(12) United States Patent
Parham et al.

(10) Patent No.: US 9,773,979 B2
(45) Date of Patent: Sep. 26, 2017

(54) MATERIALS FOR ELECTRONIC DEVICES

(75) Inventors: Amir Hossain Parham, Franfurt am Main (DE); Arne Buesing, Frankfurt am Main (DE); Christof Pflumm, Darmstadt (DE); Teresa Mujica-Fernaud, Darmstadt (DE); Philipp Stoessel, Frankfurt am Main (DE); Thomas Eberle, Landau (DE); Frank Voges, Bad Duerkheim (DE)

(73) Assignee: Merck Patent GmbH, Darmstadt (DE)

( * ) Notice: Subject to any disclaimer, the term of this patent is extended or adjusted under 35 U.S.C. 154(b) by 557 days.

(21) Appl. No.: 14/236,640

(22) PCT Filed: Jul. 5, 2012

(86) PCT No.: PCT/EP2012/002835
§ 371 (c)(1),
(2), (4) Date: Mar. 31, 2014

(87) PCT Pub. No.: WO2013/017192
PCT Pub. Date: Feb. 7, 2013

(65) Prior Publication Data
US 2014/0203216 A1 Jul. 24, 2014

(30) Foreign Application Priority Data
Aug. 3, 2011 (EP) .................... 11006384

(51) Int. Cl.
| | | |
|---|---|---|
| *H01L 51/54* | (2006.01) | |
| *C09K 11/06* | (2006.01) | |
| *H01L 51/00* | (2006.01) | |
| *C07C 255/58* | (2006.01) | |
| *C07C 209/10* | (2006.01) | |
| *C07C 211/61* | (2006.01) | |
| *C07D 403/04* | (2006.01) | |
| *C07D 209/86* | (2006.01) | |

(52) U.S. Cl.
CPC ........ *H01L 51/0035* (2013.01); *C07C 209/10* (2013.01); *C07C 211/61* (2013.01); *C07C 255/58* (2013.01); *C07D 209/86* (2013.01); *C07D 403/04* (2013.01); *C09K 11/06* (2013.01); *H01L 51/006* (2013.01); *H01L 51/0061* (2013.01); *C07C 2603/18* (2017.05); *C07C 2603/94* (2017.05); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1088* (2013.01); *C09K 2211/1092* (2013.01); *H01L 51/0072* (2013.01); *H01L 51/0073* (2013.01); *H01L 51/0074* (2013.01); *Y02E 10/549* (2013.01)

(58) Field of Classification Search
CPC ... C07C 209/00; C07C 209/10; C07C 209/86; C07C 211/61; C07C 255/00; C07C 255/58; C07C 2103/00; C07C 2103/18; C07C 2103/93; C07C 2103/94; Y02E 10/549; C09K 11/06; C09K 2211/00; C09K 2211/10; C09K 2211/1007; C09K 2211/1011; C09K 2211/1014; C09K 2211/1018; C09K 2211/1029; C09K 2211/1033; C09K 2211/1088; C09K 2211/14; C09K 2211/1092; C09K 2211/1408; C09K 2211/1416; C09K 2211/1425; C09K 2211/1433; C07D 209/82; C07D 209/86; C07D 403/00; C07D 403/02; C07D 403/04; H01L 51/0032; H01L 51/0034; H01L 51/0035; H01L 51/0039; H01L 51/005; H01L 51/0052; H01L 51/0059; H01L 51/006; H01L 51/0061; H01L 51/0071; H01L 51/0072; H01L 51/0073; H01L 51/0074; H01L 51/50; H01L 51/5012; H01L 51/5016; H01L 51/5056; H01L 51/5088
USPC ....... 428/690, 691, 917, 411.4, 336; 427/58, 427/66; 313/500–512; 257/40, 88–104, 257/E51.001–E51.052; 252/301.16–301.35, 500; 564/308; 528/422, 423, 403; 548/440; 544/102
See application file for complete search history.

(56) References Cited

U.S. PATENT DOCUMENTS

| | | |
|---|---|---|
| 8,299,459 B2 | 10/2012 | Okajima et al. |
| 9,090,532 B2 | 7/2015 | Kaiser et al. |
| 2005/0019602 A1 | 1/2005 | Sellinger |
| 2005/0221124 A1 | 10/2005 | Hwang et al. |

(Continued)

FOREIGN PATENT DOCUMENTS

| | | |
|---|---|---|
| EP | 1862524 A1 | 12/2007 |
| EP | 2182040 A2 | 5/2010 |

(Continued)

OTHER PUBLICATIONS

Thelakkat et al. Macomol. Symp. 1997, 125, 157-164. Year of publication: 1997.*

(Continued)

*Primary Examiner* — Andrew K Bohaty

(57) ABSTRACT

The present invention relates to a compound of the formula (I), (II) or (III), to the use of the compound in an electronic device, and to an electronic device comprising a compound of the formula (I), (II) or (III). The present invention furthermore relates to a process for the preparation of a compound of the formula (I), (II) or (III) and to a formulation comprising one or more compounds of the formula (I), (II) or (III).

19 Claims, No Drawings

(56) References Cited

U.S. PATENT DOCUMENTS

| | | |
|---|---|---|
| 2006/0159957 A1 | 7/2006 | Yabunouchi et al. |
| 2007/0228399 A1 | 10/2007 | Iwawaki et al. |
| 2009/0091244 A1 | 4/2009 | Negishi et al. |
| 2010/0025669 A1 | 2/2010 | Hwang et al. |
| 2010/0096982 A1 | 4/2010 | Eum et al. |
| 2011/0084255 A1* | 4/2011 | Kim .............. H01L 51/0051 257/40 |
| 2011/0114889 A1 | 5/2011 | Buesing et al. |
| 2011/0198581 A1* | 8/2011 | Yabunouchi ........ C07D 209/56 257/40 |
| 2014/0138661 A1 | 5/2014 | Ludemann et al. |

FOREIGN PATENT DOCUMENTS

| | | | |
|---|---|---|---|
| JP | 2000-056491 A | 2/2000 | |
| JP | 2005-112765 A | 4/2005 | |
| JP | 2007191465 A | 8/2007 | |
| JP | 2007318101 A | 12/2007 | |
| JP | 2009040730 A | 2/2009 | |
| JP | 2010-059158 A | 3/2010 | |
| JP | WO 2010044130 A1 * | 4/2010 | ........ C07D 209/56 |
| JP | 2010-245179 A | 10/2010 | |
| JP | 2011074037 A | 4/2011 | |
| JP | 2014-527037 A | 10/2014 | |
| KR | 2011-0041730 A | 4/2011 | |
| KR | 2011-0076271 A1 | 7/2011 | |
| WO | WO-2006/006505 A1 | 1/2006 | |
| WO | WO-2007/072838 A1 | 6/2007 | |
| WO | WO-2010110553 A2 | 9/2010 | |
| WO | WO-2011/040631 A1 | 4/2011 | |

OTHER PUBLICATIONS

Thelakkat et al. Synthetic Metals 1999, 102, 1125-1128. Year of publication: 1999.*

International Search Report for PCT/EP2012/002835 dated Aug. 20, 2012, along with English translation.

* cited by examiner

MATERIALS FOR ELECTRONIC DEVICES

RELATED APPLICATIONS

This application is a national stage application (under 35 U.S.C. §371) of PCT/EP2012/002835, filed Jul. 5, 2012, which claims benefit of European Application No. 11006384.9, filed Aug. 3, 2011, both of which are incorporated herein by reference in their entirety.

The present invention relates to a compound of the formula (I), (II) or (III), to the use of the compound in an electronic device, and to an electronic device comprising a compound of the formula (I), (II) or (III). The present invention furthermore relates to a process for the preparation of a compound of the formula (I), (II) or (III) and to a formulation comprising one or more compounds of the formula (I), (II) or (III).

The development of functional compounds for use in electronic devices is currently the subject of intensive research. The aim here is, in particular, the development of compounds with which improved properties of the electronic devices can be achieved in one or more relevant points, such as, for example, power efficiency, lifetime or colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices referred to as OLEDs. The general structure and the functional principle of OLEDs is known to the person skilled in the art and is described, inter alia, in U.S. Pat. Nos. 4,539,507, 5,151,629, EP 0676461 and WO 1998/27136.

Further improvements are still necessary regarding the performance data of OLEDs, in particular with a view to broad commercial use, for example in display devices or as light sources. Of particular importance in this connection are the lifetime, the efficiency and the operating voltage of the OLEDs and the colour values achieved. In particular in the case of blue-emitting OLEDs, there is potential for improvement with respect to the lifetime of the devices. In addition, it is desirable, for use as functional materials in electronic devices, for the compounds to have high thermal stability and a high glass-transition temperature and to be capable of sublimation without decomposition.

In this connection, there is, in particular, a need for alternative hole-transport materials. In hole-transport materials in accordance with the prior art, the voltage generally increases with the layer thickness of the hole-transport layer. In practice, a greater layer thickness of the hole-transport layer would frequently be desirable, but this often results in a higher operating voltage and worse performance data. In this connection, there is a need for novel hole-transport materials which have high charge-carrier mobility, so that thicker hole-transport layers can be achieved with only a slight increase in the operating voltage.

The use of arylamine compounds and carbazole compounds as hole-transport materials for OLEDs is known from the prior art. At this point, reference should be made, for example, to the laid-open specification EP 1661888. However, there continues to be a need for novel hole-transport materials for use in OLEDs. In particular, there is a need for materials with which the above-mentioned improvements in the performance data and properties of the OLEDs can be achieved.

The laid-open specification WO 2010/064871 discloses compounds containing a carbazole group and a fluorenyl group, where the said groups are connected directly to one another via an amino group. The compounds are disclosed for use as dopants in organic electroluminescent devices. There continues to be a need for alternative compounds for use as hole-transport material in OLEDs, in particular for those with which good efficiencies and long lifetimes of the devices can be achieved.

The laid-open specification US 2005/0221124 discloses 2-substituted fluorenyl compounds which carry a carbazole group or arylamino group. This document furthermore discloses that the said 2-fluorenyl compounds are suitable for use as hole-transport materials in OLEDs. In particular on use as hole-transport material in combination with a phosphorescent dopant in the emitting layer, however, it is highly desirable for the compound employed as hole-transport material to have a high excited triplet level. There therefore continues to be a need for alternative compounds for use as hole-transport material in OLEDs, in particular for those with which good efficiencies and long lifetimes of the devices can be achieved.

There continues to be a need for alternative matrix materials for use in OLEDs and other electronic devices. In particular, there is a need for matrix materials for phosphorescent emitters which simultaneously result in good efficiency, a long lifetime and a low operating voltage. In particular, the properties of the matrix materials are frequently limiting for the lifetime and the efficiency of the organic electroluminescent device. In particular, it is desirable for matrix materials for phosphorescent emitters to have a high excited triplet level.

The present invention is thus based on the technical object of providing compounds which are suitable for use in electronic devices, such as, for example, OLEDs, and which can be employed, in particular, as hole-transport materials and/or as matrix materials.

As part of the present invention, it has now been found that compounds of the formula (I), (II) or (III) indicated below are highly suitable for the above-mentioned uses.

The compounds according to the invention are characterised by having a fluorenyl group which is bonded in its 1-, 3- or 4-position to an arylamino group, which in turn is substituted by a further triarylamino group or carbazole group.

The present invention thus relates to a compound of the formula (I), (II) or (III)

formula (I)

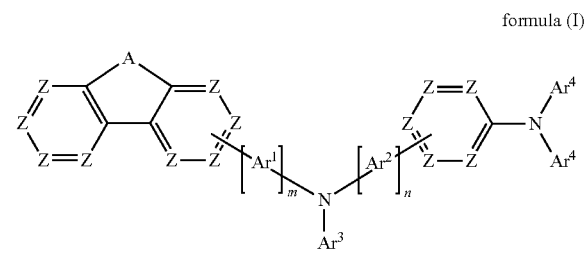

formula (II)

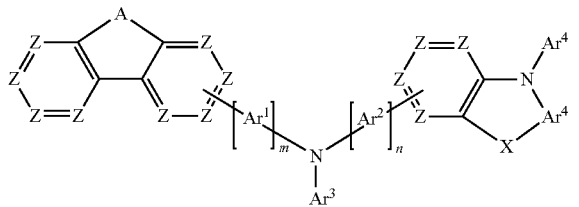

formula (III)

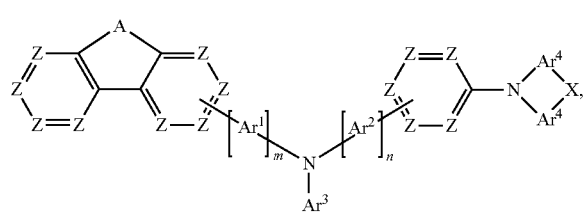

where the following applies to the symbols and indices occurring:

A is equal to $C(R^1)_2$ or equal to

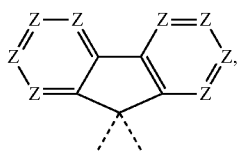

where the dashed lines represent the bonds emanating from the group A;

Z is on each occurrence, identically or differently, $CR^1$ or N or, if a group is bonded in the relevant position, is equal to C;

$Ar^1, Ar^3$ is on each occurrence, identically or differently, an aromatic or heteroaromatic ring system having 5 to 30 aromatic ring atoms, which may be substituted by one or more radicals $R^1$;

$Ar^2$ is on each occurrence, identically or differently, an arylene group having 6 to 30 aromatic ring atoms or a heteroarylene group having 5 to 14 aromatic ring atoms, which may be substituted by one or more radicals $R^1$;

$Ar^4$ is on each occurrence, identically or differently, an aryl group having 6 to 30 aromatic ring atoms or a heteroaryl group having 5 to 14 aromatic ring atoms, which may be substituted by one or more radicals $R^1$, where radicals $R^1$ on groups $Ar^4$ cannot form rings;

X is selected from a single bond, $C(R^1)_2$, C=O, $Si(R^1)_2$, $NR^1$, O, S, S=O and $S(=O)_2$;

$R^1$ is on each occurrence, identically or differently, H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^2$ and where one or more $CH_2$ groups in the above-mentioned groups may be replaced by —$R^2C=CR^2$—, —C≡C—, $Si(R^2)_2$, C=O, C=S, C=$NR^2$, —C(=O)O—, —C(=O)$NR^2$—, $NR^2$, P(=O)($R^2$), —O—, —S—, SO or $SO_2$ and where one or more H atoms in the above-mentioned groups may be replaced by D, F, Cl, Br, I, CN or $NO_2$, or an aromatic or heteroaromatic ring system having 5 to 30 aromatic ring atoms, which may in each case be substituted by one or more radicals $R^2$, or an aryloxy or heteroaryloxy group having 5 to 30 aromatic ring atoms, which may be substituted by one or more radicals $R^2$, where two or more radicals $R^1$ may be linked to one another and may form a ring;

$R^2$ is on each occurrence, identically or differently, H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^3$ and where one or more $CH_2$ groups in the above-mentioned groups may be replaced by —$R^3C=CR^3$—, —C≡C—, $Si(R^3)_2$, C=O, C=S, C=$NR^3$, —C(=O)O—, —C(=O)$NR^3$—, $NR^3$, P(=O)($R^3$), —O—, —S—, SO or $SO_2$ and where one or more H atoms in the above-mentioned groups may be replaced by D, F, Cl, Br, I, CN or $NO_2$, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which may be substituted by one or more radicals $R^3$, where two or more radicals $R^2$ may be linked to one another and may form a ring;

$R^3$ is on each occurrence, identically or differently, H, D, F or an aliphatic, aromatic or heteroaromatic organic radical having 1 to 20 C atoms, in which, in addition, one or more H atoms may be replaced by D or F; two or more substituents $R^3$ here may be linked to one another and may form a ring;

m is equal to 0, 1, 2 or 3, where m=0 means that the relevant group is not present;

n is equal to 0, 1, 2 or 3, where n=0 means that the relevant group is not present;

where the group $Ar^1$ or the nitrogen atom is bonded to the fluorene ring system in the 1-position, in the 3-position or in the 4-position;

where n in formula (II) must be equal to 1 if the group X represents a single bond; and where the compound cannot contain a heteroaryl group which contains more than 14 aromatic ring atoms.

For illustration, the structural formula of fluorene is depicted below, together with the numbering of the positions. The numbering in spiro-bifluorene derivatives is analogous, with the only difference that position 9 cannot be substituted.

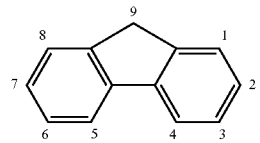

It should furthermore be emphasised that, in the case m=0 or n=0, the relevant group $Ar^1$ or $Ar^2$ respectively is not present and the two moieties bonded to this group are connected directly to one another.

If the index m or n is greater than 1, this means that a plurality of groups $Ar^1$ or $Ar^2$, more precisely m or n groups Ar$^1$ or Ar$^2$ respectively, are bonded sequentially one behind the other, so that, for example for m=2 and Ar$^1$=phenylene, a biphenylene group arises which connects the fluorenyl group and the group N(Ar$^3$). For m=3 and Ar$^1$=phenylene, for example, a terphenylene group with phenylene groups bonded in series one behind the other arises.

It should furthermore be noted that the bonding of the group X to the group Ar$^4$ in the formulae (II) and (III) can take place at any desired position of the group Ar$^4$, preferably at a directly adjacent position or at a position which is not more than one position remote from a directly adjacent position, for example a meta-position, regarded from the bonding of the group Ar$^4$ to the nitrogen atom. The group X is particularly preferably bonded to the group Ar$^4$ in a directly adjacent position, regarded from the bonding of the group Ar$^4$ to the nitrogen atom.

An aryl group in the sense of this invention contains 6 to 60 aromatic ring atoms; a heteroaryl group in the sense of this invention contains in principle 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quino-line or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benz-anthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aralkyl group in the sense of this invention is an alkyl group which is substituted by an aryl group, where the term aryl group is to be understood as defined above and the alkyl group has 1 to 20 C atoms, where, in addition, individual H atoms and/or CH$_2$ groups in the alkyl group may be replaced by the groups indicated in the definition of the alkyl groups and where the alkyl group is the group that is bonded to the remainder of the compound. Correspondingly, a heteroaralkyl group represents an alkyl group which is substituted by a heteroaryl group, where the term heteroaryl group is to be understood as defined above and the alkyl group has 1 to 20 C atoms, where, in addition, individual H atoms and/or CH$_2$ groups in the alkyl group may be replaced by the groups indicated in the definition of the alkyl groups and where the alkyl group is the group that is bonded to the remainder of the compound.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp$^3$-hybridised C, Si, N or O atom, an sp$^2$-hybridised C or N atom or an sp-hybridised C atom. Thus, for example, systems such as 9,9'-spiro-bifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, ter-phenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phen-azine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-tri-fluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoro-ethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentyn-ylthio, hexynylthio, heptynylthio or octynylthio.

The formulation that two or more radicals may form a ring with one another is, for the purposes of the present description, intended to be taken to mean, inter alia, that the two radicals are linked to one another by a chemical bond. This is illustrated by the following scheme:

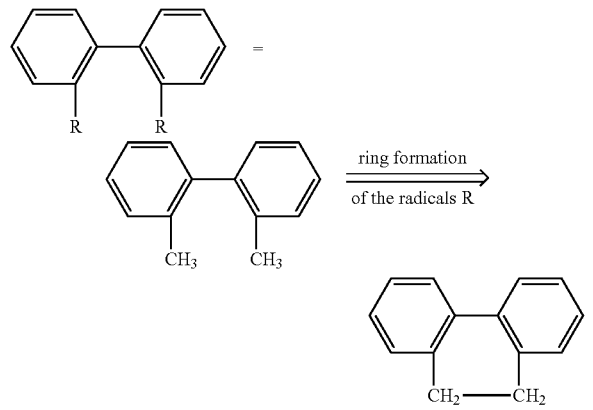

Furthermore, however, the above-mentioned formulation is also intended to be taken to mean that, in the case where one of the two radicals represents hydrogen, the second radical is bonded at the position at which the hydrogen atom was bonded, with formation of a ring. This is intended to be illustrated by the following scheme:

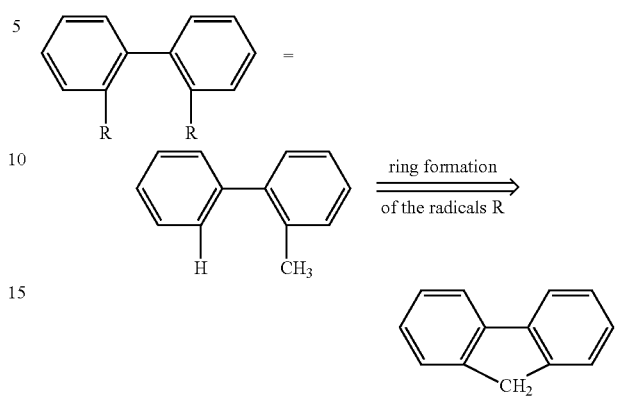

A compound of the formula (I) can, in accordance with the invention, rep-resent a compound of the following formulae (I-A) to (I-C):

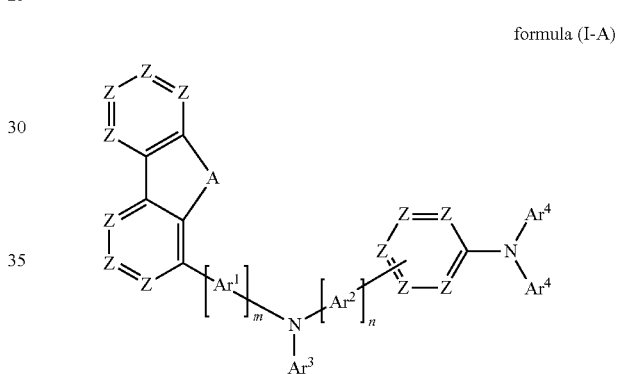

formula (I-A)

formula (I-B)

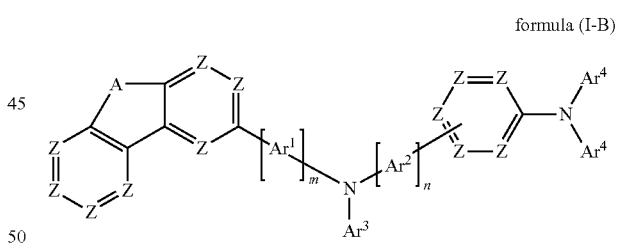

formula (I-C)

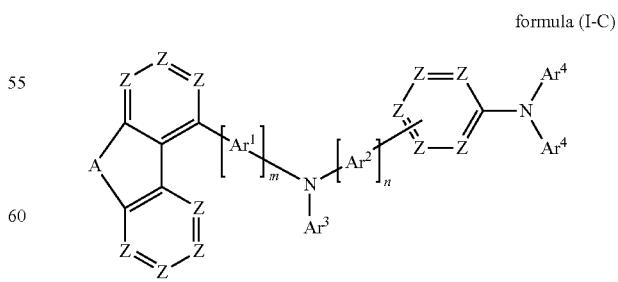

A compound of the formula (II) can, in accordance with the invention, rep-resent a compound of the following formulae (II-A) to (II-C):

formula (II-A)

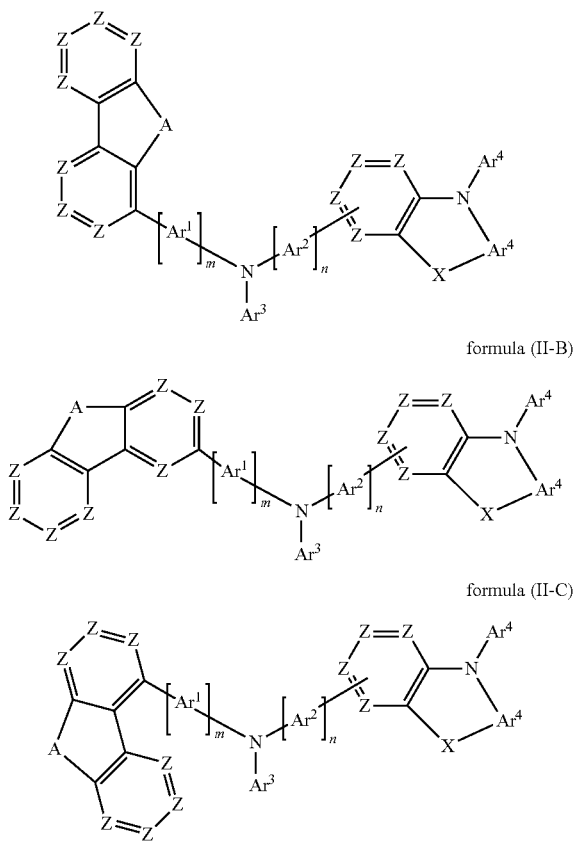

formula (II-B)

formula (II-C)

A compound of the formula (III) can, in accordance with the invention, rep-resent a compound of the following formulae (III-A) to (III-C):

formula (III-A)

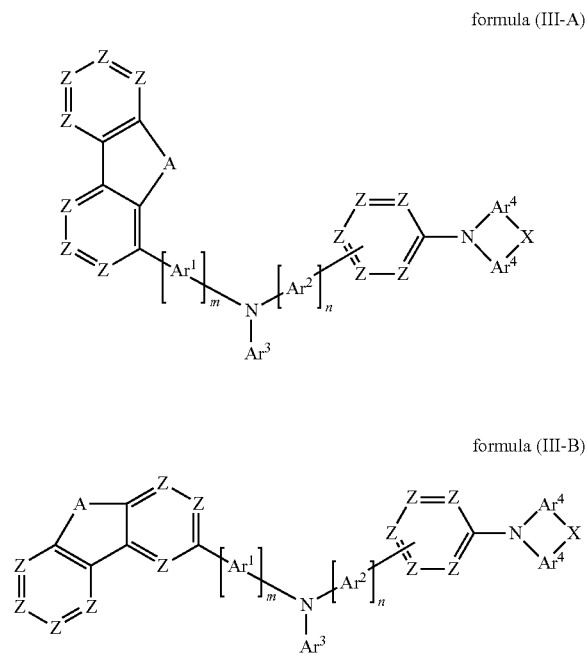

formula (III-B)

formula (III-C)

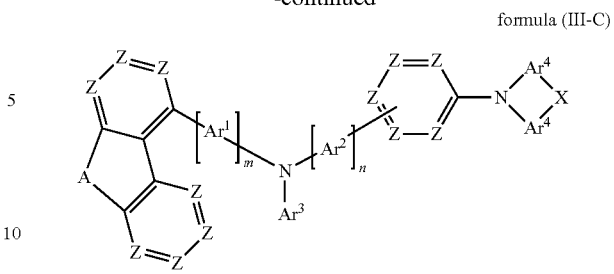

Preference is Given to Compounds of the Formulae (I-B), (II-B) and (III-B).

The following preferences for compounds of the formula (I), (II) or (III) apply in accordance with the present invention.

The group $Ar^1$ or, in the case where m=0, the group $N(Ar^3)$ is preferably bonded to the fluorenyl ring system in the 3-position.

It is preferred in accordance with the invention for not more than two Z per aromatic ring in formula (I), (II) or (III) to be equal to N, particularly preferably not more than one Z.

It is furthermore preferred for Z in the fluorenyl group to be equal to $CR^1$.

It is furthermore generally preferred for Z to be equal to $CR^1$ if no group is bonded in the relevant position and for Z to be equal to C if a group is bonded in the relevant position.

Furthermore, A is preferably equal to $C(R^1)_2$.

For formula (II), Z is preferably equal to $CR^1$ in the case where X represents a single bond or equal to C if a group is bonded in the relevant position. For formula (II), the group Z is particularly preferably equal to $CR^1$ or equal to C if a group is bonded in the relevant position.

Furthermore preferably, radicals $R^1$ which are constituent of a group Z for compounds of the formula (II) do not form rings with one another. Particularly preferably, radicals $R^1$ which are constituents of a group Z for compounds of the formula (II) do not form rings with one another in the case where X represents a single bond.

$Ar^1$ preferably represents an aromatic or heteroaromatic ring system having 5 to 24 aromatic ring atoms. $Ar^1$ is particularly preferably an aromatic ring system having 6 to 18 aromatic ring atoms, very particularly preferably 6 to 12 aromatic ring atoms. $Ar^1$ is most preferably an arylene group having 6 to 10 aromatic ring atoms. The groups indicated may generally be substituted by one or more radicals $R^1$.

$Ar^2$ preferably represents an arylene group having 6 to 10 aromatic ring atoms or a heteroarylene group having 5 to 14 aromatic ring atoms. $Ar^2$ is particularly preferably a phenylene group. The groups indicated may generally be substituted by one or more radicals $R^1$. In accordance with the invention, it is preferred for radicals $R^1$ on groups $Ar^2$ not to form rings with one another.

$Ar^3$ preferably represents an aromatic or heteroaromatic ring system having 5 to 24 aromatic ring atoms. $Ar^3$ is particularly preferably an aromatic ring system having 6 to 18 aromatic ring atoms. The groups indicated may generally be substituted by one or more radicals $R^1$.

$Ar^4$ is preferably an aryl group having 6 to 10 aromatic ring atoms or a heteroaryl group having 5 to 14 aromatic ring atoms. $Ar^4$ is particularly preferably a phenyl group. The groups indicated may generally be substituted by one or more radicals $R^1$.

The group X is preferably selected from a single bond, $C(R^1)_2$, O or S. X is very particularly preferably a single bond.

The radical $R^1$ is preferably selected on each occurrence, identically or differently, from H, D, F, CN, $Si(R^2)_3$, $N(R^2)_2$ or a straight-chain alkyl or alkoxy group having 1 to 20 C atoms or a branched or cyclic alkyl or alkoxy group having 3 to 20 C atoms, where the above-mentioned groups may each be substituted by one or more radicals $R^2$ and where one or more $CH_2$ groups in the above-mentioned groups may be replaced by —C≡C—, —$R^2$C═C$R^2$—, $Si(R^2)_2$, C═O, C═N$R^2$, —N$R^2$—, —O—, —S—, —C(═O)O— or —C(═O)N$R^2$—, or an aromatic or heteroaromatic ring system having 5 to 20 aromatic ring atoms, which may in each case be substituted by one or more radicals $R^2$, where two or more radicals $R^1$ may be linked to one another and may form a ring.

The radical $R^2$ is preferably selected on each occurrence, identically or differently, from H, D, F, CN, $Si(R^3)_3$, $N(R^3)_2$ or a straight-chain alkyl or alkoxy group having 1 to 20 C atoms or a branched or cyclic alkyl or alkoxy group having 3 to 20 C atoms, where the above-mentioned groups may each be substituted by one or more radicals $R^3$ and where one or more $CH_2$ groups in the above-mentioned groups may be replaced by —C≡C—, —$R^3$C═C$R^3$—, $Si(R^3)_2$, C═O, C═N$R^3$, —N$R^3$—, —O—, —S—, —C(═O)O— or —C(═O)N$R^3$—, or an aromatic or heteroaromatic ring system having 5 to 20 aromatic ring atoms, which may in each case be substituted by one or more radicals $R^3$, where two or more radicals $R^2$ may be linked to one another and may form a ring.

It is furthermore preferred for m to be equal to 0 or 1. m is particularly preferably equal to 0.

For formula (II) and (III), it is generally preferred for n to be equal to 1, 2 or 3. For formula (II), it is particularly preferred for n to be equal to 1.

For the formulae (I), (II) and (III), it is furthermore generally preferred for n to be equal to 1, 2 or 3, particularly preferably equal to 1 or 2, very particularly preferably equal to 1.

For the compounds according to the invention, it is generally preferred for no heteroaryl group having more than 10 aromatic ring atoms to be present. Particularly preferably, no heteroaryl group having more than 6 aromatic ring atoms is present. Very particularly preferably, the compounds according to the invention contain no heteroaryl group of whatever size.

For the compounds according to the invention, it is furthermore preferred for no condensed aryl group having more than 14 aromatic ring atoms to be present in the compound. Particularly preferably, no condensed aryl group having more than 10 aromatic ring atoms is present.

It is furthermore preferred for the group $Ar^2$ or the group $N(Ar^3)$ in compounds of the formula (I) to be bonded to the compound part shown below in the para-position to the nitrogen atom

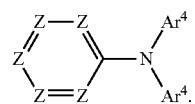

It is furthermore preferred for the group $Ar^2$ or the group $N(Ar^3)$ in compounds of the formula (II) to be bonded to the compound part shown below in the para-position to the nitrogen atom

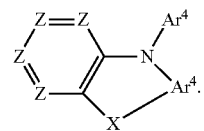

It is furthermore preferred for the group $Ar^2$ or the group $N(Ar^3)$ in compounds of the formula (III) to be bonded to the compound part shown below in the para-position to the nitrogen atom

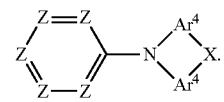

The compound of the formula (I), (II) or (II) is furthermore preferably asymmetrical. The compound can furthermore preferably not be represented in a mirror-symmetrical structural formula.

It is furthermore preferred for the compound of the formula (I), (II) or (III) to contain no further triarylamino group in addition to the two triarylamino groups depicted. It is likewise preferred for the compound to contain no further carbazole derivative apart from those which arise in formula (II) or (III) for X as single bond.

Preferred embodiments of formula (I) conform to the following formulae (I-1) to (I-48)

formula (I-1)

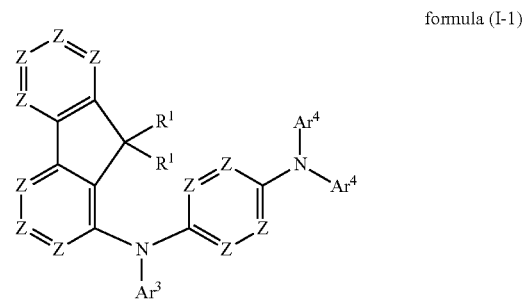

formula (I-2)

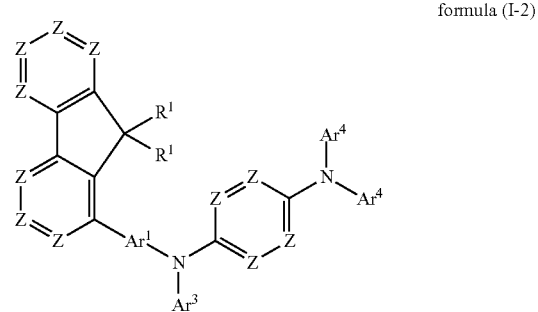

formula (I-3)

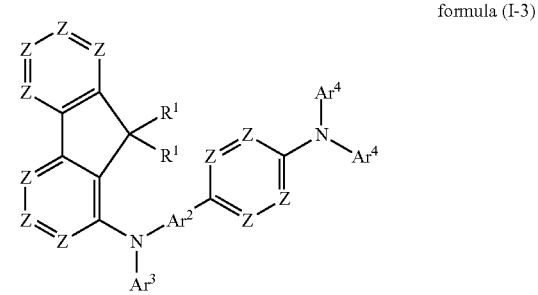

formula (I-4)
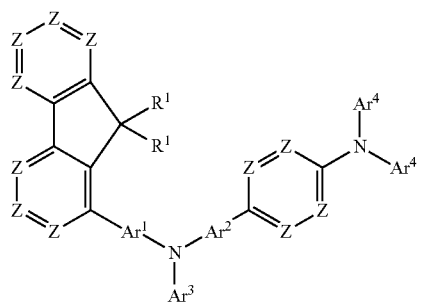
formula (I-5)
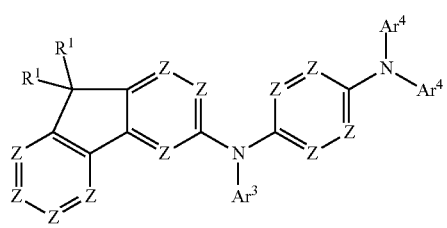
formula (I-6)
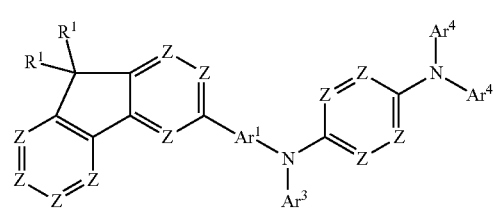
formula (I-7)
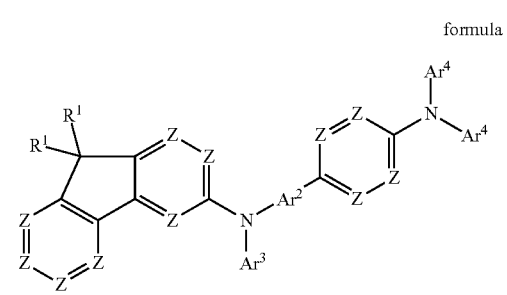
formula (I-8)
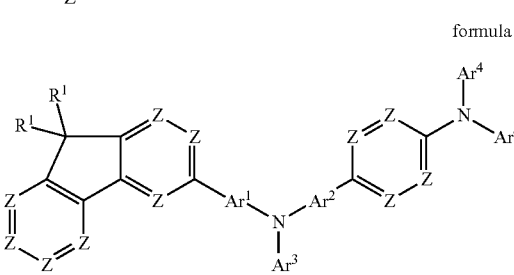
formula (I-9)
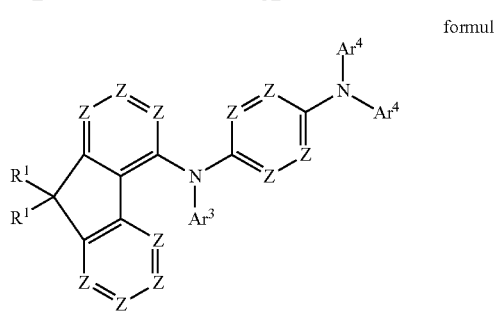
formula (I-10)
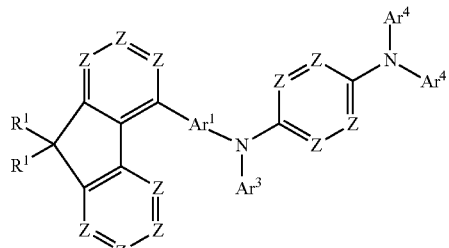
formula (I-11)
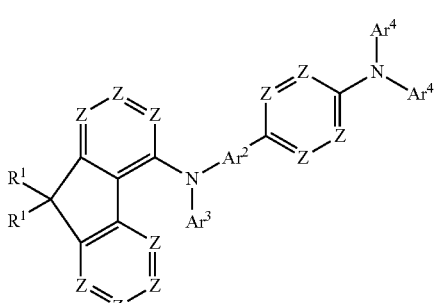
formula (I-12)
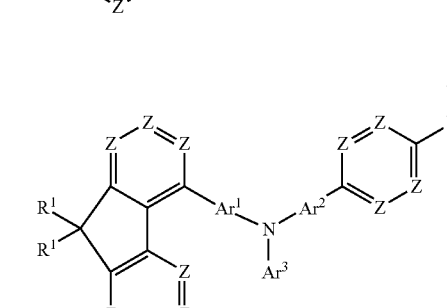
formula (I-13)
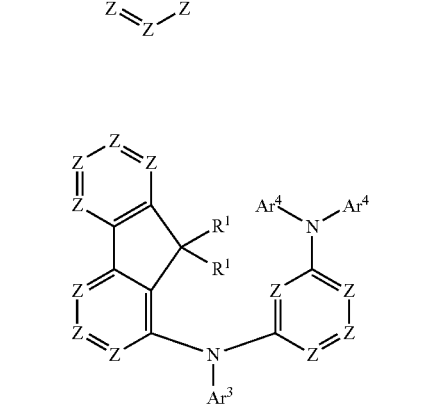
formula (I-14)
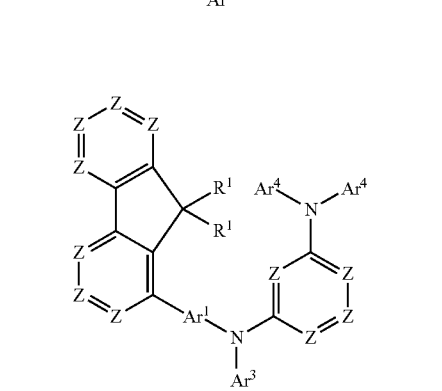

formula (I-15)
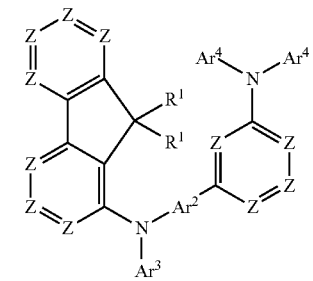
formula (I-16)
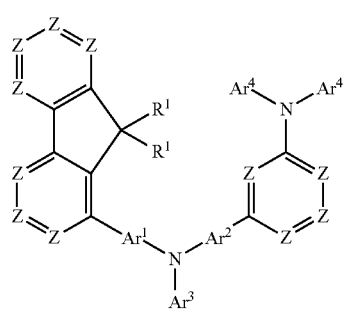
formula (I-17)
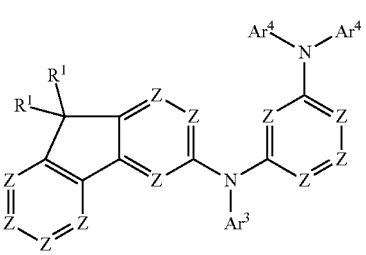
formula (I-18)
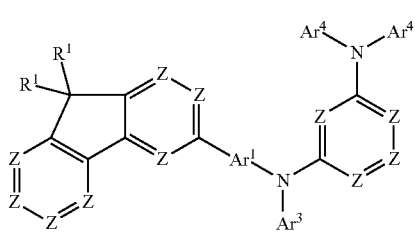
formula (I-19)
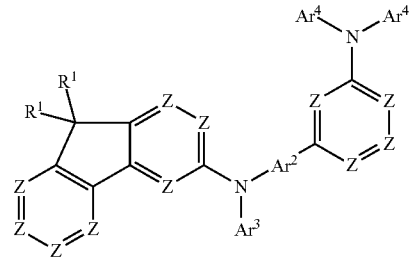
formula (I-20)
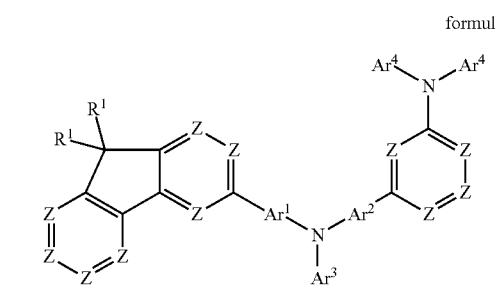
formula (I-21)
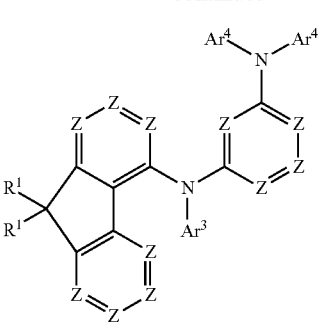
formula (I-22)
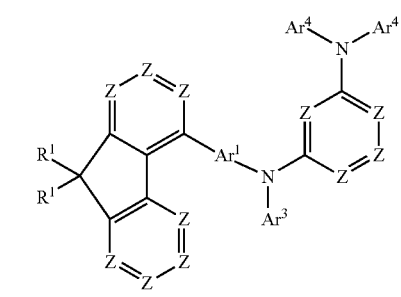
formula (I-23)
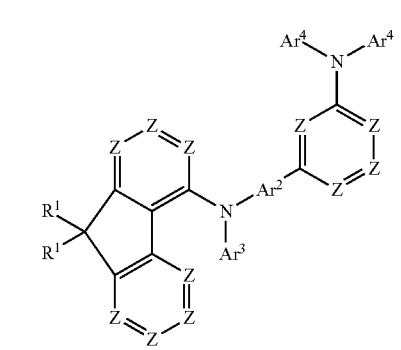
formula (I-24)
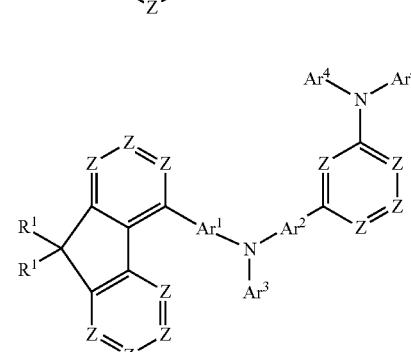
formula (I-25)
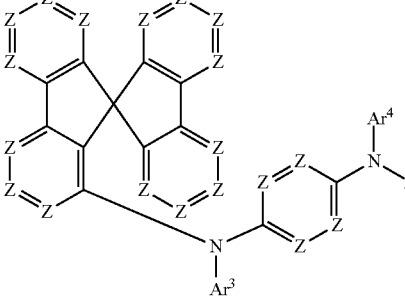

formula (I-26)
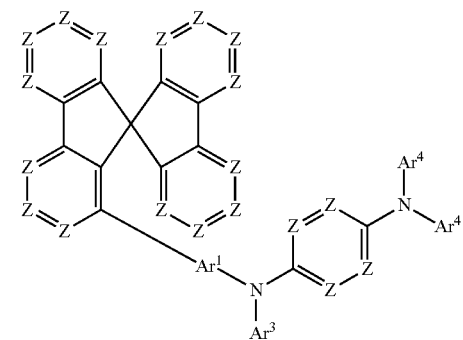
formula (I-27)
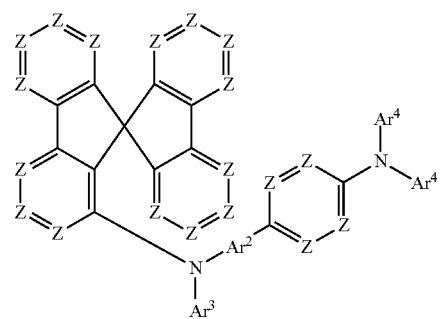
formula (I-28)
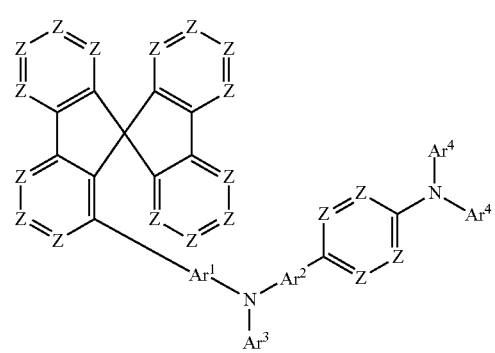
formula (I-29)
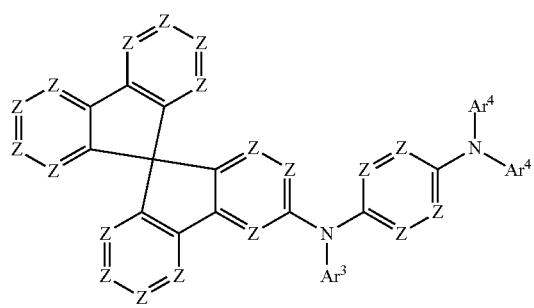
formula (I-30)
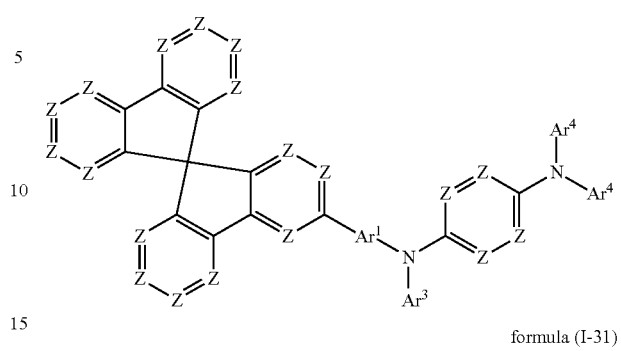
formula (I-31)
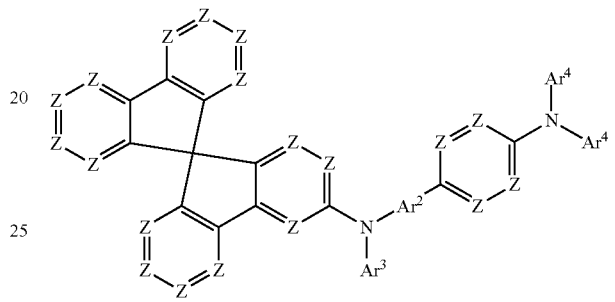
formula (I-32)
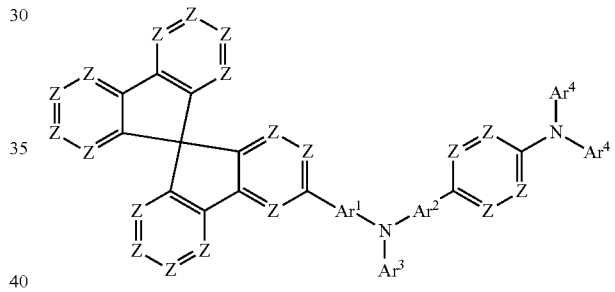
formula (I-33)
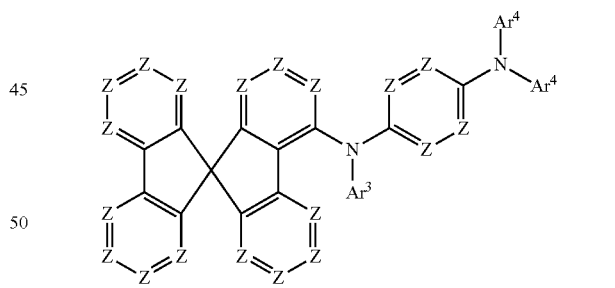
formula (I-34)
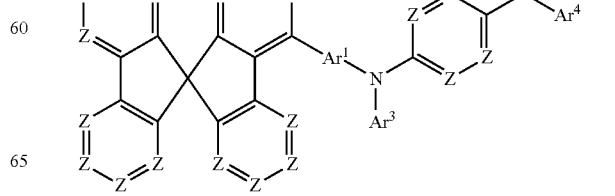

-continued
formula (I-35)
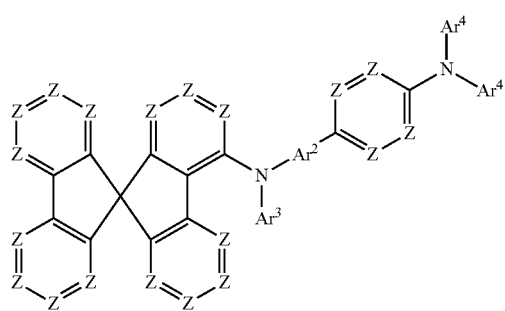
formula (I-36)
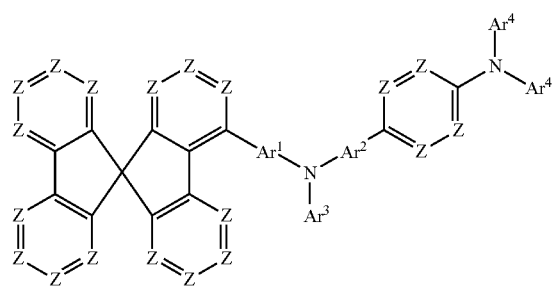
formula (I-37)
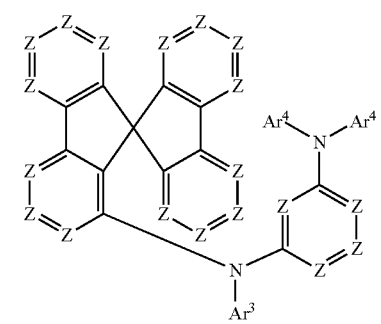
formula (I-38)
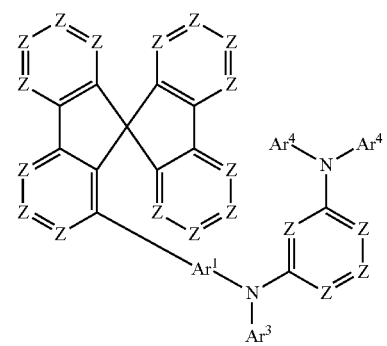
formula (I-39)
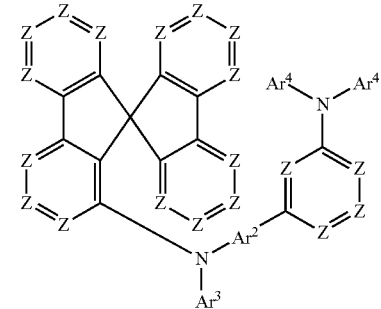
formula (I-40)
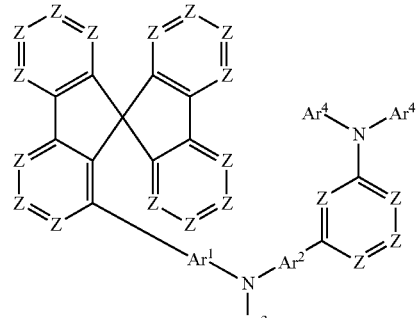
formula (I-41)
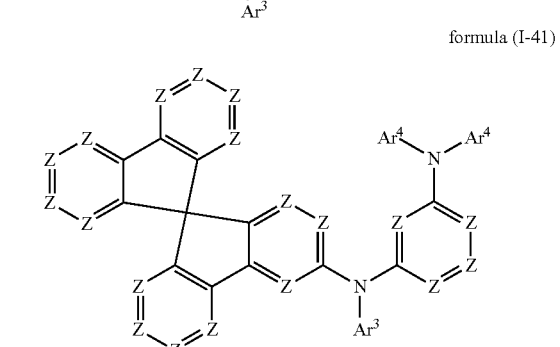
formula (I-42)
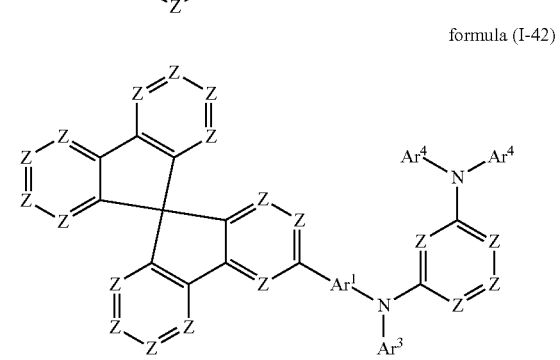
formula (I-43)
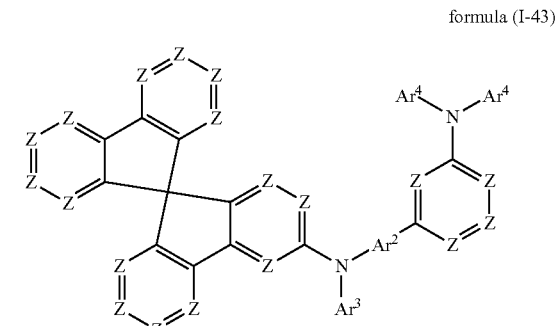
formula (I-44)
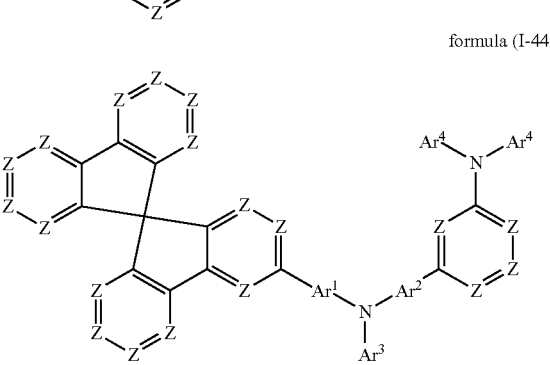

-continued formula (I-45)
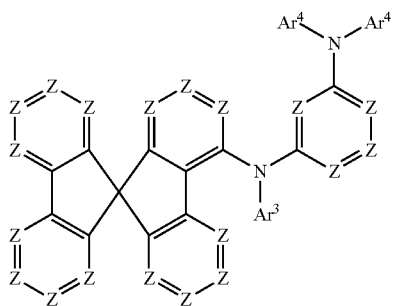

formula (I-46)
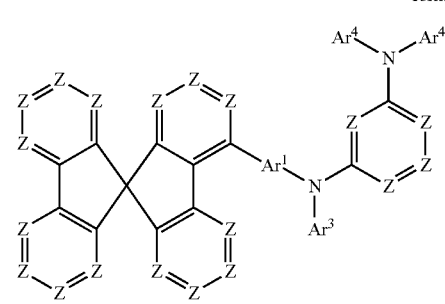

formula (I-47)
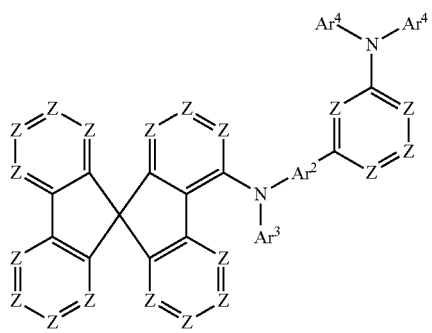

formula (I-48)
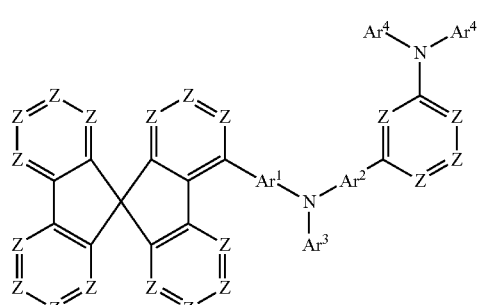

where the symbols occurring are as defined above. Furthermore, the above-mentioned preferred embodiments of the groups $Ar^1$, $Ar^2$, $Ar^3$, $Ar^4$, Z, $R^1$ and $R^2$ are also preferred here.

Preferred embodiments of formula (II) conform to the following formulae (II-1) to (II-24)

formula (II-1)
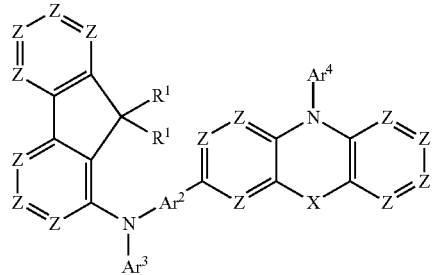

formula (II-2)
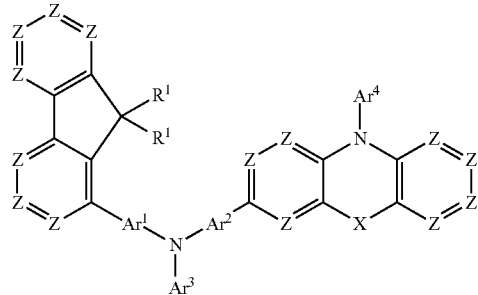

formula (II-3)
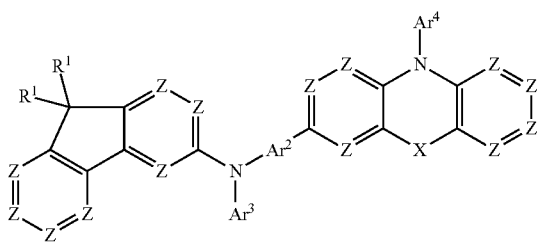

formula (II-4)
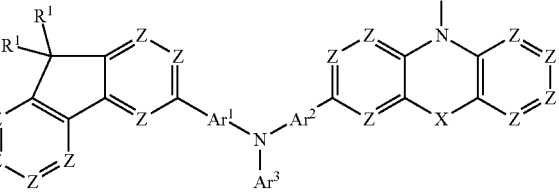

formula (II-5)
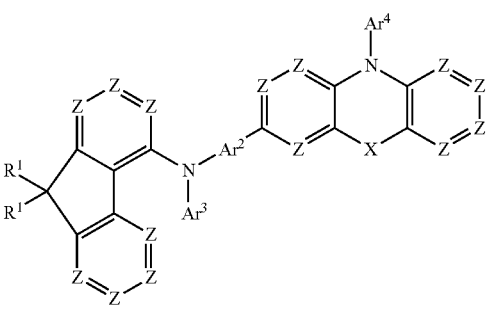

formula (II-6)
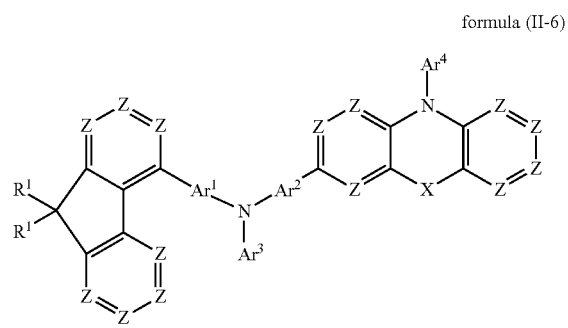
formula (II-7)
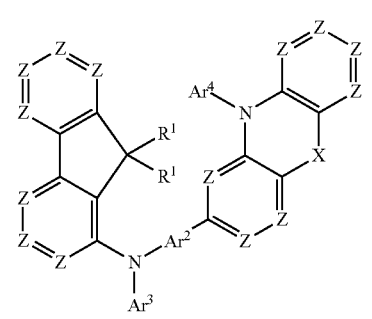
formula (II-8)
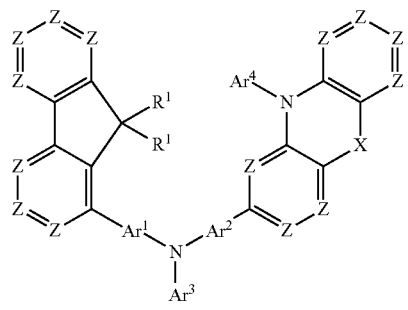
formula (II-9)
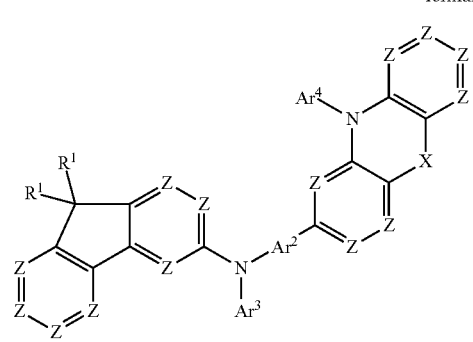
formula (II-10)
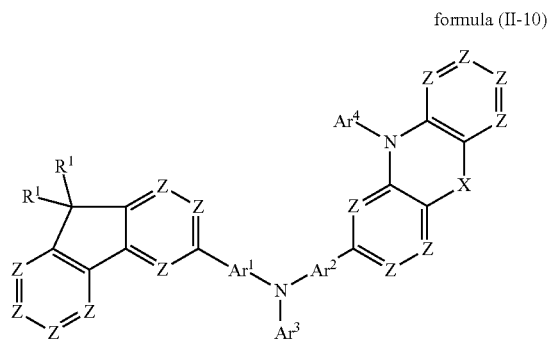
formula (II-11)
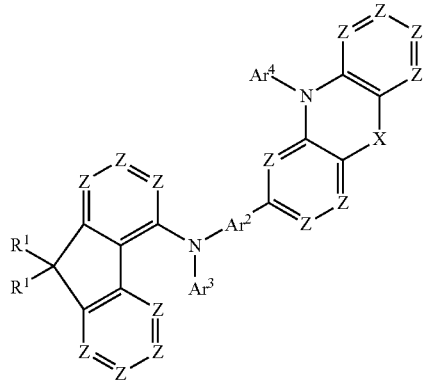
formula (II-12)
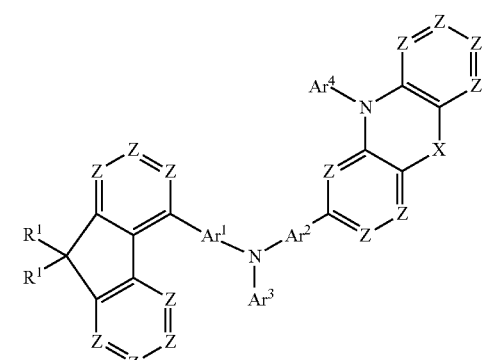
formula (II-13)
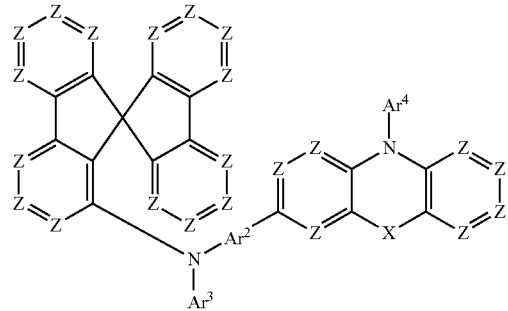
formula (II-14)
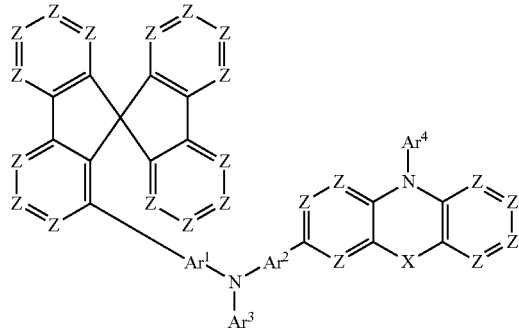

-continued
formula (II-15)
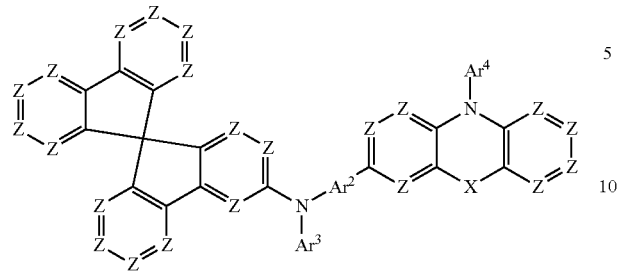
formula (II-16)
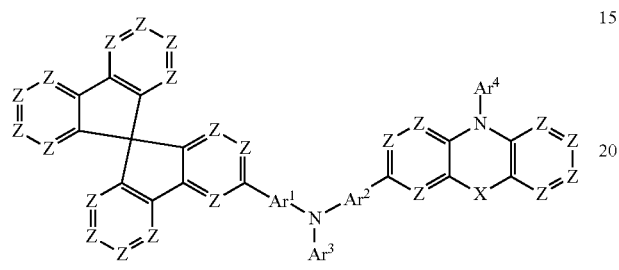
formula (II-17)
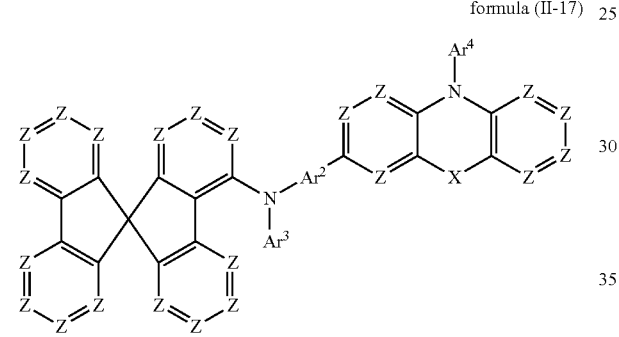
formula (II-18)
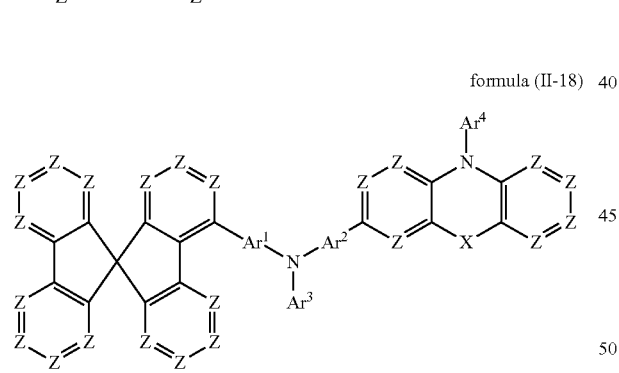
formula (II-19)
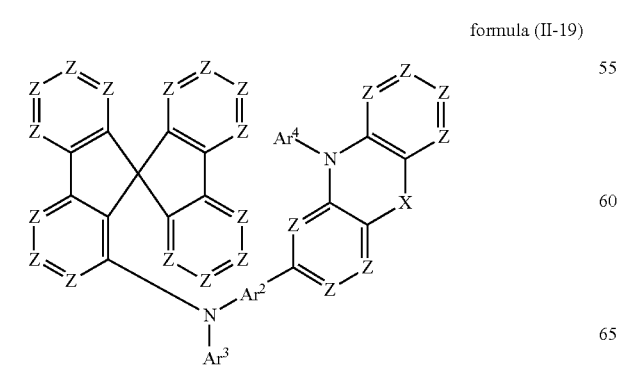
formula (II-20)
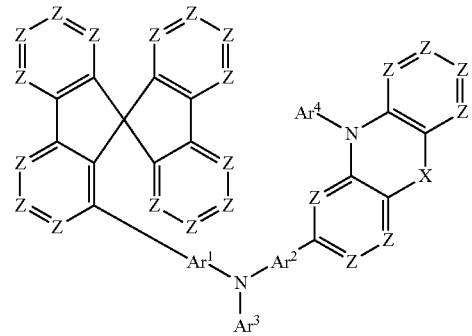
formula (II-21)
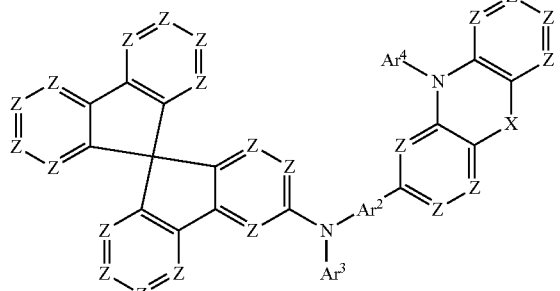
formula (II-22)
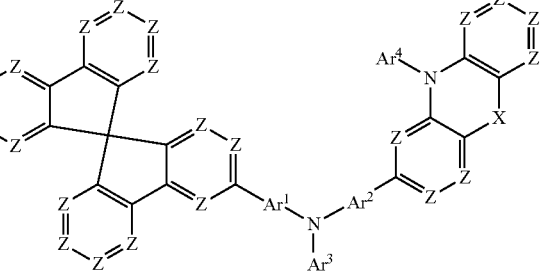
formula (II-23)
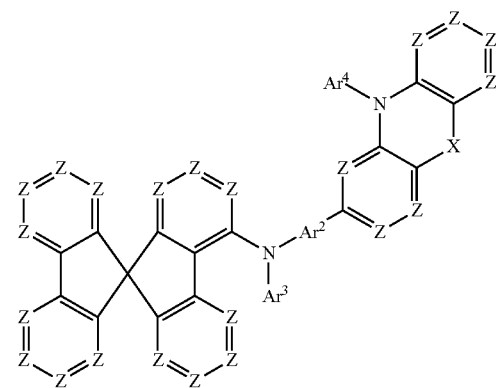

formula (II-24)

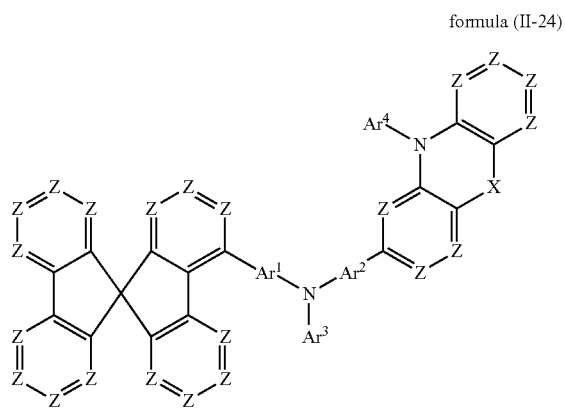

where the symbols occurring are as defined above. Furthermore, the above-mentioned preferred embodiments of the groups Ar¹, Ar², Ar³, Ar⁴, X, Z, R¹ and R² are also preferred here.

Preferred embodiments of compounds of the formula (III) conform to the following formulae (III-1) to (III-48)

formula (III-1)

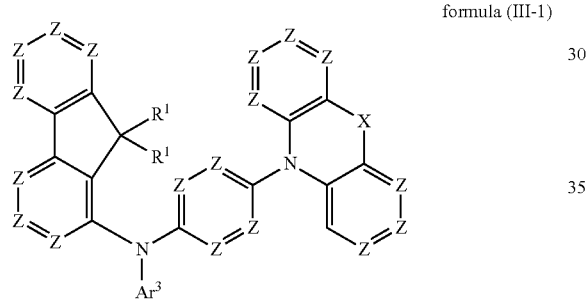

formula (III-2)

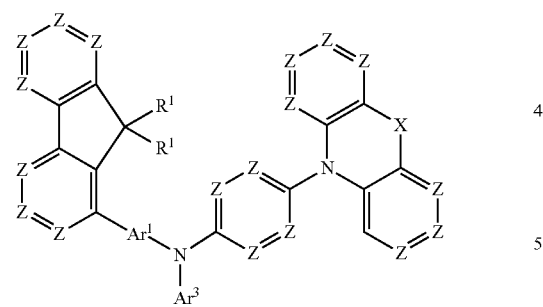

formula (III-3)

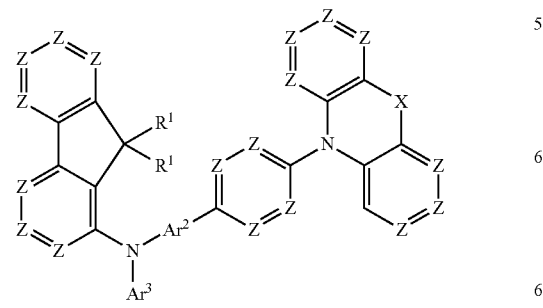

formula (III-4)

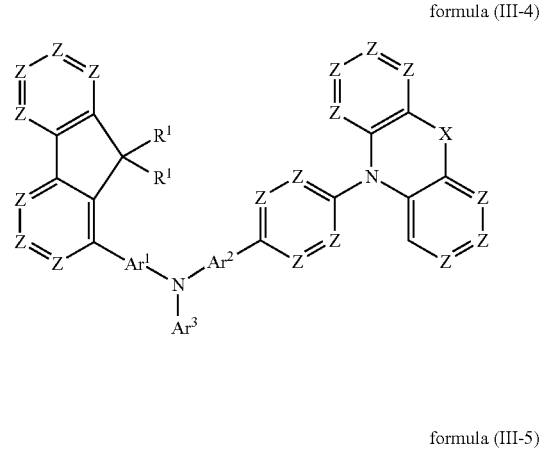

formula (III-5)

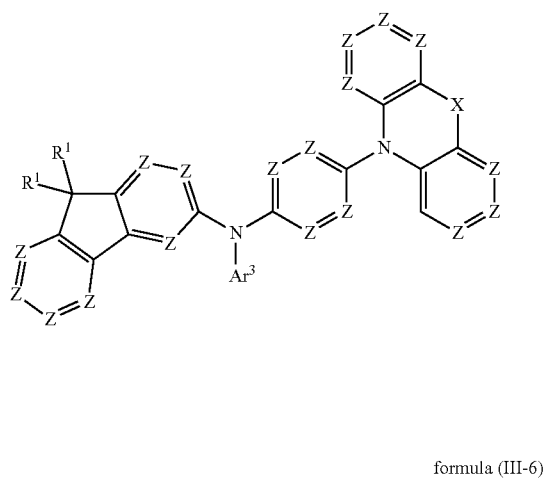

formula (III-6)

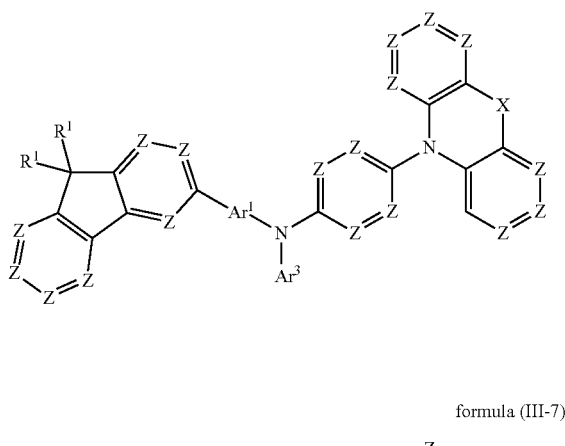

formula (III-7)

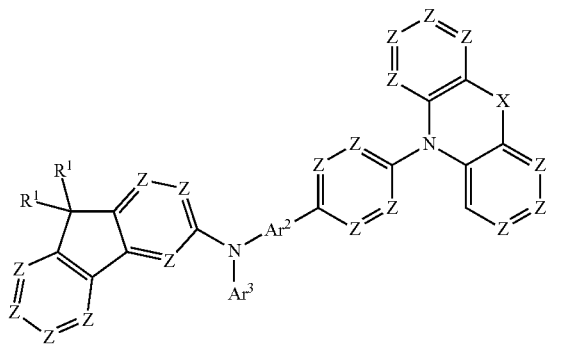

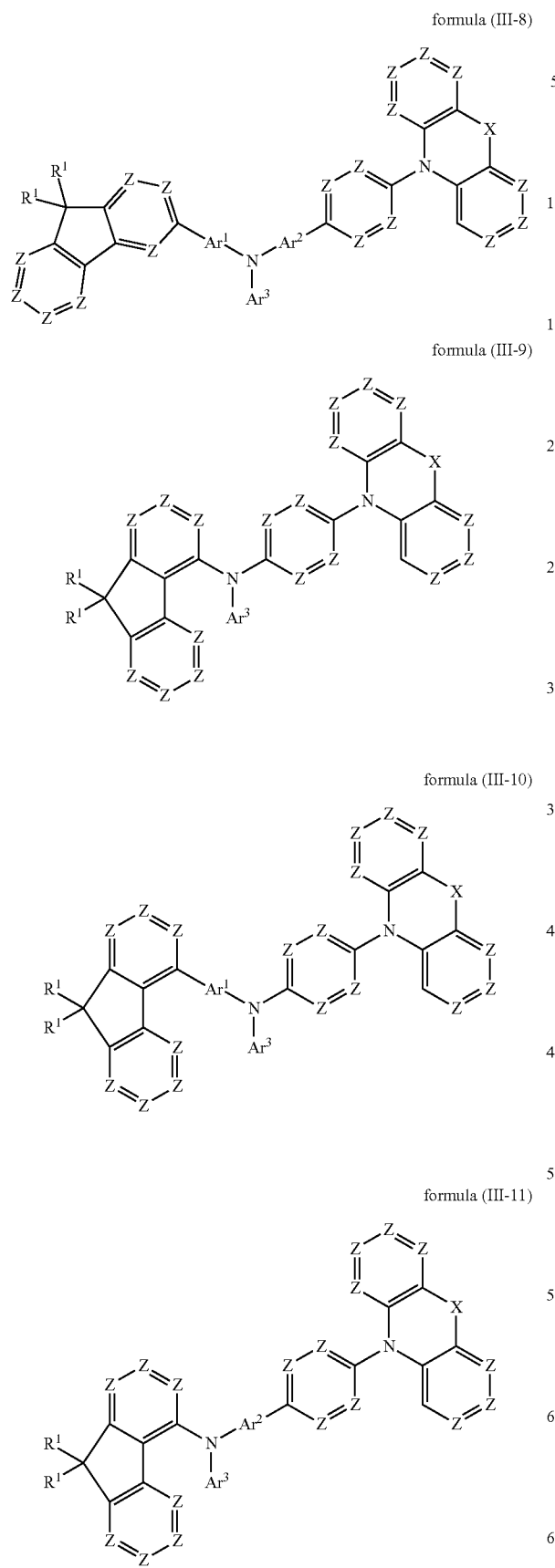
formula (III-8)
formula (III-9)
formula (III-10)
formula (III-11)
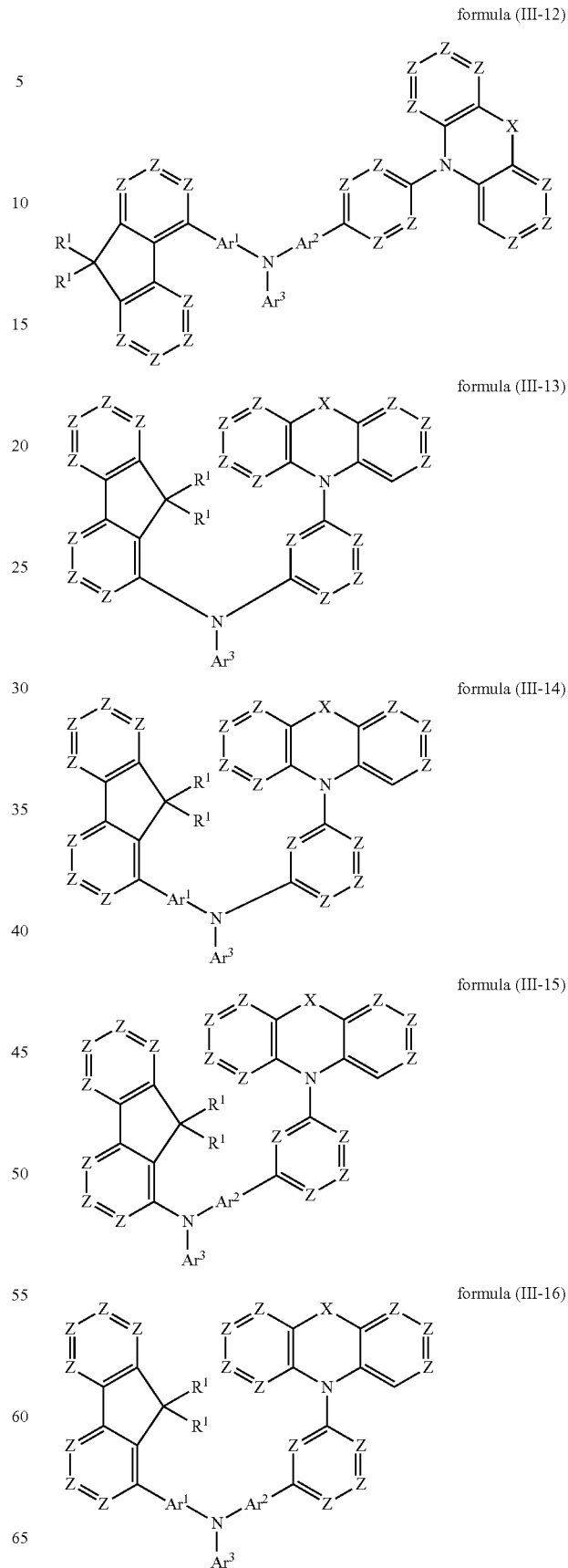
formula (III-12)
formula (III-13)
formula (III-14)
formula (III-15)
formula (III-16)

-continued
formula (III-17)
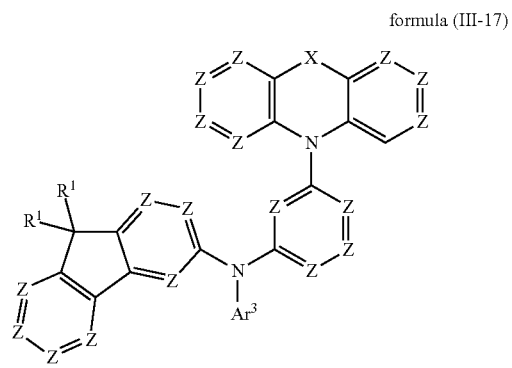
formula (III-18)
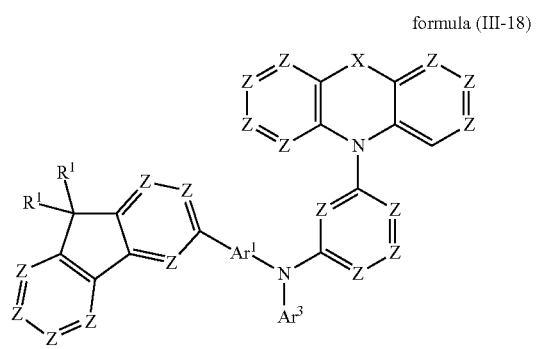
formula (III-19)
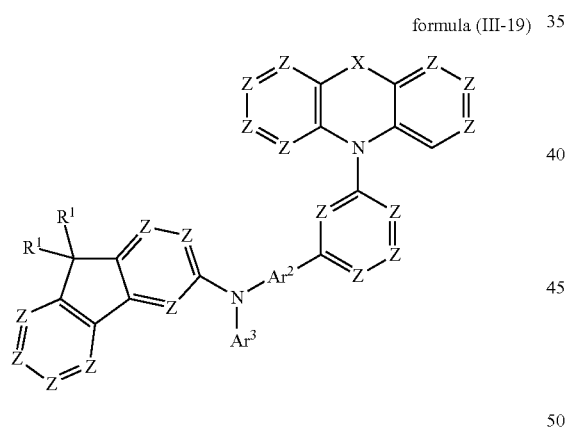
formula (III-20)
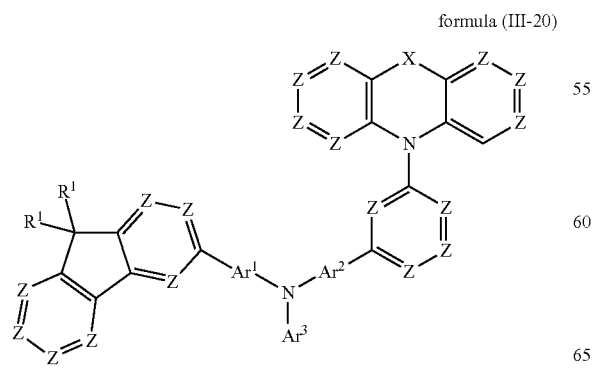
formula (III-21)
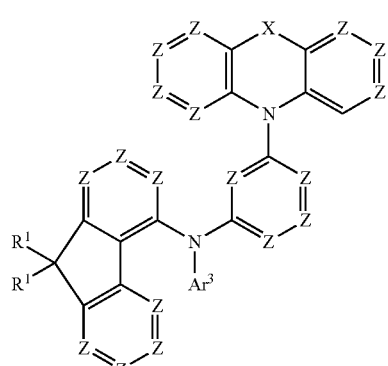
formula (III-22)
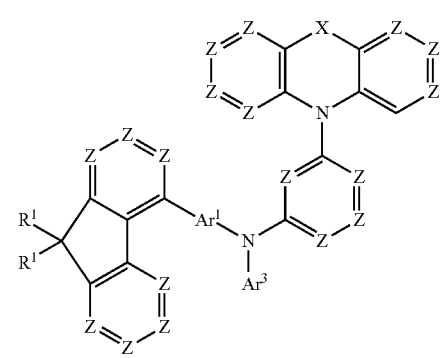
formula (III-23)
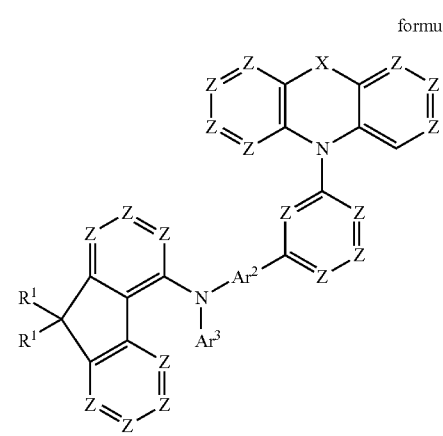
formula (III-24)
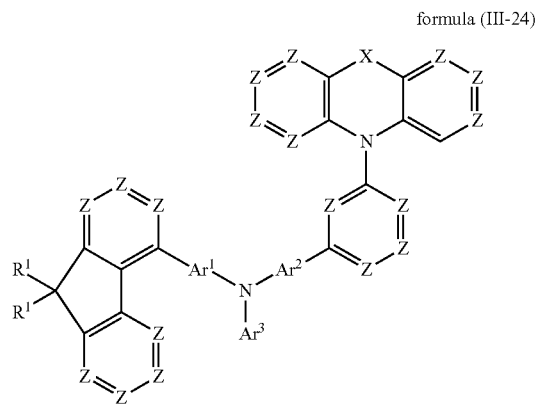

formula (III-25)
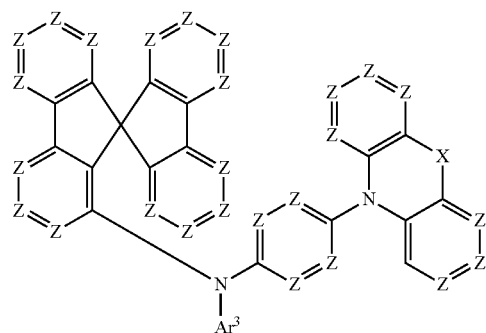
formula (III-29)
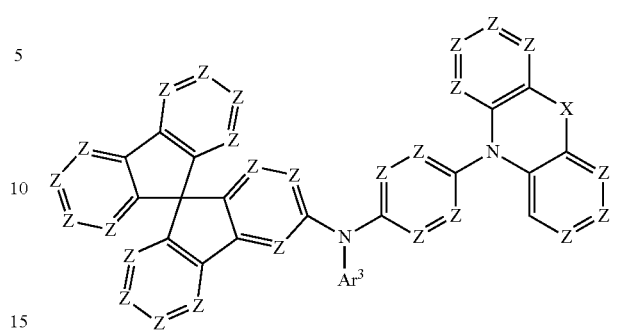
formula (III-26)
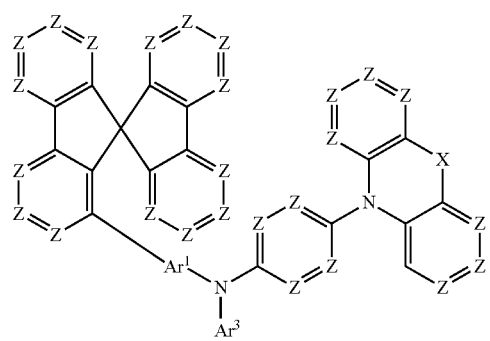
formula (III-30)
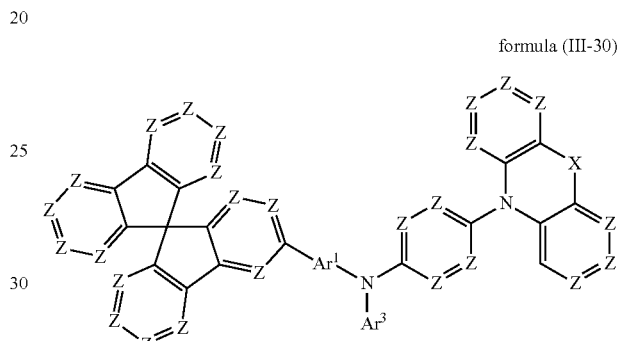
formula (III-27)
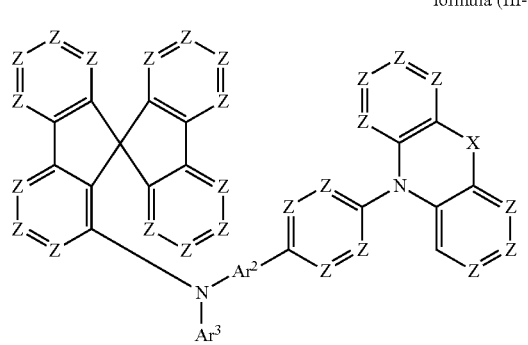
formula (III-31)
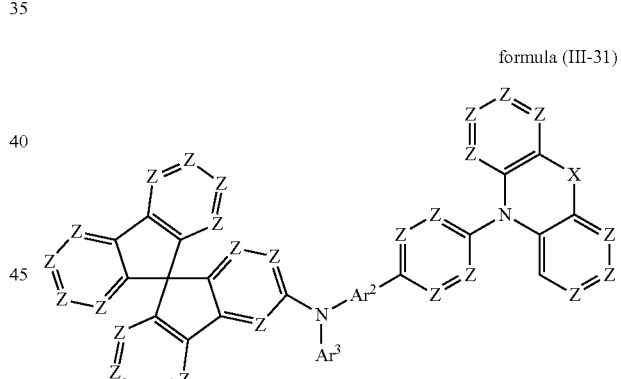
formula (III-28)
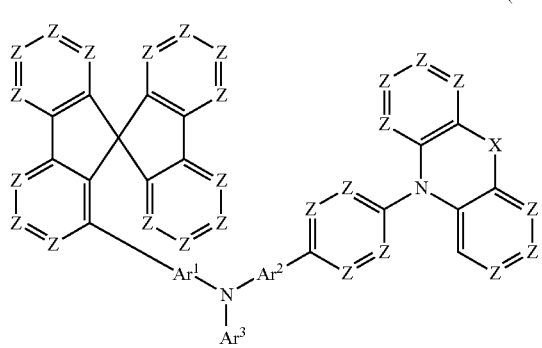
formula (III-32)
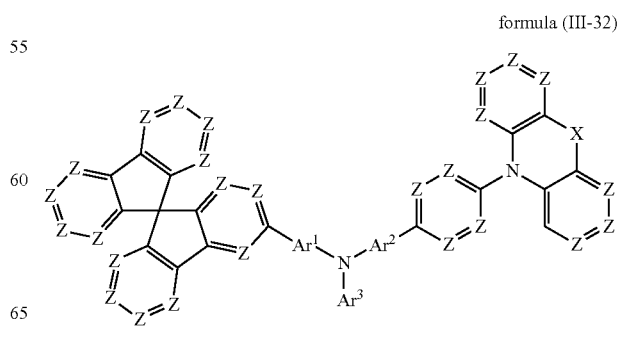

formula (III-33)
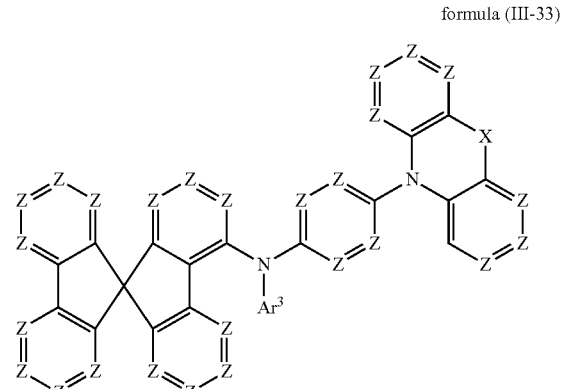
formula (III-34)
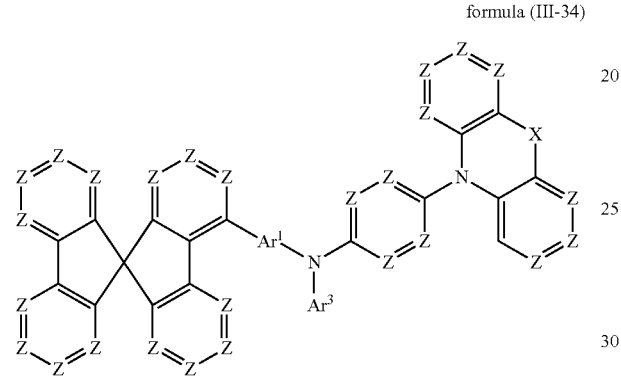
formula (III-35)
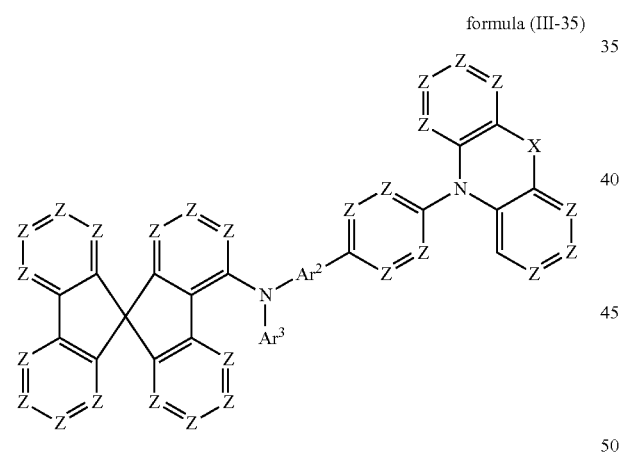
formula (III-36)
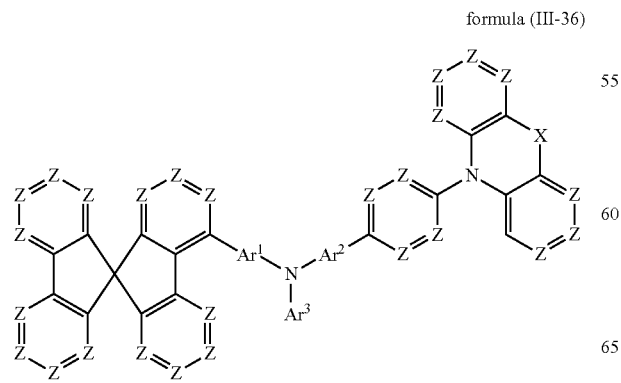
formula (III-37)
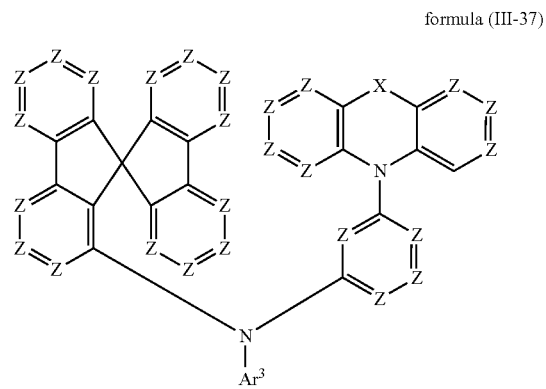
formula (III-38)
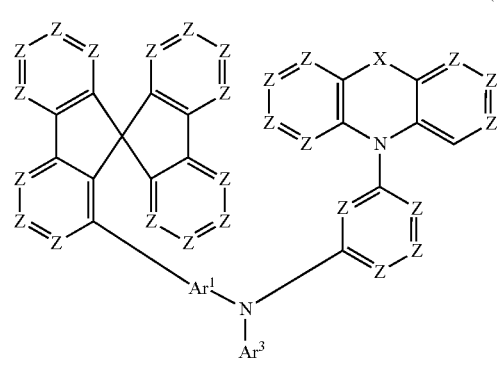
formula (III-39)
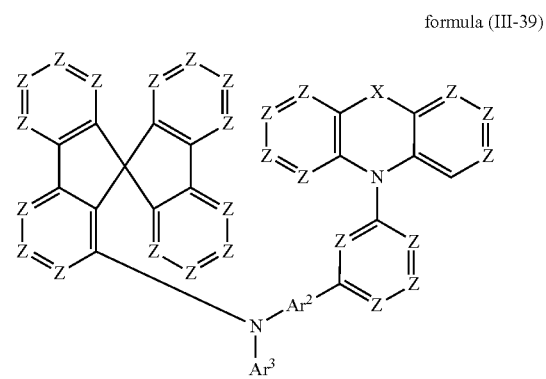
formula (III-40)
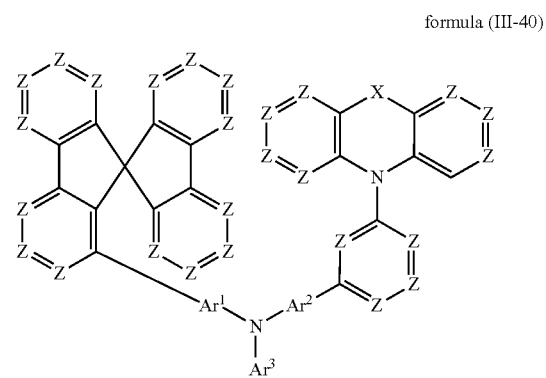

formula (III-41)
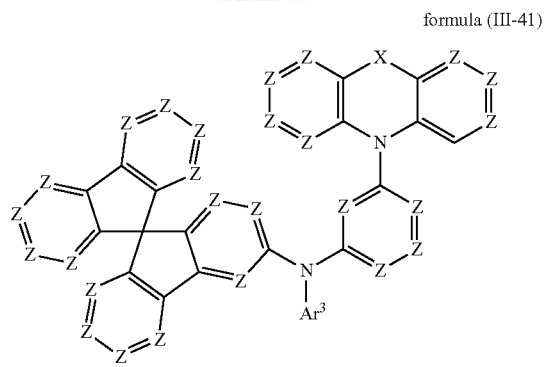
formula (III-42)
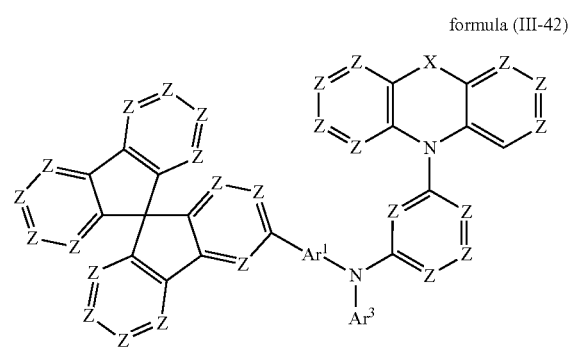
formula (III-43)
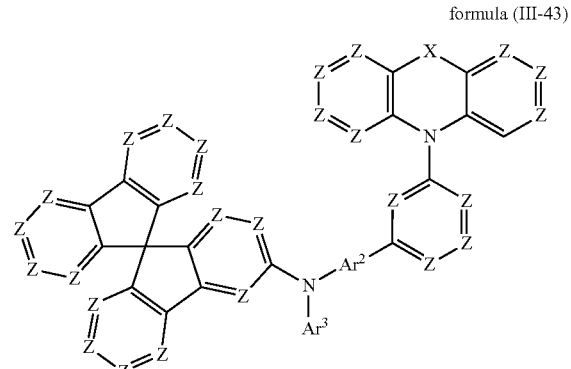
formula (III-44)
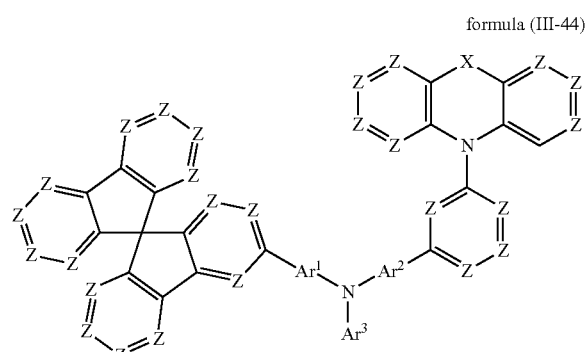
formula (III-45)
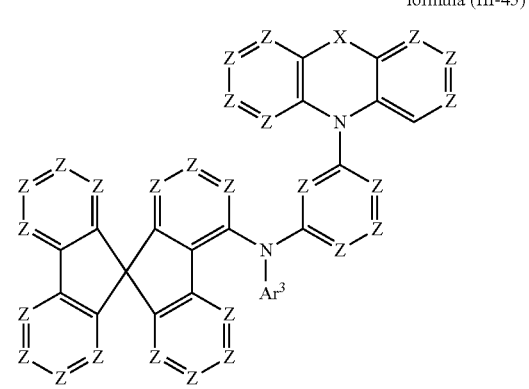
formula (III-46)
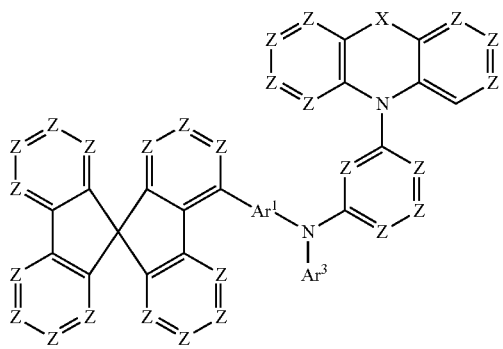
formula (III-47)
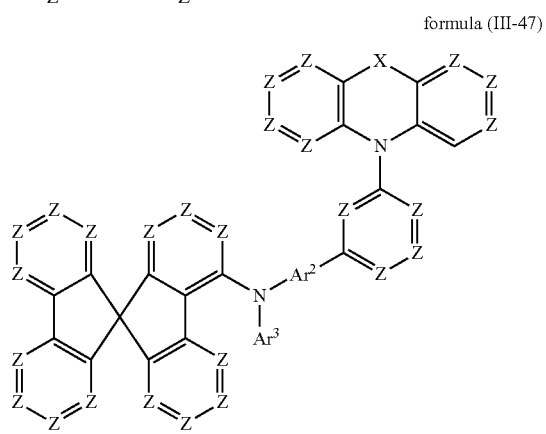
formula (III-48)
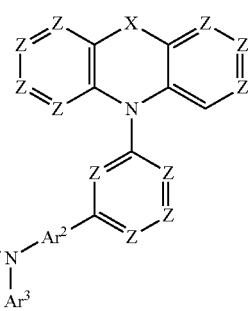
where the symbols occurring are as defined above. Furthermore, the above-mentioned preferred embodiments of the groups $Ar^1$, $Ar^2$, $Ar^3$, X, Z, $R^1$ and $R^2$ are also preferred here.

Explicit examples of compounds according to the invention are shown in the following table.
| | |
|---|---|
| 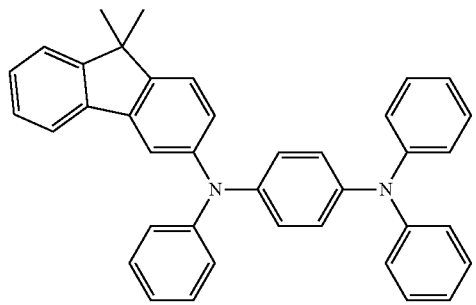 [SMILES: CC1(C)c2ccccc2-c2cc(N(c3ccccc3)c3ccc(N(c4ccccc4)c4ccccc4)cc3)ccc21] | 1 |
| 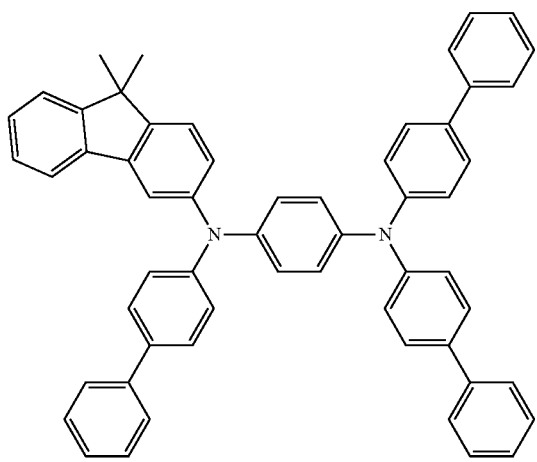 [SMILES: CC1(C)c2ccccc2-c2cc(N(c3ccc(-c4ccccc4)cc3)c3ccc(N(c4ccc(-c5ccccc5)cc4)c4ccc(-c5ccccc5)cc4)cc3)ccc21] | 2 |
| 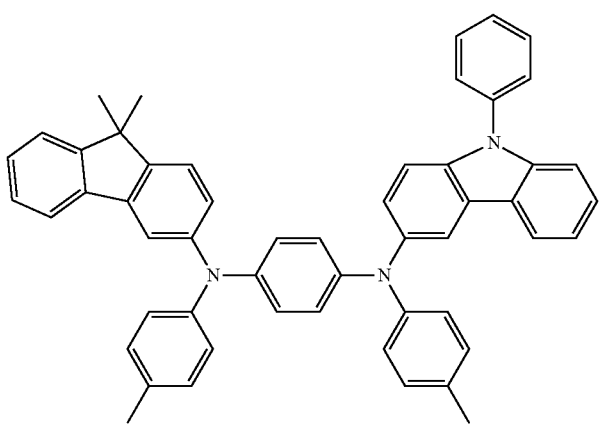 [SMILES: Cc1ccc(N(c2ccc(N(c3ccc(C)cc3)c3ccc4c(c3)c3ccccc3n4-c3ccccc3)cc2)c2ccc3c(c2)-c2ccccc2C3(C)C)cc1] | 3 |
| 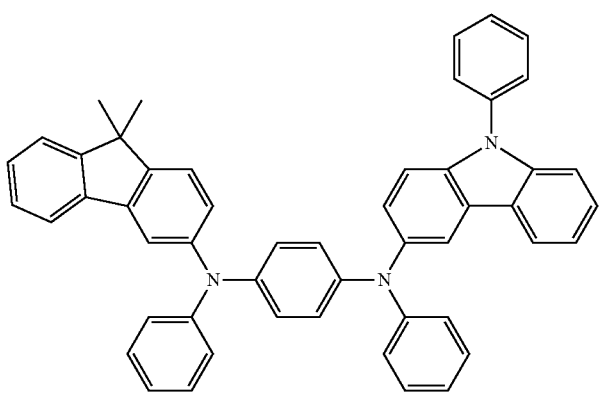 [SMILES: CC1(C)c2ccccc2-c2cc(N(c3ccccc3)c3ccc(N(c4ccccc4)c4ccc5c(c4)c4ccccc4n5-c4ccccc4)cc3)ccc21] | 4 |

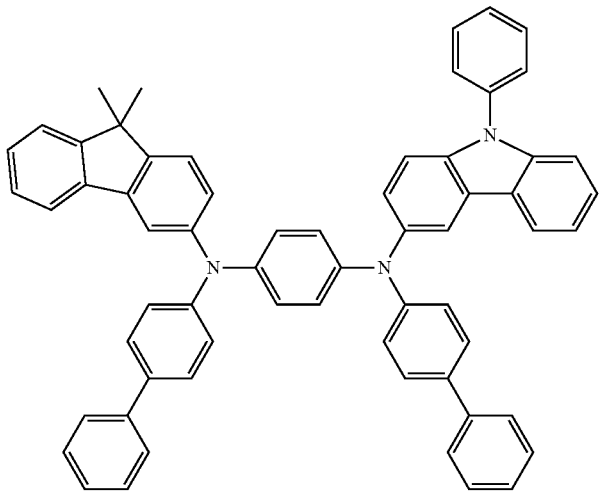 [SMILES: CC1(C)c2ccccc2-c2cc(N(c3ccc(-c4ccccc4)cc3)c3ccc(N(c4ccc(-c5ccccc5)cc4)c4ccc5c(c4)c4ccccc4n5-c4ccccc4)cc3)ccc21]

-continued
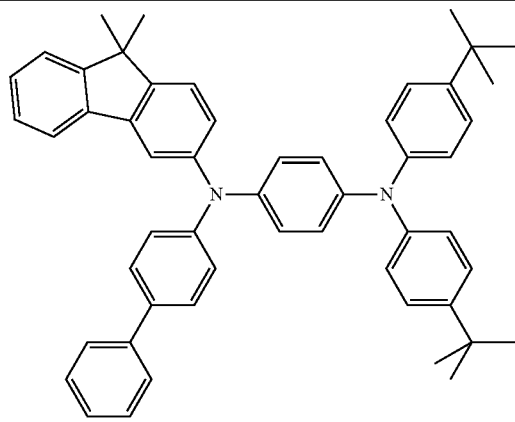
8
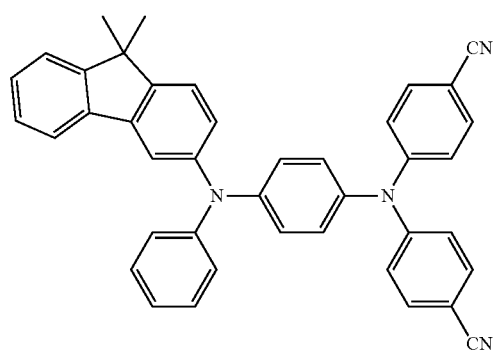 [SMILES: CC1(C)c2ccccc2-c2cc(N(c3ccccc3)c3ccc(N(c4ccc(C#N)cc4)c4ccc(C#N)cc4)cc3)ccc21]
9
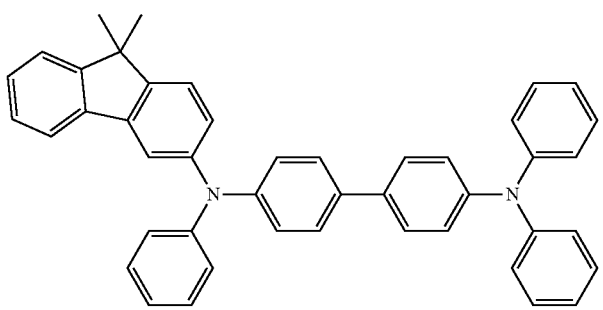 [SMILES: CC1(C)c2ccccc2-c2cc(N(c3ccccc3)c3ccc(-c4ccc(N(c5ccccc5)c5ccccc5)cc4)cc3)ccc21]
10
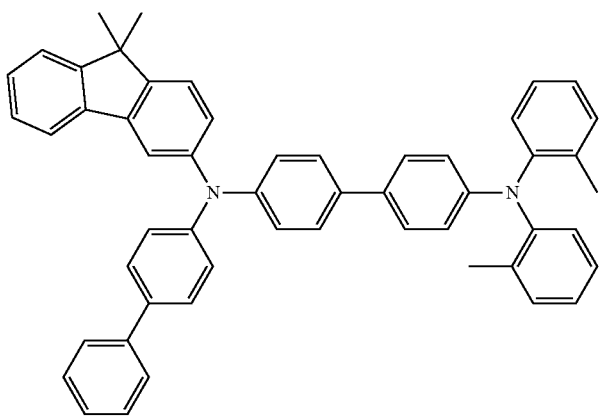
11

-continued
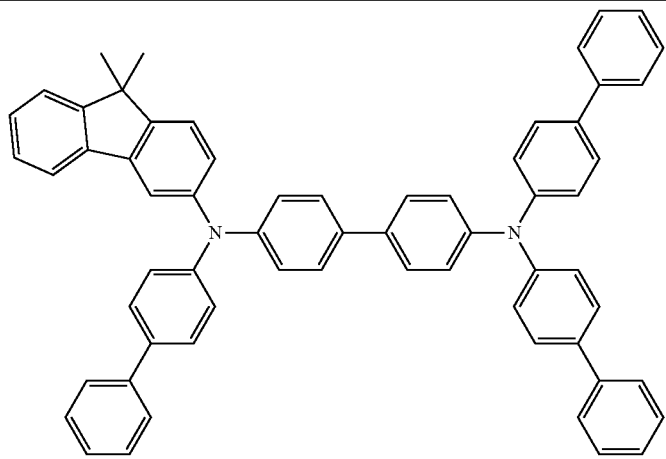
12
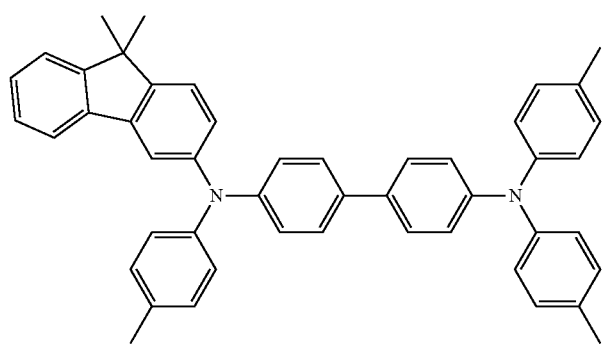 [SMILES: Cc1ccc(N(c2ccc(C)cc2)c2ccc(-c3ccc(N(c4ccc(C)cc4)c4ccc5c(c4)-c4ccccc4C5(C)C)cc3)cc2)cc1]
13
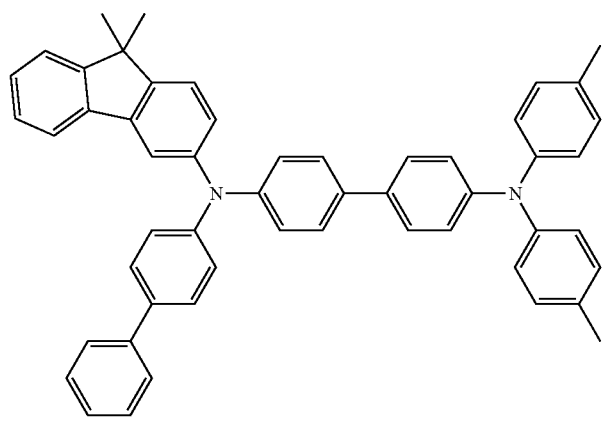 [SMILES: Cc1ccc(N(c2ccc(C)cc2)c2ccc(-c3ccc(N(c4ccc(-c5ccccc5)cc4)c4ccc5c(c4)-c4ccccc4C5(C)C)cc3)cc2)cc1]
14
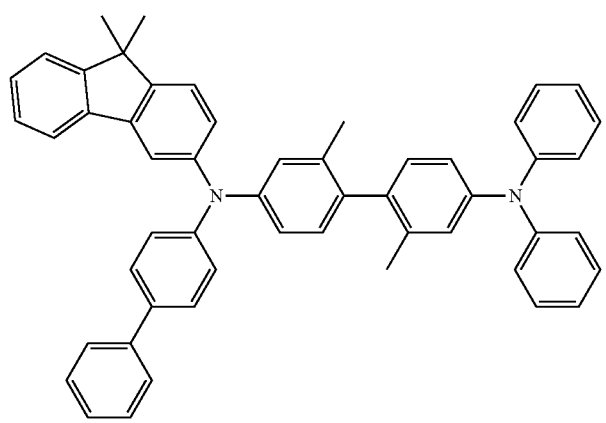 [SMILES: Cc1cc(N(c2ccccc2)c2ccccc2)ccc1-c1ccc(N(c2ccc(-c3ccccc3)cc2)c2ccc3c(c2)-c2ccccc2C3(C)C)cc1C]
15

-continued
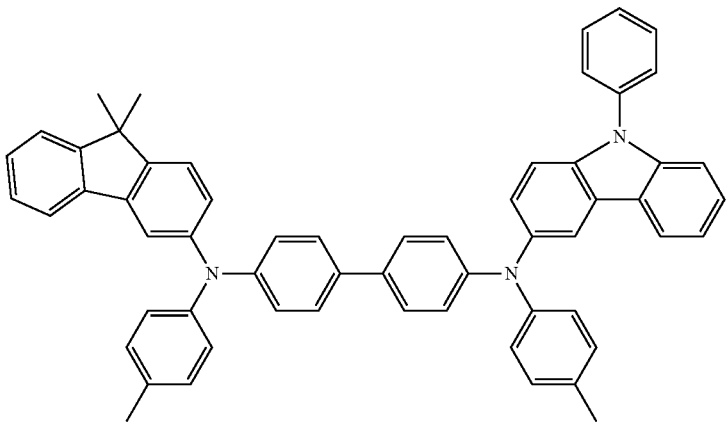 [SMILES: Cc1ccc(N(c2ccc(-c3ccc(N(c4ccc(C)cc4)c4ccc5c(c4)c4ccccc4n5-c4ccccc4)cc3)cc2)c2ccc3c(c2)-c2ccccc2C3(C)C)cc1]
16
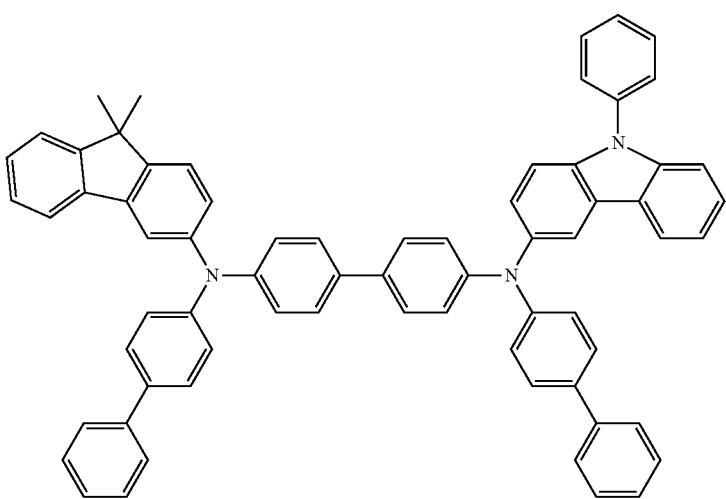 [SMILES: CC1(C)c2ccccc2-c2cc(N(c3ccc(-c4ccccc4)cc3)c3ccc(-c4ccc(N(c5ccc(-c6ccccc6)cc5)c5ccc6c(c5)c5ccccc5n6-c5ccccc5)cc4)cc3)ccc21]
17
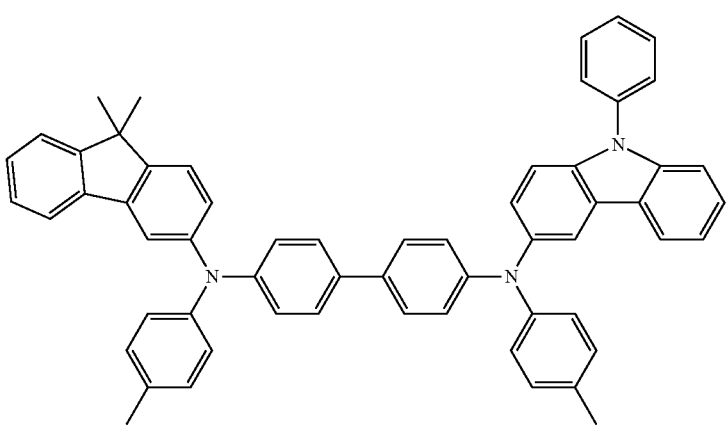 [SMILES: Cc1ccc(N(c2ccc(-c3ccc(N(c4ccc(C)cc4)c4ccc5c(c4)c4ccccc4n5-c4ccccc4)cc3)cc2)c2ccc3c(c2)-c2ccccc2C3(C)C)cc1]
18

-continued
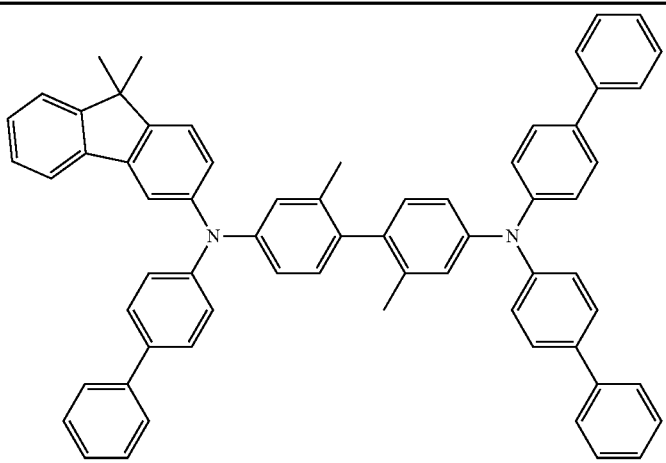
19
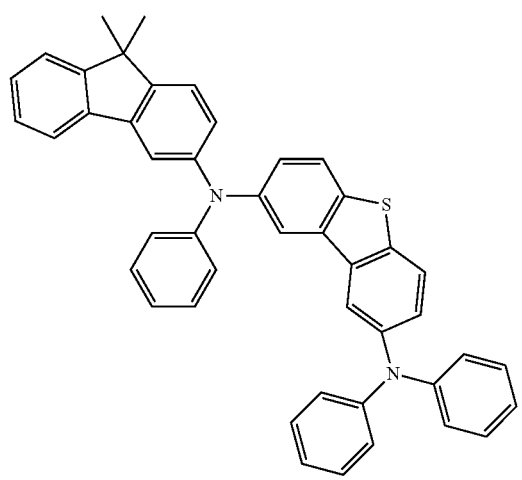 [SMILES: CC1(C)c2ccccc2-c2cc(N(c3ccccc3)c3ccc4sc5ccc(N(c6ccccc6)c6ccccc6)cc5c4c3)ccc21]
20
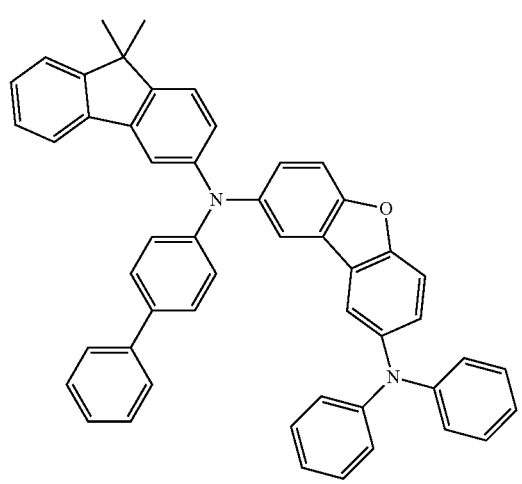 [SMILES: CC1(C)c2ccccc2-c2cc(N(c3ccc(-c4ccccc4)cc3)c3ccc4oc5ccc(N(c6ccccc6)c6ccccc6)cc5c4c3)ccc21]
21

-continued
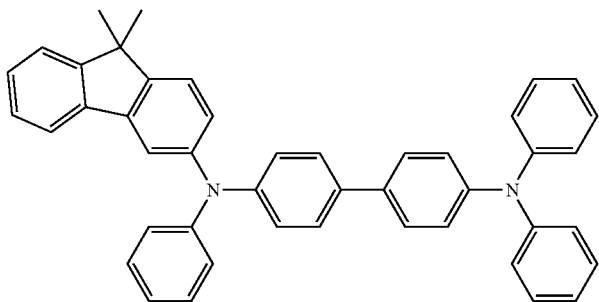
22
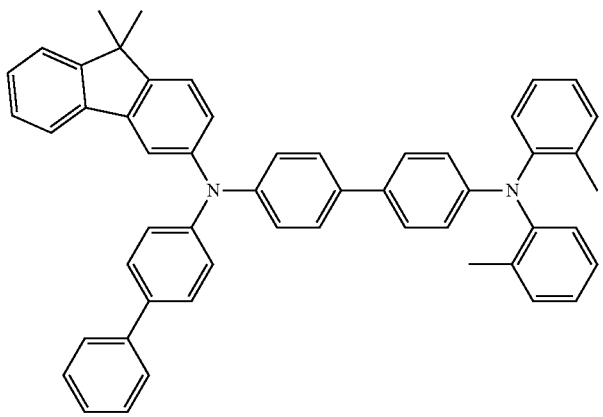 [SMILES: Cc1ccccc1N(c1ccc(-c2ccc(N(c3ccc(-c4ccccc4)cc3)c3ccc4c(c3)-c3ccccc3C4(C)C)cc2)cc1)c1ccccc1C]
23
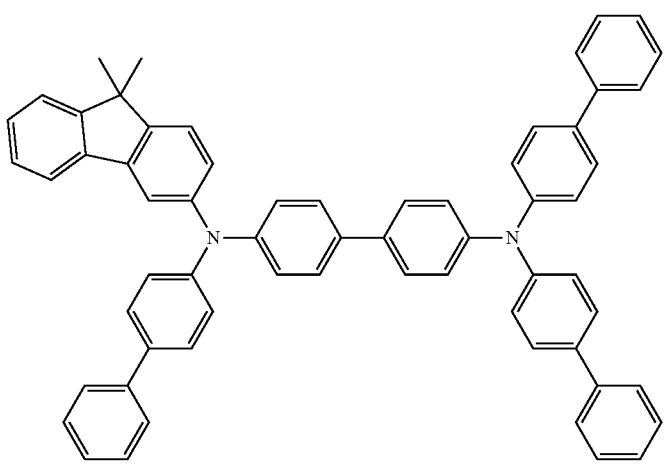
24
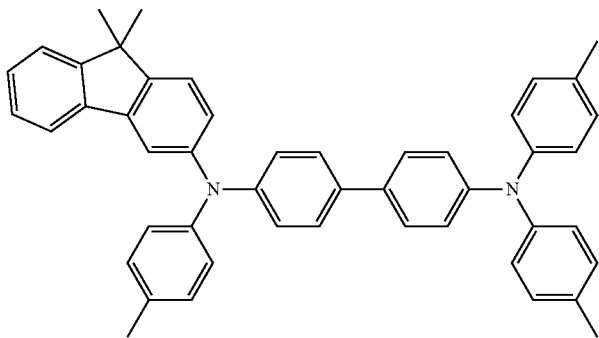 [SMILES: Cc1ccc(N(c2ccc(C)cc2)c2ccc(-c3ccc(N(c4ccc(C)cc4)c4ccc5c(c4)-c4ccccc4C5(C)C)cc3)cc2)cc1]
25

-continued
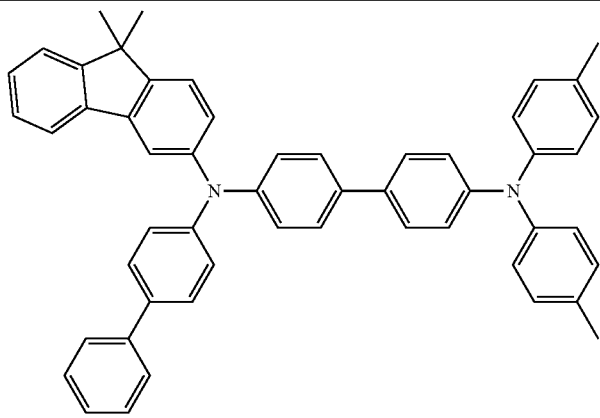
26
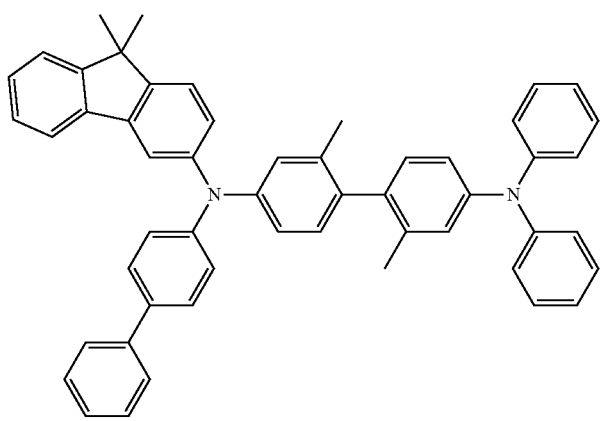 [SMILES: Cc1cc(N(c2ccccc2)c2ccccc2)ccc1-c1ccc(N(c2ccc(-c3ccccc3)cc2)c2ccc3c(c2)-c2ccccc2C3(C)C)cc1C]
27
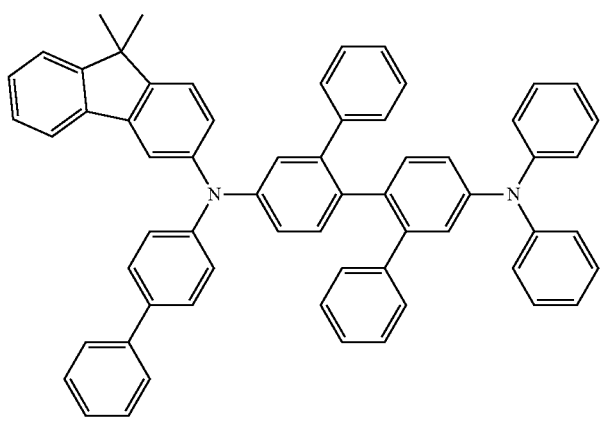 [SMILES: CC1(C)c2ccccc2-c2cc(N(c3ccc(-c4ccccc4)cc3)c3ccc(-c4ccc(N(c5ccccc5)c5ccccc5)cc4-c4ccccc4)c(-c4ccccc4)c3)ccc21]
28
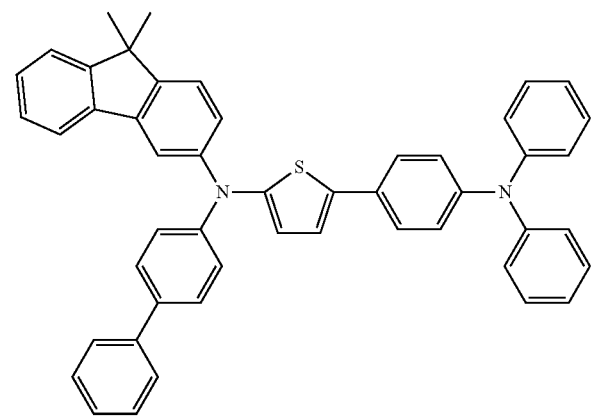 [SMILES: CC1(C)c2ccccc2-c2cc(N(c3ccc(-c4ccccc4)cc3)c3ccc(-c4ccc(N(c5ccccc5)c5ccccc5)cc4)s3)ccc21]
29

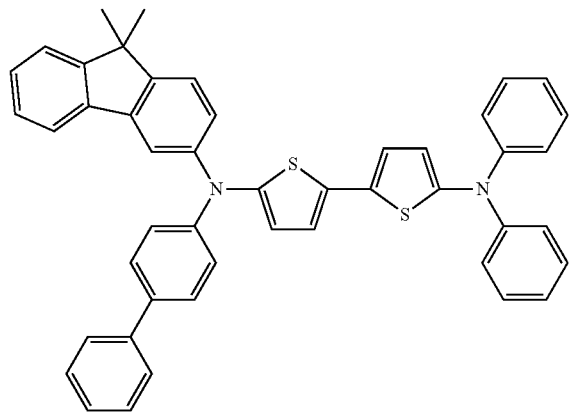 [SMILES: CC1(C)c2ccccc2-c2cc(N(c3ccc(-c4ccccc4)cc3)c3ccc(-c4ccc(N(c5ccccc5)c5ccccc5)s4)s3)ccc21]
30
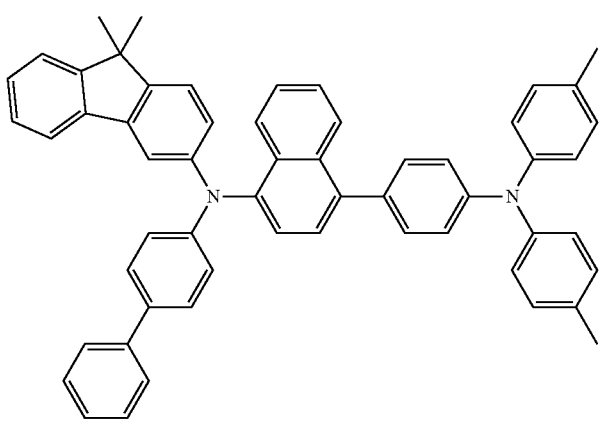 [SMILES: Cc1ccc(N(c2ccc(C)cc2)c2ccc(-c3ccc(N(c4ccc(-c5ccccc5)cc4)c4ccc5c(c4)-c4ccccc4C5(C)C)c4ccccc34)cc2)cc1]
31
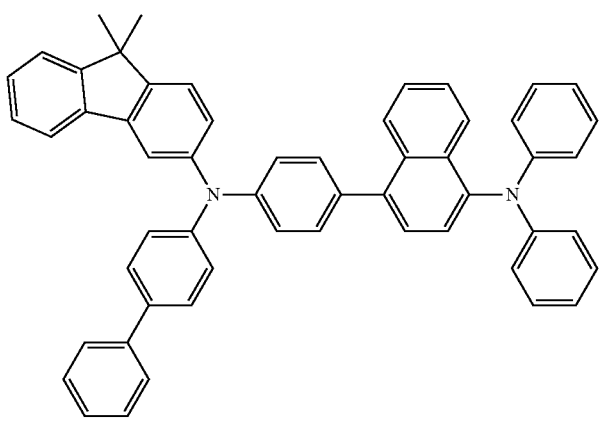 [SMILES: CC1(C)c2ccccc2-c2cc(N(c3ccc(-c4ccccc4)cc3)c3ccc(-c4ccc(N(c5ccccc5)c5ccccc5)c5ccccc45)cc3)ccc21]
32

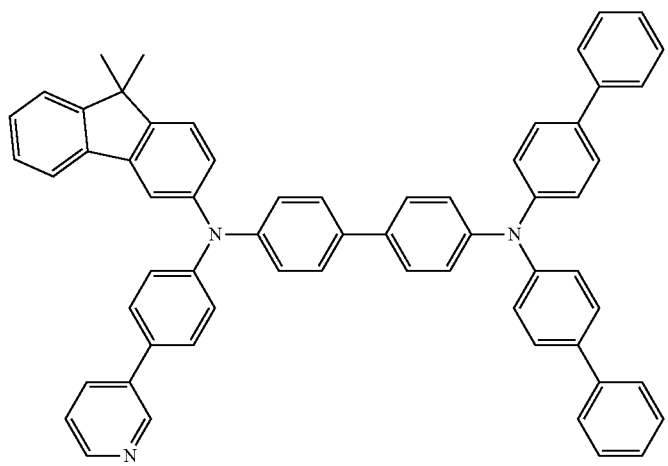 [SMILES: CC1(C)c2ccccc2-c2cc(N(c3ccc(-c4ccc(N(c5ccc(-c6ccccc6)cc5)c5ccc(-c6ccccc6)cc5)cc4)cc3)c3ccc(-c4cccnc4)cc3)ccc21]
33
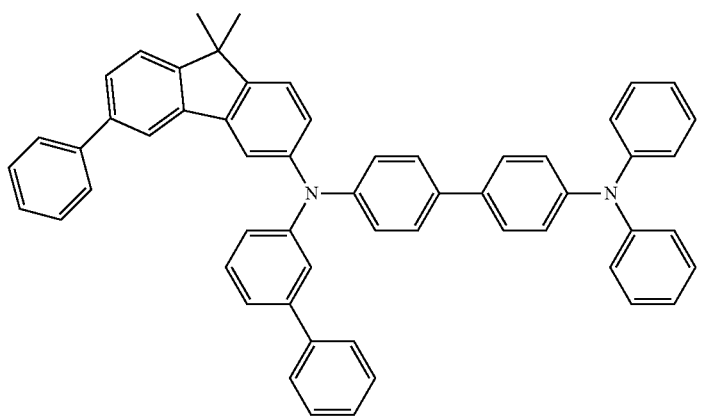 [SMILES: CC1(C)c2ccc(-c3ccccc3)cc2-c2cc(N(c3ccc(-c4ccc(N(c5ccccc5)c5ccccc5)cc4)cc3)c3cccc(-c4ccccc4)c3)ccc21]
34
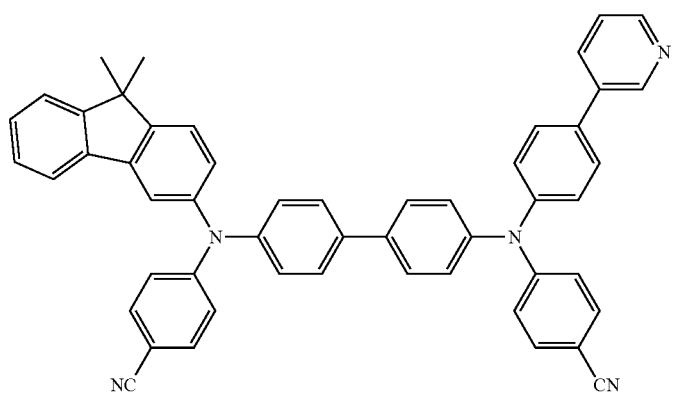 [SMILES: CC1(C)c2ccccc2-c2cc(N(c3ccc(C#N)cc3)c3ccc(-c4ccc(N(c5ccc(C#N)cc5)c5ccc(-c6cccnc6)cc5)cc4)cc3)ccc21]
35

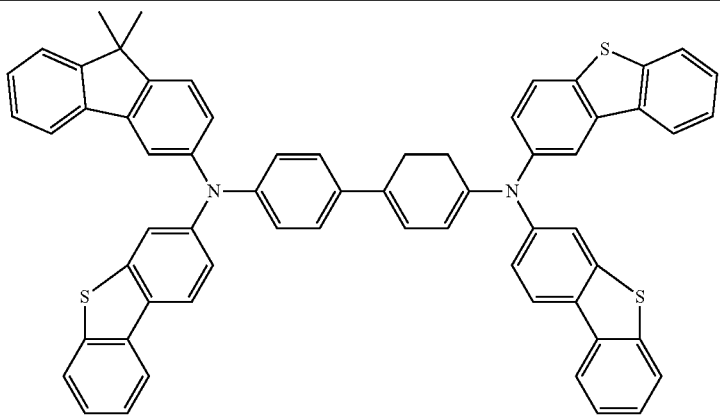
36
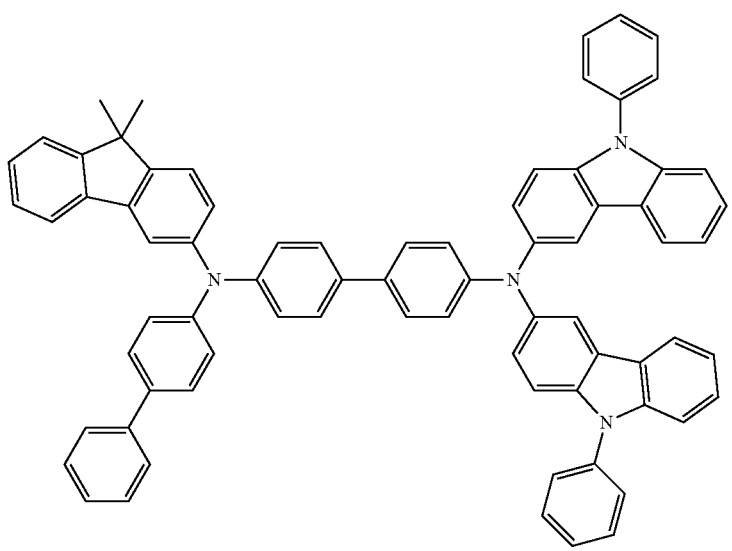 [SMILES: CC1(C)c2ccccc2-c2cc(N(c3ccc(-c4ccccc4)cc3)c3ccc(-c4ccc(N(c5ccc6c(c5)c5ccccc5n6-c5ccccc5)c5ccc6c(c5)c5ccccc5n6-c5ccccc5)cc4)cc3)ccc21]
37
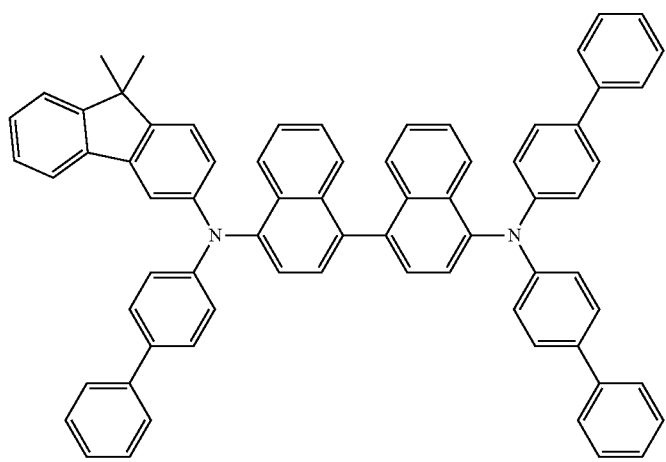 [SMILES: CC1(C)c2ccccc2-c2cc(N(c3ccc(-c4ccccc4)cc3)c3ccc(-c4ccc(N(c5ccc(-c6ccccc6)cc5)c5ccc(-c6ccccc6)cc5)c5ccccc45)c4ccccc34)ccc21]
38

-continued
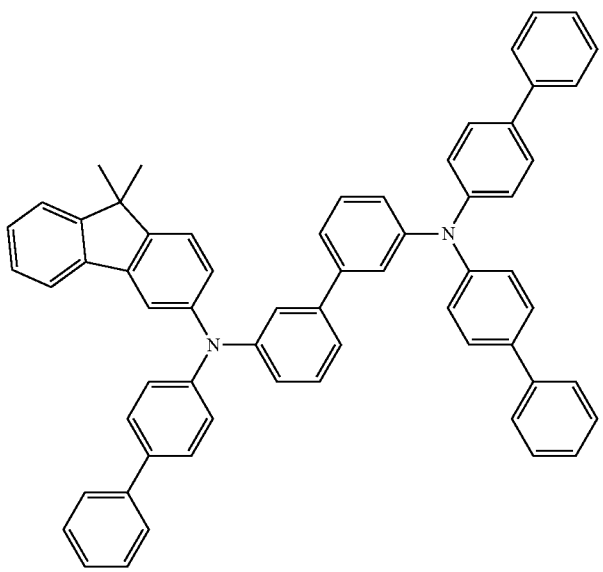 [SMILES: CC1(C)c2ccccc2-c2cc(N(c3ccc(-c4ccccc4)cc3)c3cccc(-c4cccc(N(c5ccc(-c6ccccc6)cc5)c5ccc(-c6ccccc6)cc5)c4)c3)ccc21]
39
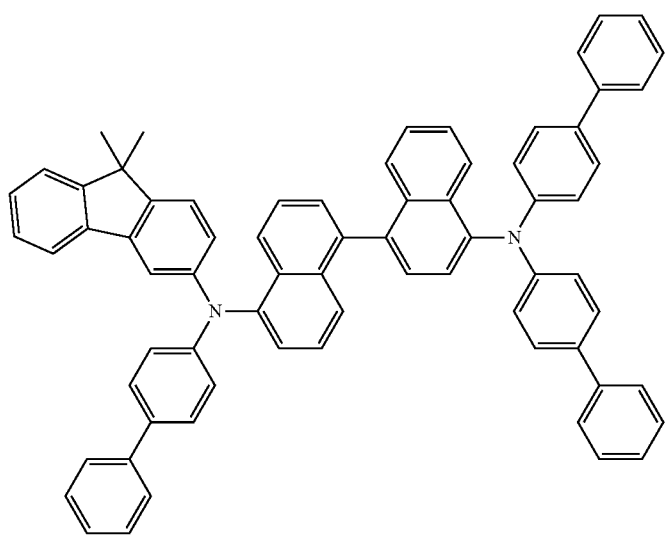 [SMILES: CC1(C)c2ccccc2-c2cc(N(c3ccc(-c4ccccc4)cc3)c3cccc4c(-c5ccc(N(c6ccc(-c7ccccc7)cc6)c6ccc(-c7ccccc7)cc6)c6ccccc56)cccc34)ccc21]
40
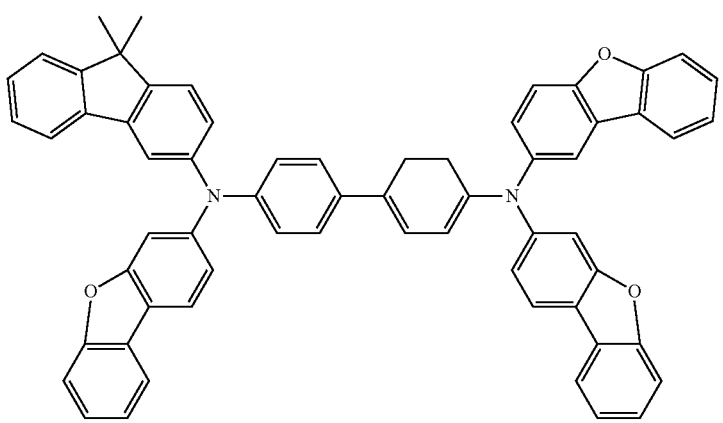 [SMILES: CC1(C)c2ccccc2-c2cc(N(c3ccc(C4=CC=C(N(c5ccc6c(c5)oc5ccccc56)c5ccc6oc7ccccc7c6c5)CC4)cc3)c3ccc4c(c3)oc3ccccc34)ccc21]
41

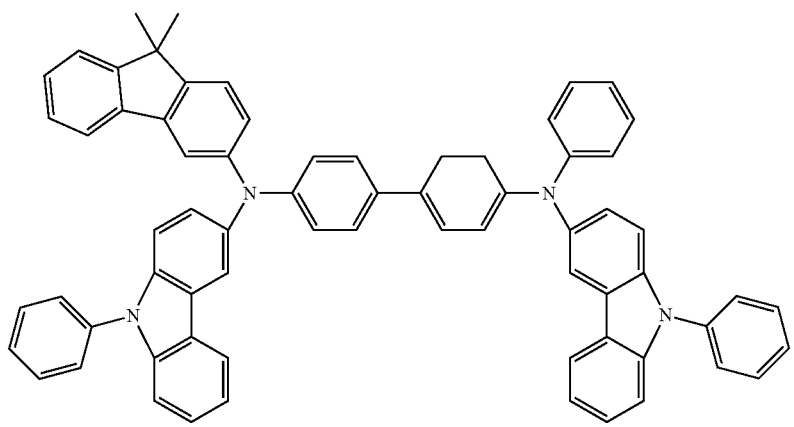 [SMILES: CC1(C)c2ccccc2-c2cc(N(c3ccc(C4=CC=C(N(c5ccccc5)c5ccc6c(c5)c5ccccc5n6-c5ccccc5)CC4)cc3)c3ccc4c(c3)c3ccccc3n4-c3ccccc3)ccc21]
42
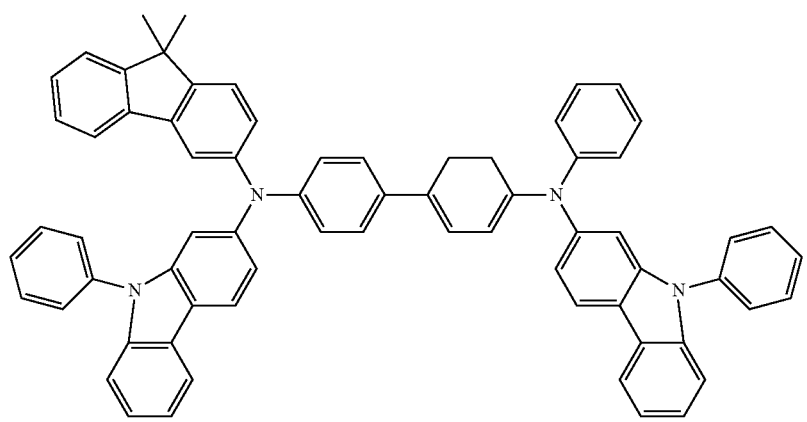 [SMILES: CC1(C)c2ccccc2-c2cc(N(c3ccc(C4=CC=C(N(c5ccccc5)c5ccc6c7ccccc7n(-c7ccccc7)c6c5)CC4)cc3)c3ccc4c5ccccc5n(-c5ccccc5)c4c3)ccc21]
43
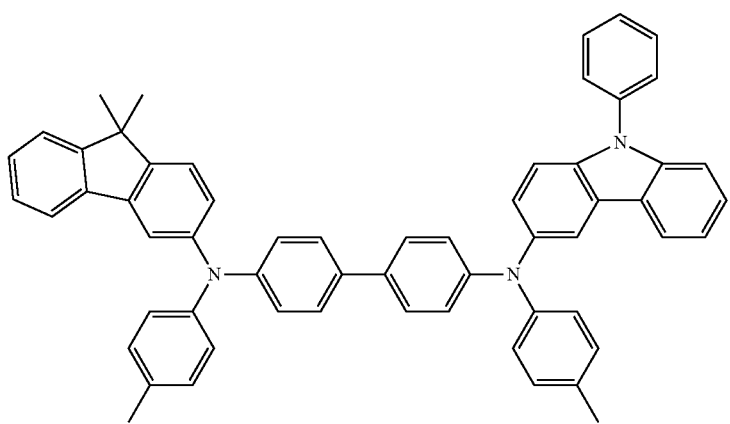 [SMILES: Cc1ccc(N(c2ccc(-c3ccc(N(c4ccc(C)cc4)c4ccc5c(c4)c4ccccc4n5-c4ccccc4)cc3)cc2)c2ccc3c(c2)-c2ccccc2C3(C)C)cc1]
44

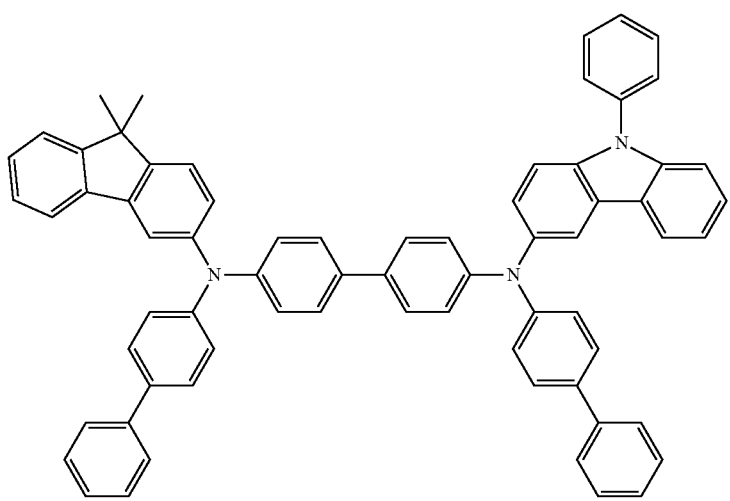 [SMILES: CC1(C)c2ccccc2-c2cc(N(c3ccc(-c4ccccc4)cc3)c3ccc(-c4ccc(N(c5ccc(-c6ccccc6)cc5)c5ccc6c(c5)c5ccccc5n6-c5ccccc5)cc4)cc3)ccc21]
45
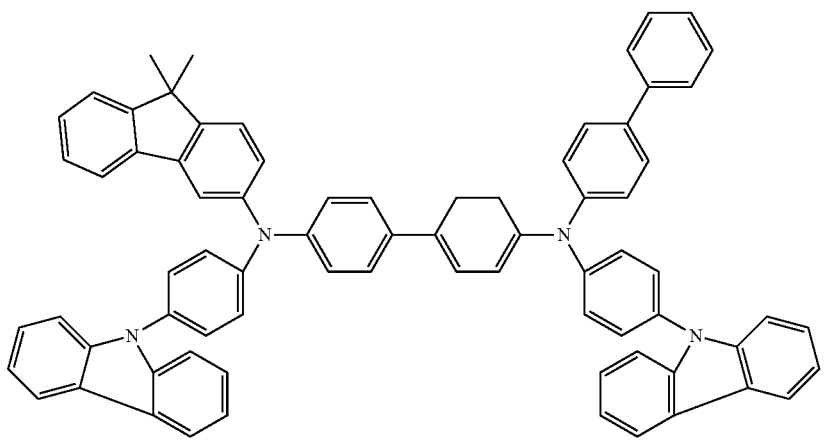 [SMILES: CC1(C)c2ccccc2-c2cc(N(c3ccc(C4=CC=C(N(c5ccc(-c6ccccc6)cc5)c5ccc(-n6c7ccccc7c7ccccc76)cc5)CC4)cc3)c3ccc(-n4c5ccccc5c5ccccc54)cc3)ccc21]
46
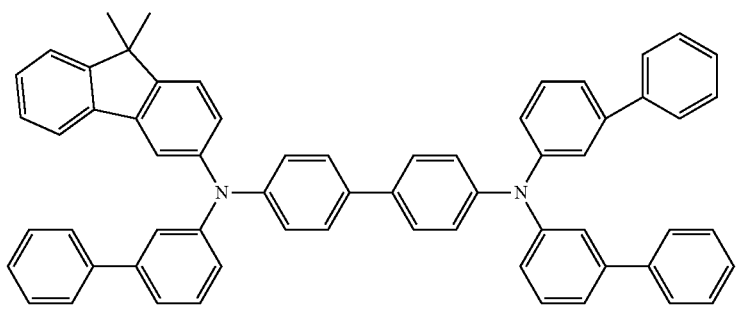 [SMILES: CC1(C)c2ccccc2-c2cc(N(c3ccc(-c4ccc(N(c5cccc(-c6ccccc6)c5)c5cccc(-c6ccccc6)c5)cc4)cc3)c3cccc(-c4ccccc4)c3)ccc21]
47
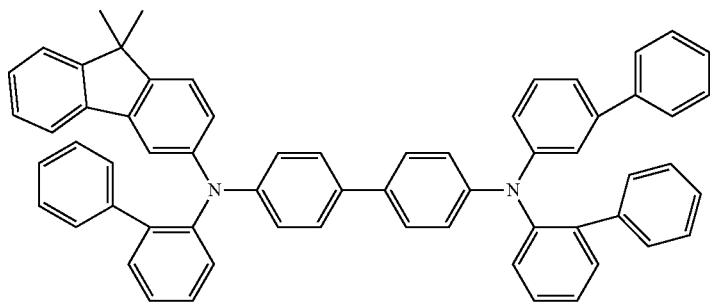 [SMILES: CC1(C)c2ccccc2-c2cc(N(c3ccc(-c4ccc(N(c5cccc(-c6ccccc6)c5)c5ccccc5-c5ccccc5)cc4)cc3)c3ccccc3-c3ccccc3)ccc21]
48

-continued
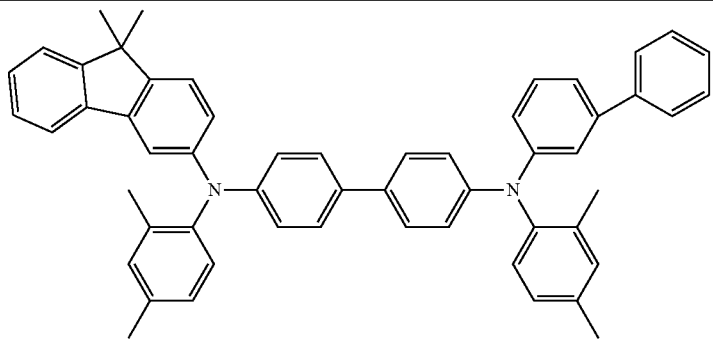
49
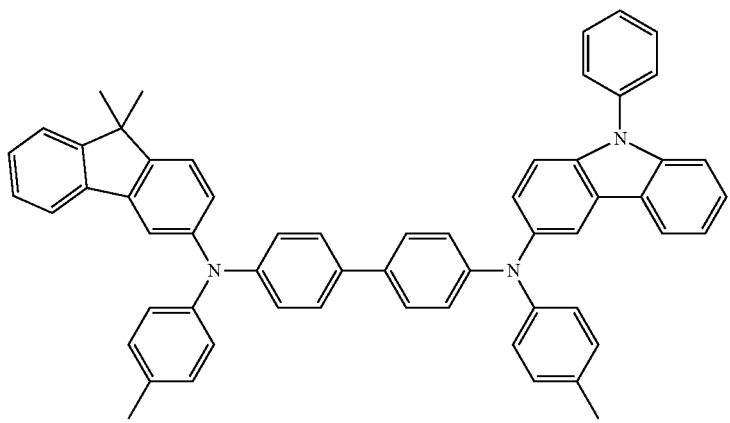 [SMILES: Cc1ccc(N(c2ccc(-c3ccc(N(c4ccc(C)cc4)c4ccc5c(c4)c4ccccc4n5-c4ccccc4)cc3)cc2)c2ccc3c(c2)-c2ccccc2C3(C)C)cc1]
50
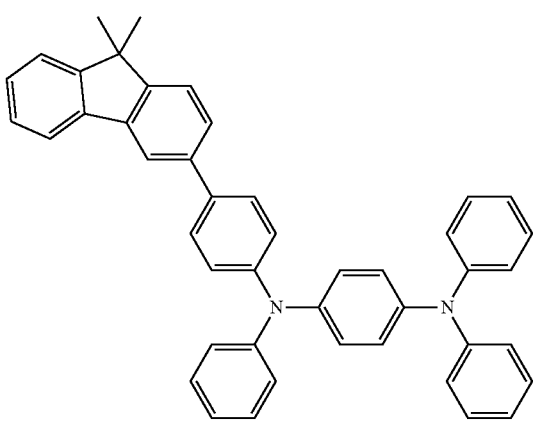 [SMILES: CC1(C)c2ccccc2-c2cc(-c3ccc(N(c4ccccc4)c4ccc(N(c5ccccc5)c5ccccc5)cc4)cc3)ccc21]
51
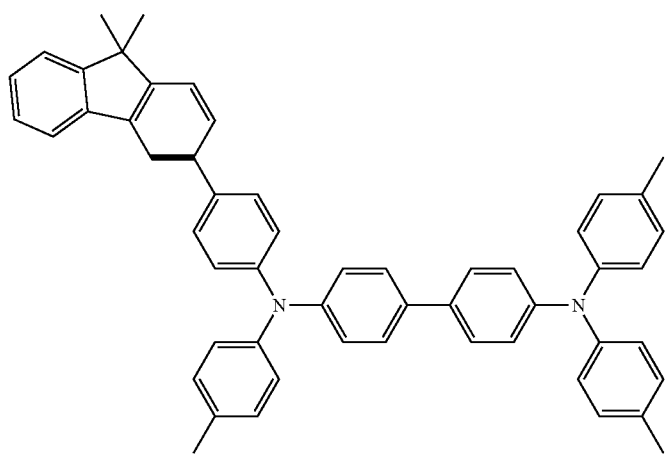
52

-continued
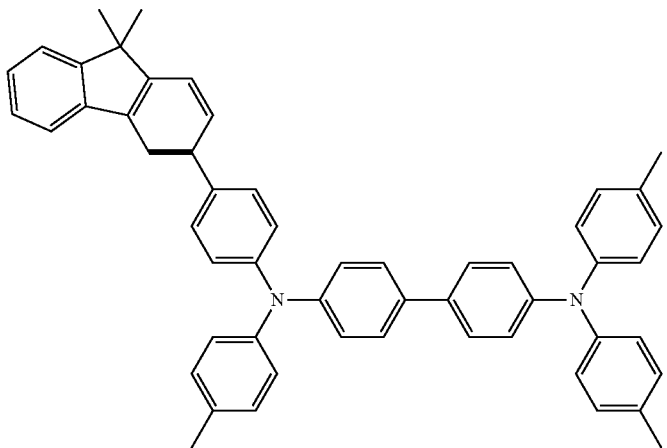
53
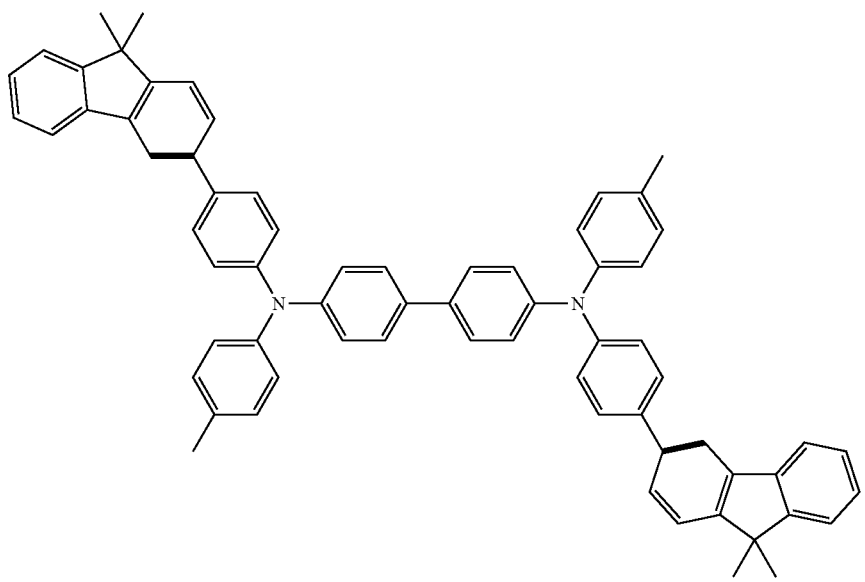
54
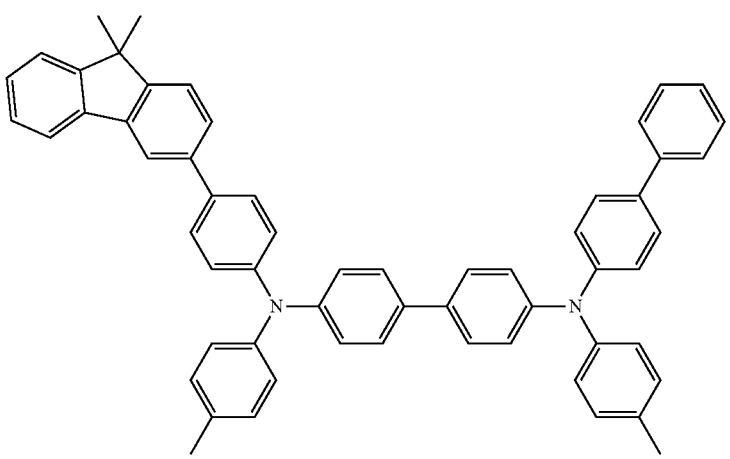 [SMILES: Cc1ccc(N(c2ccc(-c3ccccc3)cc2)c2ccc(-c3ccc(N(c4ccc(C)cc4)c4ccc(-c5ccc6c(c5)-c5ccccc5C6(C)C)cc4)cc3)cc2)cc1]
55

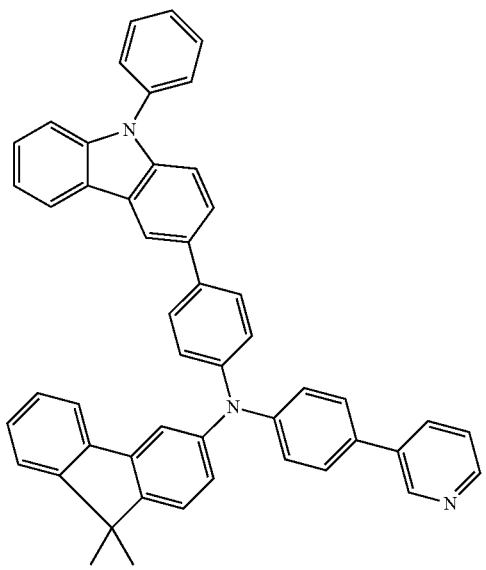
56
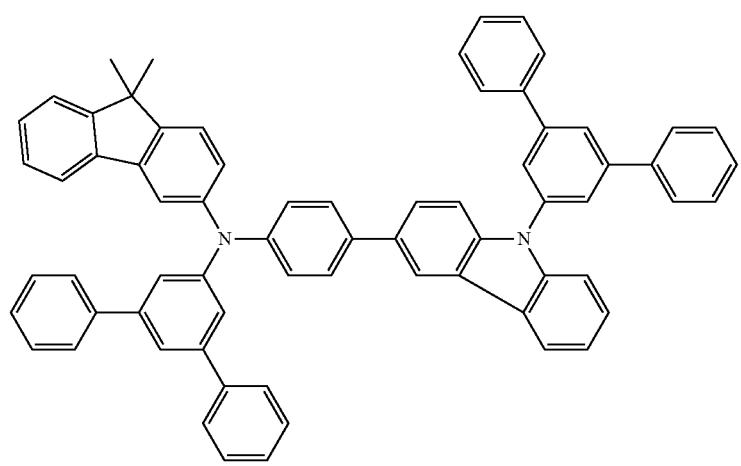 [SMILES: CC1(C)c2ccccc2-c2cc(N(c3ccc(-c4ccc5c(c4)c4ccccc4n5-c4cc(-c5ccccc5)cc(-c5ccccc5)c4)cc3)c3cc(-c4ccccc4)cc(-c4ccccc4)c3)ccc21]
57

-continued
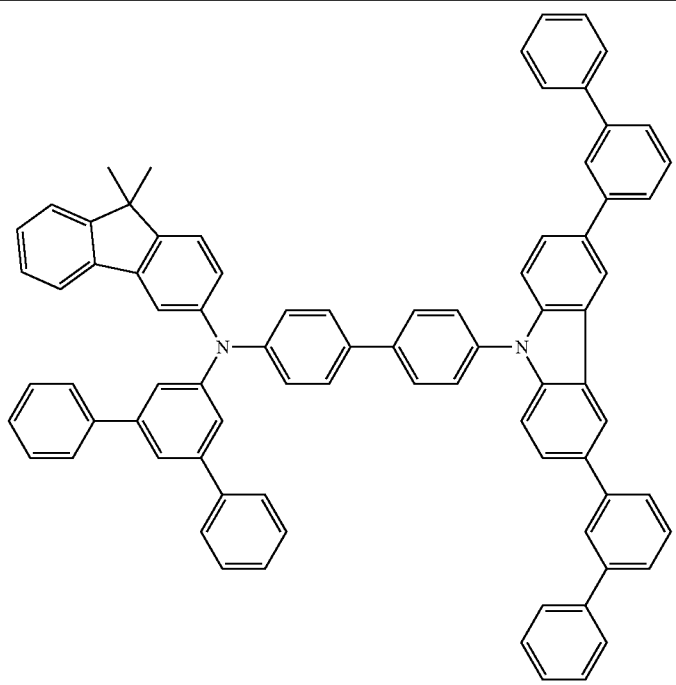
58
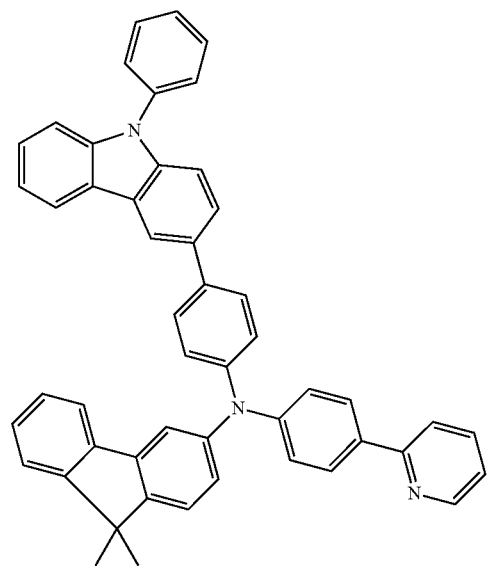 [SMILES: CC1(C)c2ccccc2-c2cc(N(c3ccc(-c4ccc5c(c4)c4ccccc4n5-c4ccccc4)cc3)c3ccc(-c4ccccn4)cc3)ccc21]
59

-continued
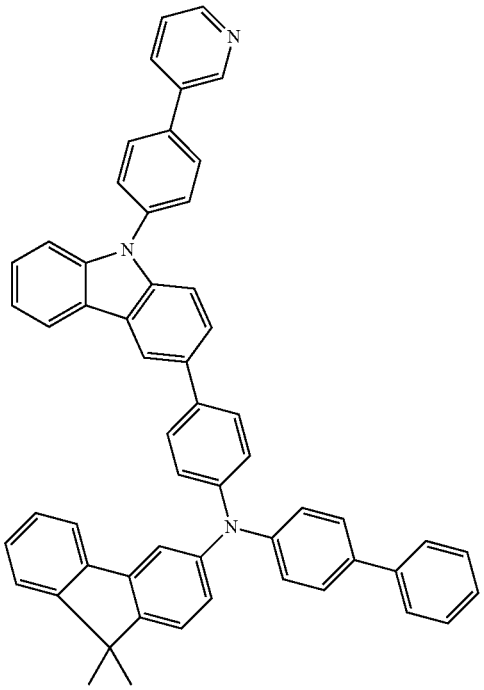 [SMILES: CC1(C)c2ccccc2-c2cc(N(c3ccc(-c4ccccc4)cc3)c3ccc(-c4ccc5c(c4)c4ccccc4n5-c4ccc(-c5cccnc5)cc4)cc3)ccc21]
60
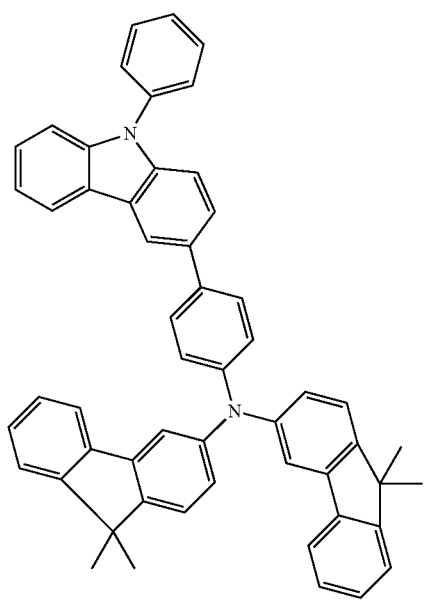 [SMILES: CC1(C)c2ccccc2-c2cc(N(c3ccc(-c4ccc5c(c4)c4ccccc4n5-c4ccccc4)cc3)c3ccc4c(c3)-c3ccccc3C4(C)C)ccc21]
61

-continued
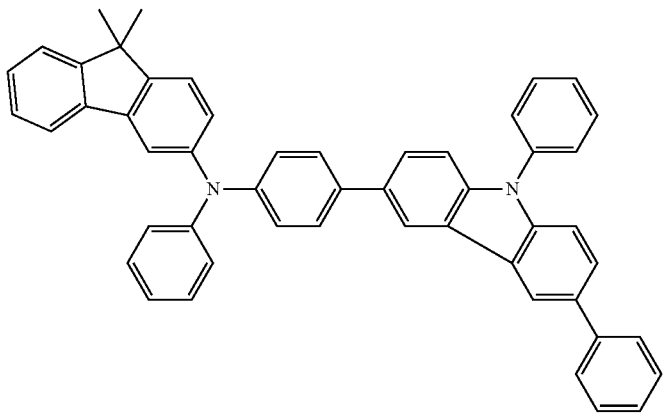 [SMILES: CC1(C)c2ccccc2-c2cc(N(c3ccccc3)c3ccc(-c4ccc5c(c4)c4cc(-c6ccccc6)ccc4n5-c4ccccc4)cc3)ccc21]
62
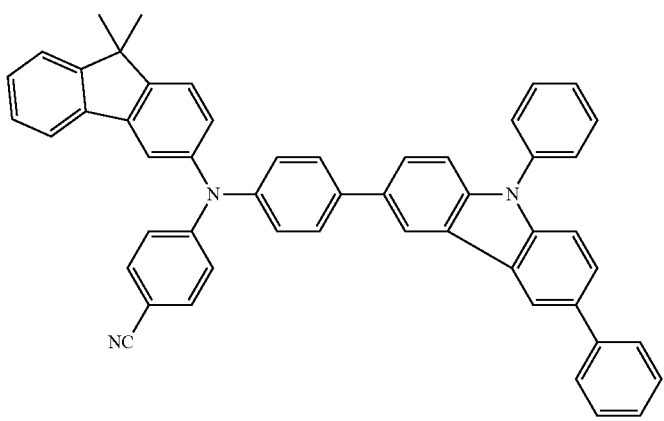 [SMILES: CC1(C)c2ccccc2-c2cc(N(c3ccc(C#N)cc3)c3ccc(-c4ccc5c(c4)c4cc(-c6ccccc6)ccc4n5-c4ccccc4)cc3)ccc21]
63
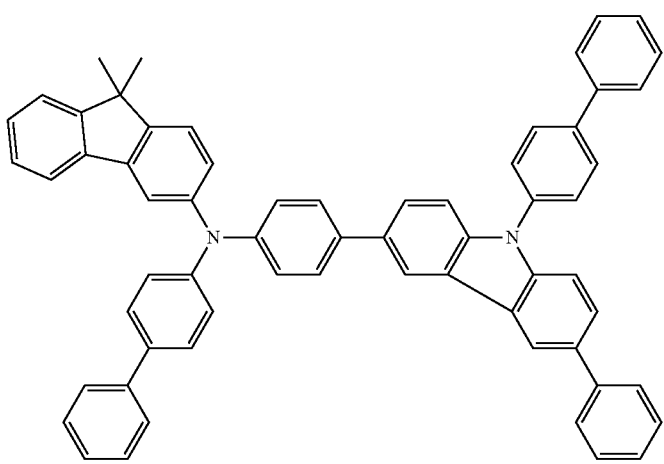 [SMILES: CC1(C)c2ccccc2-c2cc(N(c3ccc(-c4ccccc4)cc3)c3ccc(-c4ccc5c(c4)c4cc(-c6ccccc6)ccc4n5-c4ccc(-c5ccccc5)cc4)cc3)ccc21]
64
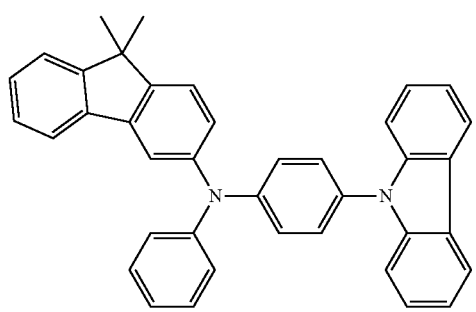 [SMILES: CC1(C)c2ccccc2-c2cc(N(c3ccccc3)c3ccc(-n4c5ccccc5c5ccccc54)cc3)ccc21]
65

66
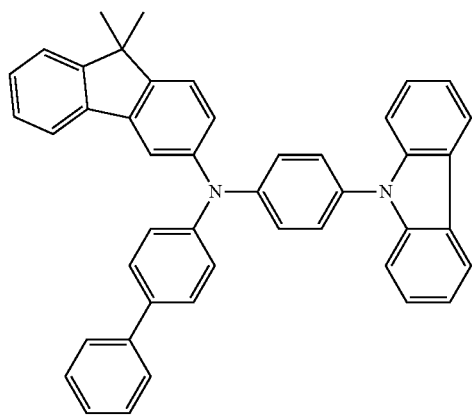 [SMILES: CC1(C)c2ccccc2-c2cc(N(c3ccc(-c4ccccc4)cc3)c3ccc(-n4c5ccccc5c5ccccc54)cc3)ccc21]
67
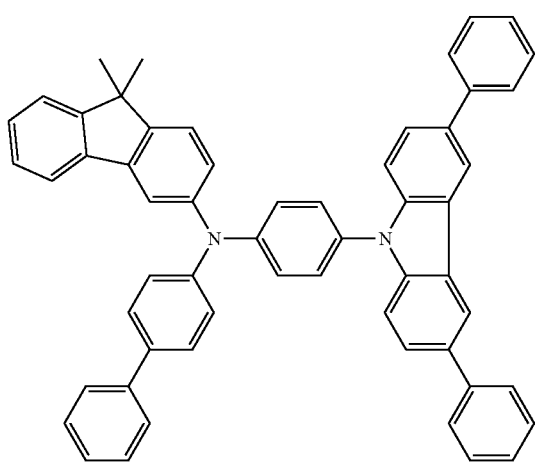 [SMILES: CC1(C)c2ccccc2-c2cc(N(c3ccc(-c4ccccc4)cc3)c3ccc(-n4c5ccc(-c6ccccc6)cc5c5cc(-c6ccccc6)ccc54)cc3)ccc21]
68
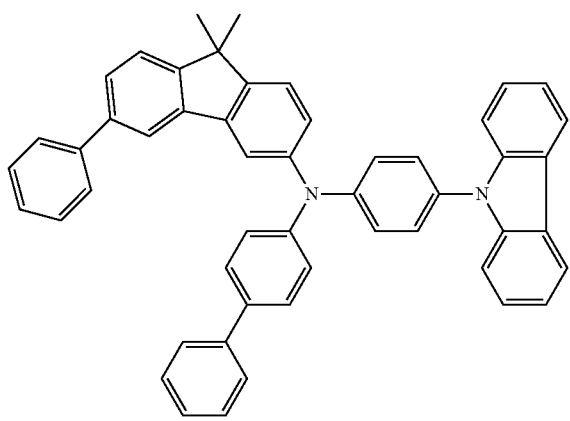 [SMILES: CC1(C)c2ccc(-c3ccccc3)cc2-c2cc(N(c3ccc(-c4ccccc4)cc3)c3ccc(-n4c5ccccc5c5ccccc54)cc3)ccc21]

-continued
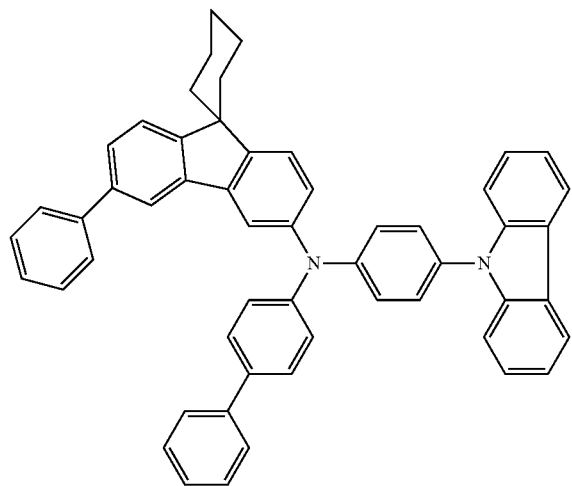 [SMILES: c1ccc(-c2ccc(N(c3ccc(-n4c5ccccc5c5ccccc54)cc3)c3ccc4c(c3)-c3cc(-c5ccccc5)ccc3C43CCCCC3)cc2)cc1]
69
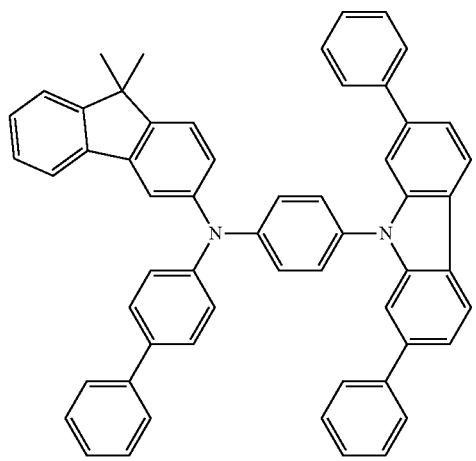 [SMILES: CC1(C)c2ccccc2-c2cc(N(c3ccc(-c4ccccc4)cc3)c3ccc(-n4c5cc(-c6ccccc6)ccc5c5ccc(-c6ccccc6)cc54)cc3)ccc21]
70
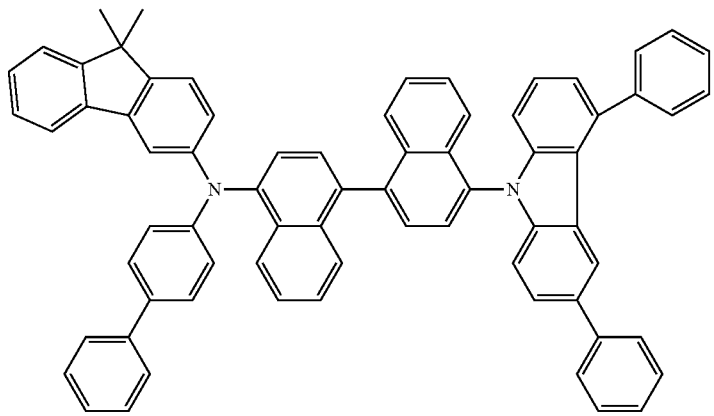 [SMILES: CC1(C)c2ccccc2-c2cc(N(c3ccc(-c4ccccc4)cc3)c3ccc(-c4ccc(-n5c6ccc(-c7ccccc7)cc6c6c(-c7ccccc7)cccc65)c5ccccc45)c4ccccc34)ccc21]
71

-continued
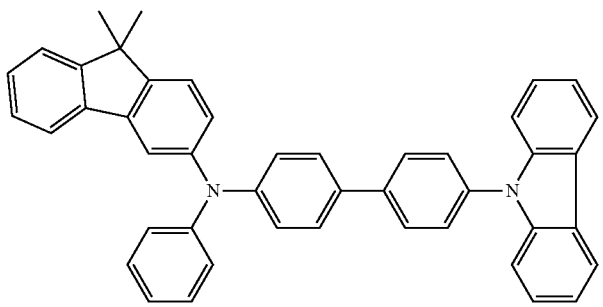 [SMILES: CC1(C)c2ccccc2-c2cc(N(c3ccccc3)c3ccc(-c4ccc(-n5c6ccccc6c6ccccc65)cc4)cc3)ccc21]
72
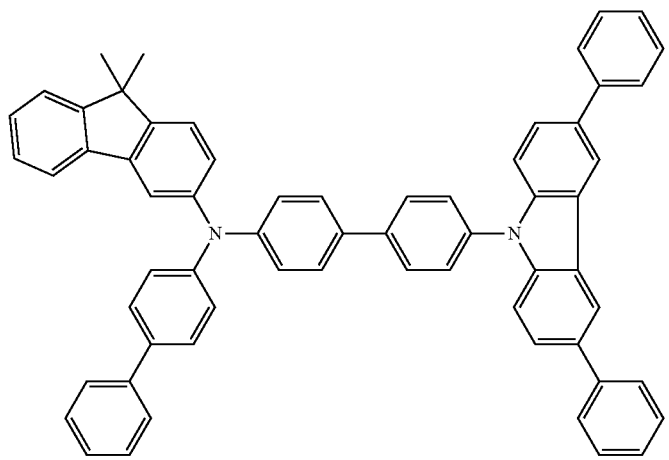 [SMILES: CC1(C)c2ccccc2-c2cc(N(c3ccc(-c4ccccc4)cc3)c3ccc(-c4ccc(-n5c6ccc(-c7ccccc7)cc6c6cc(-c7ccccc7)ccc65)cc4)cc3)ccc21]
73
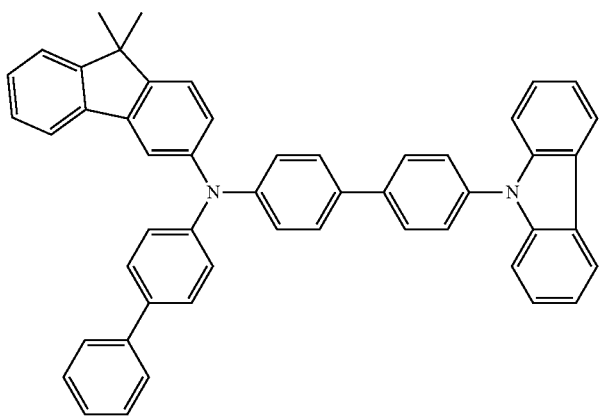 [SMILES: CC1(C)c2ccccc2-c2cc(N(c3ccc(-c4ccccc4)cc3)c3ccc(-c4ccc(-n5c6ccccc6c6ccccc65)cc4)cc3)ccc21]
74
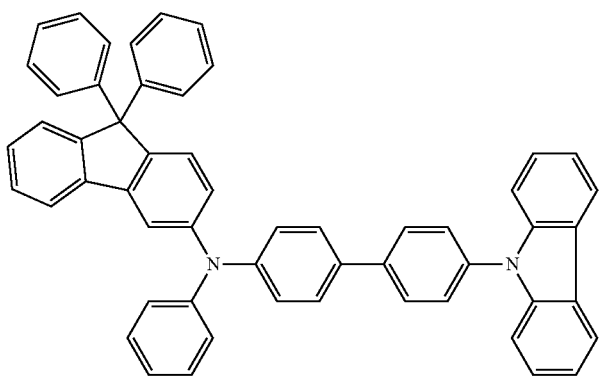 [SMILES: c1ccc(N(c2ccc(-c3ccc(-n4c5ccccc5c5ccccc54)cc3)cc2)c2ccc3c(c2)-c2ccccc2C3(c2ccccc2)c2ccccc2)cc1]
75

| | |
|---|---|
| 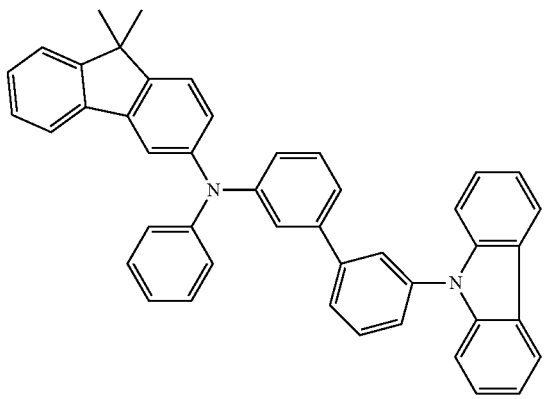 [SMILES: CC1(C)c2ccccc2-c2cc(N(c3ccccc3)c3cccc(-c4cccc(-n5c6ccccc6c6ccccc65)c4)c3)ccc21] | 76 |
| 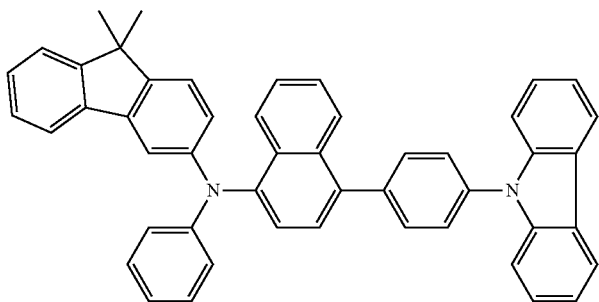 [SMILES: CC1(C)c2ccccc2-c2cc(N(c3ccccc3)c3ccc(-c4ccc(-n5c6ccccc6c6ccccc65)cc4)c4ccccc34)ccc21] | 77 |
| 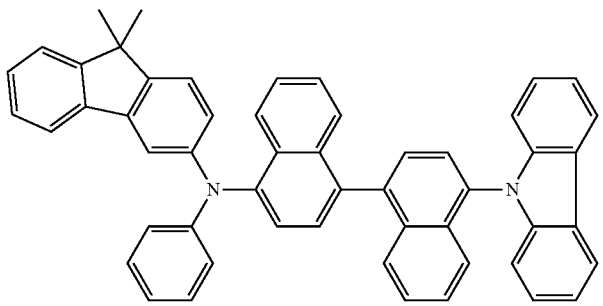 [SMILES: CC1(C)c2ccccc2-c2cc(N(c3ccccc3)c3ccc(-c4ccc(-n5c6ccccc6c6ccccc65)c5ccccc45)c4ccccc34)ccc21] | 78 |
| 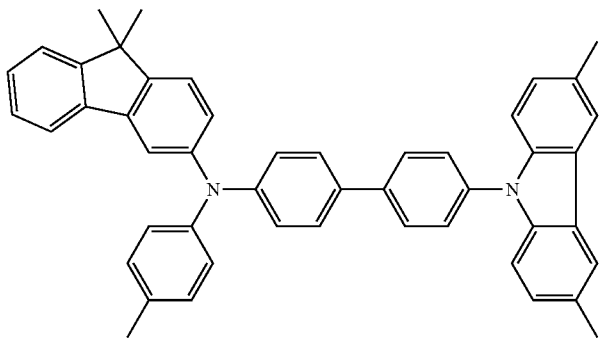 | 79 |

-continued
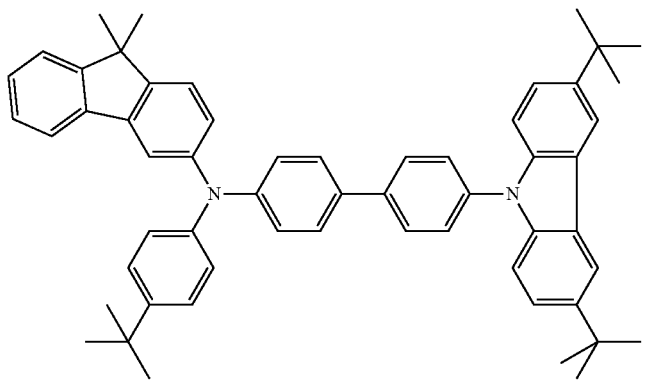 [SMILES: CC(C)(C)c1ccc(N(c2ccc(-c3ccc(-n4c5ccc(C(C)(C)C)cc5c5cc(C(C)(C)C)ccc54)cc3)cc2)c2ccc3c(c2)-c2ccccc2C3(C)C)cc1]
80
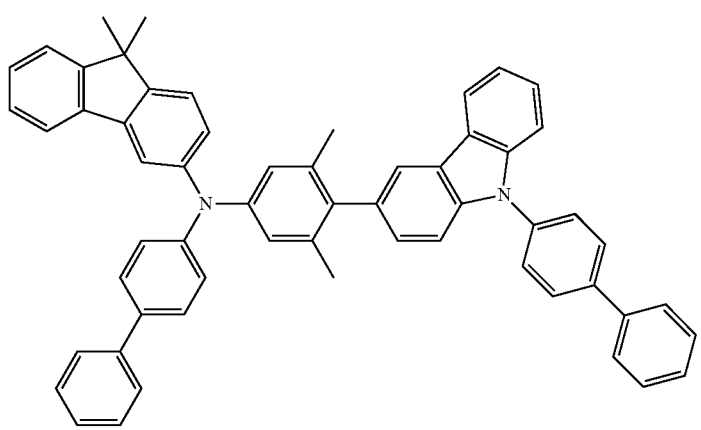 [SMILES: Cc1cc(N(c2ccc(-c3ccccc3)cc2)c2ccc3c(c2)-c2ccccc2C3(C)C)cc(C)c1-c1ccc2c(c1)c1ccccc1n2-c1ccc(-c2ccccc2)cc1]
81
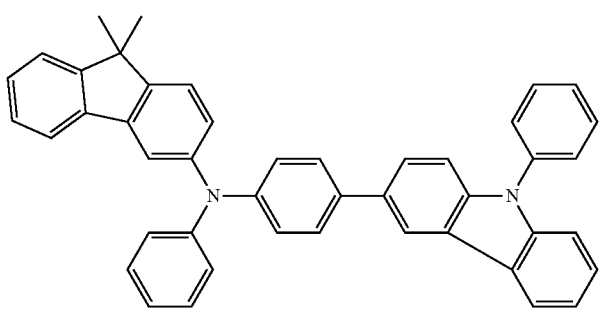 [SMILES: CC1(C)c2ccccc2-c2cc(N(c3ccccc3)c3ccc(-c4ccc5c(c4)c4ccccc4n5-c4ccccc4)cc3)ccc21]
82
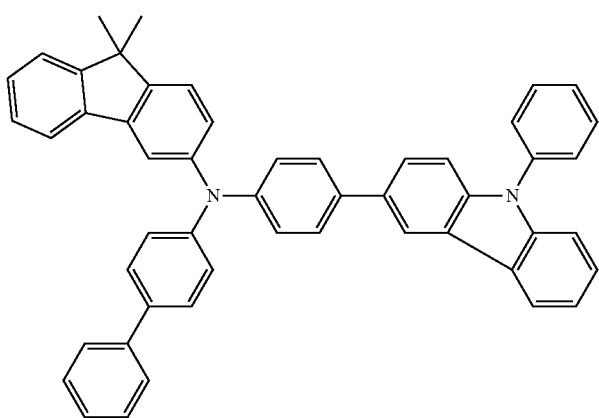 [SMILES: CC1(C)c2ccccc2-c2cc(N(c3ccc(-c4ccccc4)cc3)c3ccc(-c4ccc5c(c4)c4ccccc4n5-c4ccccc4)cc3)ccc21]
83

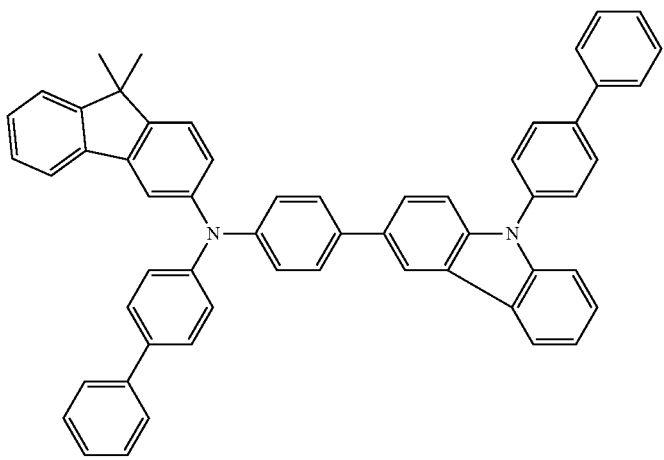 [SMILES: CC1(C)c2ccccc2-c2cc(N(c3ccc(-c4ccccc4)cc3)c3ccc(-c4ccc5c(c4)c4ccccc4n5-c4ccc(-c5ccccc5)cc4)cc3)ccc21]
84
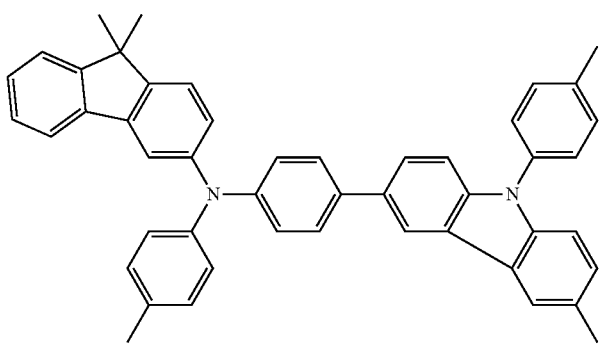 [SMILES: Cc1ccc(N(c2ccc(-c3ccc4c(c3)c3cc(C)ccc3n4-c3ccc(C)cc3)cc2)c2ccc3c(c2)-c2ccccc2C3(C)C)cc1]
85
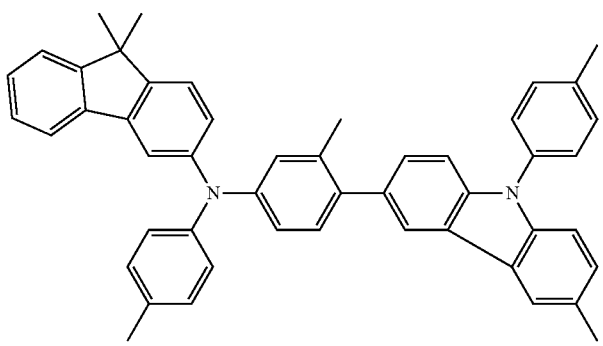
86
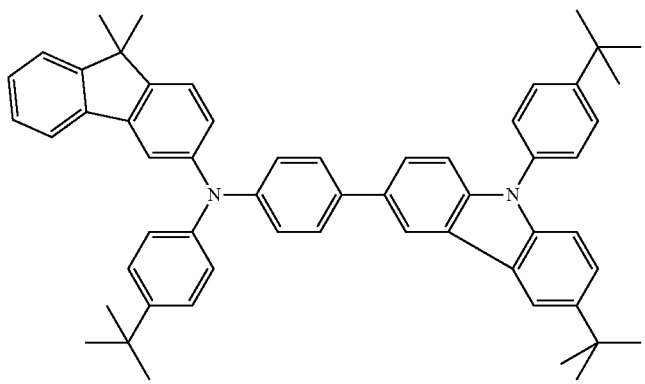 [SMILES: CC(C)(C)c1ccc(N(c2ccc(-c3ccc4c(c3)c3cc(C(C)(C)C)ccc3n4-c3ccc(C(C)(C)C)cc3)cc2)c2ccc3c(c2)-c2ccccc2C3(C)C)cc1]
87

-continued
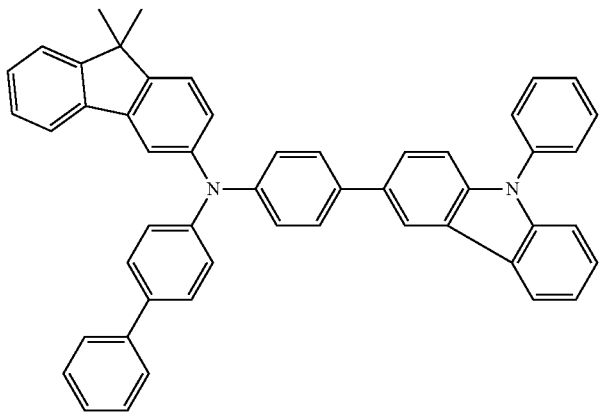 [SMILES: CC1(C)c2ccccc2-c2cc(N(c3ccc(-c4ccccc4)cc3)c3ccc(-c4ccc5c(c4)c4ccccc4n5-c4ccccc4)cc3)ccc21]
88
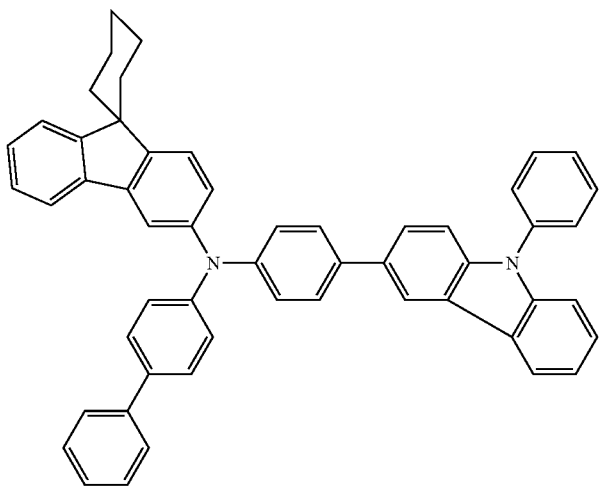 [SMILES: c1ccc(-c2ccc(N(c3ccc(-c4ccc5c(c4)c4ccccc4n5-c4ccccc4)cc3)c3ccc4c(c3)-c3ccccc3C43CCCCC3)cc2)cc1]
89
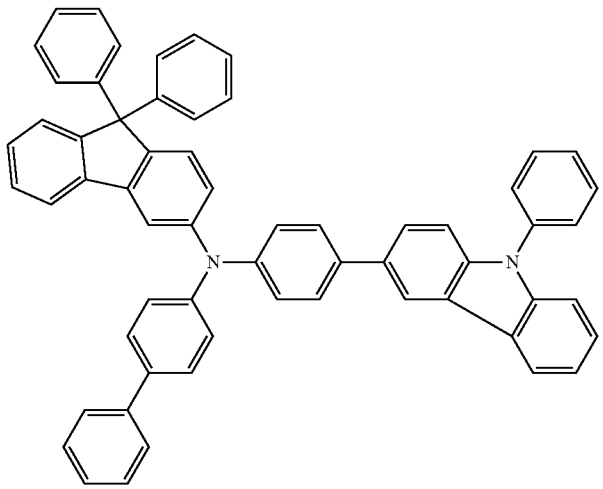 [SMILES: c1ccc(-c2ccc(N(c3ccc(-c4ccc5c(c4)c4ccccc4n5-c4ccccc4)cc3)c3ccc4c(c3)-c3ccccc3C4(c3ccccc3)c3ccccc3)cc2)cc1]
90

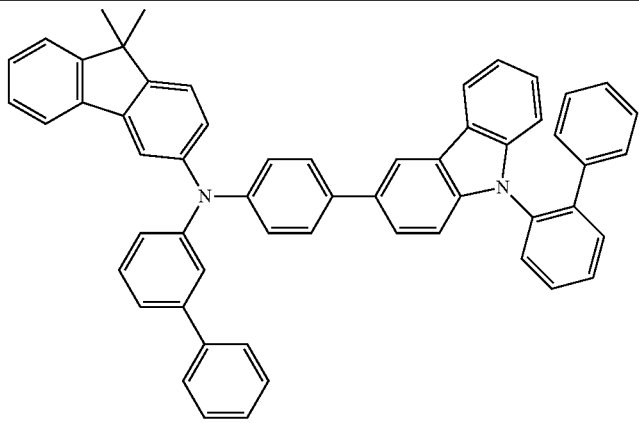
91
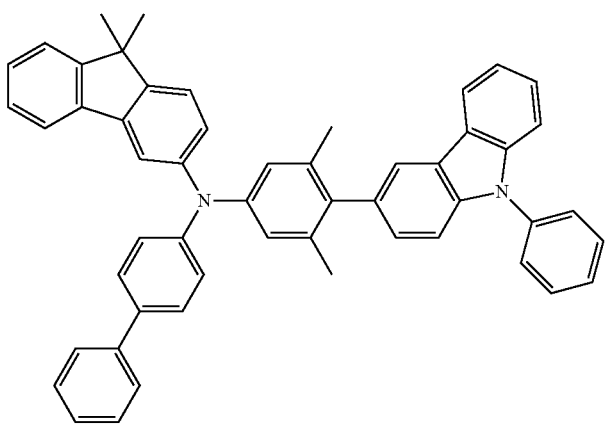 [SMILES: Cc1cc(N(c2ccc(-c3ccccc3)cc2)c2ccc3c(c2)-c2ccccc2C3(C)C)cc(C)c1-c1ccc2c(c1)c1ccccc1n2-c1ccccc1]
92
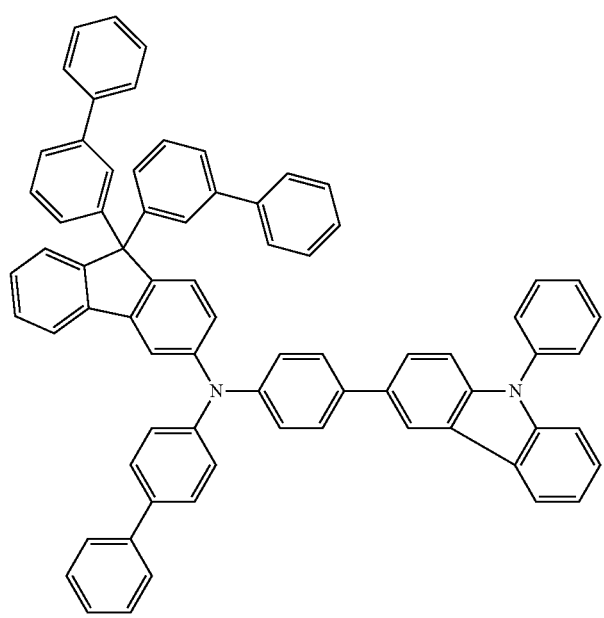 [SMILES: c1ccc(-c2ccc(N(c3ccc(-c4ccc5c(c4)c4ccccc4n5-c4ccccc4)cc3)c3ccc4c(c3)-c3ccccc3C4(c3cccc(-c4ccccc4)c3)c3cccc(-c4ccccc4)c3)cc2)cc1]
93

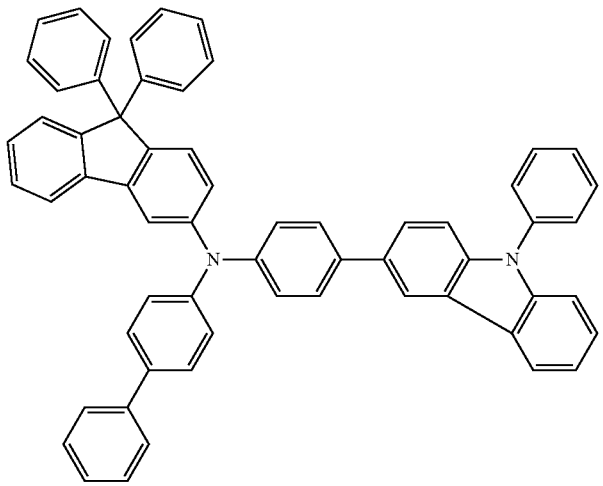 [SMILES: c1ccc(-c2ccc(N(c3ccc(-c4ccc5c(c4)c4ccccc4n5-c4ccccc4)cc3)c3ccc4c(c3)-c3ccccc3C4(c3ccccc3)c3ccccc3)cc2)cc1]
94
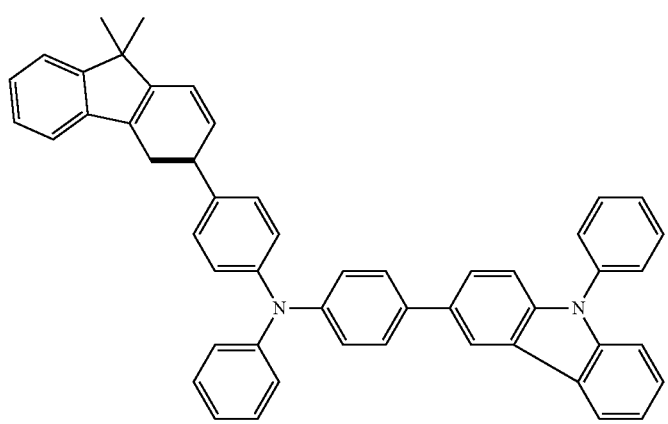
95
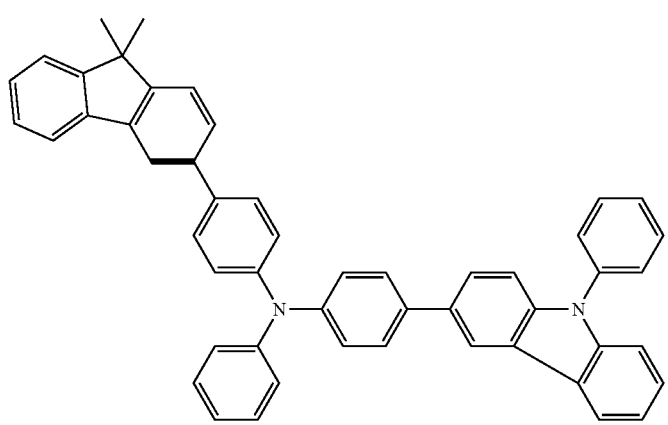
96
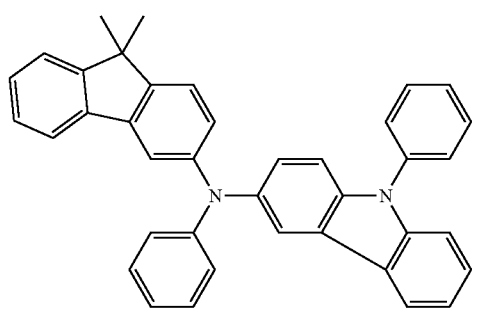 [SMILES: CC1(C)c2ccccc2-c2cc(N(c3ccccc3)c3ccc4c(c3)c3ccccc3n4-c3ccccc3)ccc21]
97

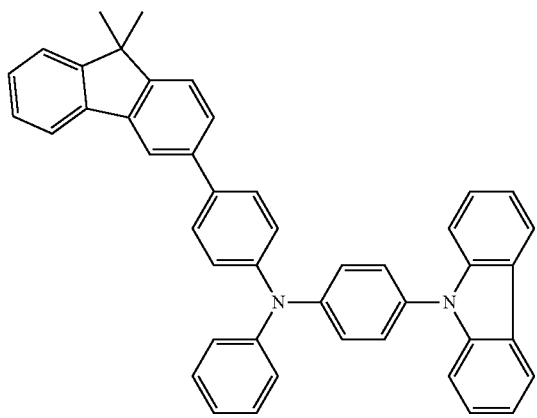 [SMILES: CC1(C)c2ccccc2-c2cc(-c3ccc(N(c4ccccc4)c4ccc(-n5c6ccccc6c6ccccc65)cc4)cc3)ccc21]
98
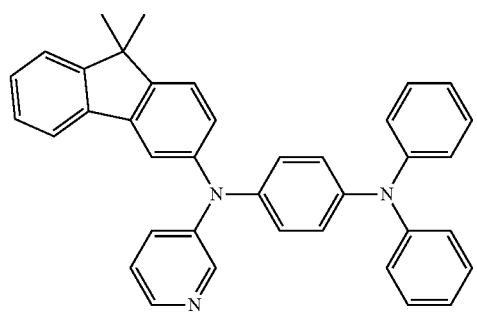 [SMILES: CC1(C)c2ccccc2-c2cc(N(c3ccc(N(c4ccccc4)c4ccccc4)cc3)c3cccnc3)ccc21]
99
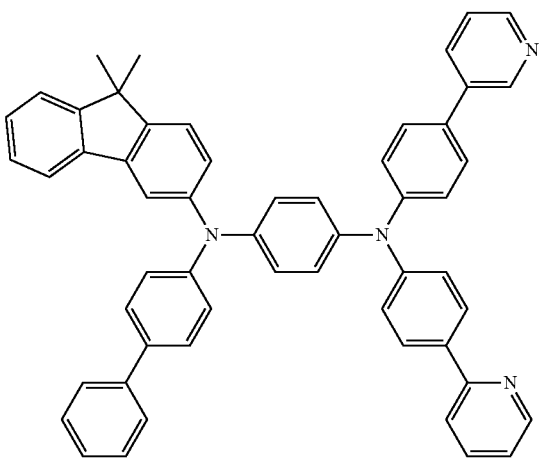 [SMILES: CC1(C)c2ccccc2-c2cc(N(c3ccc(-c4ccccc4)cc3)c3ccc(N(c4ccc(-c5cccnc5)cc4)c4ccc(-c5ccccn5)cc4)cc3)ccc21]
100
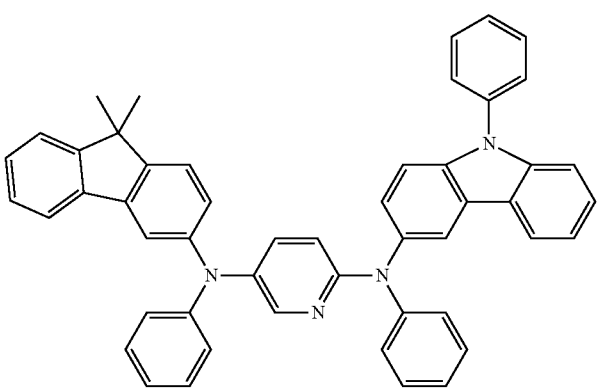 [SMILES: CC1(C)c2ccccc2-c2cc(N(c3ccccc3)c3ccc(N(c4ccccc4)c4ccc5c(c4)c4ccccc4n5-c4ccccc4)nc3)ccc21]
101

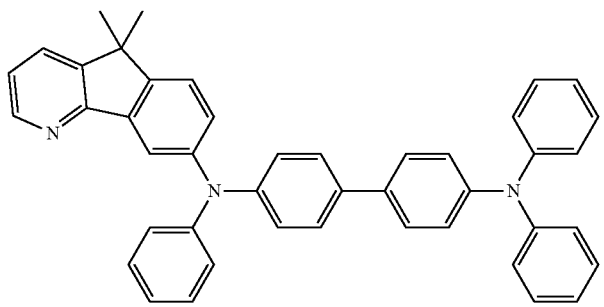 [SMILES: CC1(C)c2ccc(N(c3ccccc3)c3ccc(-c4ccc(N(c5ccccc5)c5ccccc5)cc4)cc3)cc2-c2ncccc21]
102
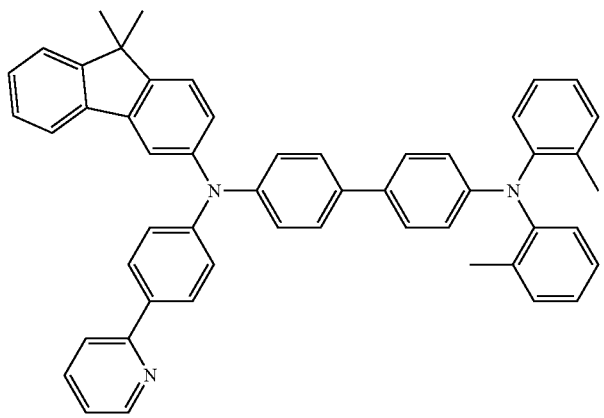
103
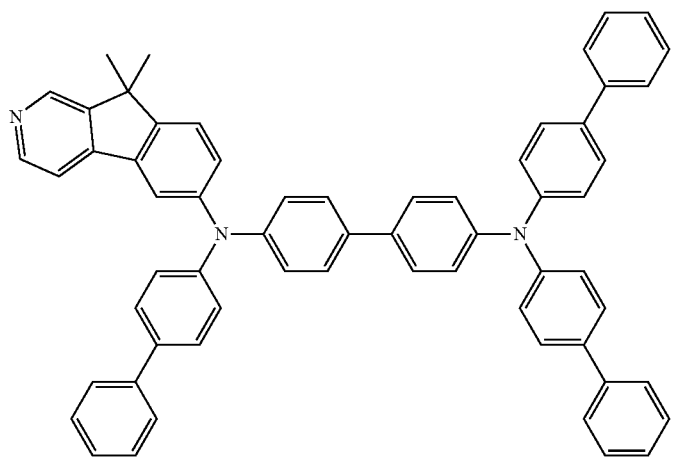 [SMILES: CC1(C)c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2-c2ccncc21]
104
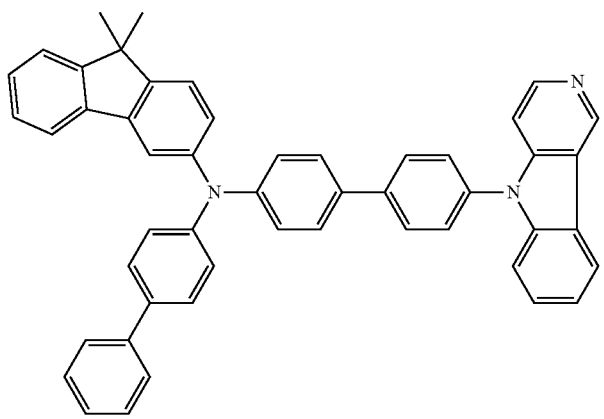 [SMILES: CC1(C)c2ccccc2-c2cc(N(c3ccc(-c4ccccc4)cc3)c3ccc(-c4ccc(-n5c6ccccc6c6cnccc65)cc4)cc3)ccc21]
105

-continued
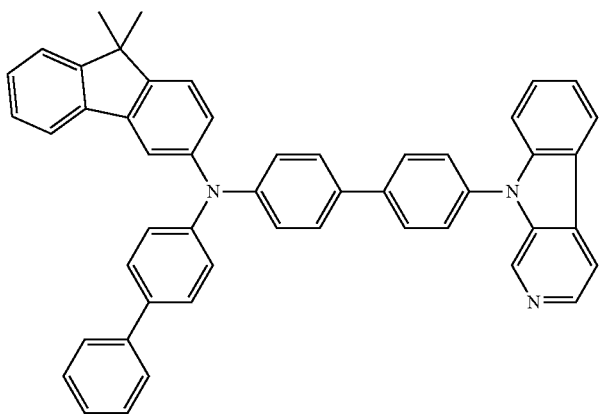 [SMILES: CC1(C)c2ccccc2-c2cc(N(c3ccc(-c4ccccc4)cc3)c3ccc(-c4ccc(-n5c6ccccc6c6ccncc65)cc4)cc3)ccc21]
106
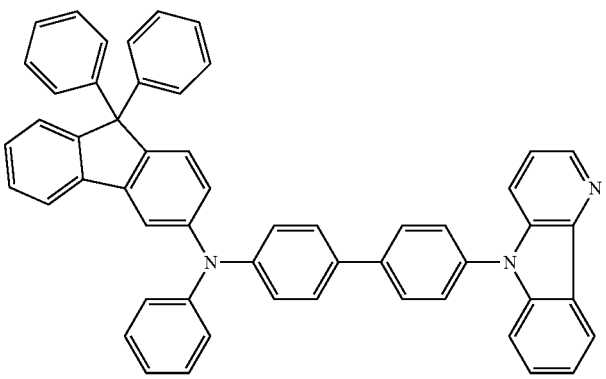 [SMILES: c1ccc(N(c2ccc(-c3ccc(-n4c5ccccc5c5ncccc54)cc3)cc2)c2ccc3c(c2)-c2ccccc2C3(c2ccccc2)c2ccccc2)cc1]
107
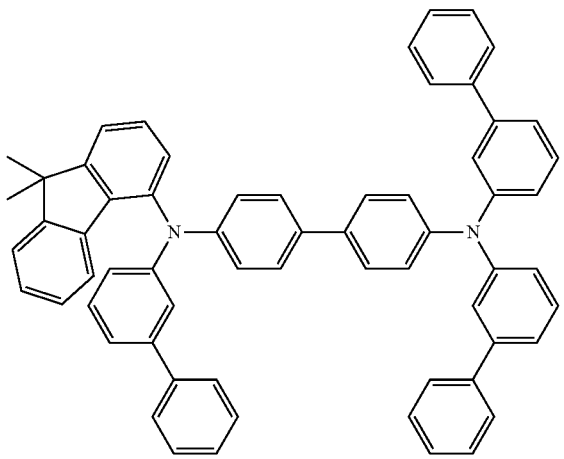 [SMILES: CC1(C)c2ccccc2-c2c(N(c3ccc(-c4ccc(N(c5cccc(-c6ccccc6)c5)c5cccc(-c6ccccc6)c5)cc4)cc3)c3cccc(-c4ccccc4)c3)cccc21]
108
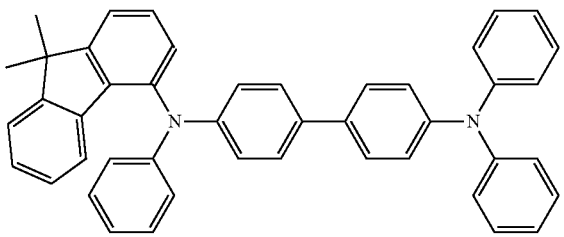 [SMILES: CC1(C)c2ccccc2-c2c(N(c3ccccc3)c3ccc(-c4ccc(N(c5ccccc5)c5ccccc5)cc4)cc3)cccc21]
109

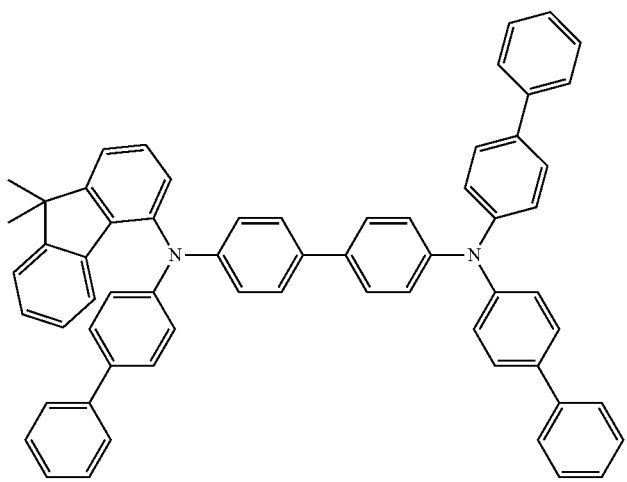 [SMILES: CC1(C)c2ccccc2-c2c(N(c3ccc(-c4ccccc4)cc3)c3ccc(-c4ccc(N(c5ccc(-c6ccccc6)cc5)c5ccc(-c6ccccc6)cc5)cc4)cc3)cccc21]
110
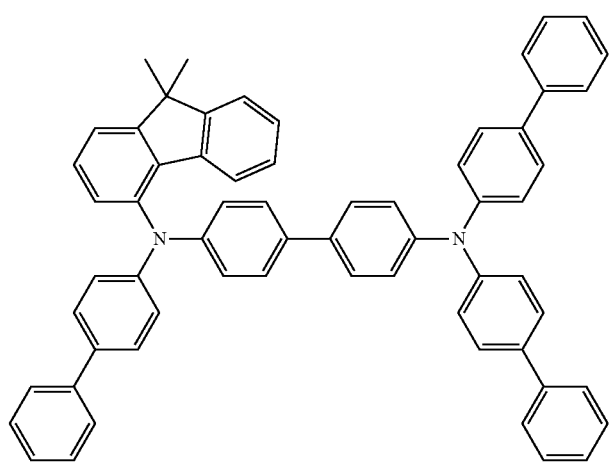 [SMILES: CC1(C)c2ccccc2-c2c(N(c3ccc(-c4ccccc4)cc3)c3ccc(-c4ccc(N(c5ccc(-c6ccccc6)cc5)c5ccc(-c6ccccc6)cc5)cc4)cc3)cccc21]
111
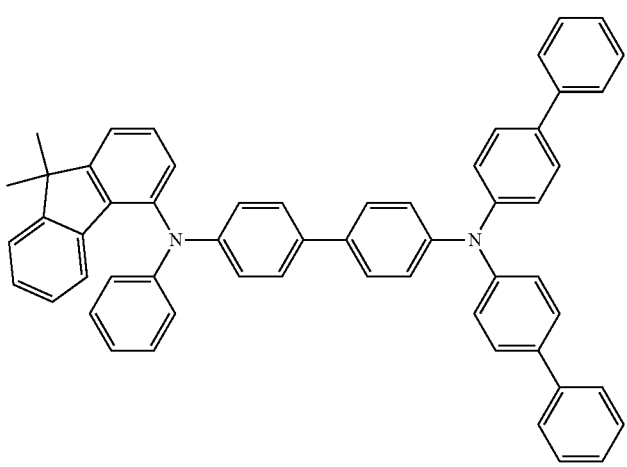 [SMILES: CC1(C)c2ccccc2-c2c(N(c3ccccc3)c3ccc(-c4ccc(N(c5ccc(-c6ccccc6)cc5)c5ccc(-c6ccccc6)cc5)cc4)cc3)cccc21]
112

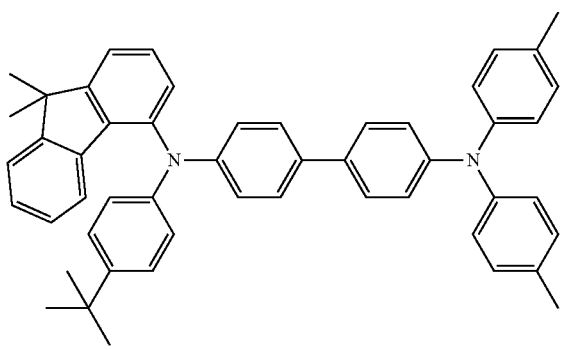 [SMILES: Cc1ccc(N(c2ccc(C)cc2)c2ccc(-c3ccc(N(c4ccc(C(C)(C)C)cc4)c4cccc5c4-c4ccccc4C5(C)C)cc3)cc2)cc1]
113
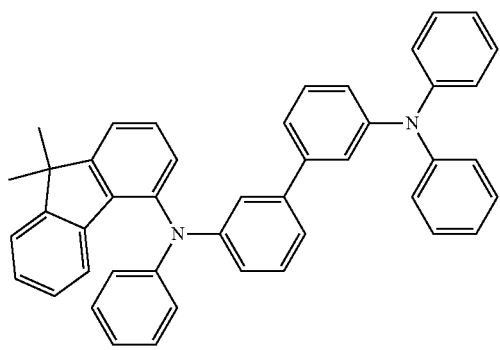 [SMILES: CC1(C)c2ccccc2-c2c(N(c3ccccc3)c3cccc(-c4cccc(N(c5ccccc5)c5ccccc5)c4)c3)cccc21]
114
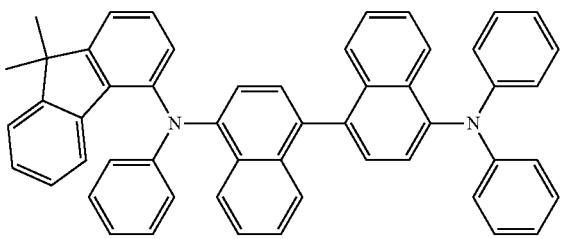 [SMILES: CC1(C)c2ccccc2-c2c(N(c3ccccc3)c3ccc(-c4ccc(N(c5ccccc5)c5ccccc5)c5ccccc45)c4ccccc34)cccc21]
115
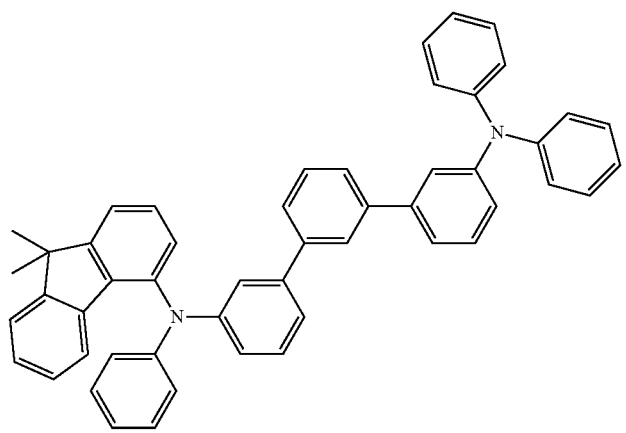 [SMILES: CC1(C)c2ccccc2-c2c(N(c3ccccc3)c3cccc(-c4cccc(-c5cccc(N(c6ccccc6)c6ccccc6)c5)c4)c3)cccc21]
116

-continued
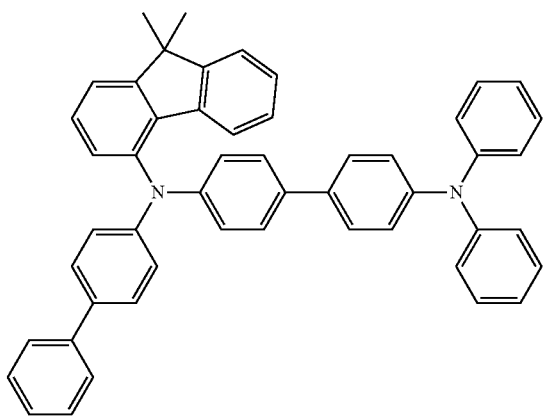 [SMILES: CC1(C)c2ccccc2-c2c(N(c3ccc(-c4ccccc4)cc3)c3ccc(-c4ccc(N(c5ccccc5)c5ccccc5)cc4)cc3)cccc21]
117
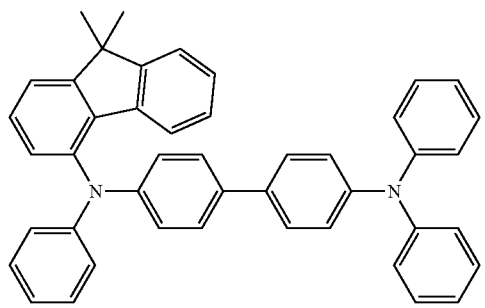 [SMILES: CC1(C)c2ccccc2-c2c(N(c3ccccc3)c3ccc(-c4ccc(N(c5ccccc5)c5ccccc5)cc4)cc3)cccc21]
118
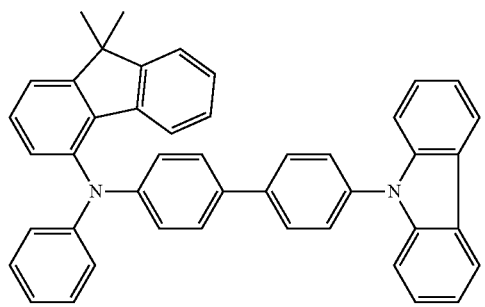 [SMILES: CC1(C)c2ccccc2-c2c(N(c3ccccc3)c3ccc(-c4ccc(-n5c6ccccc6c6ccccc65)cc4)cc3)cccc21]
119
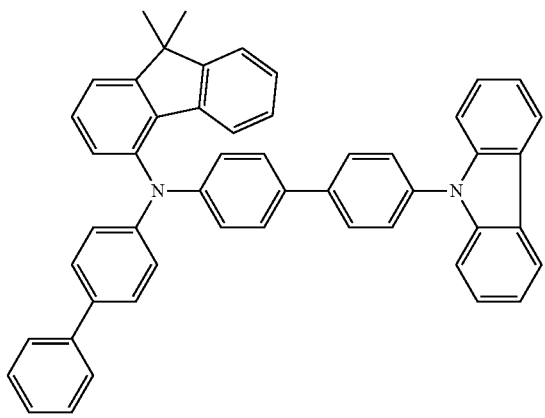 [SMILES: CC1(C)c2ccccc2-c2c(N(c3ccc(-c4ccccc4)cc3)c3ccc(-c4ccc(-n5c6ccccc6c6ccccc65)cc4)cc3)cccc21]
120

-continued
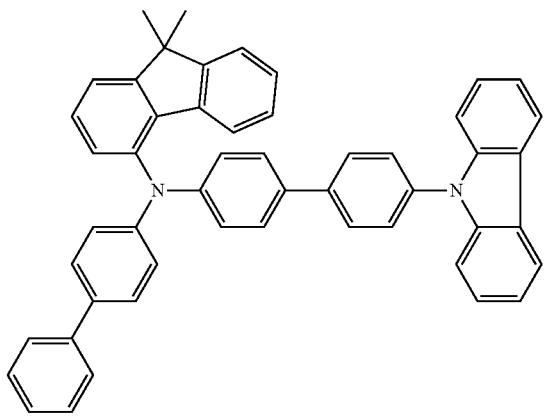 [SMILES: CC1(C)c2ccccc2-c2c(N(c3ccc(-c4ccccc4)cc3)c3ccc(-c4ccc(-n5c6ccccc6c6ccccc65)cc4)cc3)cccc21]
121
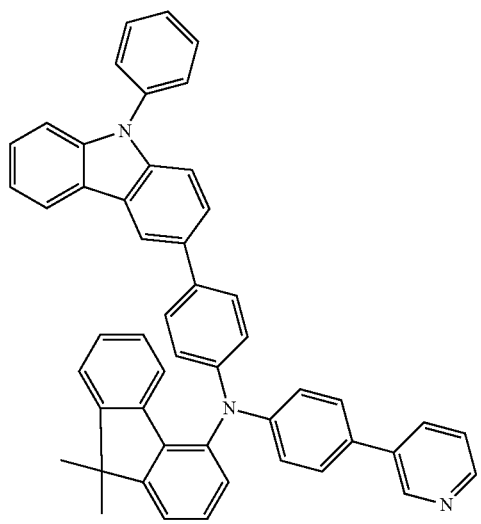 [SMILES: CC1(C)c2ccccc2-c2c(N(c3ccc(-c4cccnc4)cc3)c3ccc(-c4ccc5c(c4)c4ccccc4n5-c4ccccc4)cc3)cccc21]
122
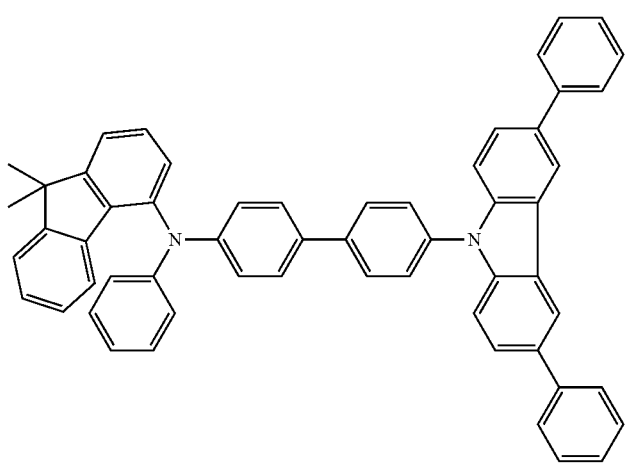 [SMILES: CC1(C)c2ccccc2-c2c(N(c3ccccc3)c3ccc(-c4ccc(-n5c6ccc(-c7ccccc7)cc6c6cc(-c7ccccc7)ccc65)cc4)cc3)cccc21]
123

-continued
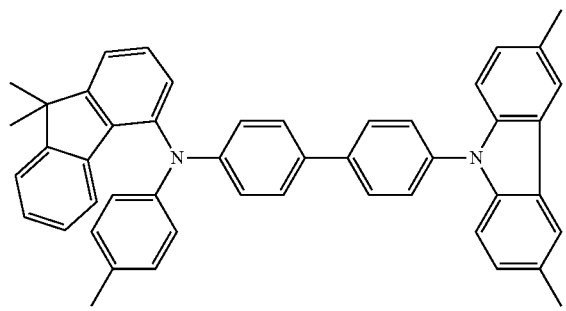
124
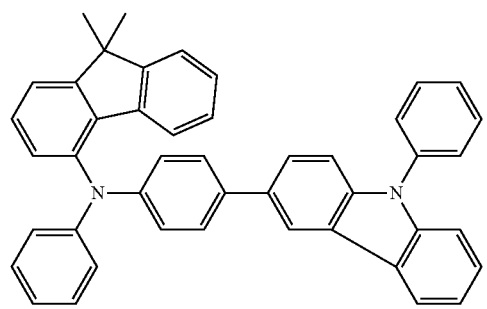 [SMILES: CC1(C)c2ccccc2-c2c(N(c3ccccc3)c3ccc(-c4ccc5c(c4)c4ccccc4n5-c4ccccc4)cc3)cccc21]
125
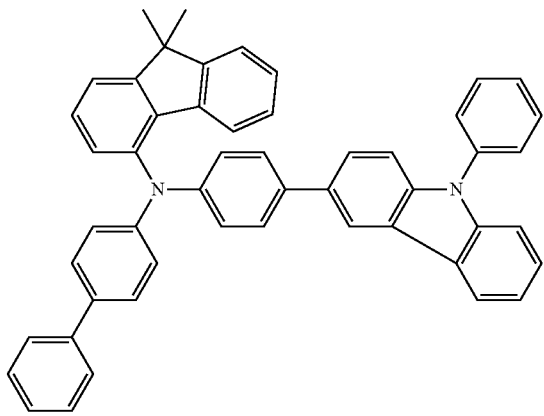 [SMILES: CC1(C)c2ccccc2-c2c(N(c3ccc(-c4ccccc4)cc3)c3ccc(-c4ccc5c(c4)c4ccccc4n5-c4ccccc4)cc3)cccc21]
126
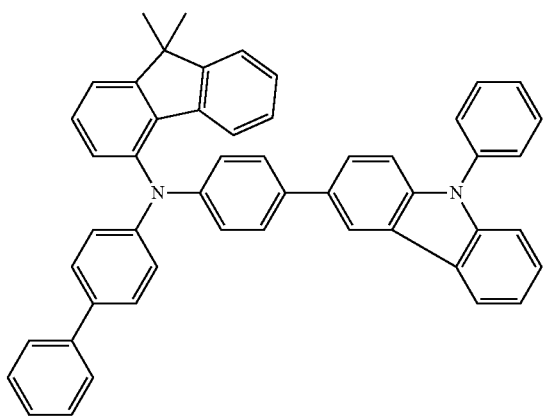 [SMILES: CC1(C)c2ccccc2-c2c(N(c3ccc(-c4ccccc4)cc3)c3ccc(-c4ccc5c(c4)c4ccccc4n5-c4ccccc4)cc3)cccc21]
127

-continued
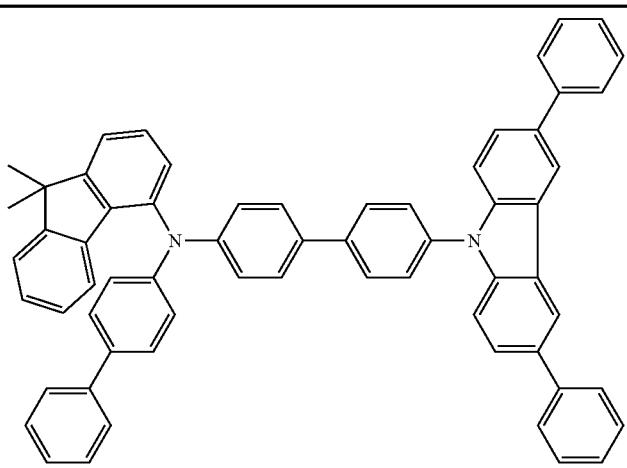
128
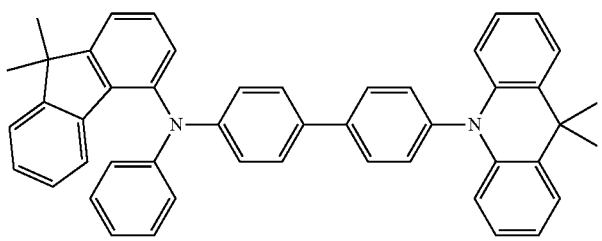
129
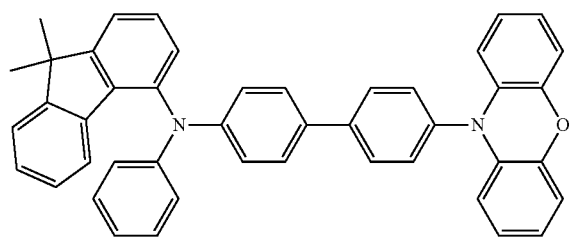 [SMILES: CC1(C)c2ccccc2-c2c(N(c3ccccc3)c3ccc(-c4ccc(N5c6ccccc6Oc6ccccc65)cc4)cc3)cccc21]
130
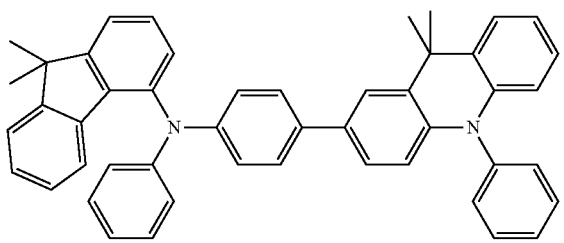 [SMILES: CC1(C)c2ccccc2N(c2ccccc2)c2ccc(-c3ccc(N(c4ccccc4)c4cccc5c4-c4ccccc4C5(C)C)cc3)cc21]
131
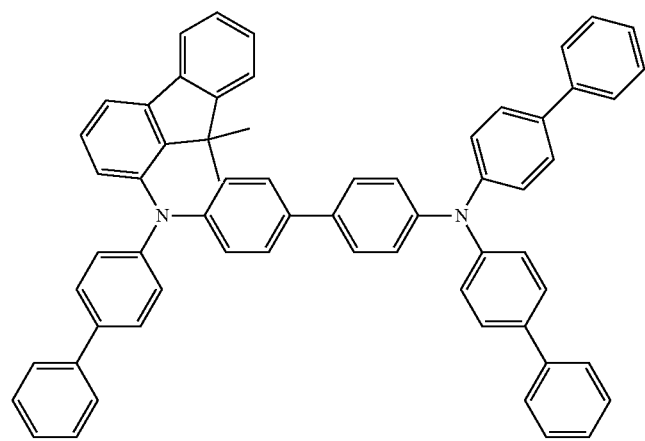 [SMILES: CC1(C)c2ccccc2-c2cccc(N(c3ccc(-c4ccccc4)cc3)c3ccc(-c4ccc(N(c5ccc(-c6ccccc6)cc5)c5ccc(-c6ccccc6)cc5)cc4)cc3)c21]
132

-continued
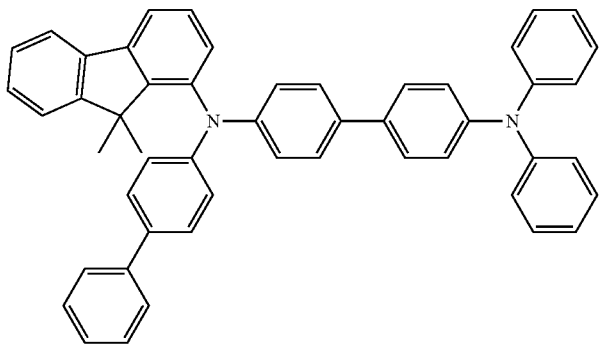 [SMILES: CC1(C)c2ccccc2-c2cccc(N(c3ccc(-c4ccccc4)cc3)c3ccc(-c4ccc(N(c5ccccc5)c5ccccc5)cc4)cc3)c21]
133
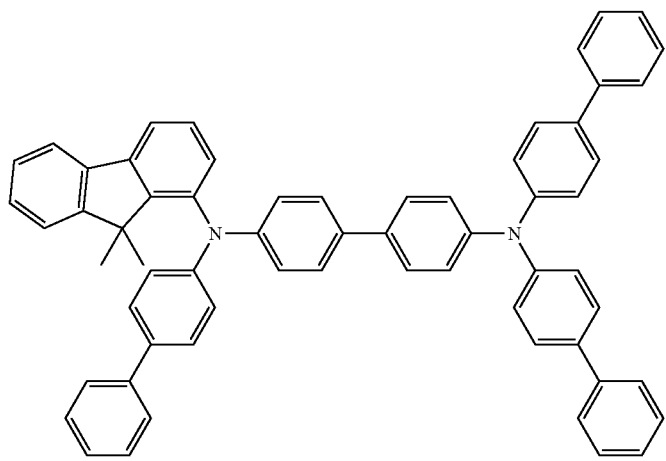 [SMILES: CC1(C)c2ccccc2-c2cccc(N(c3ccc(-c4ccccc4)cc3)c3ccc(-c4ccc(N(c5ccc(-c6ccccc6)cc5)c5ccc(-c6ccccc6)cc5)cc4)cc3)c21]
134
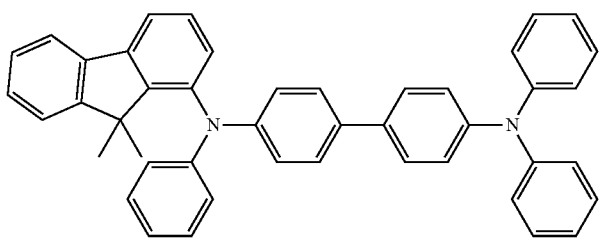 [SMILES: CC1(C)c2ccccc2-c2cccc(N(c3ccccc3)c3ccc(-c4ccc(N(c5ccccc5)c5ccccc5)cc4)cc3)c21]
135
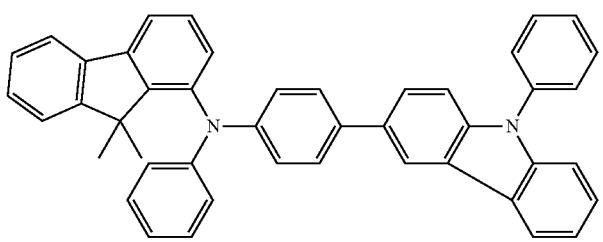 [SMILES: CC1(C)c2ccccc2-c2cccc(N(c3ccccc3)c3ccc(-c4ccc5c(c4)c4ccccc4n5-c4ccccc4)cc3)c21]
136
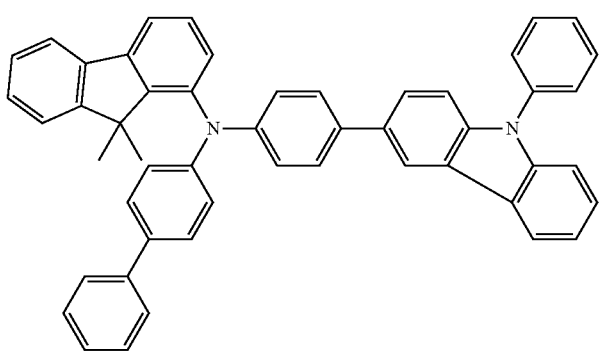 [SMILES: CC1(C)c2ccccc2-c2cccc(N(c3ccc(-c4ccccc4)cc3)c3ccc(-c4ccc5c(c4)c4ccccc4n5-c4ccccc4)cc3)c21]
137

-continued
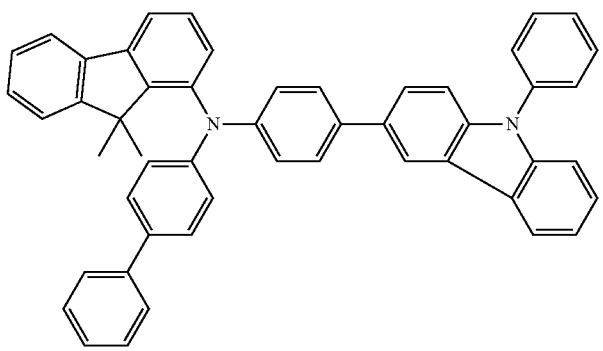 [SMILES: CC1(C)c2ccccc2-c2cccc(N(c3ccc(-c4ccccc4)cc3)c3ccc(-c4ccc5c(c4)c4ccccc4n5-c4ccccc4)cc3)c21]
138
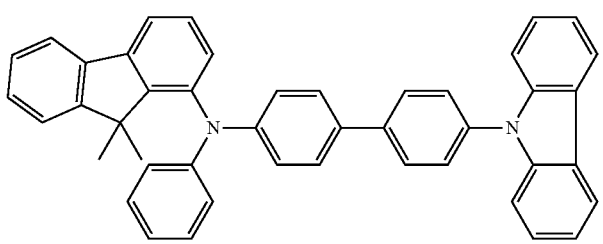
139
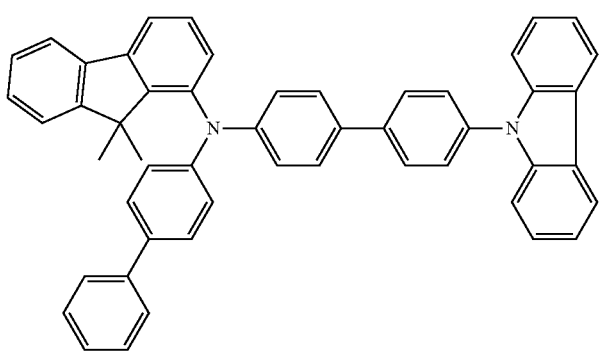 [SMILES: CC1(C)c2ccccc2-c2cccc(N(c3ccc(-c4ccccc4)cc3)c3ccc(-c4ccc(-n5c6ccccc6c6ccccc65)cc4)cc3)c21]
140
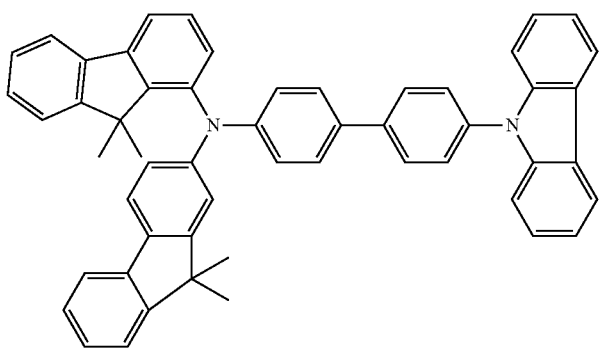 [SMILES: CC1(C)c2ccccc2-c2ccc(N(c3ccc(-c4ccc(-n5c6ccccc6c6ccccc65)cc4)cc3)c3cccc4c3C(C)(C)c3ccccc3-4)cc21]
141
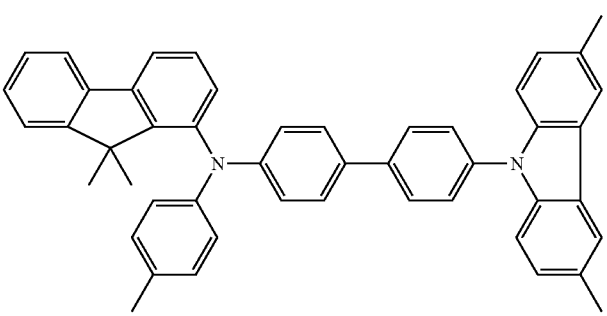 [SMILES: Cc1ccc(N(c2ccc(-c3ccc(-n4c5ccc(C)cc5c5cc(C)ccc54)cc3)cc2)c2cccc3c2C(C)(C)c2ccccc2-3)cc1]
142

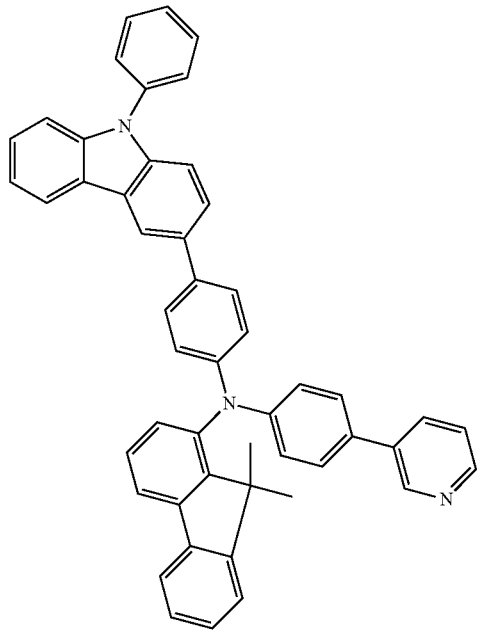 [SMILES: CC1(C)c2ccccc2-c2cccc(N(c3ccc(-c4cccnc4)cc3)c3ccc(-c4ccc5c(c4)c4ccccc4n5-c4ccccc4)cc3)c21]
143
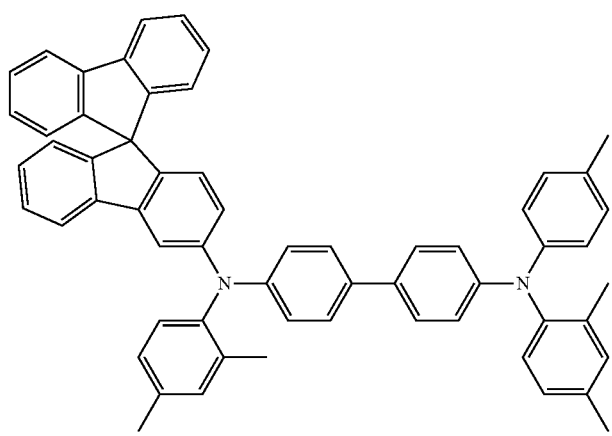 [SMILES: Cc1ccc(N(c2ccc(-c3ccc(N(c4ccc5c(c4)-c4ccccc4C54c5ccccc5-c5ccccc54)c4ccc(C)cc4C)cc3)cc2)c2ccc(C)cc2C)cc1]
144
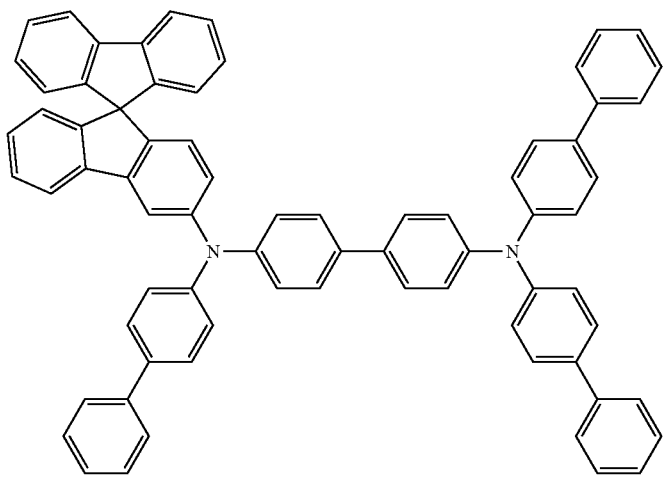 [SMILES: c1ccc(-c2ccc(N(c3ccc(-c4ccccc4)cc3)c3ccc(-c4ccc(N(c5ccc(-c6ccccc6)cc5)c5ccc6c(c5)-c5ccccc5C65c6ccccc6-c6ccccc65)cc4)cc3)cc2)cc1]
145

-continued
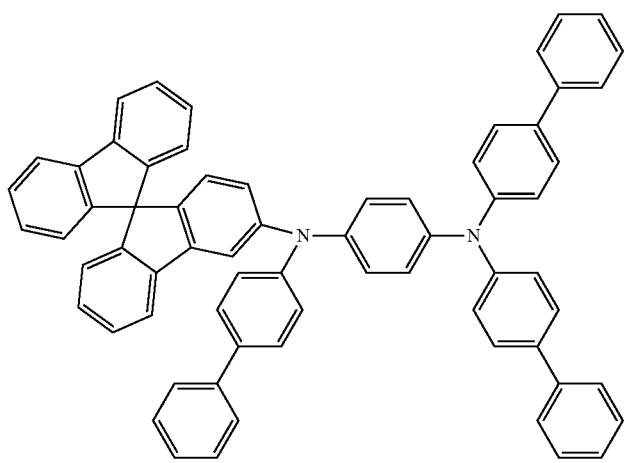 [SMILES: c1ccc(-c2ccc(N(c3ccc(-c4ccccc4)cc3)c3ccc(N(c4ccc(-c5ccccc5)cc4)c4ccc5c(c4)-c4ccccc4C54c5ccccc5-c5ccccc54)cc3)cc2)cc1]
146
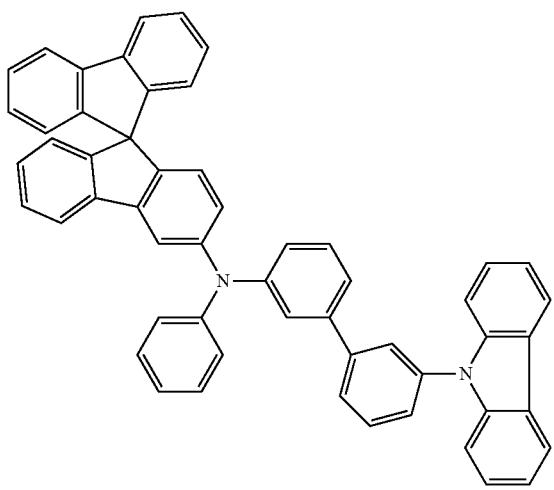 [SMILES: c1ccc(N(c2cccc(-c3cccc(-n4c5ccccc5c5ccccc54)c3)c2)c2ccc3c(c2)-c2ccccc2C32c3ccccc3-c3ccccc32)cc1]
147
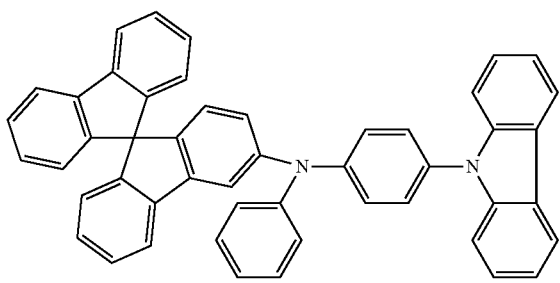 [SMILES: c1ccc(N(c2ccc(-n3c4ccccc4c4ccccc43)cc2)c2ccc3c(c2)-c2ccccc2C32c3ccccc3-c3ccccc32)cc1]
148

149
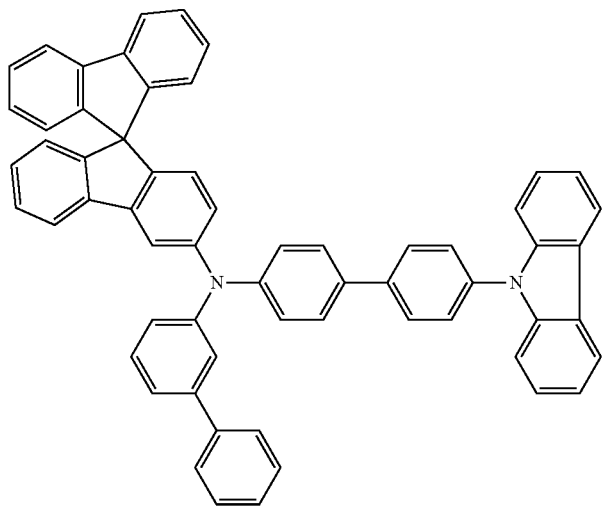 [SMILES: c1ccc(-c2cccc(N(c3ccc(-c4ccc(-n5c6ccccc6c6ccccc65)cc4)cc3)c3ccc4c(c3)-c3ccccc3C43c4ccccc4-c4ccccc43)c2)cc1]
150
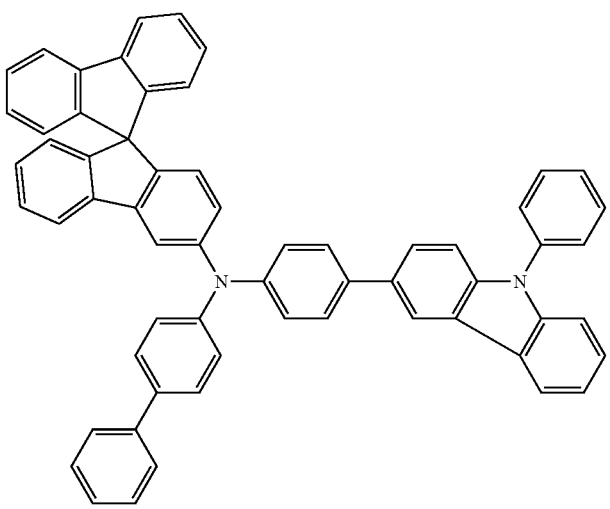 [SMILES: c1ccc(-c2ccc(N(c3ccc(-c4ccc5c(c4)c4ccccc4n5-c4ccccc4)cc3)c3ccc4c(c3)-c3ccccc3C43c4ccccc4-c4ccccc43)cc2)cc1]
151
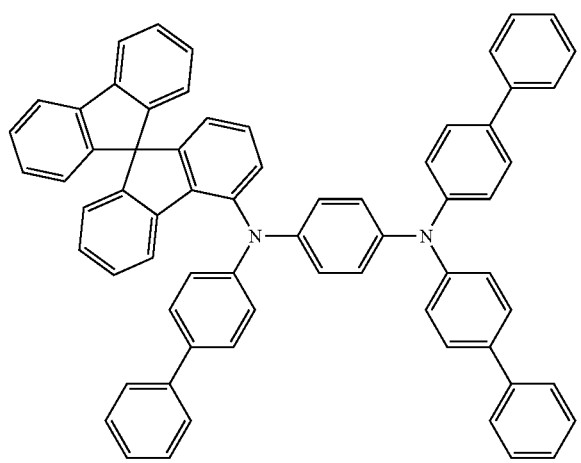 [SMILES: c1ccc(-c2ccc(N(c3ccc(-c4ccccc4)cc3)c3ccc(N(c4ccc(-c5ccccc5)cc4)c4cccc5c4-c4ccccc4C54c5ccccc5-c5ccccc54)cc3)cc2)cc1]

-continued
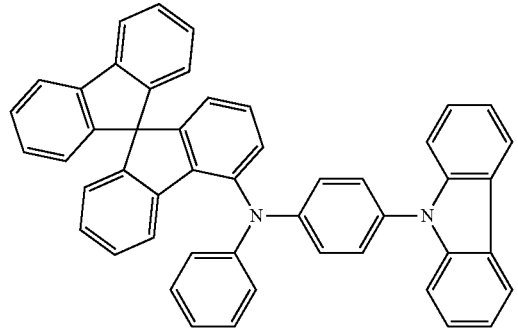 [SMILES: c1ccc(N(c2ccc(-n3c4ccccc4c4ccccc43)cc2)c2cccc3c2-c2ccccc2C32c3ccccc3-c3ccccc32)cc1]
152
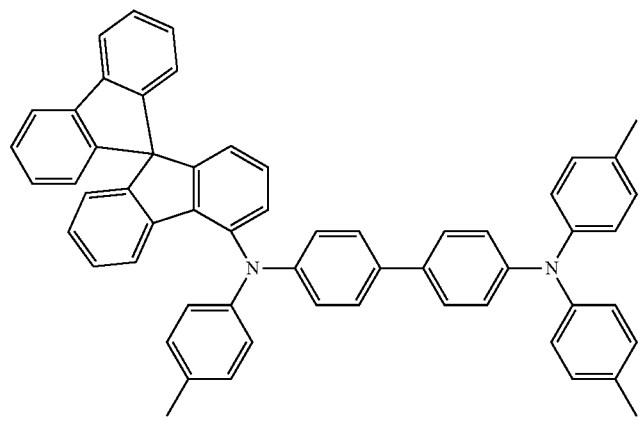 [SMILES: Cc1ccc(N(c2ccc(C)cc2)c2ccc(-c3ccc(N(c4ccc(C)cc4)c4cccc5c4-c4ccccc4C54c5ccccc5-c5ccccc54)cc3)cc2)cc1]
153
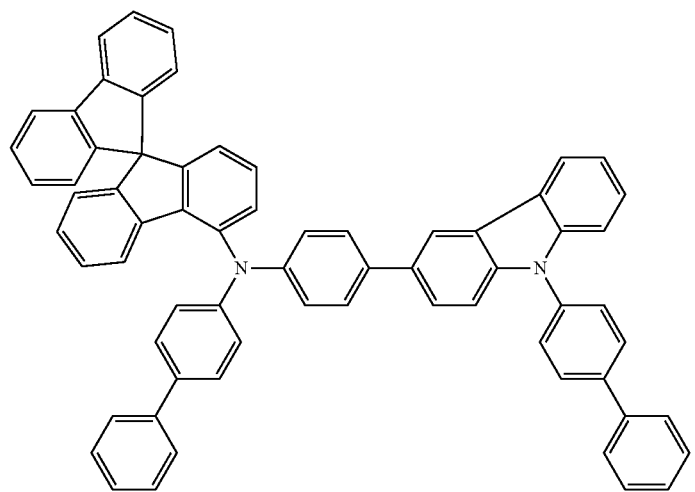 [SMILES: c1ccc(-c2ccc(N(c3ccc(-c4ccc5c(c4)c4ccccc4n5-c4ccc(-c5ccccc5)cc4)cc3)c3cccc4c3-c3ccccc3C43c4ccccc4-c4ccccc43)cc2)cc1]
154

155
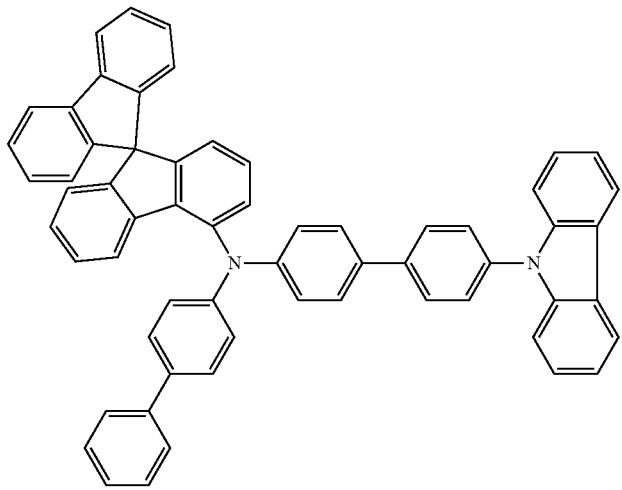 [SMILES: c1ccc(-c2ccc(N(c3ccc(-c4ccc(-n5c6ccccc6c6ccccc65)cc4)cc3)c3cccc4c3-c3ccccc3C43c4ccccc4-c4ccccc43)cc2)cc1]
156
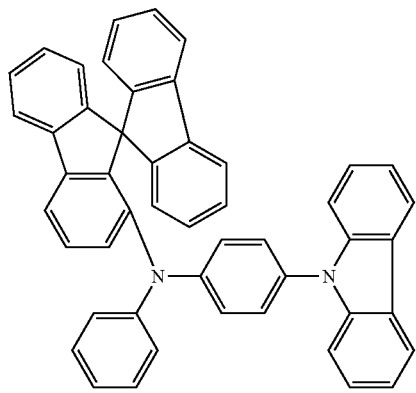 [SMILES: c1ccc(N(c2ccc(-n3c4ccccc4c4ccccc43)cc2)c2cccc3c2C2(c4ccccc4-c4ccccc42)c2ccccc2-3)cc1]
157
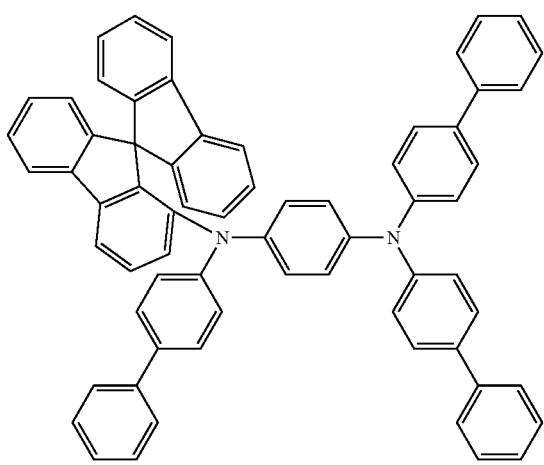 [SMILES: c1ccc(-c2ccc(N(c3ccc(-c4ccccc4)cc3)c3ccc(N(c4ccc(-c5ccccc5)cc4)c4cccc5c4C4(c6ccccc6-c6ccccc64)c4ccccc4-5)cc3)cc2)cc1]

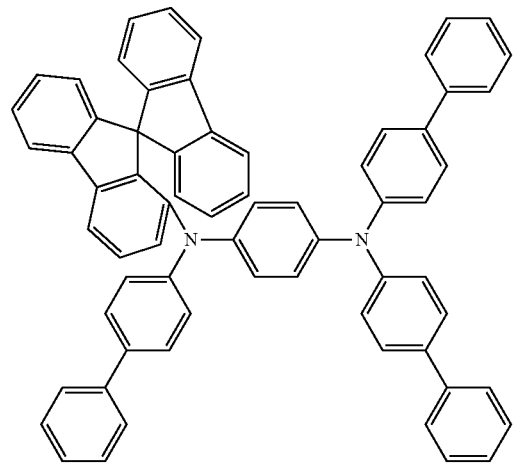 [SMILES: c1ccc(-c2ccc(N(c3ccc(-c4ccccc4)cc3)c3ccc(N(c4ccc(-c5ccccc5)cc4)c4cccc5c4C4(c6ccccc6-c6ccccc64)c4ccccc4-5)cc3)cc2)cc1]
158
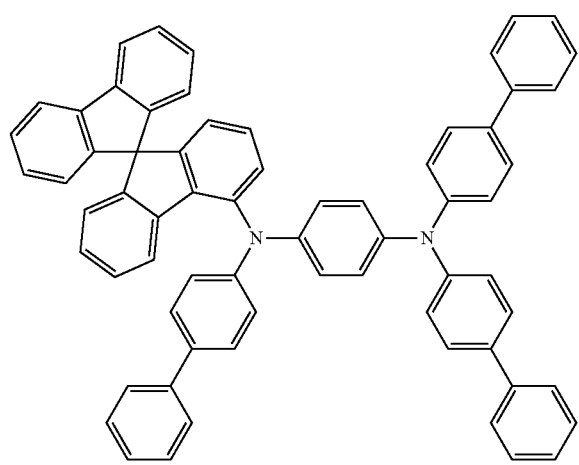 [SMILES: c1ccc(-c2ccc(N(c3ccc(-c4ccccc4)cc3)c3ccc(N(c4ccc(-c5ccccc5)cc4)c4cccc5c4-c4ccccc4C54c5ccccc5-c5ccccc54)cc3)cc2)cc1]
159
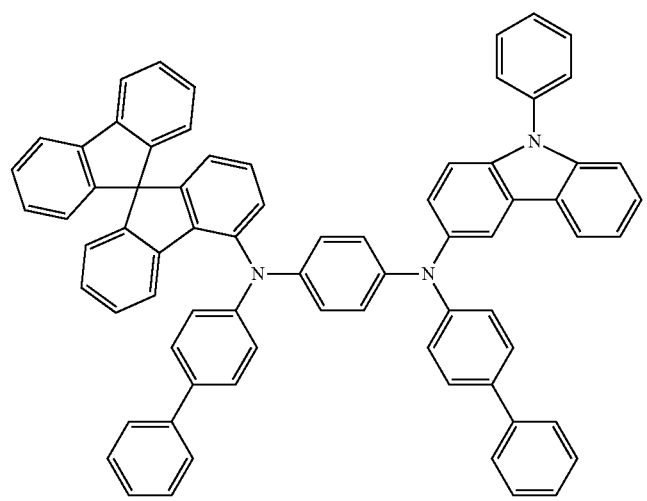 [SMILES: c1ccc(-c2ccc(N(c3ccc(N(c4ccc(-c5ccccc5)cc4)c4cccc5c4-c4ccccc4C54c5ccccc5-c5ccccc54)cc3)c3ccc4c(c3)c3ccccc3n4-c3ccccc3)cc2)cc1]
160

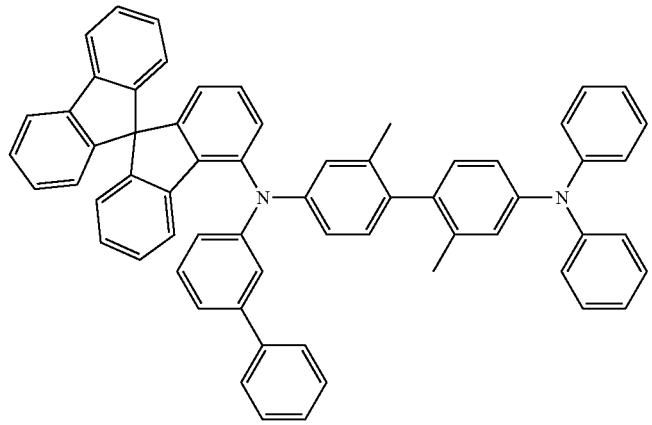 [SMILES: Cc1cc(N(c2ccccc2)c2ccccc2)ccc1-c1ccc(N(c2cccc(-c3ccccc3)c2)c2cccc3c2-c2ccccc2C32c3ccccc3-c3ccccc32)cc1C]
161
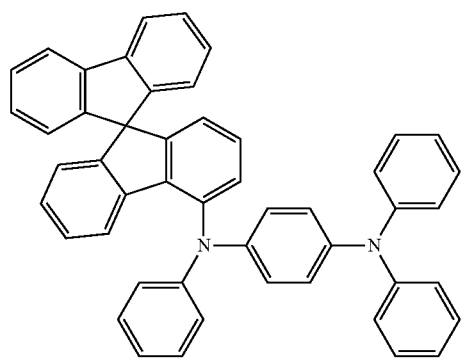 [SMILES: c1ccc(N(c2ccccc2)c2ccc(N(c3ccccc3)c3cccc4c3-c3ccccc3C43c4ccccc4-c4ccccc43)cc2)cc1]
162
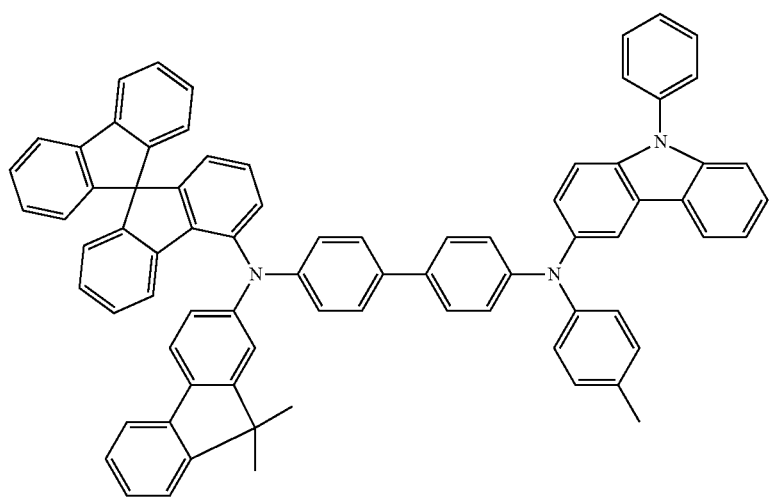 [SMILES: Cc1ccc(N(c2ccc(-c3ccc(N(c4ccc5c(c4)C(C)(C)c4ccccc4-5)c4cccc5c4-c4ccccc4C54c5ccccc5-c5ccccc54)cc3)cc2)c2ccc3c(c2)c2ccccc2n3-c2ccccc2)cc1]
163

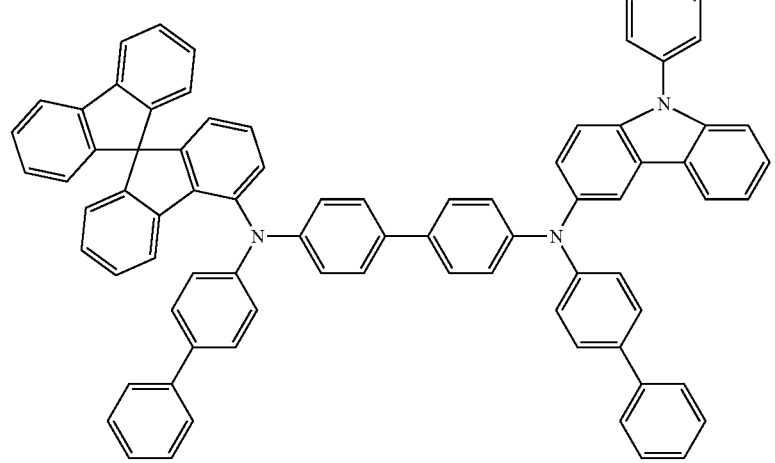
164
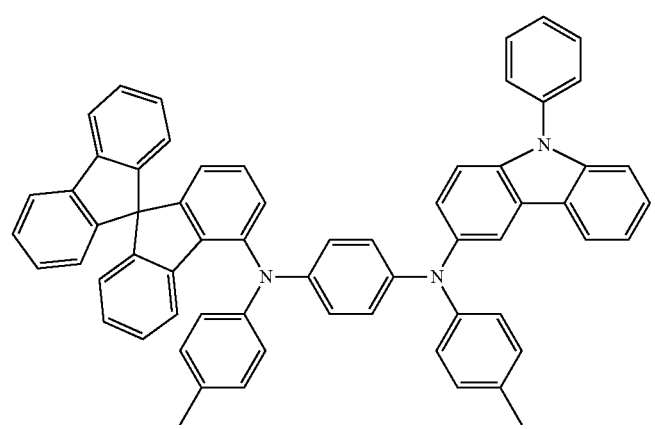 [SMILES: Cc1ccc(N(c2ccc(N(c3ccc(C)cc3)c3cccc4c3-c3ccccc3C43c4ccccc4-c4ccccc43)cc2)c2ccc3c(c2)c2ccccc2n3-c2ccccc2)cc1]
165
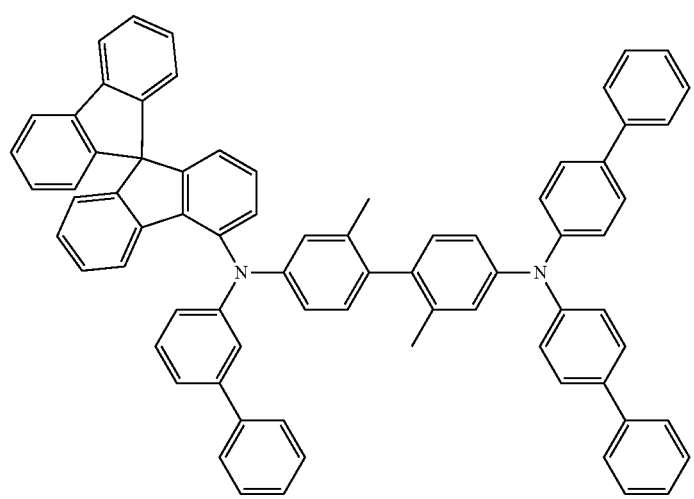 [SMILES: Cc1cc(N(c2ccc(-c3ccccc3)cc2)c2ccc(-c3ccccc3)cc2)ccc1-c1ccc(N(c2cccc(-c3ccccc3)c2)c2cccc3c2-c2ccccc2C32c3ccccc3-c3ccccc32)cc1C]
166

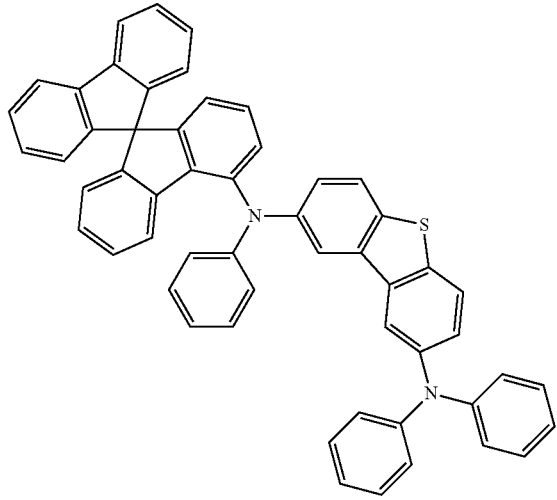 [SMILES: c1ccc(N(c2ccccc2)c2ccc3sc4ccc(N(c5ccccc5)c5cccc6c5-c5ccccc5C65c6ccccc6-c6ccccc65)cc4c3c2)cc1]
167
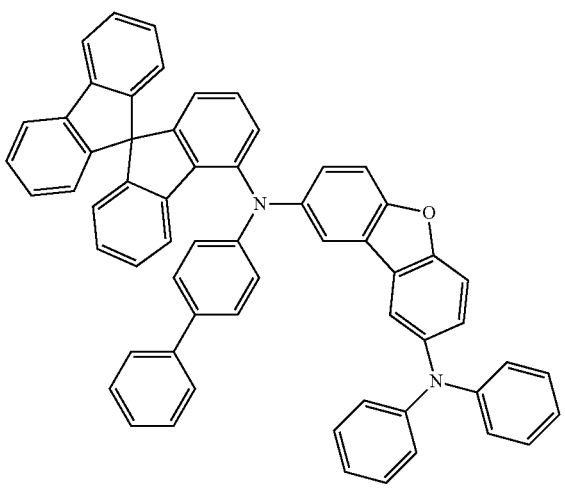 [SMILES: c1ccc(-c2ccc(N(c3ccc4oc5ccc(N(c6ccccc6)c6ccccc6)cc5c4c3)c3cccc4c3-c3ccccc3C43c4ccccc4-c4ccccc43)cc2)cc1]
168
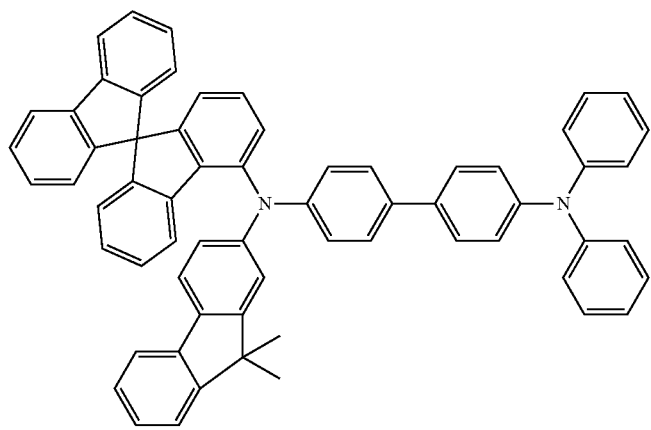 [SMILES: CC1(C)c2ccccc2-c2ccc(N(c3ccc(-c4ccc(N(c5ccccc5)c5ccccc5)cc4)cc3)c3cccc4c3-c3ccccc3C43c4ccccc4-c4ccccc43)cc21]
169

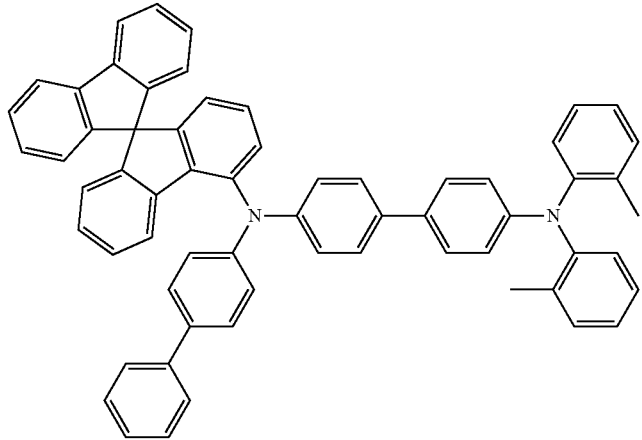 [SMILES: Cc1ccccc1N(c1ccc(-c2ccc(N(c3ccc(-c4ccccc4)cc3)c3cccc4c3-c3ccccc3C43c4ccccc4-c4ccccc43)cc2)cc1)c1ccccc1C]
170
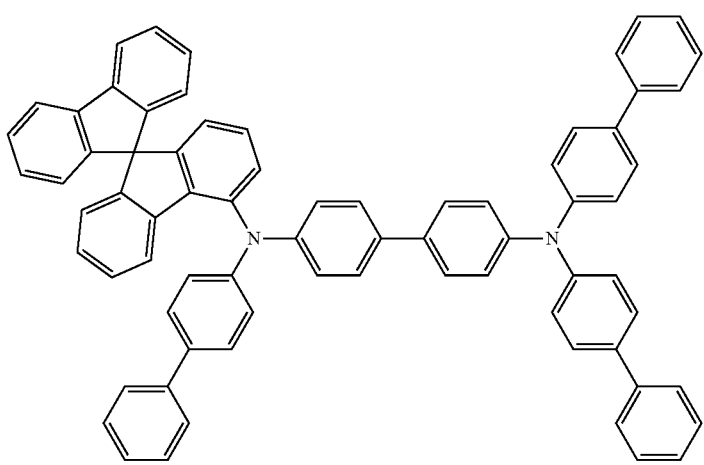 [SMILES: c1ccc(-c2ccc(N(c3ccc(-c4ccccc4)cc3)c3ccc(-c4ccc(N(c5ccc(-c6ccccc6)cc5)c5cccc6c5-c5ccccc5C65c6ccccc6-c6ccccc65)cc4)cc3)cc2)cc1]
171
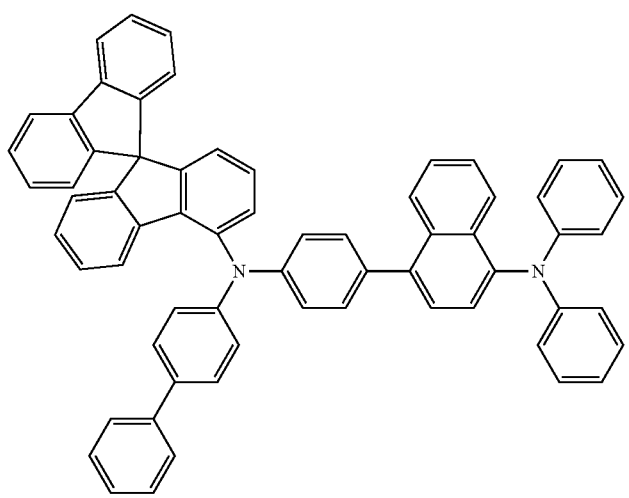 [SMILES: c1ccc(-c2ccc(N(c3ccc(-c4ccc(N(c5ccccc5)c5ccccc5)c5ccccc45)cc3)c3cccc4c3-c3ccccc3C43c4ccccc4-c4ccccc43)cc2)cc1]
172

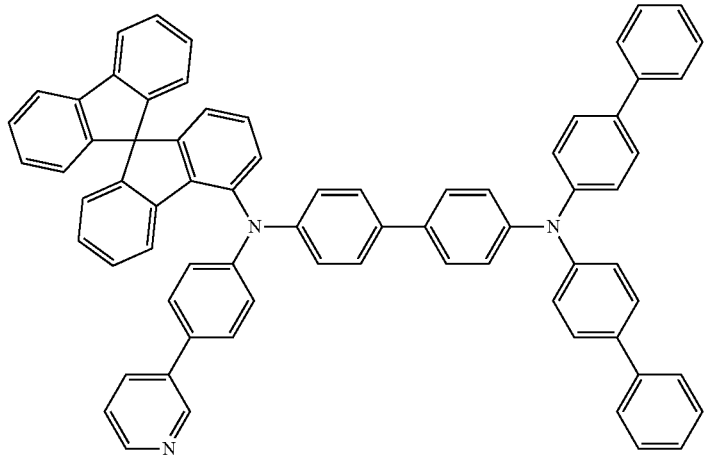 [SMILES: c1ccc(-c2ccc(N(c3ccc(-c4ccccc4)cc3)c3ccc(-c4ccc(N(c5ccc(-c6cccnc6)cc5)c5cccc6c5-c5ccccc5C65c6ccccc6-c6ccccc65)cc4)cc3)cc2)cc1]
173
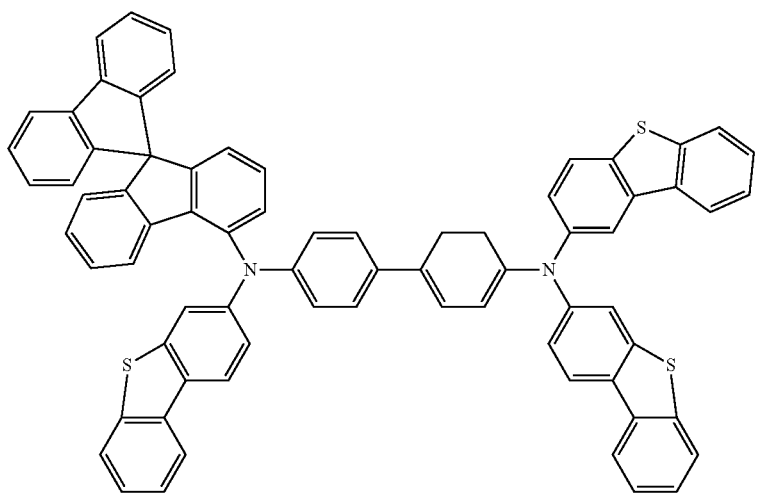 [SMILES: C1=C(c2ccc(N(c3ccc4c(c3)sc3ccccc34)c3cccc4c3-c3ccccc3C43c4ccccc4-c4ccccc43)cc2)CCC(N(c2ccc3c(c2)sc2ccccc23)c2ccc3sc4ccccc4c3c2)=C1]
174
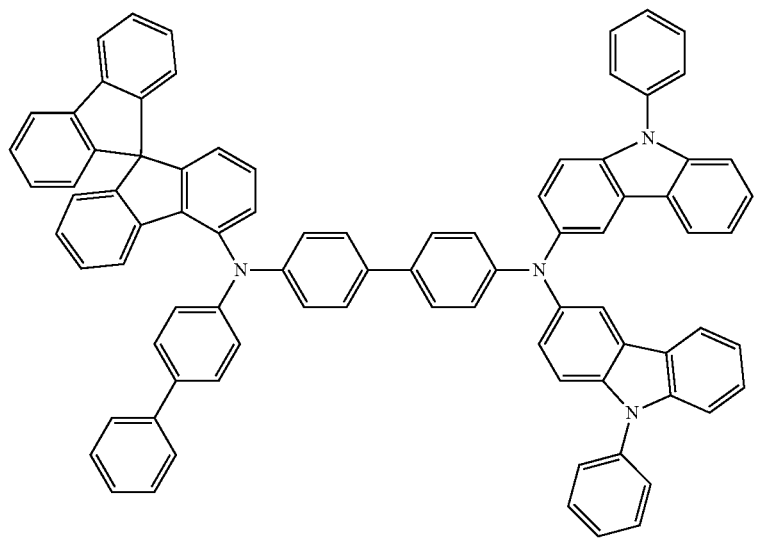 [SMILES: c1ccc(-c2ccc(N(c3ccc(-c4ccc(N(c5ccc6c(c5)c5ccccc5n6-c5ccccc5)c5ccc6c(c5)c5ccccc5n6-c5ccccc5)cc4)cc3)c3cccc4c3-c3ccccc3C43c4ccccc4-c4ccccc43)cc2)cc1]
175

-continued
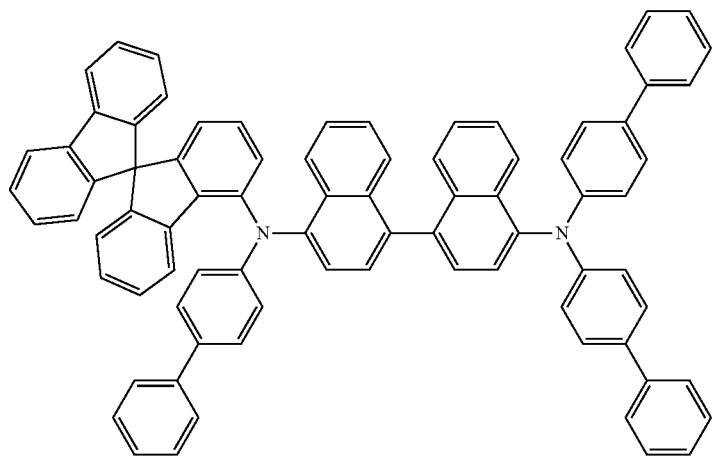 [SMILES: c1ccc(-c2ccc(N(c3ccc(-c4ccccc4)cc3)c3ccc(-c4ccc(N(c5ccc(-c6ccccc6)cc5)c5cccc6c5-c5ccccc5C65c6ccccc6-c6ccccc65)c5ccccc45)c4ccccc34)cc2)cc1]
176
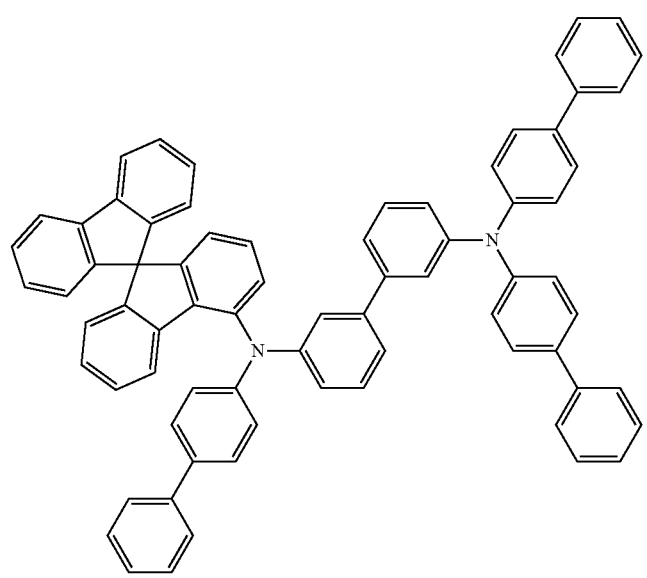 [SMILES: c1ccc(-c2ccc(N(c3ccc(-c4ccccc4)cc3)c3cccc(-c4cccc(N(c5ccc(-c6ccccc6)cc5)c5cccc6c5-c5ccccc5C65c6ccccc6-c6ccccc65)c4)c3)cc2)cc1]
177
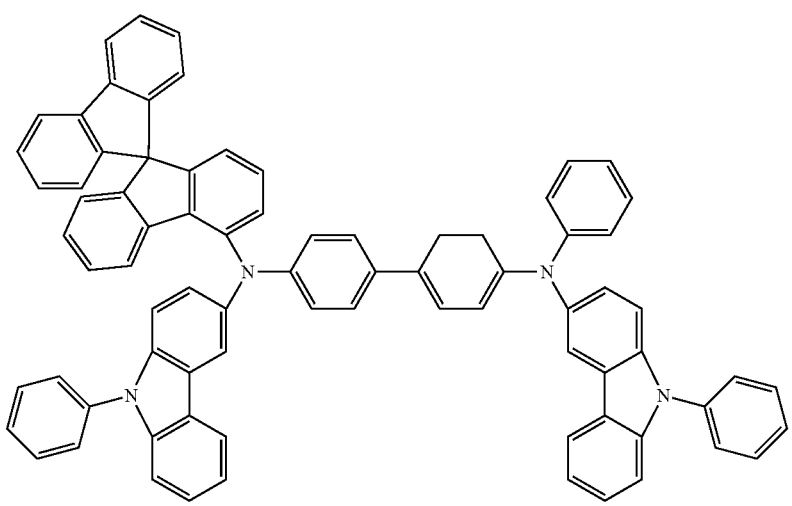 [SMILES: C1=C(c2ccc(N(c3ccc4c(c3)c3ccccc3n4-c3ccccc3)c3cccc4c3-c3ccccc3C43c4ccccc4-c4ccccc43)cc2)CCC(N(c2ccccc2)c2ccc3c(c2)c2ccccc2n3-c2ccccc2)=C1]
178

-continued
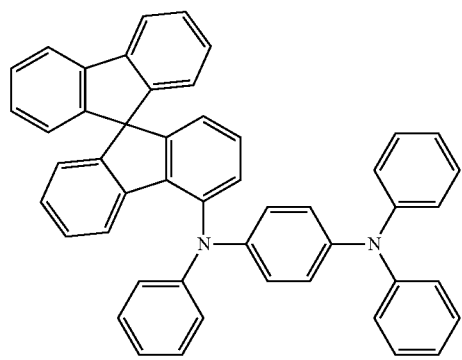 [SMILES: c1ccc(N(c2ccccc2)c2ccc(N(c3ccccc3)c3cccc4c3-c3ccccc3C43c4ccccc4-c4ccccc43)cc2)cc1]
179
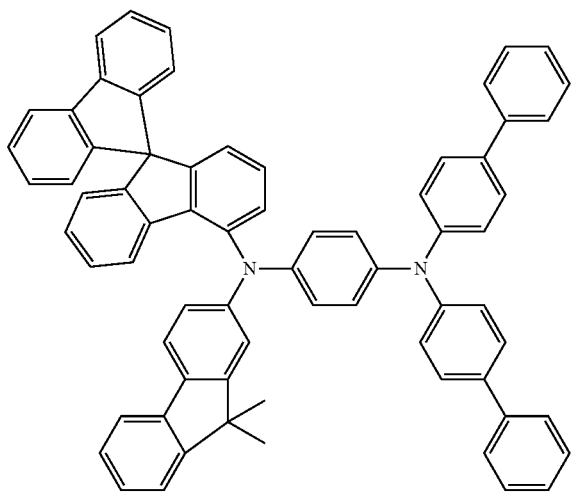 [SMILES: CC1(C)c2ccccc2-c2ccc(N(c3ccc(N(c4ccc(-c5ccccc5)cc4)c4ccc(-c5ccccc5)cc4)cc3)c3cccc4c3-c3ccccc3C43c4ccccc4-c4ccccc43)cc21]
180
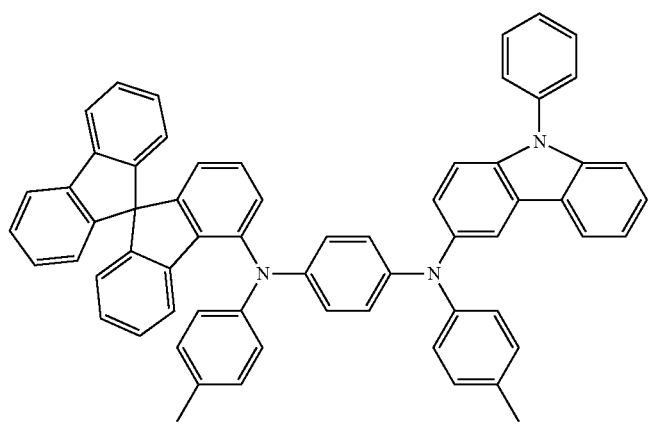 [SMILES: Cc1ccc(N(c2ccc(N(c3ccc(C)cc3)c3cccc4c3-c3ccccc3C43c4ccccc4-c4ccccc43)cc2)c2ccc3c(c2)c2ccccc2n3-c2ccccc2)cc1]
181

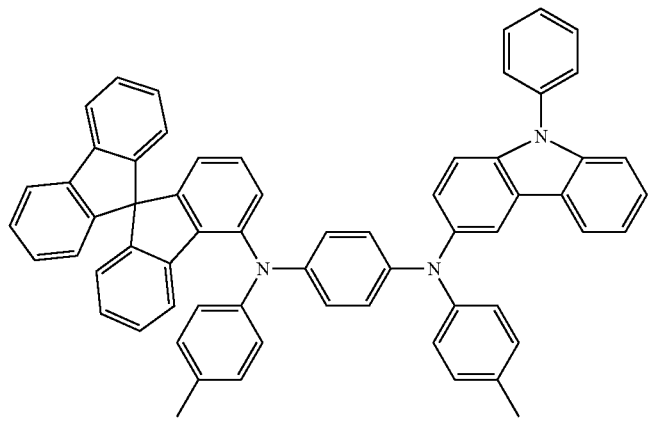 [SMILES: Cc1ccc(N(c2ccc(N(c3ccc(C)cc3)c3cccc4c3-c3ccccc3C43c4ccccc4-c4ccccc43)cc2)c2ccc3c(c2)c2ccccc2n3-c2ccccc2)cc1]
182
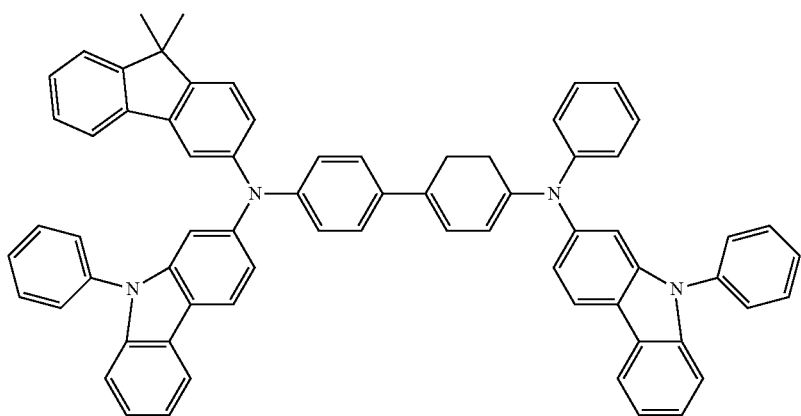 [SMILES: CC1(C)c2ccccc2-c2cc(N(c3ccc(C4=CC=C(N(c5ccccc5)c5ccc6c7ccccc7n(-c7ccccc7)c6c5)CC4)cc3)c3ccc4c5ccccc5n(-c5ccccc5)c4c3)ccc21]
183
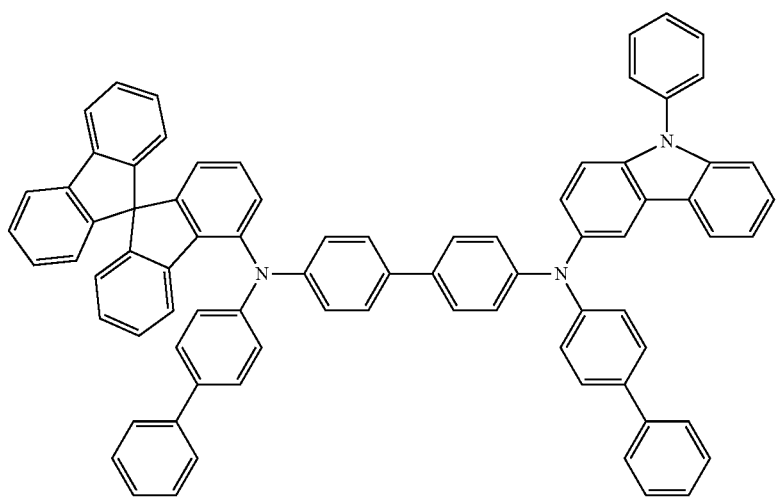 [SMILES: c1ccc(-c2ccc(N(c3ccc(-c4ccc(N(c5ccc(-c6ccccc6)cc5)c5cccc6c5-c5ccccc5C65c6ccccc6-c6ccccc65)cc4)cc3)c3ccc4c(c3)c3ccccc3n4-c3ccccc3)cc2)cc1]
184

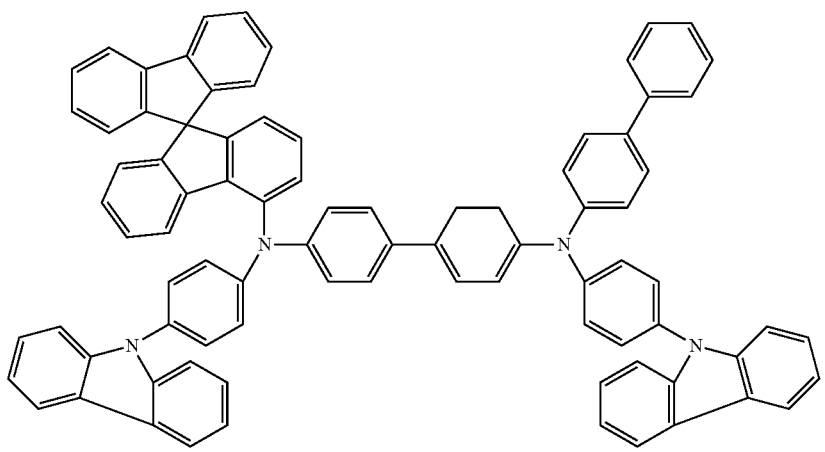 [SMILES: C1=C(c2ccc(N(c3ccc(-n4c5ccccc5c5ccccc54)cc3)c3cccc4c3-c3ccccc3C43c4ccccc4-c4ccccc43)cc2)CCC(N(c2ccc(-c3ccccc3)cc2)c2ccc(-n3c4ccccc4c4ccccc43)cc2)=C1]
185
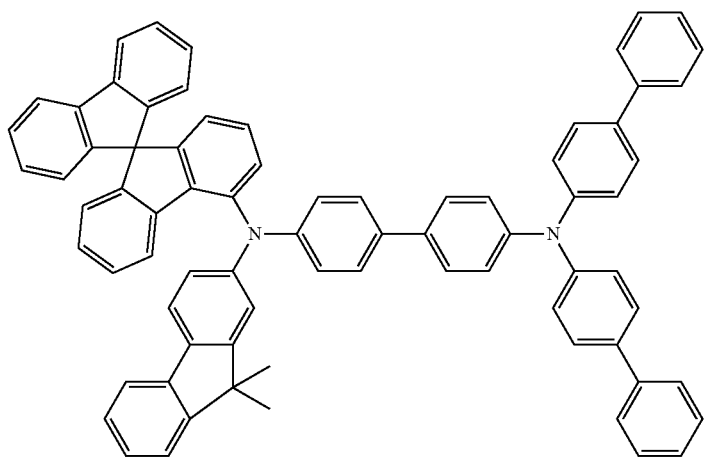 [SMILES: CC1(C)c2ccccc2-c2ccc(N(c3ccc(-c4ccc(N(c5ccc(-c6ccccc6)cc5)c5ccc(-c6ccccc6)cc5)cc4)cc3)c3cccc4c3-c3ccccc3C43c4ccccc4-c4ccccc43)cc21]
186
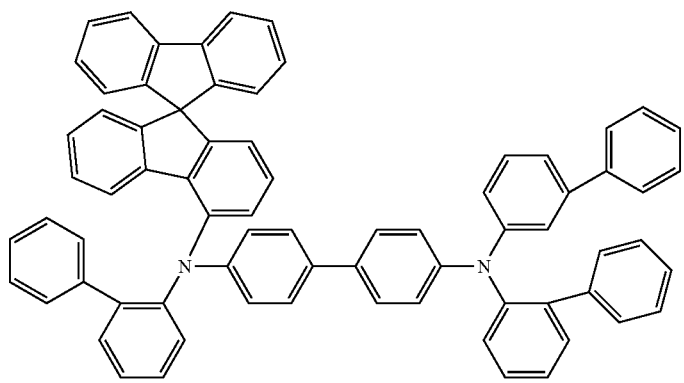 [SMILES: c1ccc(-c2cccc(N(c3ccc(-c4ccc(N(c5ccccc5-c5ccccc5)c5cccc6c5-c5ccccc5C65c6ccccc6-c6ccccc65)cc4)cc3)c3ccccc3-c3ccccc3)c2)cc1]
187

188
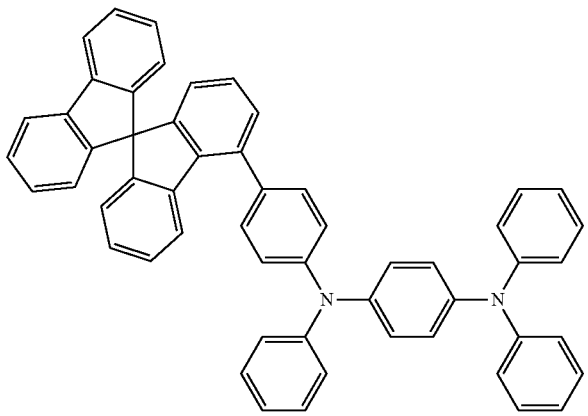 [SMILES: c1ccc(N(c2ccccc2)c2ccc(N(c3ccccc3)c3ccc(-c4cccc5c4-c4ccccc4C54c5ccccc5-c5ccccc54)cc3)cc2)cc1]
189
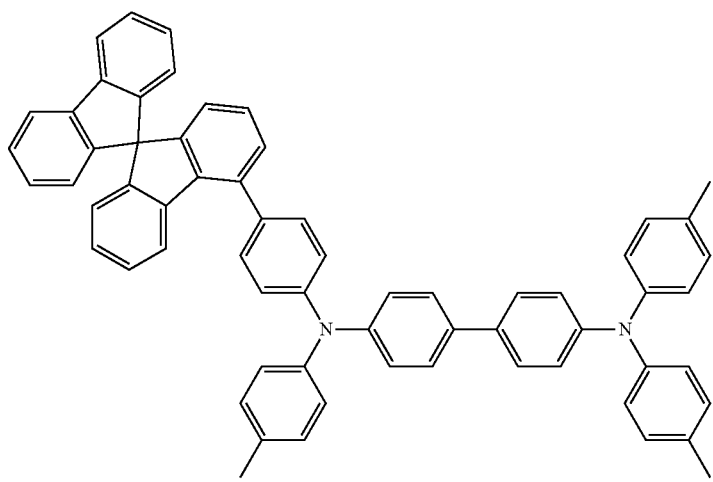 [SMILES: Cc1ccc(N(c2ccc(C)cc2)c2ccc(-c3ccc(N(c4ccc(C)cc4)c4ccc(-c5cccc6c5-c5ccccc5C65c6ccccc6-c6ccccc65)cc4)cc3)cc2)cc1]
190
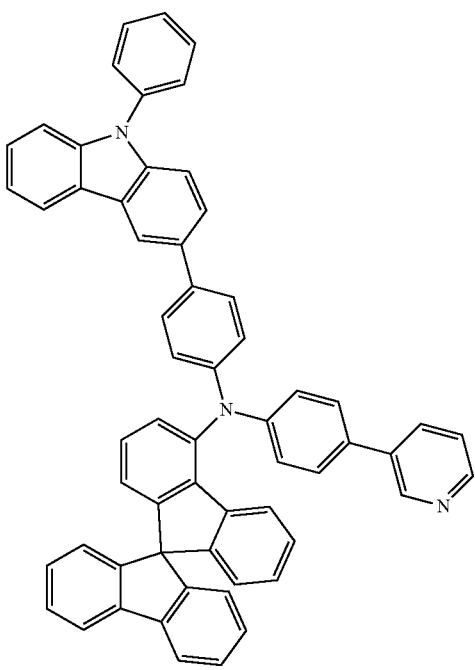 [SMILES: c1ccc(-n2c3ccccc3c3cc(-c4ccc(N(c5ccc(-c6cccnc6)cc5)c5cccc6c5-c5ccccc5C65c6ccccc6-c6ccccc65)cc4)ccc32)cc1]

| 191 |
|---|
| 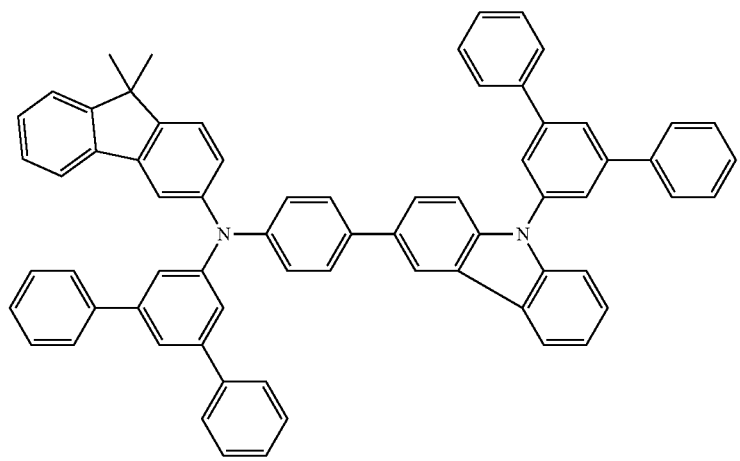 [SMILES: CC1(C)c2ccccc2-c2cc(N(c3ccc(-c4ccc5c(c4)c4ccccc4n5-c4cc(-c5ccccc5)cc(-c5ccccc5)c4)cc3)c3cc(-c4ccccc4)cc(-c4ccccc4)c3)ccc21] |
| 192 |
|---|
| 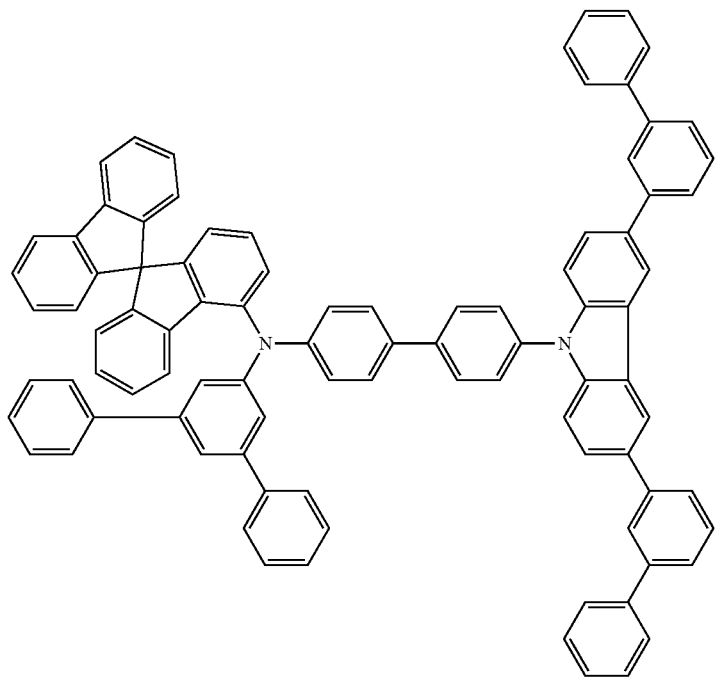 [SMILES: c1ccc(-c2cccc(-c3ccc4c(c3)c3cc(-c5cccc(-c6ccccc6)c5)ccc3n4-c3ccc(-c4ccc(N(c5cc(-c6ccccc6)cc(-c6ccccc6)c5)c5cccc6c5-c5ccccc5C65c6ccccc6-c6ccccc65)cc4)cc3)c2)cc1] |

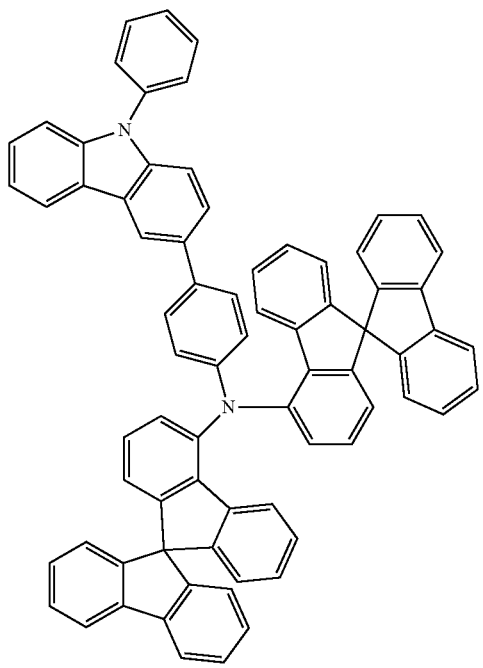 [SMILES: c1ccc(-n2c3ccccc3c3cc(-c4ccc(N(c5cccc6c5-c5ccccc5C65c6ccccc6-c6ccccc65)c5cccc6c5-c5ccccc5C65c6ccccc6-c6ccccc65)cc4)ccc32)cc1]
193
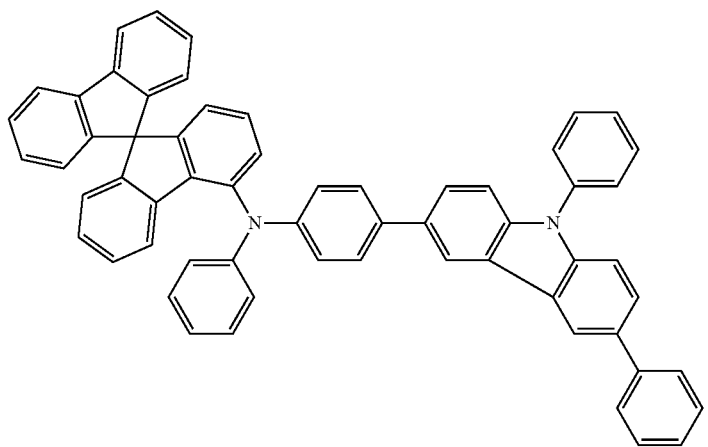 [SMILES: c1ccc(-c2ccc3c(c2)c2cc(-c4ccc(N(c5ccccc5)c5cccc6c5-c5ccccc5C65c6ccccc6-c6ccccc65)cc4)ccc2n3-c2ccccc2)cc1]
194

-continued
195
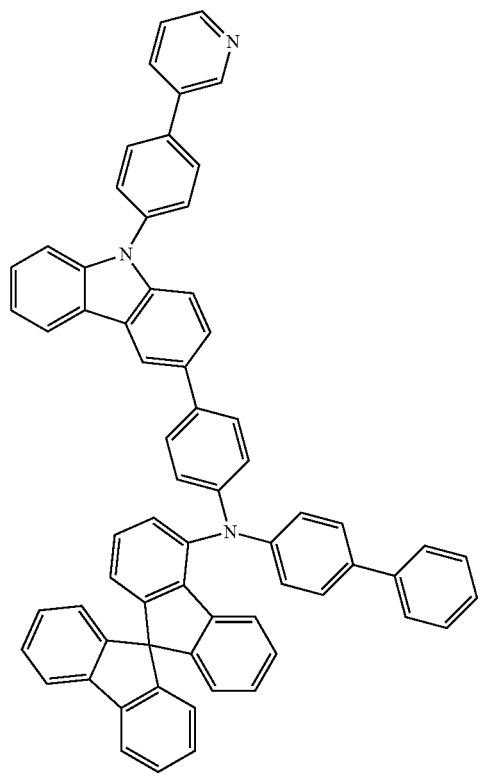 [SMILES: c1ccc(-c2ccc(N(c3ccc(-c4ccc5c(c4)c4ccccc4n5-c4ccc(-c5cccnc5)cc4)cc3)c3cccc4c3-c3ccccc3C43c4ccccc4-c4ccccc43)cc2)cc1]
196
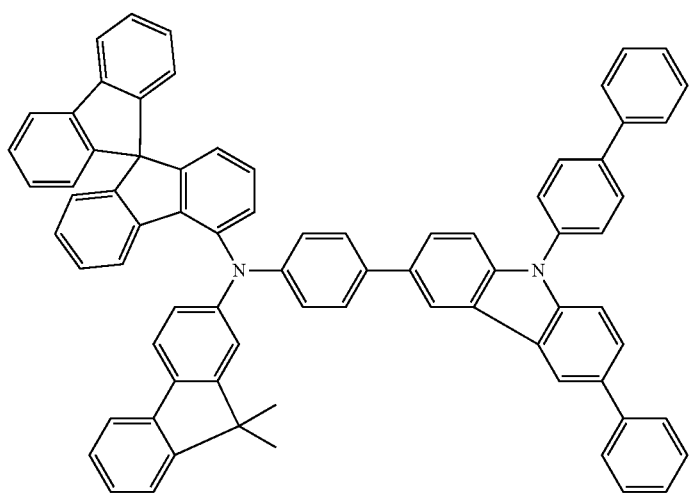 [SMILES: CC1(C)c2ccccc2-c2ccc(N(c3ccc(-c4ccc5c(c4)c4cc(-c6ccccc6)ccc4n5-c4ccc(-c5ccccc5)cc4)cc3)c3cccc4c3-c3ccccc3C43c4ccccc4-c4ccccc43)cc21]
197
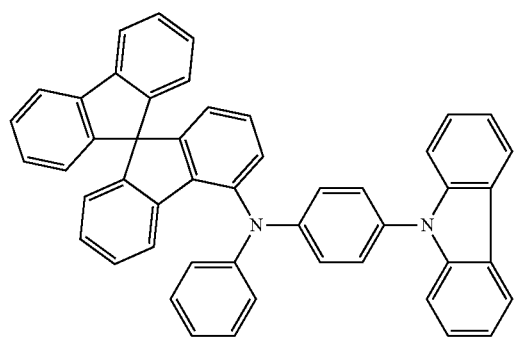 [SMILES: c1ccc(N(c2ccc(-n3c4ccccc4c4ccccc43)cc2)c2cccc3c2-c2ccccc2C32c3ccccc3-c3ccccc32)cc1]

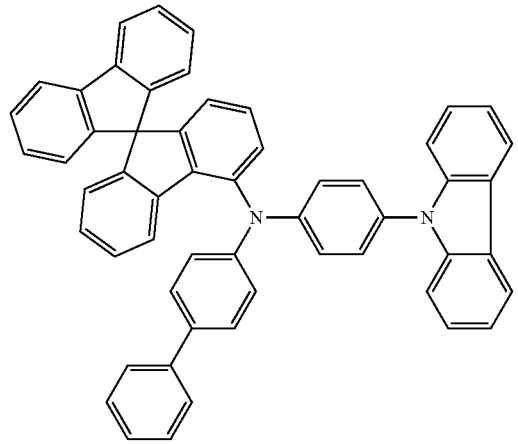 [SMILES: c1ccc(-c2ccc(N(c3ccc(-n4c5ccccc5c5ccccc54)cc3)c3cccc4c3-c3ccccc3C43c4ccccc4-c4ccccc43)cc2)cc1]
198
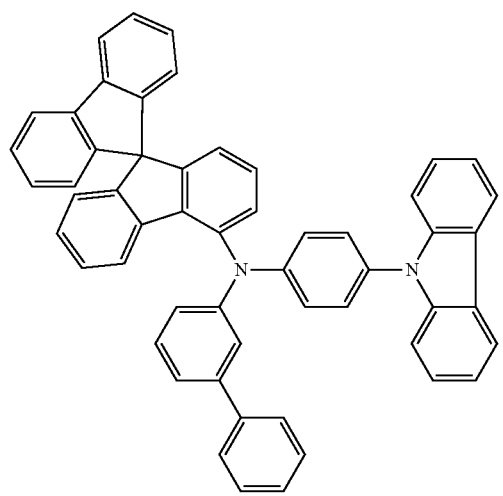 [SMILES: c1ccc(-c2cccc(N(c3ccc(-n4c5ccccc5c5ccccc54)cc3)c3cccc4c3-c3ccccc3C43c4ccccc4-c4ccccc43)c2)cc1]
199
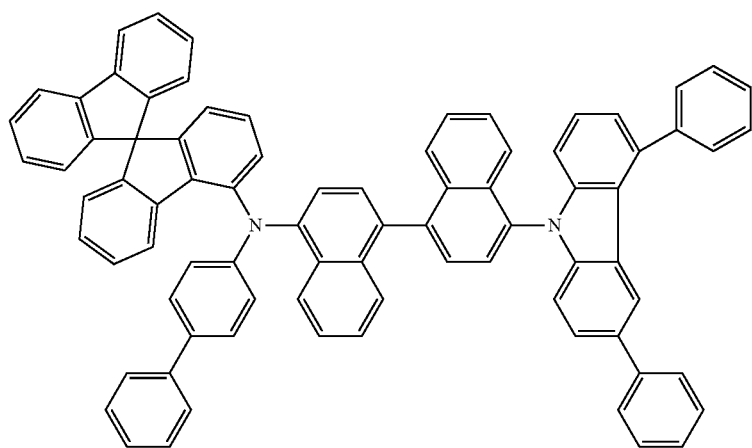 [SMILES: c1ccc(-c2ccc(N(c3cccc4c3-c3ccccc3C43c4ccccc4-c4ccccc43)c3ccc(-c4ccc(-n5c6ccc(-c7ccccc7)cc6c6c(-c7ccccc7)cccc65)c5ccccc45)c4ccccc34)cc2)cc1]
200

201
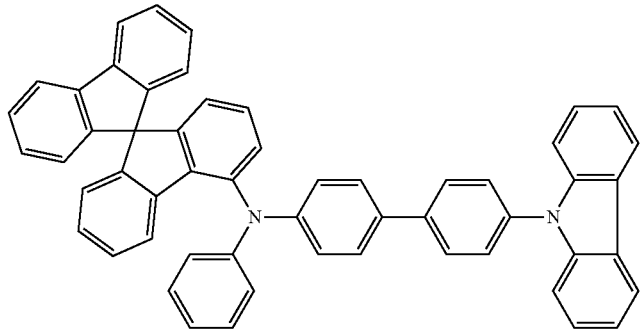 [SMILES: c1ccc(N(c2ccc(-c3ccc(-n4c5ccccc5c5ccccc54)cc3)cc2)c2cccc3c2-c2ccccc2C32c3ccccc3-c3ccccc32)cc1]
202
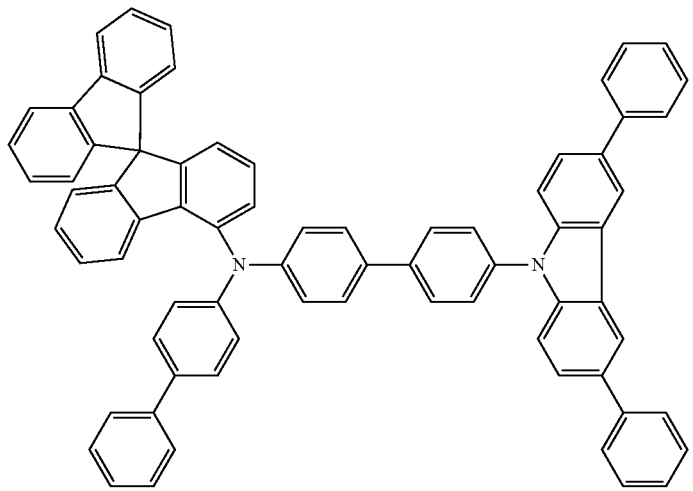 [SMILES: c1ccc(-c2ccc(N(c3ccc(-c4ccc(-n5c6ccc(-c7ccccc7)cc6c6cc(-c7ccccc7)ccc65)cc4)cc3)c3cccc4c3-c3ccccc3C43c4ccccc4-c4ccccc43)cc2)cc1]
203
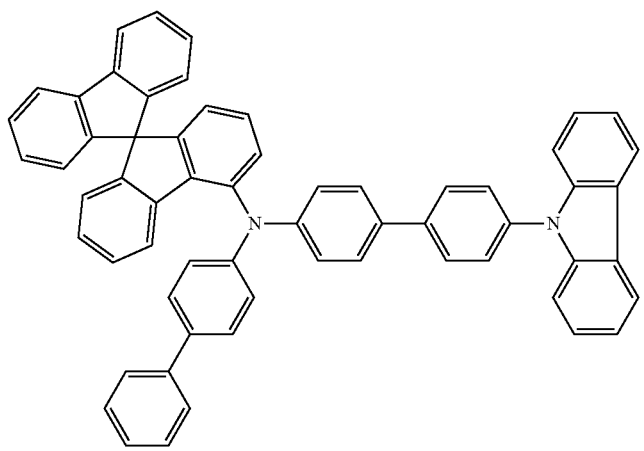 [SMILES: c1ccc(-c2ccc(N(c3ccc(-c4ccc(-n5c6ccccc6c6ccccc65)cc4)cc3)c3cccc4c3-c3ccccc3C43c4ccccc4-c4ccccc43)cc2)cc1]
204
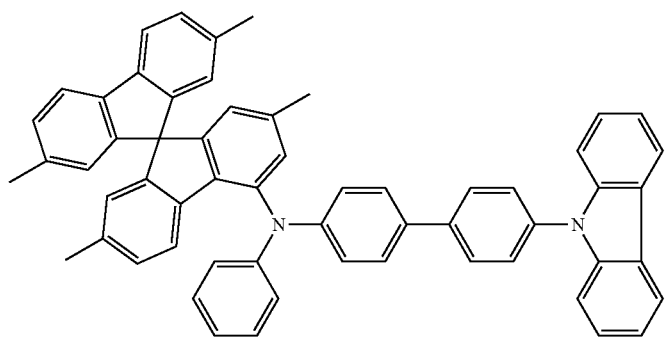 [SMILES: Cc1ccc2c(c1)C1(c3cc(C)ccc3-2)c2cc(C)ccc2-c2c(N(c3ccccc3)c3ccc(-c4ccc(-n5c6ccccc6c6ccccc65)cc4)cc3)cc(C)cc21]

205
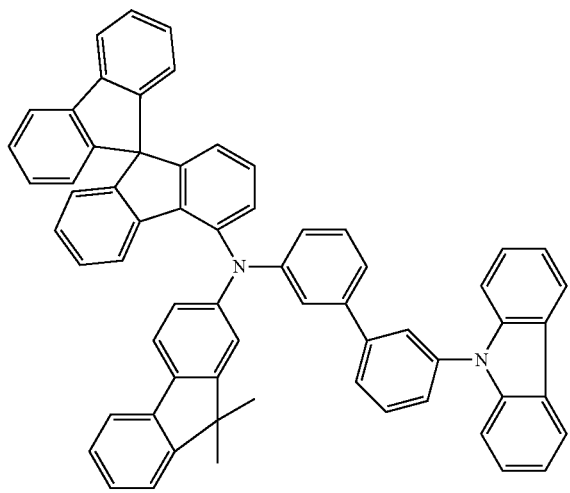 [SMILES: CC1(C)c2ccccc2-c2ccc(N(c3cccc(-c4cccc(-n5c6ccccc6c6ccccc65)c4)c3)c3cccc4c3-c3ccccc3C43c4ccccc4-c4ccccc43)cc21]
206
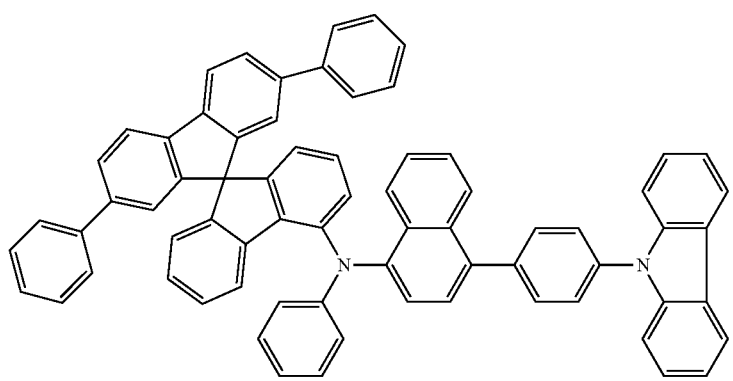 [SMILES: c1ccc(-c2ccc3c(c2)C2(c4cc(-c5ccccc5)ccc4-3)c3ccccc3-c3c(N(c4ccccc4)c4ccc(-c5ccc(-n6c7ccccc7c7ccccc76)cc5)c5ccccc45)cccc32)cc1]
207
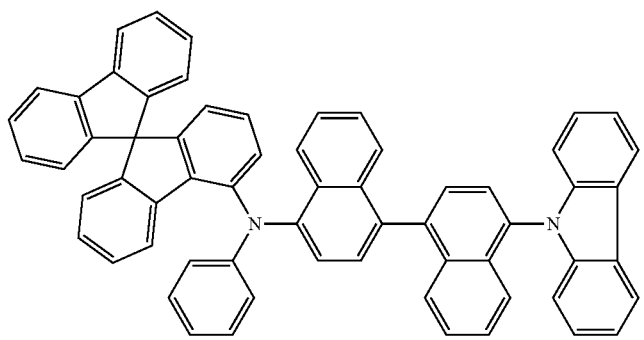 [SMILES: c1ccc(N(c2cccc3c2-c2ccccc2C32c3ccccc3-c3ccccc32)c2ccc(-c3ccc(-n4c5ccccc5c5ccccc54)c4ccccc34)c3ccccc23)cc1]
208
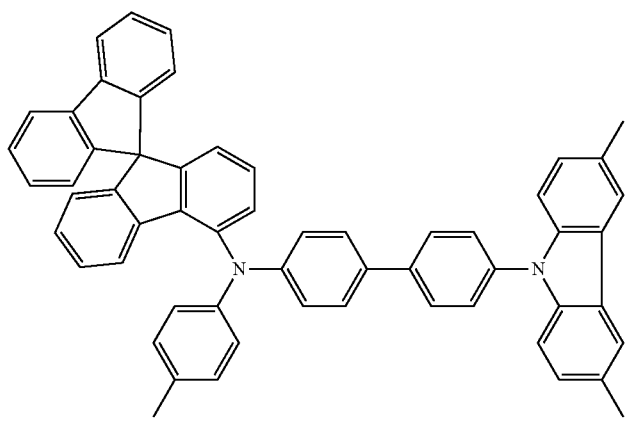 [SMILES: Cc1ccc(N(c2ccc(-c3ccc(-n4c5ccc(C)cc5c5cc(C)ccc54)cc3)cc2)c2cccc3c2-c2ccccc2C32c3ccccc3-c3ccccc32)cc1]

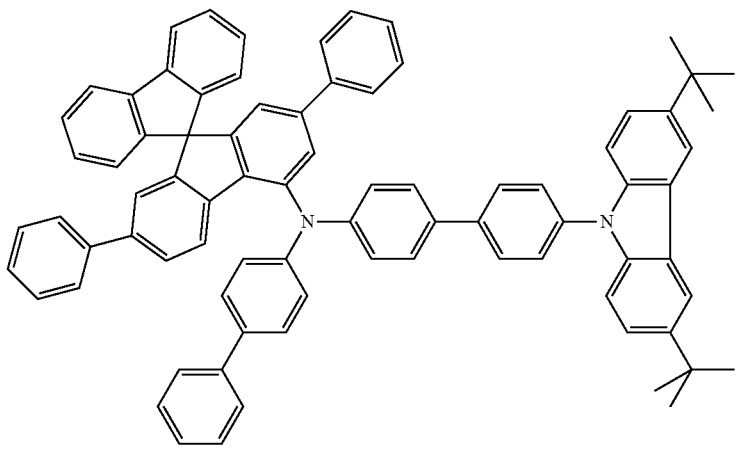 [SMILES: CC(C)(C)c1ccc2c(c1)c1cc(C(C)(C)C)ccc1n2-c1ccc(-c2ccc(N(c3ccc(-c4ccccc4)cc3)c3cc(-c4ccccc4)cc4c3-c3ccc(-c5ccccc5)cc3C43c4ccccc4-c4ccccc43)cc2)cc1]
209
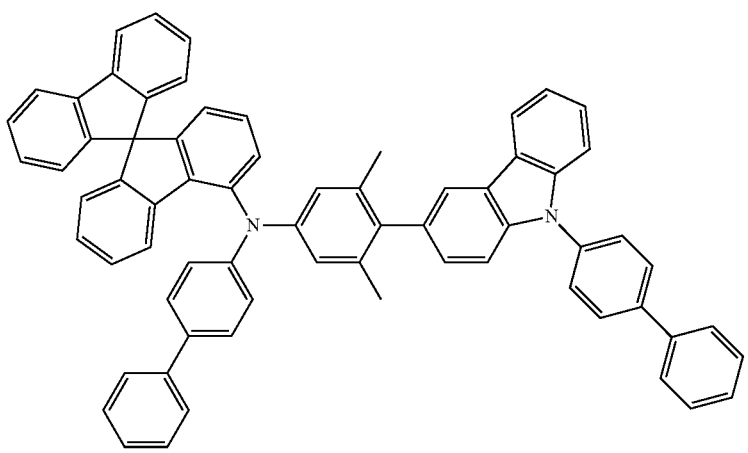 [SMILES: Cc1cc(N(c2ccc(-c3ccccc3)cc2)c2cccc3c2-c2ccccc2C32c3ccccc3-c3ccccc32)cc(C)c1-c1ccc2c(c1)c1ccccc1n2-c1ccc(-c2ccccc2)cc1]
210
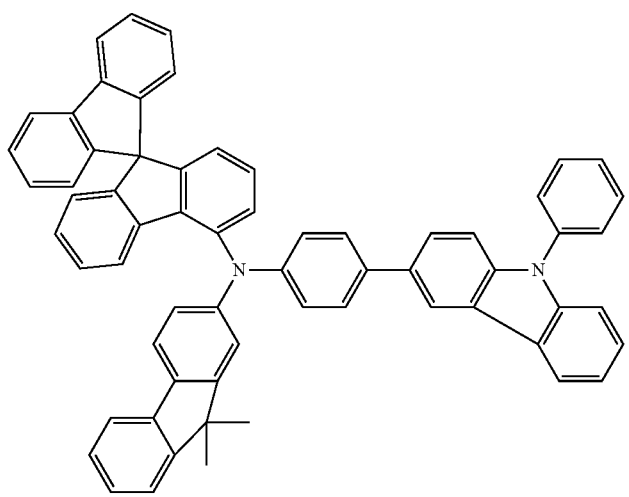 [SMILES: CC1(C)c2ccccc2-c2ccc(N(c3ccc(-c4ccc5c(c4)c4ccccc4n5-c4ccccc4)cc3)c3cccc4c3-c3ccccc3C43c4ccccc4-c4ccccc43)cc21]
211

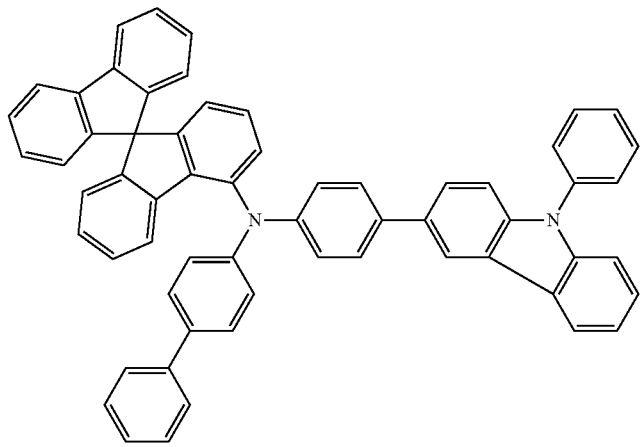 [SMILES: c1ccc(-c2ccc(N(c3ccc(-c4ccc5c(c4)c4ccccc4n5-c4ccccc4)cc3)c3cccc4c3-c3ccccc3C43c4ccccc4-c4ccccc43)cc2)cc1]
212
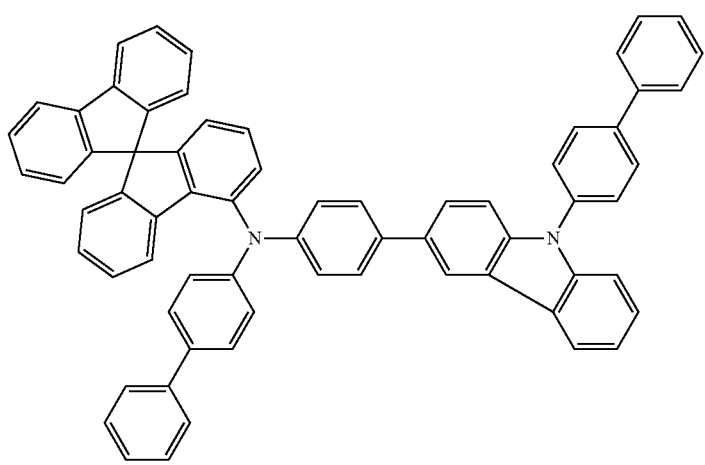 [SMILES: c1ccc(-c2ccc(N(c3ccc(-c4ccc5c(c4)c4ccccc4n5-c4ccc(-c5ccccc5)cc4)cc3)c3cccc4c3-c3ccccc3C43c4ccccc4-c4ccccc43)cc2)cc1]
213
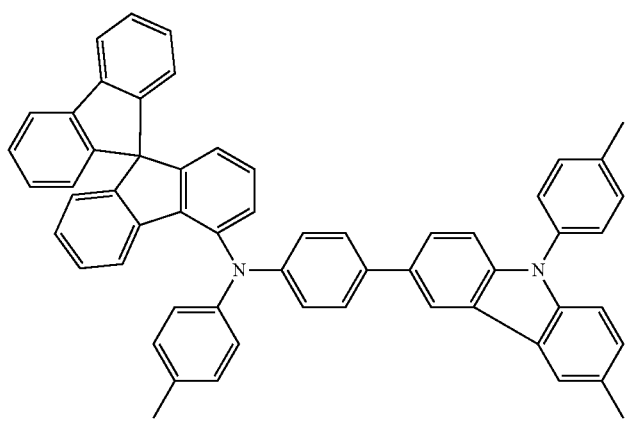 [SMILES: Cc1ccc(N(c2ccc(-c3ccc4c(c3)c3cc(C)ccc3n4-c3ccc(C)cc3)cc2)c2cccc3c2-c2ccccc2C32c3ccccc3-c3ccccc32)cc1]
214

215
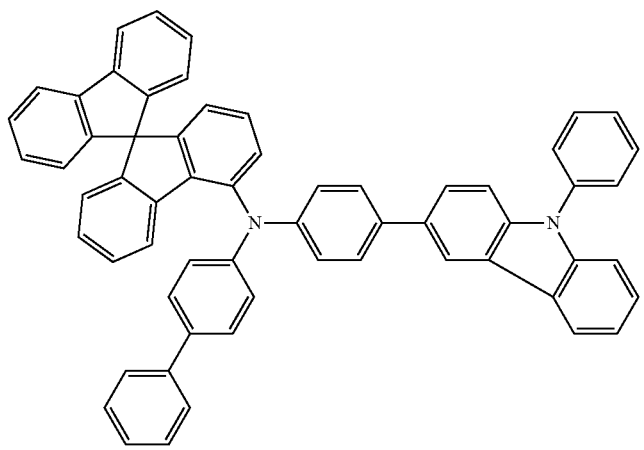 [SMILES: c1ccc(-c2ccc(N(c3ccc(-c4ccc5c(c4)c4ccccc4n5-c4ccccc4)cc3)c3cccc4c3-c3ccccc3C43c4ccccc4-c4ccccc43)cc2)cc1]
216
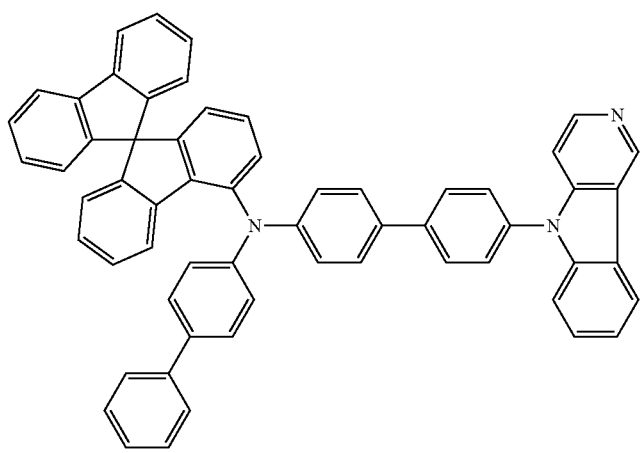
217
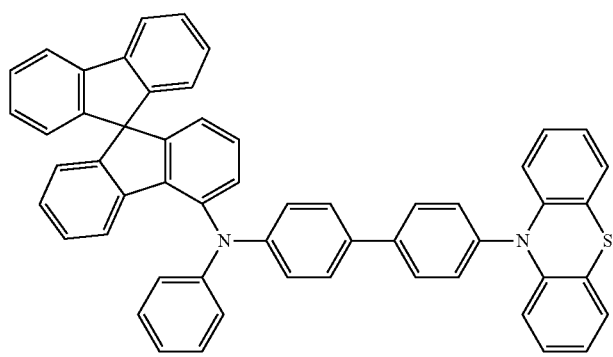 [SMILES: c1ccc(N(c2ccc(-c3ccc(N4c5ccccc5Sc5ccccc54)cc3)cc2)c2cccc3c2-c2ccccc2C32c3ccccc3-c3ccccc32)cc1]
218
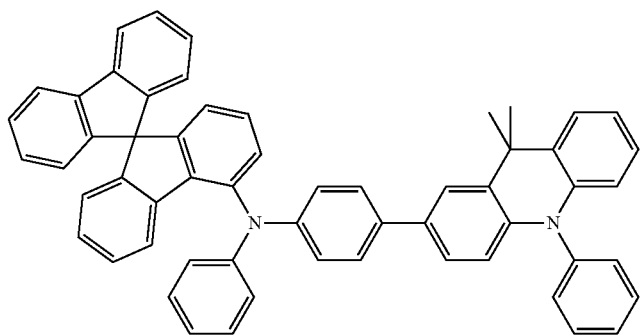 [SMILES: CC1(C)c2ccccc2N(c2ccccc2)c2ccc(-c3ccc(N(c4ccccc4)c4cccc5c4-c4ccccc4C54c5ccccc5-c5ccccc54)cc3)cc21]

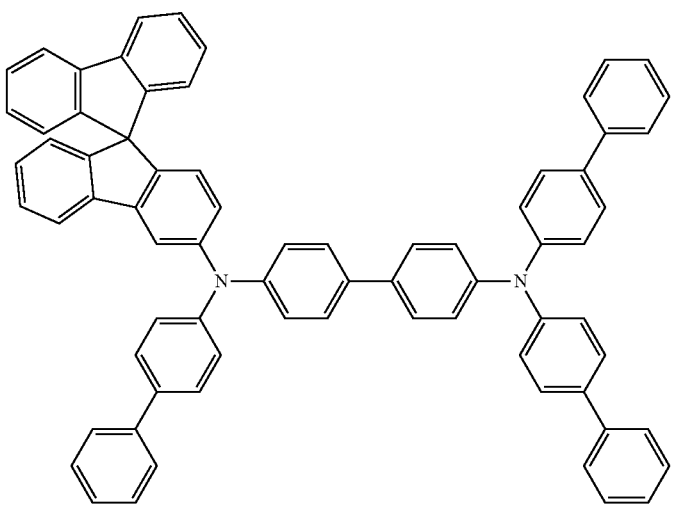 [SMILES: c1ccc(-c2ccc(N(c3ccc(-c4ccccc4)cc3)c3ccc(-c4ccc(N(c5ccc(-c6ccccc6)cc5)c5ccc6c(c5)-c5ccccc5C65c6ccccc6-c6ccccc65)cc4)cc3)cc2)cc1]
219
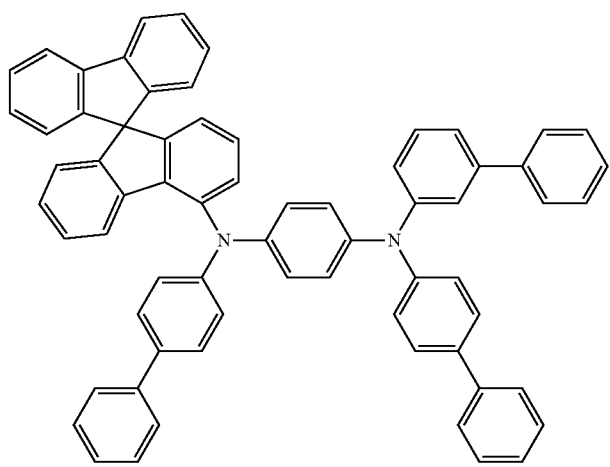 [SMILES: c1ccc(-c2ccc(N(c3ccc(N(c4ccc(-c5ccccc5)cc4)c4cccc5c4-c4ccccc4C54c5ccccc5-c5ccccc54)cc3)c3cccc(-c4ccccc4)c3)cc2)cc1]
220
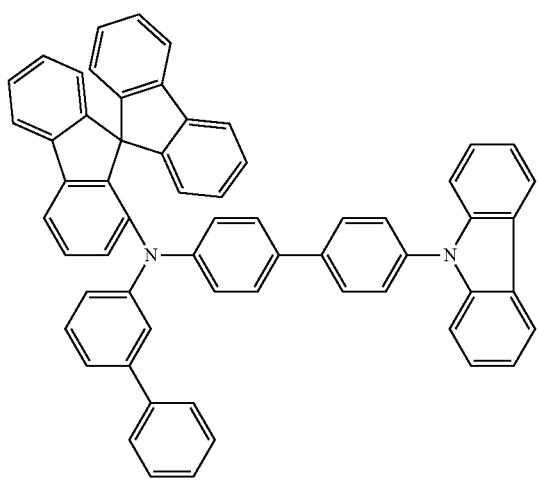 [SMILES: c1ccc(-c2cccc(N(c3ccc(-c4ccc(-n5c6ccccc6c6ccccc65)cc4)cc3)c3cccc4c3C3(c5ccccc5-c5ccccc53)c3ccccc3-4)c2)cc1]
221

-continued
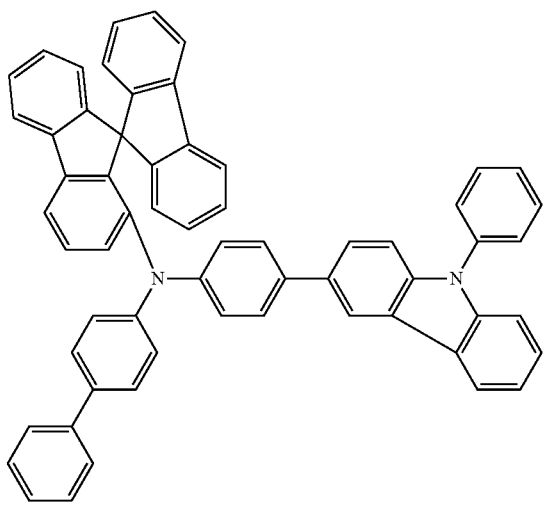 [SMILES: c1ccc(-c2ccc(N(c3ccc(-c4ccc5c(c4)c4ccccc4n5-c4ccccc4)cc3)c3cccc4c3C3(c5ccccc5-c5ccccc53)c3ccccc3-4)cc2)cc1]
222
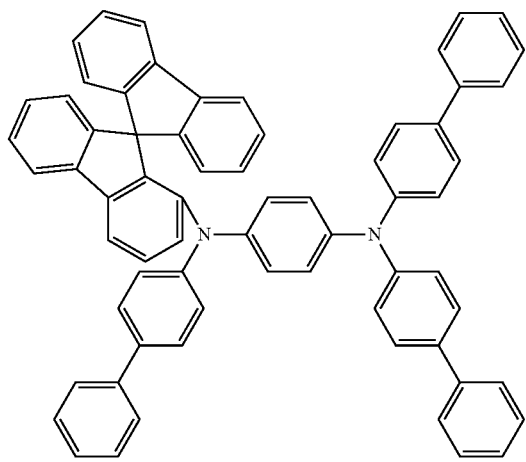 [SMILES: c1ccc(-c2ccc(N(c3ccc(-c4ccccc4)cc3)c3ccc(N(c4ccc(-c5ccccc5)cc4)c4cccc5c4C4(c6ccccc6-c6ccccc64)c4ccccc4-5)cc3)cc2)cc1]
223
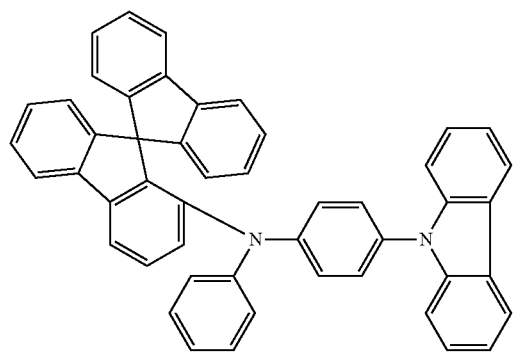 [SMILES: c1ccc(N(c2ccc(-n3c4ccccc4c4ccccc43)cc2)c2cccc3c2C2(c4ccccc4-c4ccccc42)c2ccccc2-3)cc1]
224

-continued
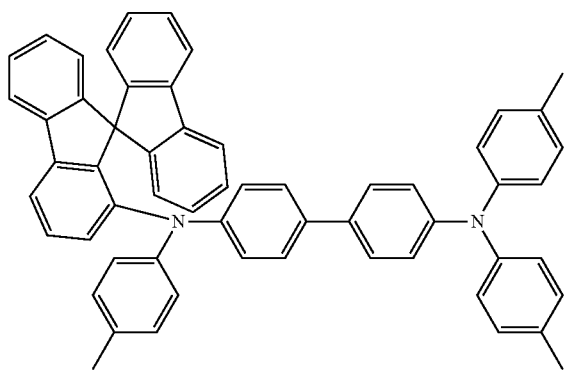 [SMILES: Cc1ccc(N(c2ccc(C)cc2)c2ccc(-c3ccc(N(c4ccc(C)cc4)c4cccc5c4C4(c6ccccc6-c6ccccc64)c4ccccc4-5)cc3)cc2)cc1]
225
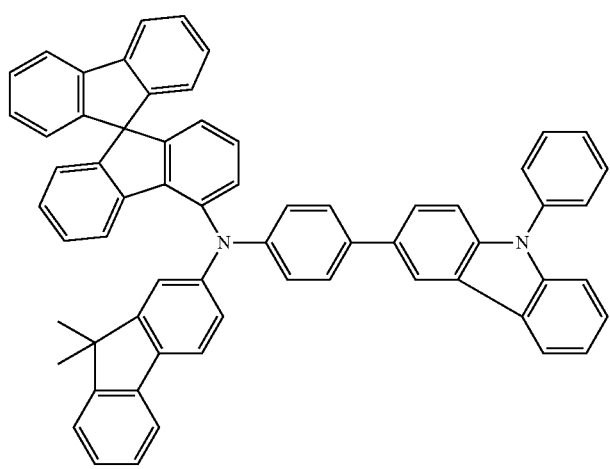 [SMILES: CC1(C)c2ccccc2-c2ccc(N(c3ccc(-c4ccc5c(c4)c4ccccc4n5-c4ccccc4)cc3)c3cccc4c3-c3ccccc3C43c4ccccc4-c4ccccc43)cc21]
226
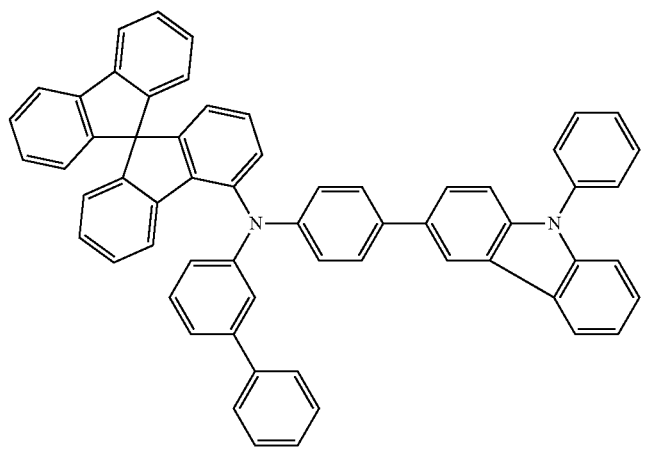 [SMILES: c1ccc(-c2cccc(N(c3ccc(-c4ccc5c(c4)c4ccccc4n5-c4ccccc4)cc3)c3cccc4c3-c3ccccc3C43c4ccccc4-c4ccccc43)c2)cc1]
227

-continued
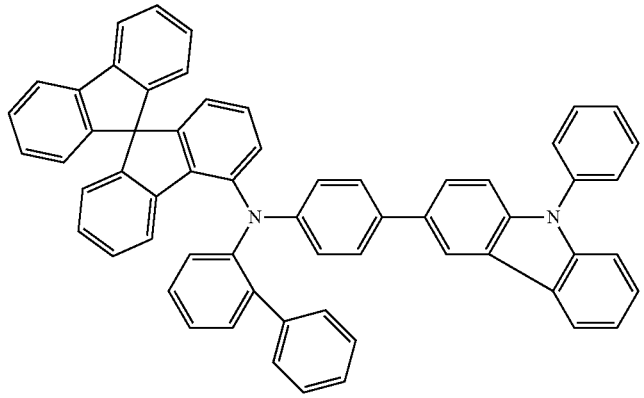 [SMILES: c1ccc(-c2ccccc2N(c2ccc(-c3ccc4c(c3)c3ccccc3n4-c3ccccc3)cc2)c2cccc3c2-c2ccccc2C32c3ccccc3-c3ccccc32)cc1]
228
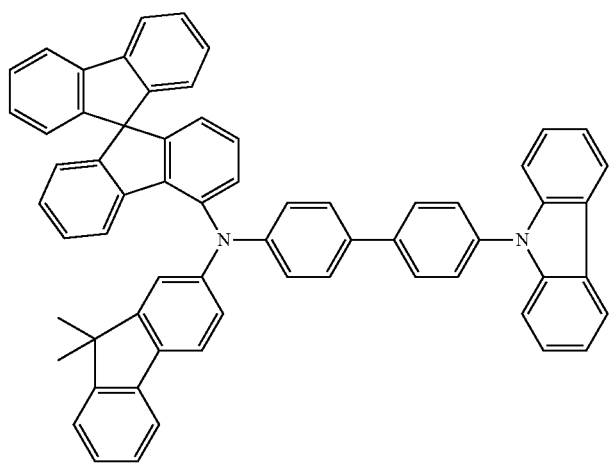 [SMILES: CC1(C)c2ccccc2-c2ccc(N(c3ccc(-c4ccc(-n5c6ccccc6c6ccccc65)cc4)cc3)c3cccc4c3-c3ccccc3C43c4ccccc4-c4ccccc43)cc21]
229
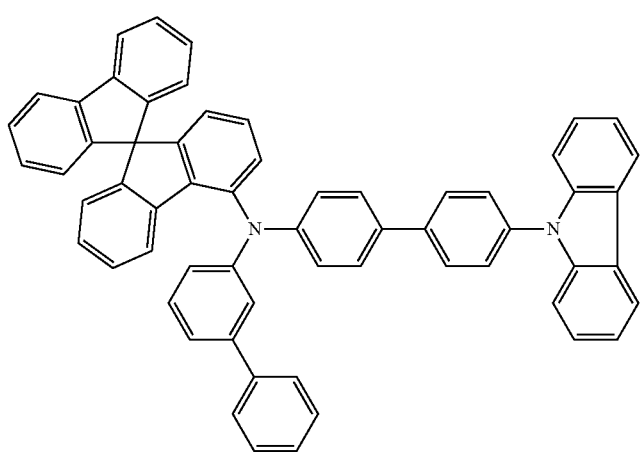 [SMILES: c1ccc(-c2cccc(N(c3ccc(-c4ccc(-n5c6ccccc6c6ccccc65)cc4)cc3)c3cccc4c3-c3ccccc3C43c4ccccc4-c4ccccc43)c2)cc1]
230

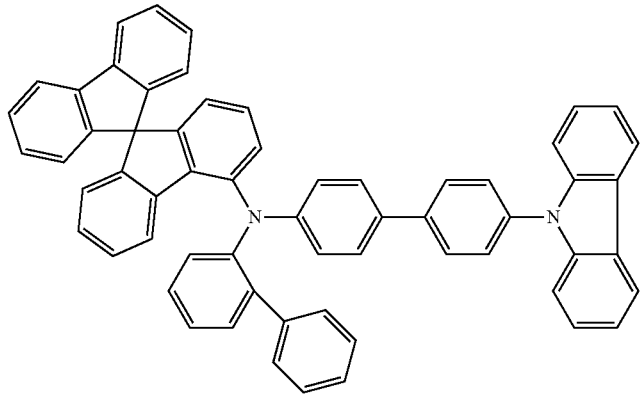 [SMILES: c1ccc(-c2ccccc2N(c2ccc(-c3ccc(-n4c5ccccc5c5ccccc54)cc3)cc2)c2cccc3c2-c2ccccc2C32c3ccccc3-c3ccccc32)cc1]
231
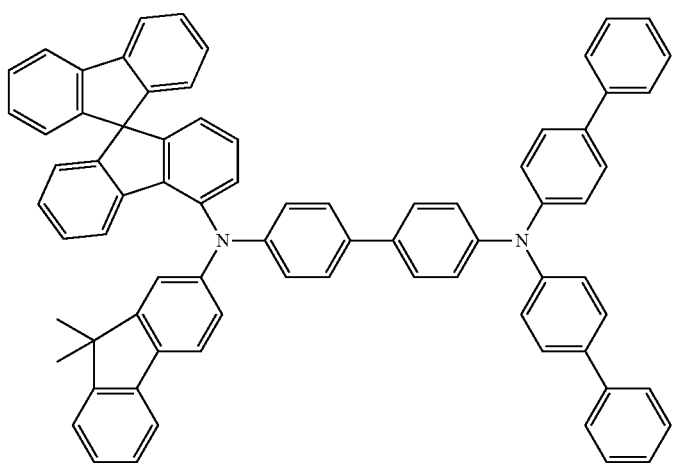 [SMILES: CC1(C)c2ccccc2-c2ccc(N(c3ccc(-c4ccc(N(c5ccc(-c6ccccc6)cc5)c5ccc(-c6ccccc6)cc5)cc4)cc3)c3cccc4c3-c3ccccc3C43c4ccccc4-c4ccccc43)cc21]
232
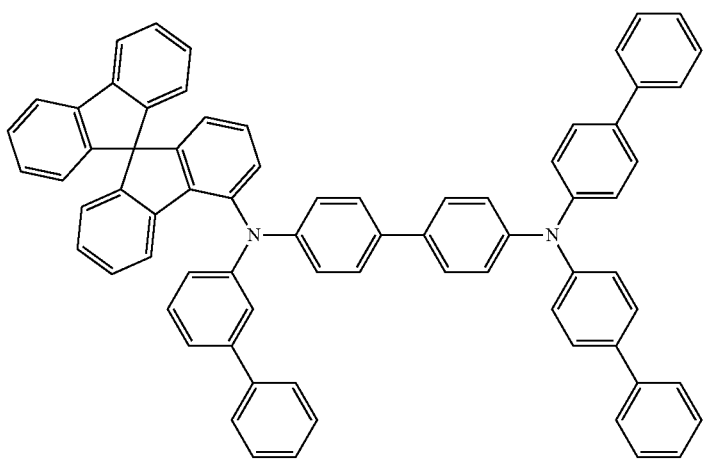 [SMILES: c1ccc(-c2ccc(N(c3ccc(-c4ccccc4)cc3)c3ccc(-c4ccc(N(c5cccc(-c6ccccc6)c5)c5cccc6c5-c5ccccc5C65c6ccccc6-c6ccccc65)cc4)cc3)cc2)cc1]
233

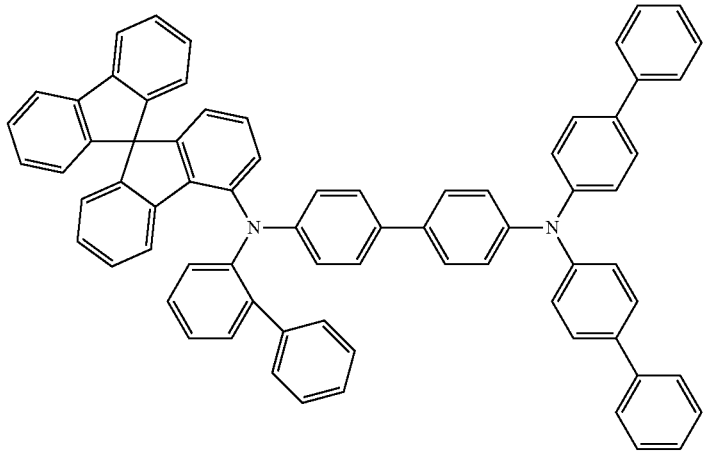 [SMILES: c1ccc(-c2ccc(N(c3ccc(-c4ccccc4)cc3)c3ccc(-c4ccc(N(c5ccccc5-c5ccccc5)c5cccc6c5-c5ccccc5C65c6ccccc6-c6ccccc65)cc4)cc3)cc2)cc1]
234
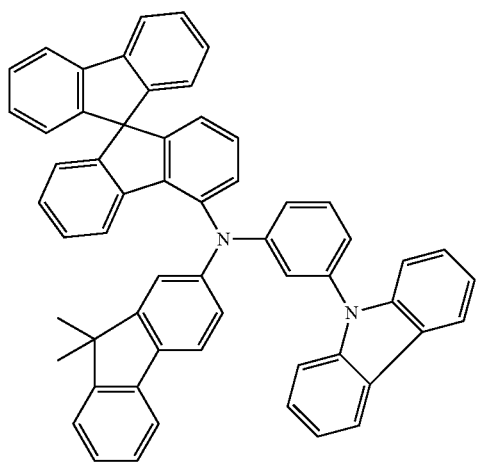 [SMILES: CC1(C)c2ccccc2-c2ccc(N(c3cccc(-n4c5ccccc5c5ccccc54)c3)c3cccc4c3-c3ccccc3C43c4ccccc4-c4ccccc43)cc21]
235
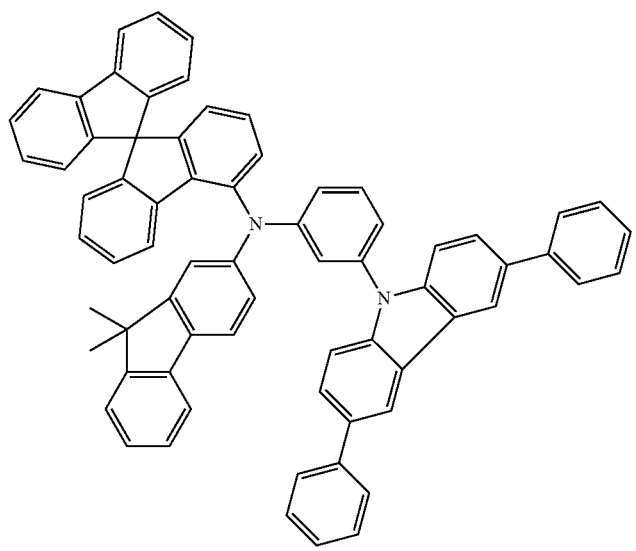 [SMILES: CC1(C)c2ccccc2-c2ccc(N(c3cccc(-n4c5ccc(-c6ccccc6)cc5c5cc(-c6ccccc6)ccc54)c3)c3cccc4c3-c3ccccc3C43c4ccccc4-c4ccccc43)cc21]
236

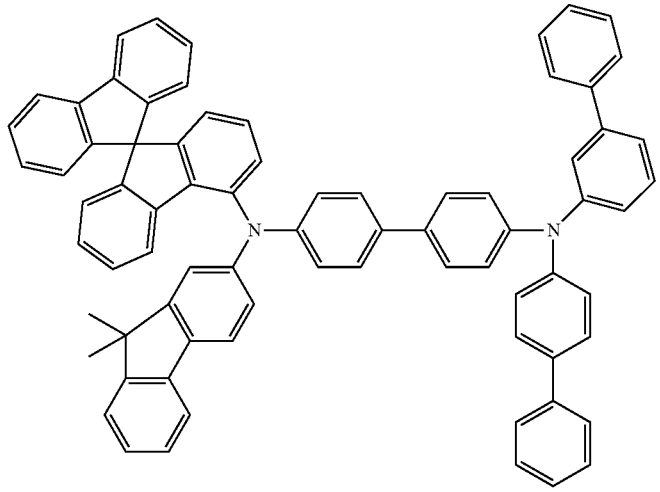 [SMILES: CC1(C)c2ccccc2-c2ccc(N(c3ccc(-c4ccc(N(c5ccc(-c6ccccc6)cc5)c5cccc(-c6ccccc6)c5)cc4)cc3)c3cccc4c3-c3ccccc3C43c4ccccc4-c4ccccc43)cc21]

237

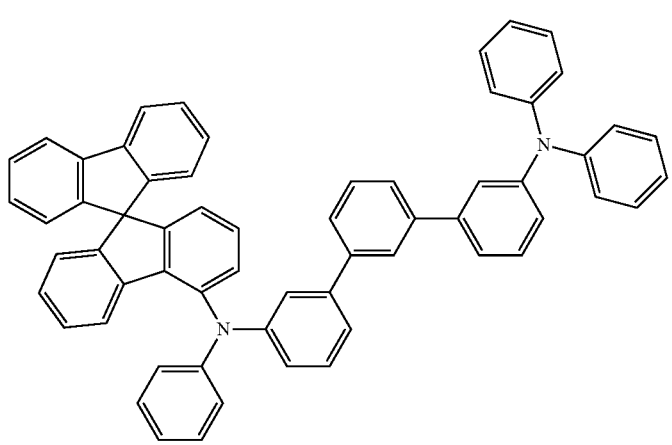 [SMILES: c1ccc(N(c2ccccc2)c2cccc(-c3cccc(-c4cccc(N(c5ccccc5)c5cccc6c5-c5ccccc5C65c6ccccc6-c6ccccc65)c4)c3)c2)cc1]

238

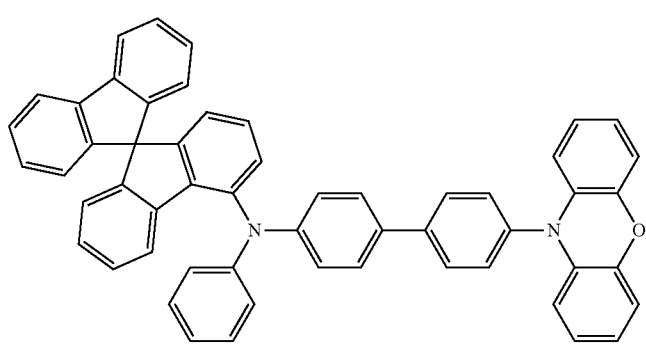 [SMILES: c1ccc(N(c2ccc(-c3ccc(N4c5ccccc5Oc5ccccc54)cc3)cc2)c2cccc3c2-c2ccccc2C32c3ccccc3-c3ccccc32)cc1]

239

The synthesis of the compounds according to the invention can be carried out by processes and reaction types known from the prior art, for example halogenation, Buchwald coupling and Suzuki coupling.

A preferred synthetic route for the preparation of the compounds according to the invention is depicted below. The synthetic route comprises two coupling reactions: firstly, the fluorene or spirobifluorene derivative is reacted with an amine of the formula $Ar^3$—$NH_2$ (cf. formulae (I) to (III) of the compounds according to the invention) in a first Buchwald coupling. Finally, a second Buchwald coupling is carried out in order to introduce the moiety containing the second arylamino or carbazole group.

The synthetic route is depicted below by way of example with reference to a compound of the formula (I) (Scheme 1). However, it should be emphasised that compounds of the formula (II) or (III) according to the invention can equally also be prepared by this synthetic route. Spirobifluorenyl compounds can also be employed analogously to the fluorenyl starting compounds depicted, so that compounds according to the invention containing spirobifluorene units are obtained.

Scheme 1:

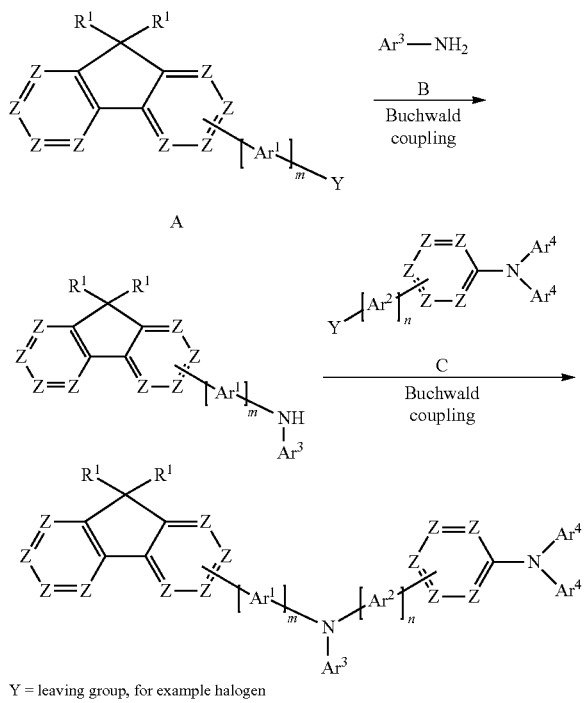

Y = leaving group, for example halogen

Synthetic routes for starting compounds A, B and C which are employed in the synthesis of the compounds according to the invention (cf. Scheme 1) are known to the person skilled in the art. Furthermore, some explicit synthetic processes are described in detail in the working examples.

The present invention thus relates to a process for the preparation of a compound of the formula (I), (II) or (III), characterised in that a fluorenyl or spirobifluorenyl derivative is reacted with an arylamino compound in a first coupling reaction, and the resultant product is reacted with a triarylamino or carbazole compound in a second coupling reaction.

The coupling reactions here are preferably Buchwald couplings.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. The oligomerisation or polymerisation here preferably takes place via the halogen functionality or the boronic acid functionality.

The invention therefore furthermore relates to oligomers, polymers or dendrimers containing one or more compounds of the formula (I), (II) or (III), where the bond(s) to the polymer, oligomer or dendrimer can be localised at any desired positions in formula (I), (II) or (III) that are substituted by $R^1$.

Depending on the linking of the compound according to the invention, the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I), (II) or (III) may be linked directly to one another or they may be linked to one another via a divalent group, for example via a substituted or unsubstituted alkylene group, via a hetero-atom or via a divalent aromatic or heteroaromatic group. In branched and dendritic structures, for example, three or more units of the formula (I), (II) or (III) may be linked via a trivalent or polyvalent group, for example via a trivalent or polyvalent aromatic or heteroaromatic group, to form a branched or dendritic oligomer or polymer. The same preferences as described above for the compounds according to the invention apply to the recurring units of the formula (I), (II) or (III) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, of which at least one monomer results in recurring units of the formula (I), (II) or (III) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(I-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds of the formula (I), (II) or (III) from liquid phase, for example by spin coating or by printing processes, formulations of the compounds are necessary. These formulations can be, for example, solutions, dispersions or mini-emulsions.

The invention therefore furthermore relates to a formulation, in particular a solution, dispersion or mini-emulsion, comprising at least one compound of the formula (I), (II) or (III) or at least one polymer, oligomer or dendrimer containing at least one unit of the formula (I), (II) or (III) and at least one solvent, preferably an organic solvent. The way in which solutions of this type can be prepared is known to the person skilled in the art and is described, for example, in the applications WO 2002/072714 and WO 2003/019694 and the literature cited therein.

The compounds of the formula (I), (II) or (III) are suitable for use in electronic devices, in particular in organic electroluminescent devices (OLEDs). Depending on the substitution, the compounds are employed in different functions and in different layers of the organic electroluminescent device. The compounds are preferably employed as hole-transport materials in a hole-transport or hole-injection layer, as matrix materials in an emitting layer, as electron-blocking materials, as exciton-blocking materials and/or as materials for an interlayer.

The invention therefore furthermore relates to the use of the compounds of the formula (I), (II) or (III) in electronic devices and to electronic devices themselves which comprise one or more compounds of the formula (I), (II) or (III). The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably organic electroluminescent devices (OLEDs). Particular preference is given to organic electroluminescent devices comprising anode, cathode and at least one emitting layer, characterised in that at least one organic layer, which may be an emitting layer, a hole-transport layer or another layer, comprises at least one compound of the formula (I), (II) or (III).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device may also comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue, yellow, orange or red light are used in the emitting layers. Particular preference is given to three-layer systems, i.e. systems having three emitting layers, where at least one of these layers comprises at least one compound of the formula (I), (II) or (III) and where the three layers exhibit blue, green and orange or red emission (for the basic structure see, for example, WO 2005/011013). Alternatively and/or additionally, the compounds according to the invention may also be present in the hole-transport layer or in an interlayer. It should be noted that, for the generation of white light, an emitter compound used individually which emits in a broad wavelength range may also be suitable instead of a plurality of emitter compounds emitting in colour.

It is preferred in accordance with the invention for the compound of the formula (I), (II) or (III) to be employed in an electronic device comprising one or more phosphorescent dopants. The compound can be used in various layers here, preferably in a hole-transport layer, a hole-injection layer or in an emitting layer. However, the compound of the formula (I), (II) or (III) can also be employed in accordance with the invention in an electronic device comprising one or more fluorescent dopants.

The term phosphorescent dopants typically encompasses compounds in which the light emission takes place by a spin-forbidden transition, for example a transition from an excited triplet state or a state having a relatively high spin quantum number, for example a quintet state.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescence emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent dopants described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to employ further phosphorescent complexes without inventive step in combination with the compounds of the formula (I), (II) or (III) in organic electroluminescent devices.

Explicit examples of suitable phosphorescent emitter compounds can furthermore be obtained from a table depicted below.

In a preferred embodiment of the invention, the compounds of the formula (I), (II) or (III) are employed as hole-transport material. The compounds are then preferably employed in a hole-transport layer and/or in a hole-injection layer. A hole-injection layer in the sense of this invention is a layer which is directly adjacent to the anode. A hole-transport layer in the sense of this invention is a layer which is located between the hole-injection layer and the emission layer. The hole-transport layer may be directly adjacent to the emission layer. If the compounds of the formula (I), (II) or (III) are used as hole-transport material or as hole-injection material, it may be preferred for them to be doped with electron-acceptor compounds, for example with $F_4$-TCNQ or with compounds as described in EP 1476881 or EP 1596445. In a further preferred embodiment of the invention, a compound of the formula (I), (II) or (III) is used as hole-transport material in combination with a hexaazatriphenylene derivative, as described in US 2007/0092755. The hexaazatriphenylene derivative here is particularly preferably employed in a separate layer. If the compound of the formula (I), (II) or (III) is employed as hole-transport material in a hole-transport layer, the compound may be employed as pure material, i.e. in a proportion of 100%, in the hole-transport layer, or it may be employed in combination with one or more further compounds in the hole-transport layer.

In a further embodiment of the present invention, the compounds of the formula (I), (II) or (III) are employed as matrix material in combination with one or more dopants, preferably phosphorescent dopants.

A dopant in a system comprising a matrix material and a dopant is taken to mean the component whose proportion in the mixture is the smaller. Correspondingly, a matrix material is taken to mean the component whose proportion in the mixture is the greater in a system comprising a matrix material and a dopant.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In a preferred embodiment of the invention, the compounds of the formula (I), (II) or (III) are used as a component of mixed-matrix systems. The mixed-matrix systems preferably comprise two or three different matrix materials, particularly preferably two different matrix materials. The two different matrix materials here may be present in a ratio of 1:10 to 1:1, preferably in a ratio of 1:4 to 1:1. The mixed-matrix systems may comprise one or more dopants. The dopant compound or the dopant compounds together have, in accordance with the invention, a proportion of 0.1 to 50.0% by vol. in the mixture as a whole and preferably a proportion of 0.5 to 20.0% by vol. in the mixture as a whole. Correspondingly, the matrix components together have a proportion of 50.0 to 99.9% by vol. in the mixture as a whole and preferably a proportion of 80.0 to 99.5% by vol. in the mixture as a whole.

Mixed-matrix systems are preferably employed in phosphorescent organic electroluminescent devices.

Particularly suitable matrix materials which can be employed in combination with the compounds according to the invention as matrix components of a mixed-matrix system are aromatic ketones, aromatic phosphine oxides or aromatic sulfoxides or sulfones, for example in accordance with WO 04/013080, WO 04/093207, WO 06/005627 or WO 10/006,680, triaryl-amines, carbazole derivatives, for example CBP (N,N-biscarbazolyl-biphenyl) or the carbazole derivatives disclosed in WO 05/039246, US 2005/0069729, JP 2004/288381, EP 1205527 or WO 08/086,851, indolocarbazole derivatives, for example in accordance with WO 07/063754 or WO 08/056746, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with WO 10/015306, WO 07/063,754 or WO 08/056,746, zinc complexes, for example in accordance with EP 652273 or WO 09/062,578, diazasilole or tetraazasilole derivatives, for example in accordance with WO 10/054729, diazaphosphole derivatives, for example in accordance with WO 10/054730, or indenocarbazole derivatives, for example in accordance with WO 10/136109.

Preferred phosphorescent dopants for use in mixed-matrix systems comprising the compounds according to the invention are the phosphorescent dopants shown in a following table.

According to a further preferred embodiment of the invention, the compounds of formula (I), (II) or (III) are employed in an interlayer. Interlayers are preferably employed in organic electroluminescent devices comprising a plurality of emitting layers, for example in white-emitting OLEDs, which comprise in each case a red-emitting layer, a green-emitting layer and a blue-emitting layer. Interlayers are particularly preferably arranged between two emitting layers. An interlayer comprising a compound according to the invention is, in accordance with a preferred embodiment of the invention, arranged between the blue-emitting layer and the green-emitting layer of an OLED emitting white light which comprises a red-emitting layer, a green-emitting layer and a blue-emitting layer. The blue-emitting layer here is particularly preferably a fluorescent layer, and the green-emitting layer is a phosphorescent layer.

The compounds shown in the following table are particularly suitable phosphorescent dopants.

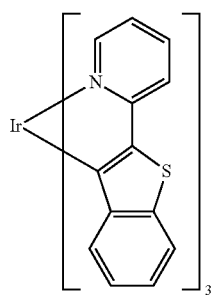
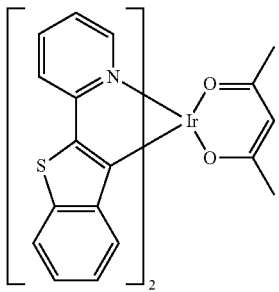
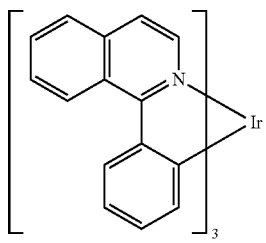
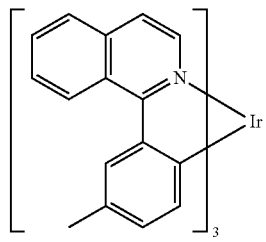
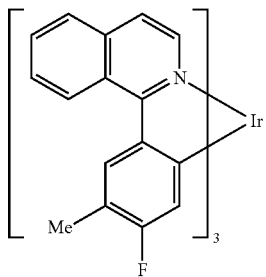
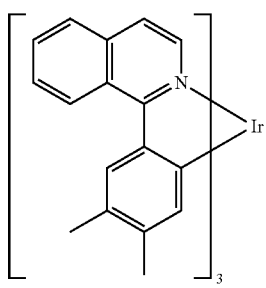
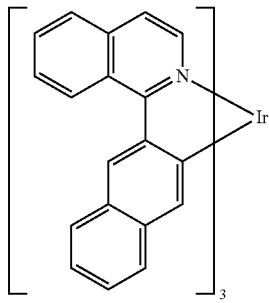
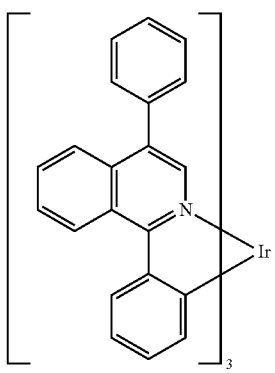
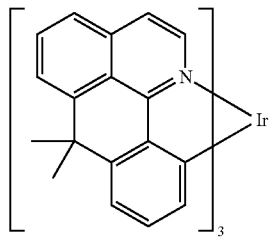
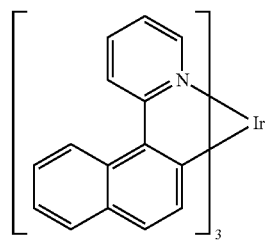
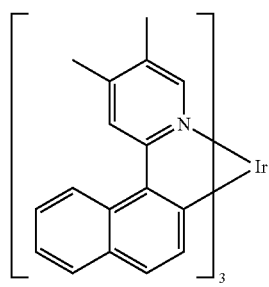

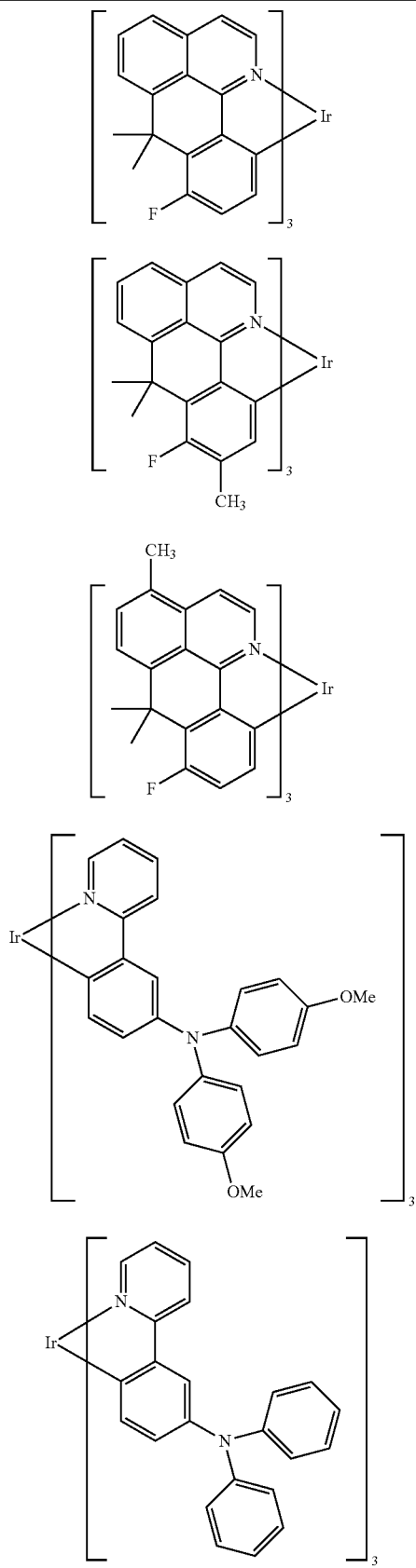
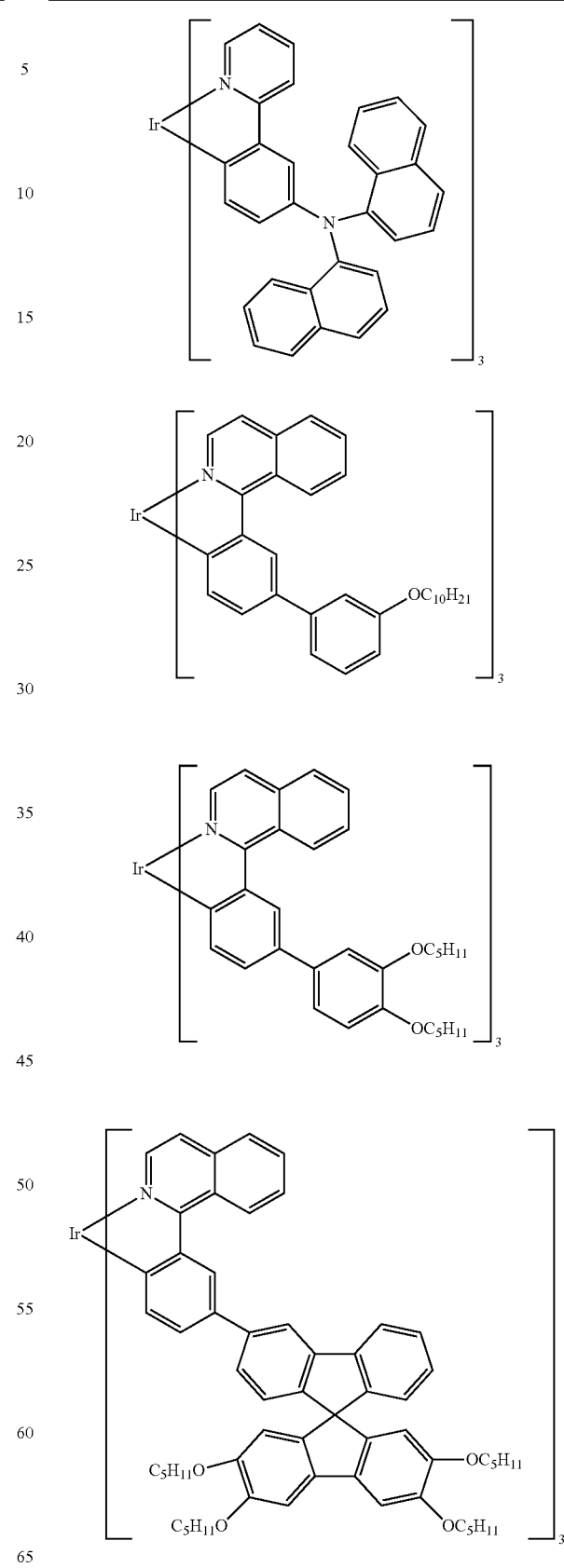

-continued
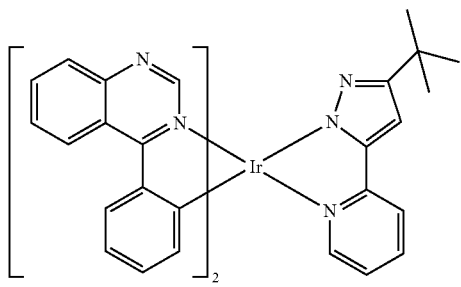
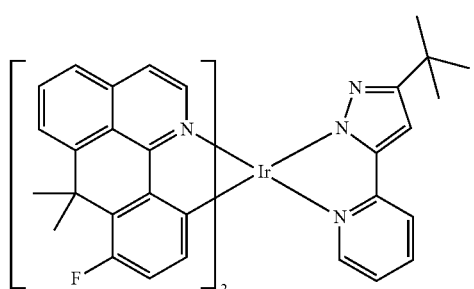
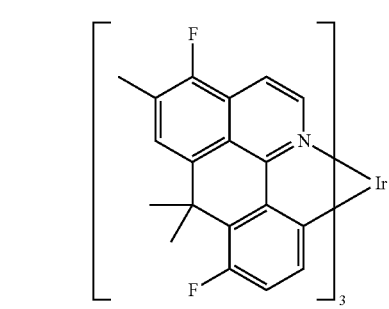
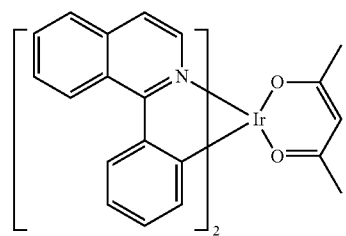
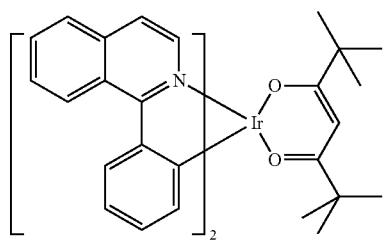
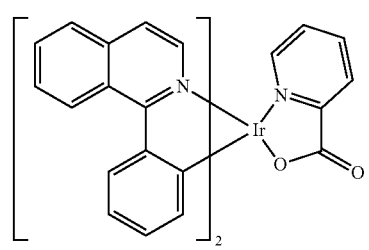
-continued
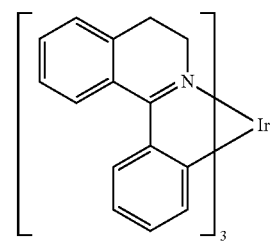
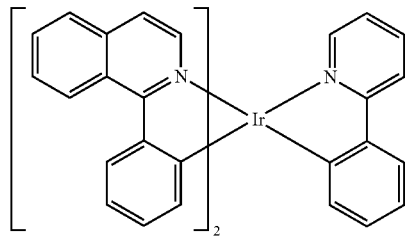
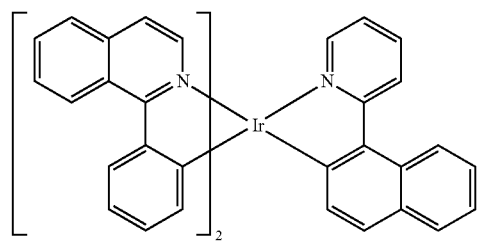
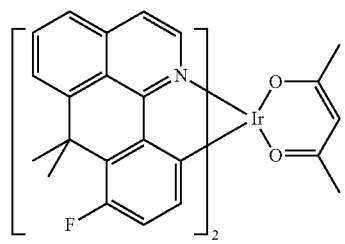
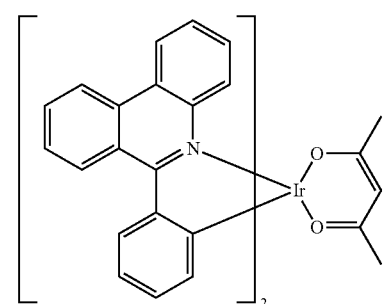
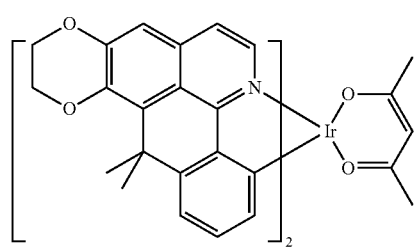

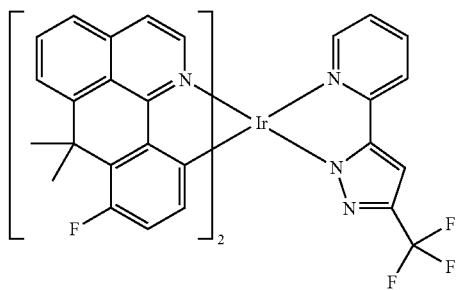
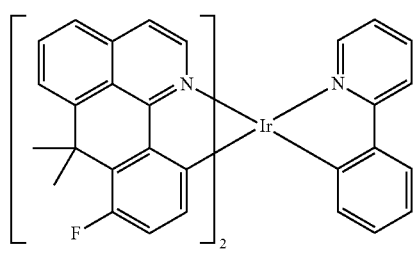
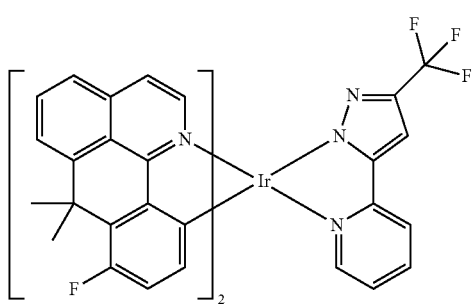
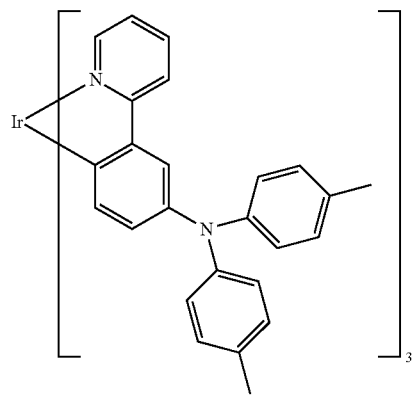
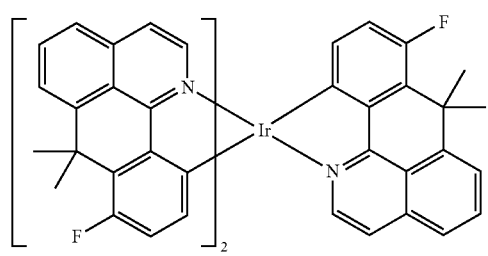
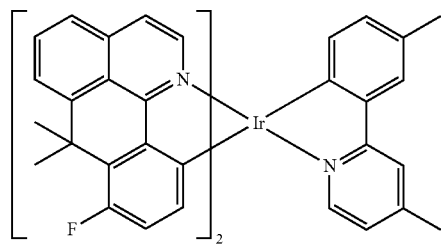
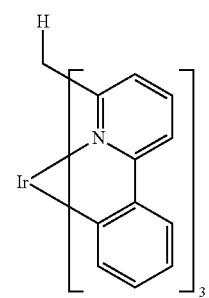
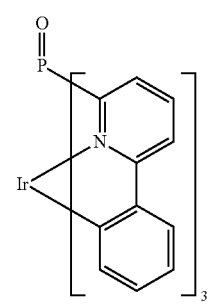
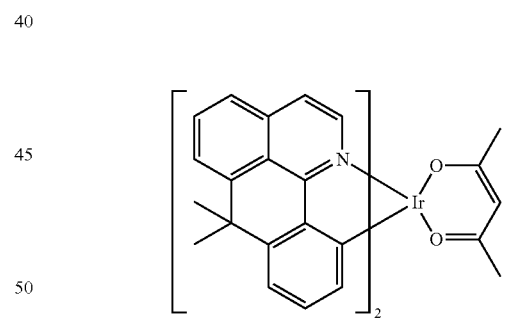
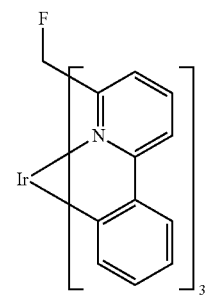

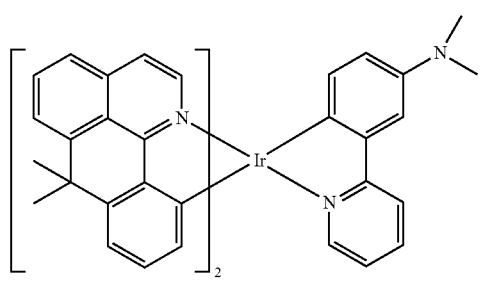
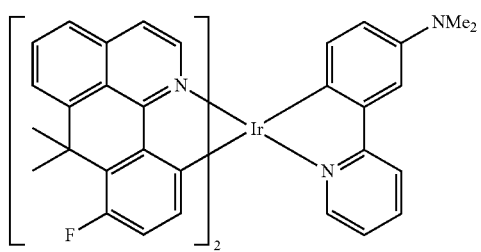
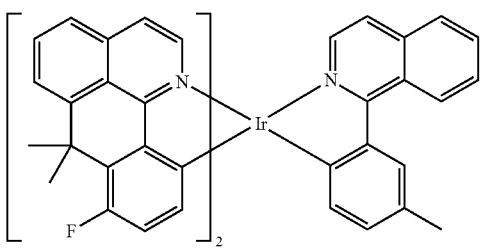
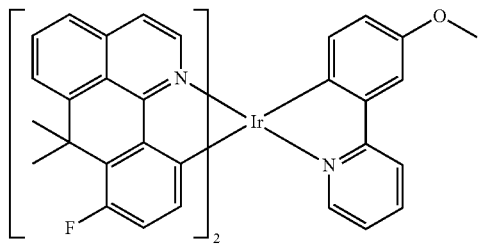
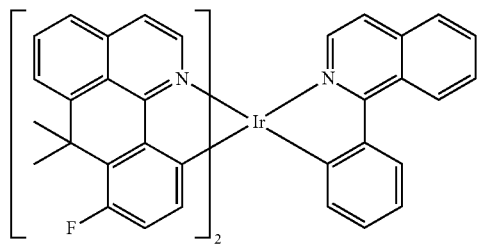
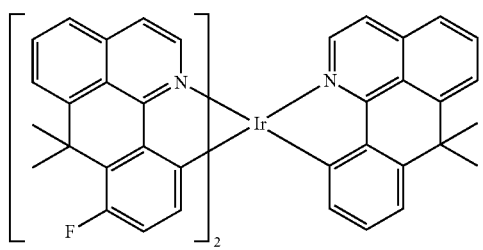
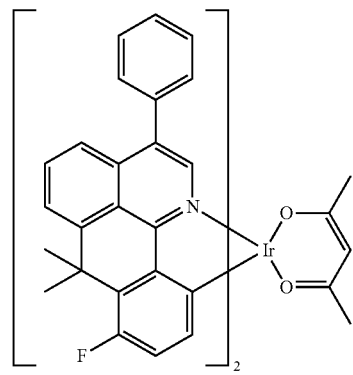
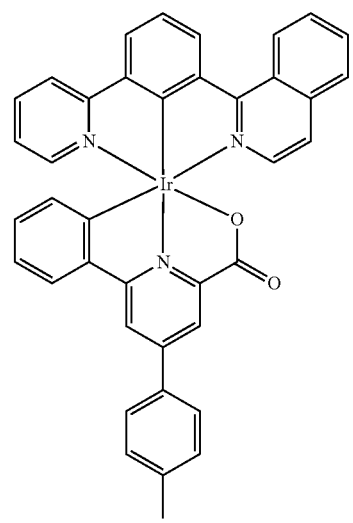
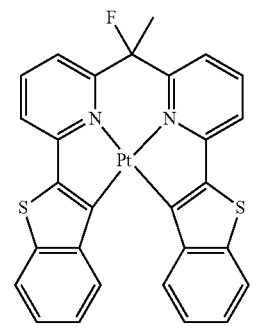

199
-continued
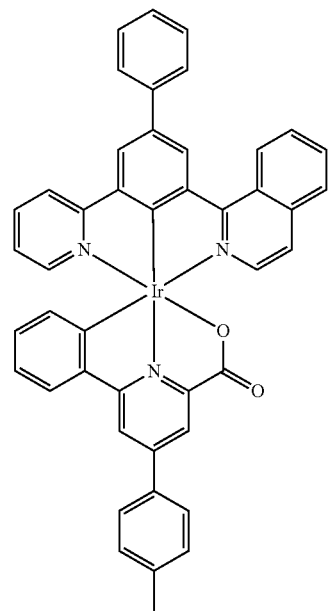
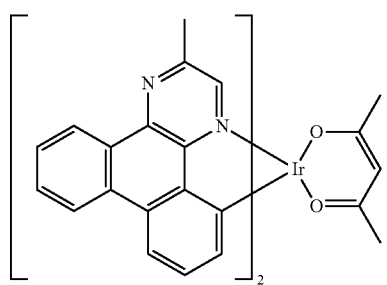
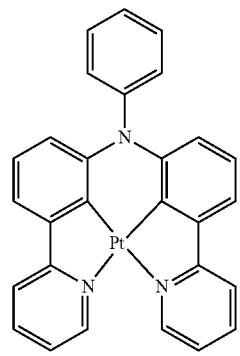
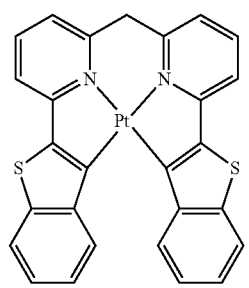
200
-continued
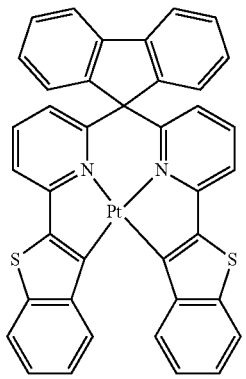
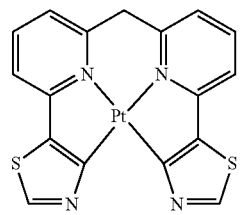
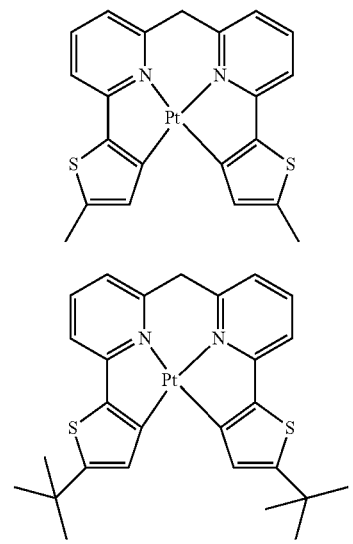
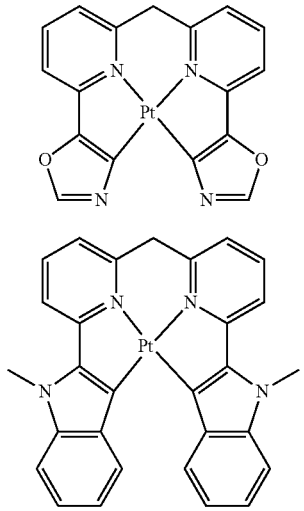

| 201 -continued | 202 -continued |
|---|---|
| 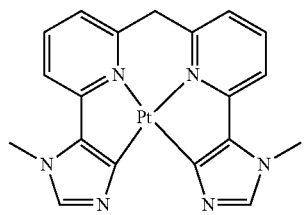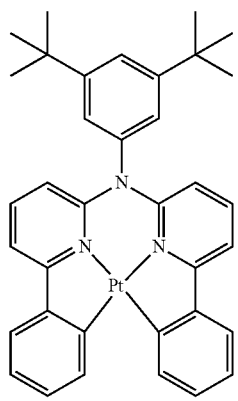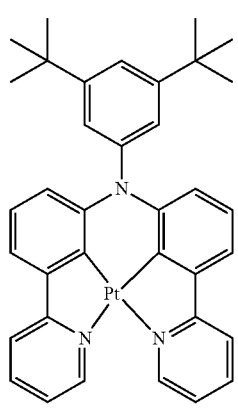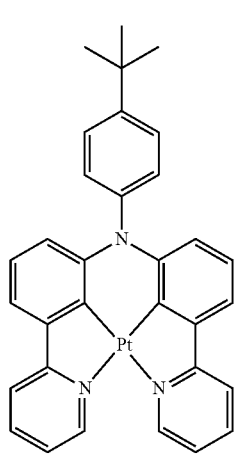 | 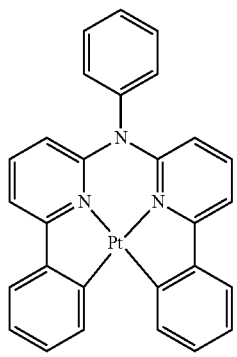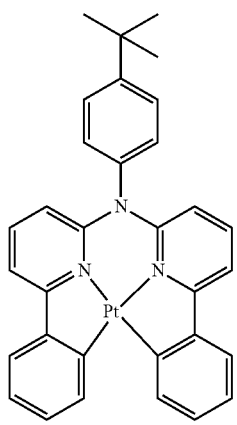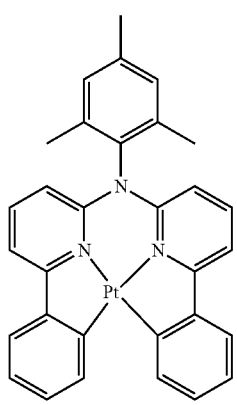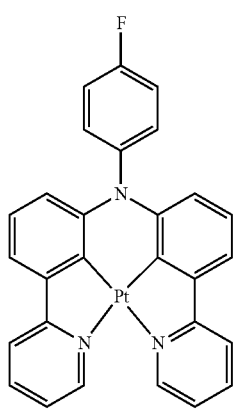 |

| 203 -continued | 204 -continued |
|---|---|
| 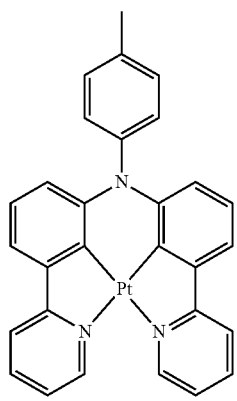 | 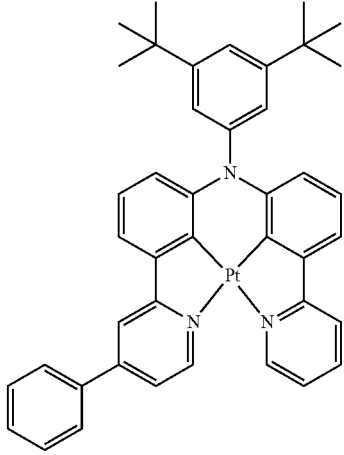 |
| 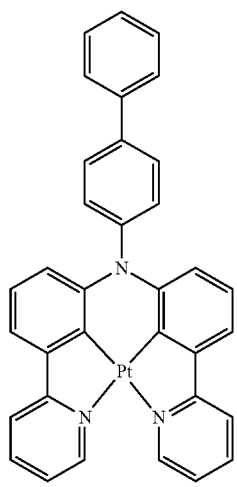 | 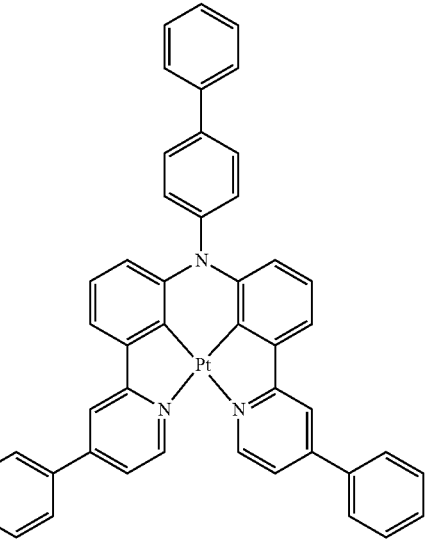 |
| 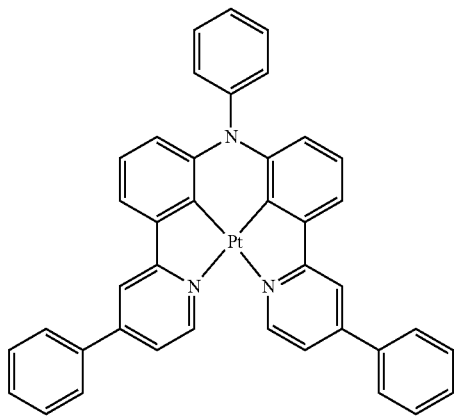 | 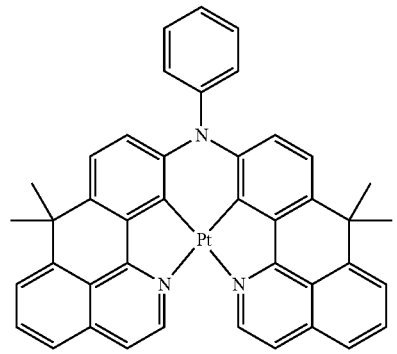 |

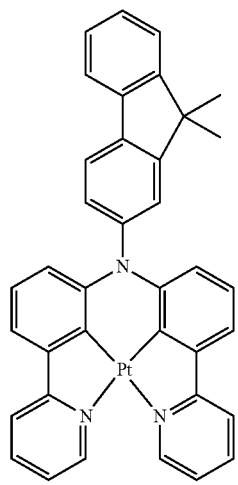
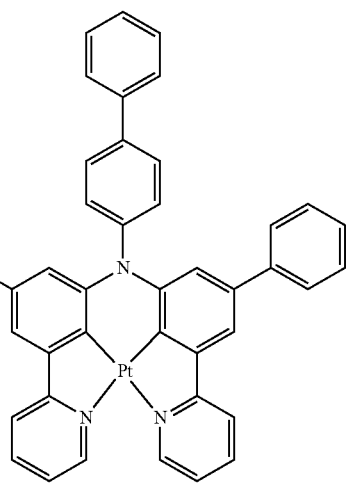
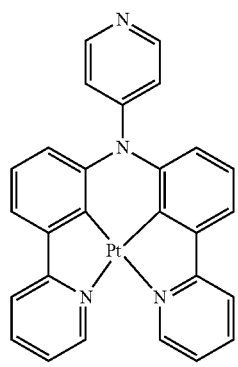
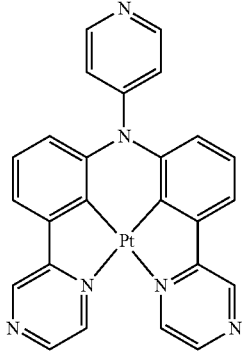
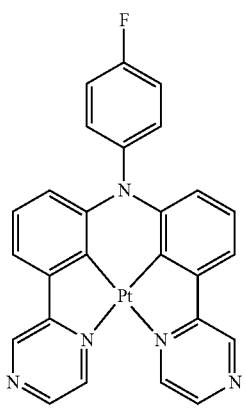
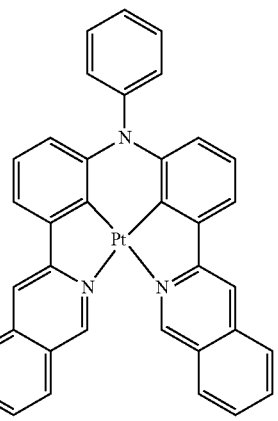
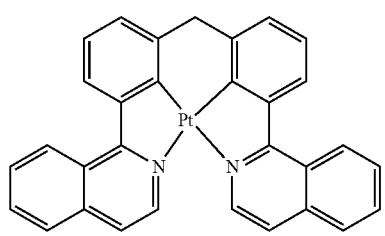

207
-continued
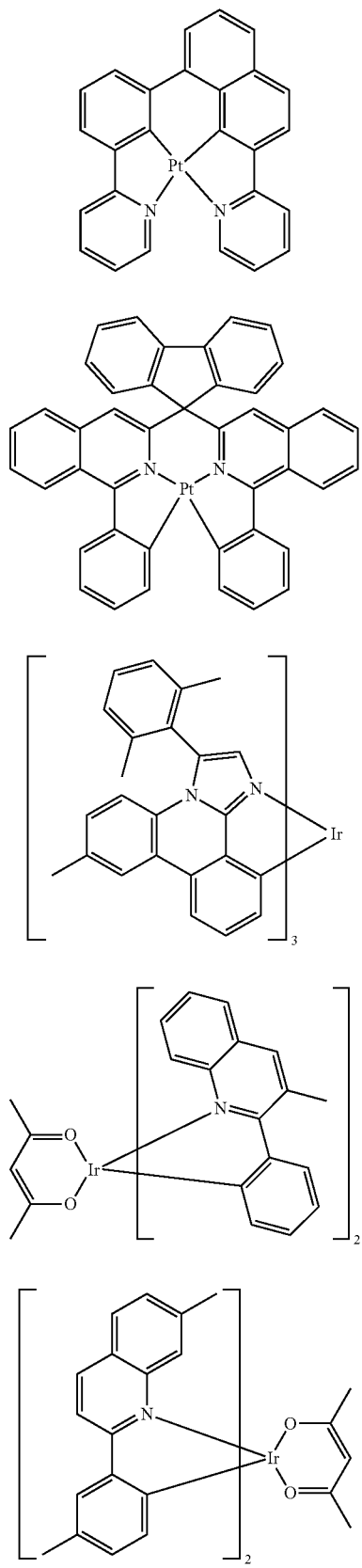
208
-continued
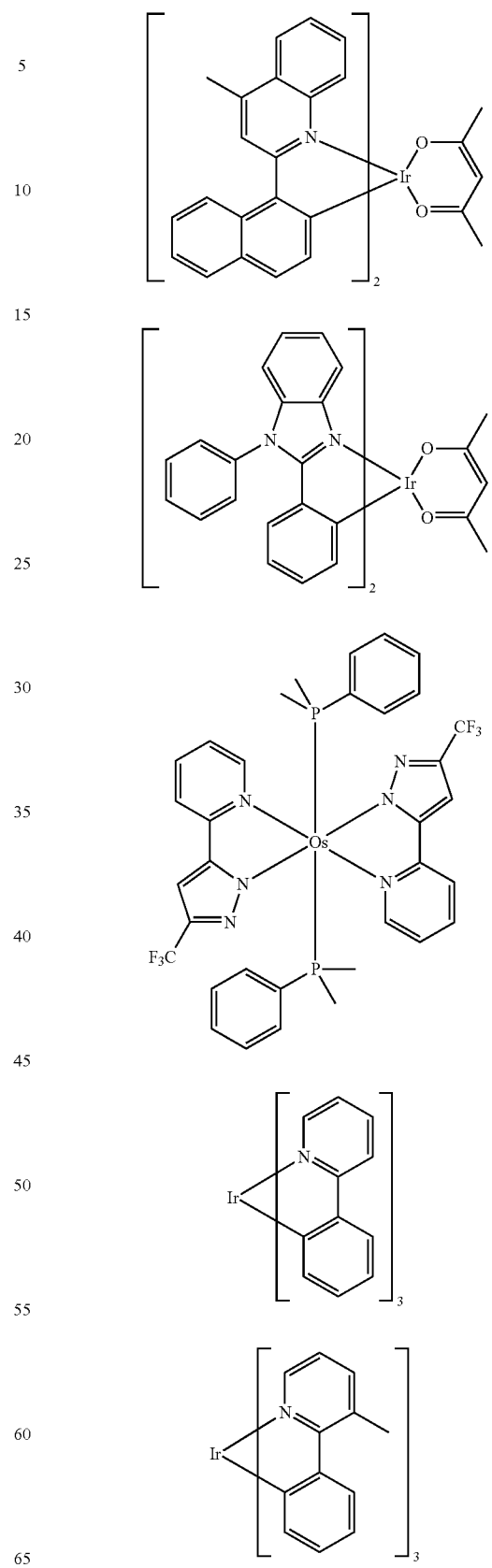

209
-continued
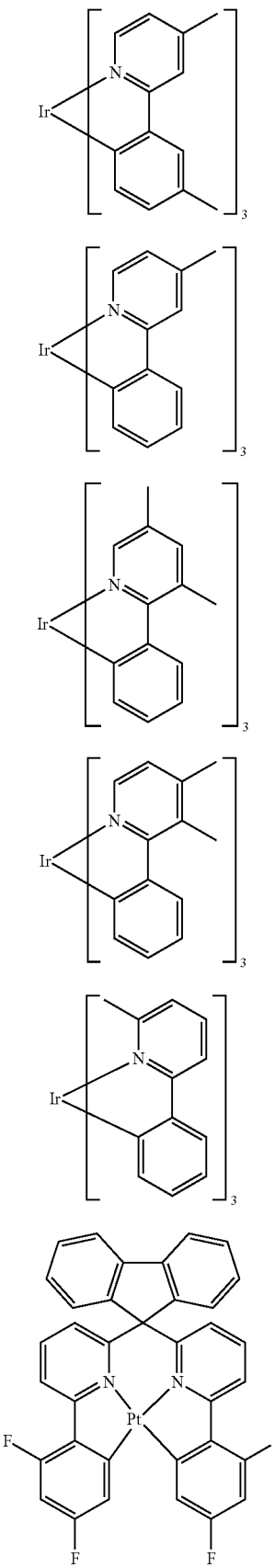
210
-continued
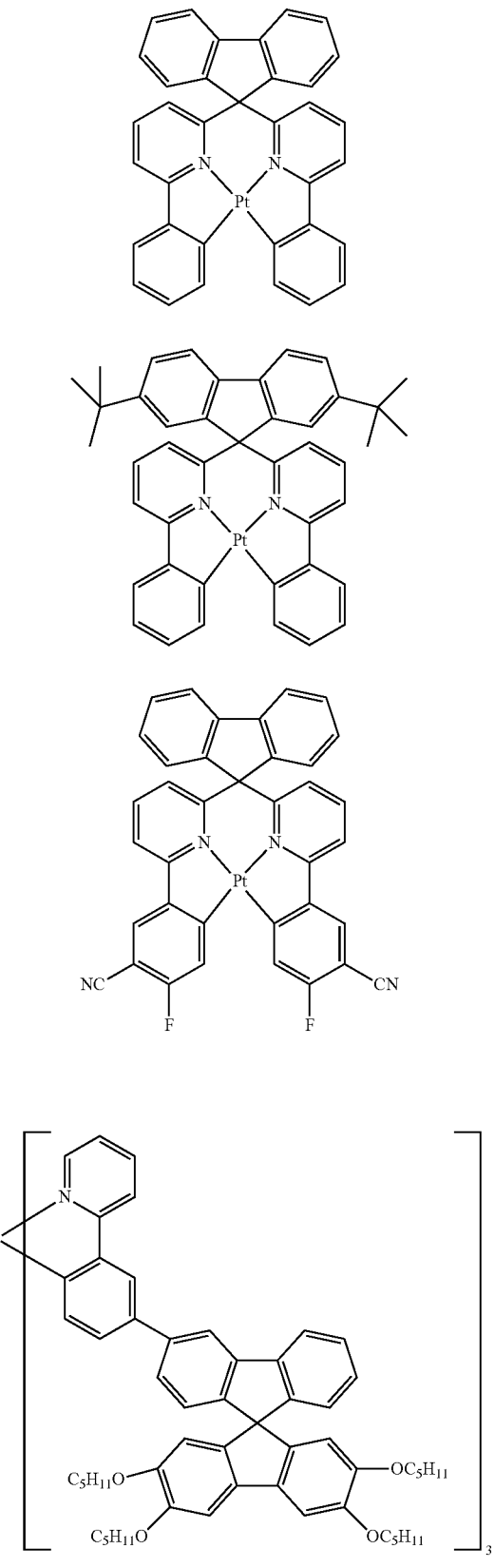

211
-continued
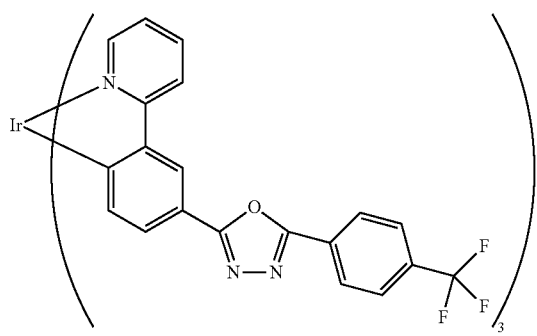
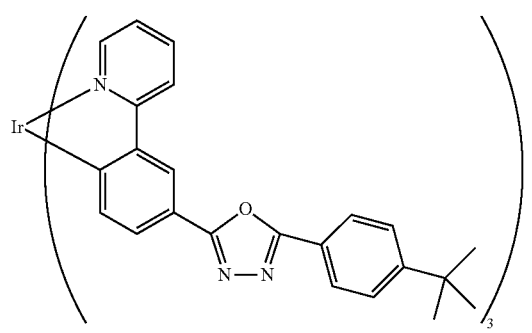
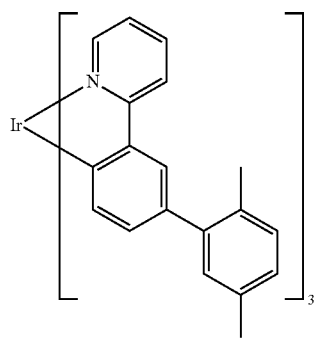
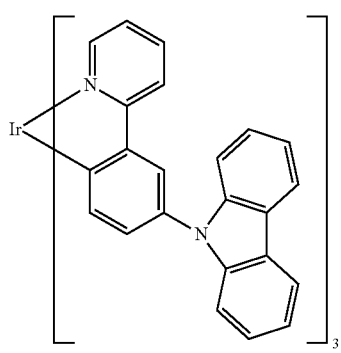
212
-continued
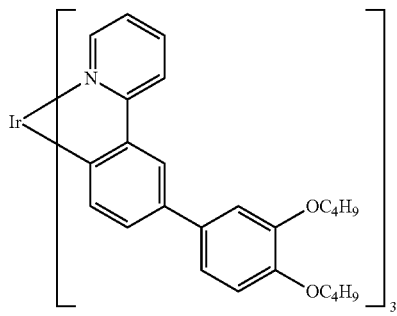
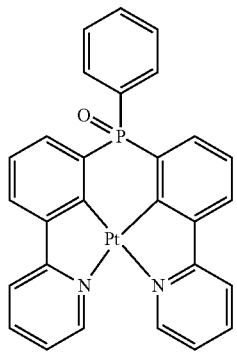
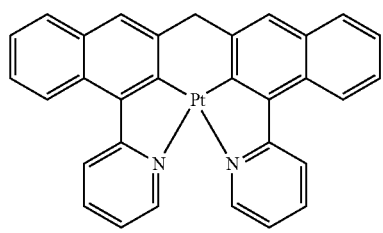
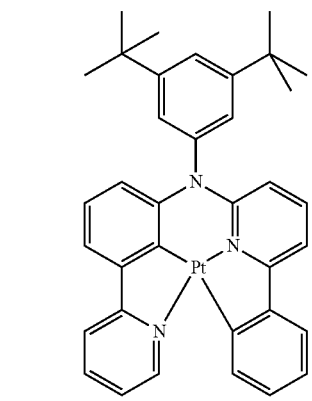
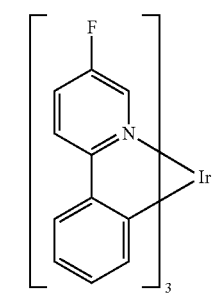

213
-continued
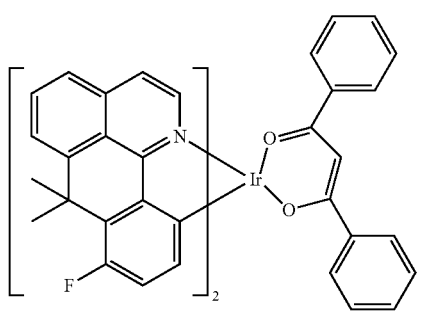
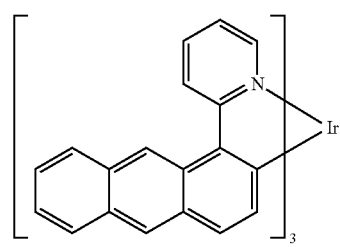
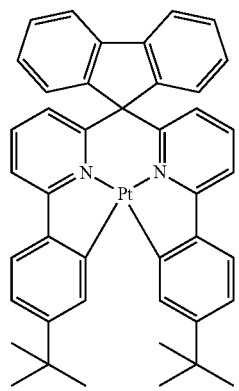
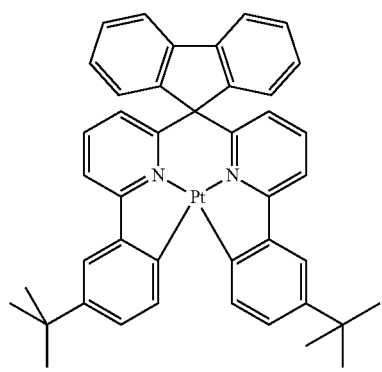
214
-continued
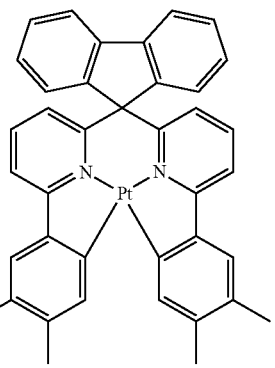
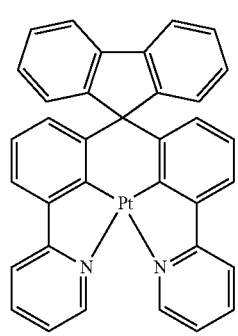
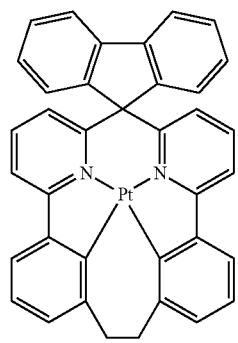
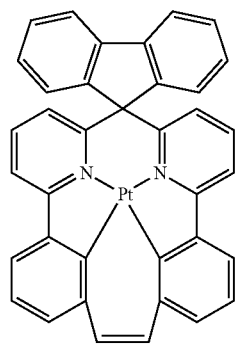

215
-continued
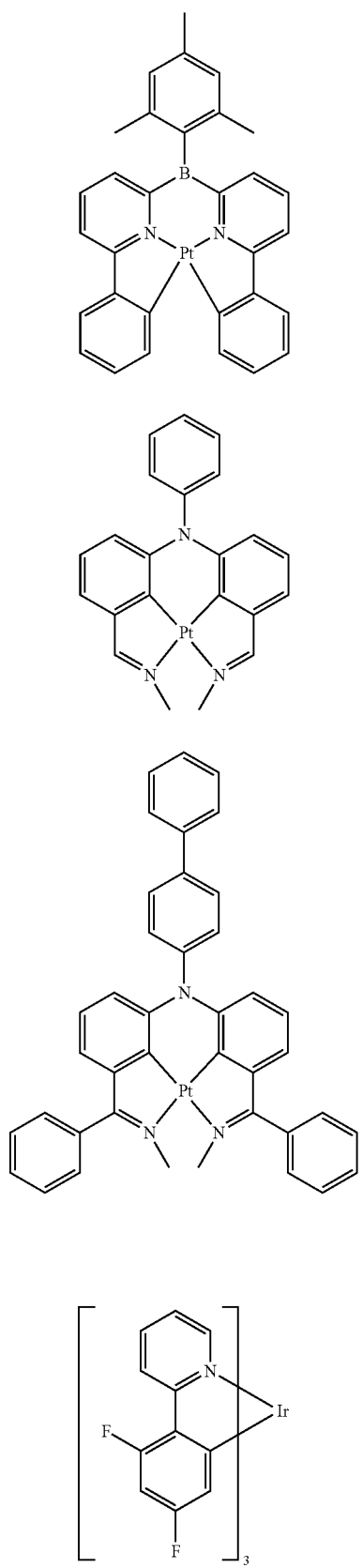
216
-continued
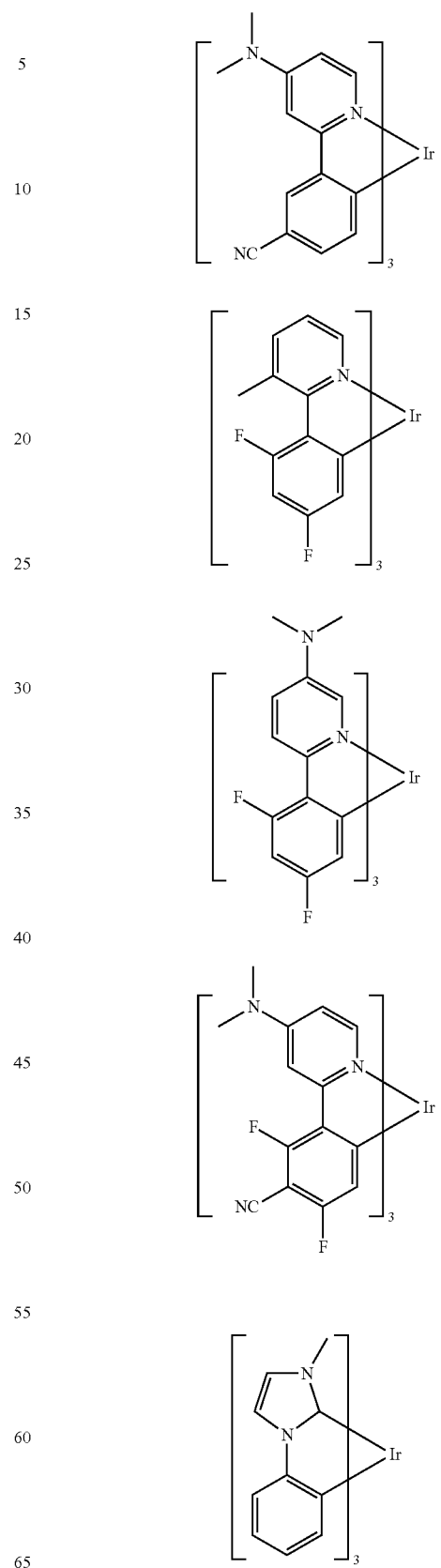

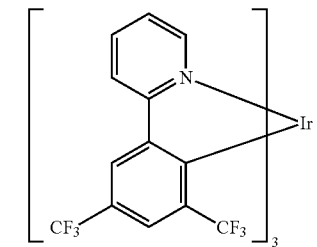
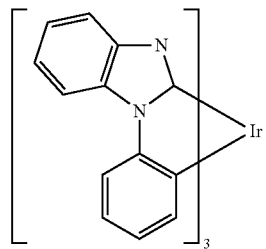
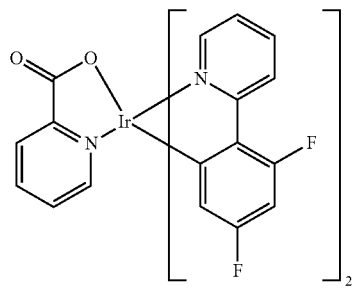
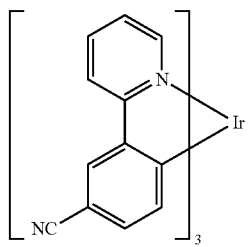
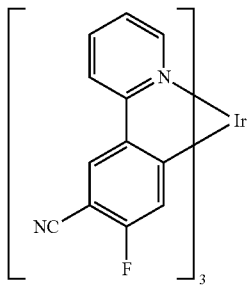
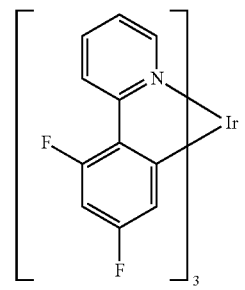
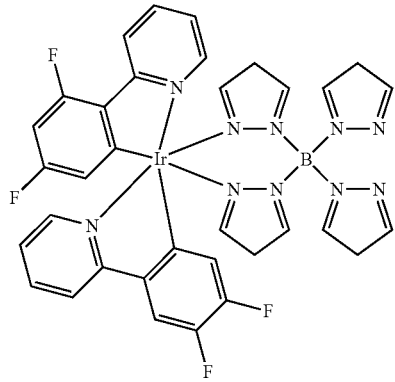
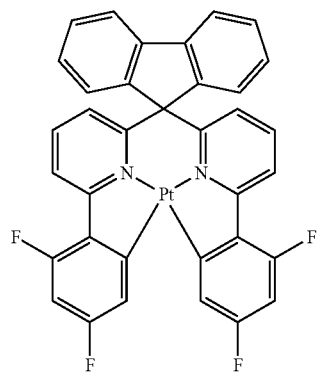
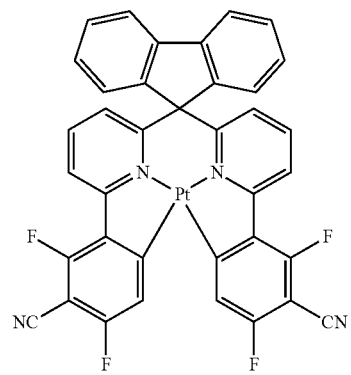
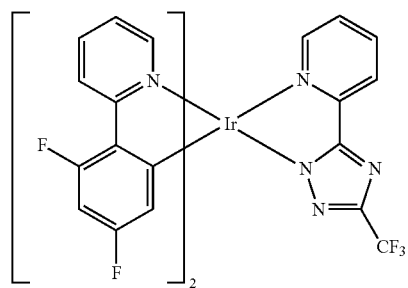

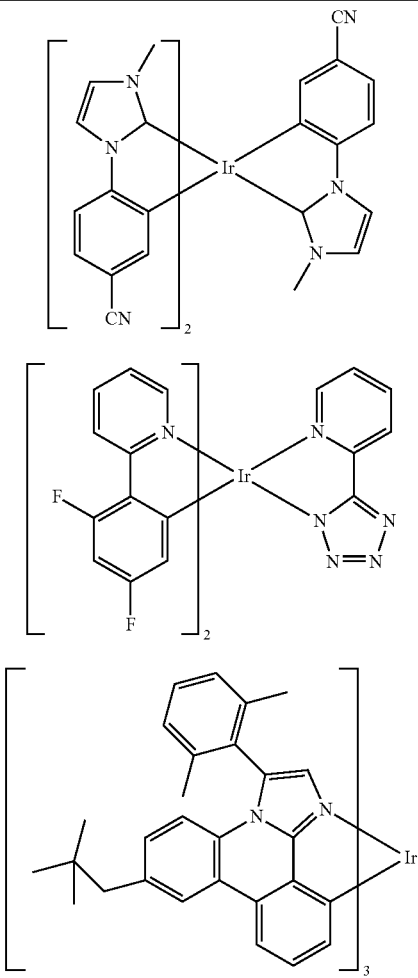

Preferred fluorescent dopants are selected from the class of the aryl-amines. An arylamine or aromatic amine in the sense of this invention is taken to mean a compound which contains three substituted or unsubstituted aromatic or heteroaromatic ring systems bonded directly to the nitro-gen. At least one of these aromatic or heteroaromatic ring systems is preferably a condensed ring system, particularly preferably having at least 14 aromatic ring atoms. Preferred examples thereof are aromatic anthracen-amines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrene-diamines, chrysenamines and chrysenediamines are defined analogously thereto, where the diarylamino groups are preferably bonded to the pyrene in the 1-position or in the 1,6-position. Further preferred fluorescent dopants are selected from indenofluorenamines or indenofluorene-diamines, for example in accordance with WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847. Preference is furthermore given to the condensed hydrocarbons disclosed in WO 2010/012328.

Suitable fluorescent dopants are furthermore the derivatives of these structures disclosed in JP 2006/001973, WO 2004/047499, WO 2006/098080, WO 2007/065678, US 2005/0260442 and WO 2004/092111.

Suitable matrix materials, preferably for fluorescent dopants, are materials from various classes of substance. Preferred matrix materials are selected from the classes of the oligoarylenes (for example 2, 2',7,7'-tetraphenyl-spirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008 145239). Particularly preferred matrix materials are selected from the classes of the oligoarylenes containing naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes containing anthracene, benzanthracene, benzophenanthrene and/or pyrene or atropisomers of these compounds.

An oligoarylene in the sense of this invention is intended to be taken to mean a compound in which at least three aryl or arylene groups are bonded to one another.

Preferred matrix materials for phosphorescent dopants, besides the compounds according to the invention, are carbazole derivatives (for example CBP (N,N-biscarbazolyl-biphenyl) or compounds in accordance with WO 2005/039246, US 2005/0069729, JP 2004/288381, EP 1205527 or WO 2008/086851), triarylamines, azacarbazoles (for example in accordance with EP 1617710, EP 1617711, EP 1731584, JP 2005/347160), indolocarbazole derivatives, for example in accordance with WO 2007/063754 or WO 2008/056746, ketones (for example in accordance with WO 2004/093207 or WO 2010/006680), phosphine oxides, sulfoxides and sulfones (for example in accordance with WO 2005/003253), oligophenylenes, aromatic amines (for example in accordance with US 2005/0069729), bipolar matrix materials (for example in accordance with WO 2007/137725), silanes (for example in accordance with WO 2005/111172), azaboroles or boronic esters, for example in accordance with WO 2006/117052, triazine derivatives, for example in accordance with WO 2010/015306, WO 2007/063754 or WO 2008/056746, zinc complexes (for example in accordance with WO 2009/062578), aluminium complexes (for example BAlq), diazasilole and tetraazasilole derivatives, for example in accordance with WO 2010/054730, indenocarbazole derivatives, for example in accordance with WO 2010/136109 and WO 2011/000455 or diazaphospholes, for example in accordance with WO 2010/054730.

Suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as are employed in these layers in accordance with the prior art.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Ba/Ag or Mg/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, pro-vided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I), (II) or (III) are necessary for this purpose. High solubility can be achieved through suitable substitution of the compounds.

For the production of an organic electroluminescent device according to the invention, it is furthermore preferred to apply one or more layers from solution and one or more layers by a sublimation process.

The organic electroluminescent devices comprising one or more compounds according to the invention can be employed in displays, as light sources in lighting applications and as light sources in medical and/or cosmetic applications (for example light therapy).

The compounds according to the invention are distinguished, in particular, by the fact that they cause good performance efficiencies, low operating voltages and long lifetimes of the devices on use in organic electroluminescent devices.

Furthermore, the compounds are oxidation-stable, temperature-stable and have a high glass-transition temperature, which is advantageous both for the processability, for example from solution or from the gas phase, and also for use in electronic devices.

Furthermore, the compounds have a high excited triplet level, which is highly desired, in particular, on use in an emitting layer in combination with a phosphorescent emitter compound. In particular, the compounds have a higher excited triplet level than the corresponding 2-fluorenyl derivatives.

Furthermore, the compounds have high hole mobility, which is highly desired, in particular, on use as hole-transport material or hole-injection material.

The invention is explained in greater detail by the following use examples, where the invention is not restricted to the scope of the examples.

WORKING EXAMPLES

Syntheses of Compounds 1 to 13 According to the Invention

The following syntheses are carried out, unless indicated otherwise, under a protective-gas atmosphere. The starting materials can be purchased from ALDRICH or ABCR (palladium(II) acetate, tri-o-tolylphosphine, inorganics, solvents). The synthesis of 3-bromofluorenone (Tetrahedron, 51, 7, 2039-54; 1995) and 3-bromofluorene can be carried out in accordance with the literature (Tetrahedron Letters, 51, 37, 4894-4897; 2010), as can the synthesis of bisbiphenyl-4-yl-(4'-bromobiphenyl-4-yl)amine (JP 2010-111605).

Precursor A: 3-Bromo-9H-fluorene

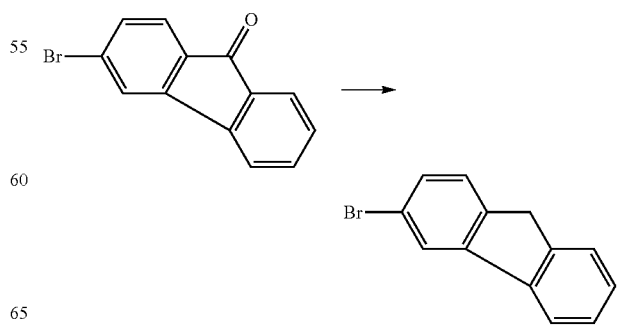

49 ml (1000 mmol) of hydrazine hydrate and then 3 g of freshly prepared Raney nickel are added to a vigorously stirred, refluxing suspension of 64 g (250 mmol) of 3-bromofluorene in a mixture of 1000 ml of toluene and 2000 ml of ethanol. After 2 h under reflux, the mixture is allowed to cool, the solvent is removed in vacuo, the residue is taken up in 1000 ml of warm chloroform, the solution is filtered through silica gel, the clear solution is evaporated to 100 ml, and 300 ml of ethanol are added. After the mixture has been left to stand for 12 h, the colourless crystals are filtered off with suction and subsequently recrystallised twice from chloroform/ethanol. Yield: 60 g (240 mmol), 98% of theory; purity: 97% according to $^1$H-NMR.

Precursor B: 3-Bromo-9,9-dimethyl-9H-fluorene

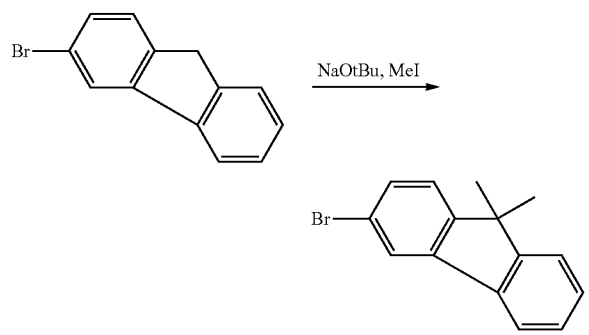

37 g (152 mmol) of 3-bromo-9H-fluorene are dissolved in 600 ml of dried DMSO in a flask which has been dried by heating. 43.9 g (457 mmol) of NaO$^t$Bu are added at room temperature. The suspension, which is now blue, is brought to an internal temperature of 80° C. At this temperature, 64.8 g (457 mmol) of iodomethane are added dropwise to the solution, which is now violet, at such a rate that the internal temperature does not exceed 90° C. (duration: about 30 min). The batch is kept at an internal temperature of 80-90° C. for a further 30 min, then poured into 1500 ml of ice-water and stirred for about 20 min. The precipitated solid is filtered off with suction and washed successively with about 200 ml of H$_2$O and methanol. Yield: 39 g (144 mmol), 96% of theory; purity: 95% according to $^1$H-NMR.

Precursor C: 3-Bromo-9,9'-spirobifluorene

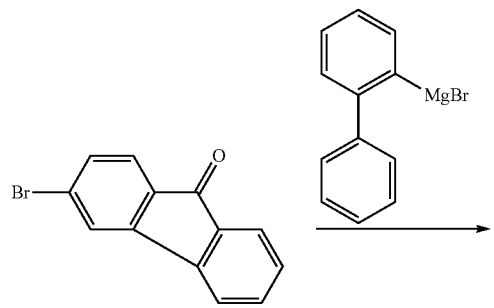

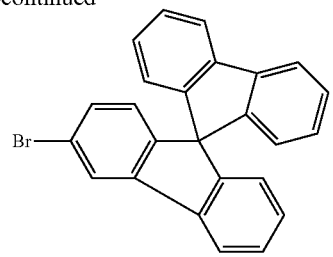

The Grignard reagent prepared from 9.9 g (400 mmol) of magnesium turnings and 93.2 g (68 ml, 400 mmol) of 2-bromobiphenyl in 500 ml of dry diethyl ether is added dropwise over the course of 2 h to a boiling solution of 103 g (400 mmol) of 3-bromo-9-fluorenone in 100 ml of dry diethyl ether. When the addition is complete, the mixture is heated at the boil for a further 3 hours. After cooling overnight, the deposited precipitate is filtered off with suction and washed with cold ether. The residue is hydrolysed in a solution of 15 g of ammonium chloride in 250 ml of ice-water. After 1 h, the alcohol formed is filtered off with suction, washed with water and sucked dry.

For the ring-closure reaction, the dried fluorenol is boiled for 6 hours in 100 ml of glacial acetic acid, after addition of 3 drops of conc. HCl. The mixture is allowed to crystallise overnight, the product formed is filtered off with suction and washed with glacial acetic acid and water. Yield: 141 g (356 mmol), 95% of theory; purity: 96% according to $^1$H-NMR.

Precursor D: Synthesis of
9,9-dimethyl-9,9'-spirobifluorene-3-boronic acid

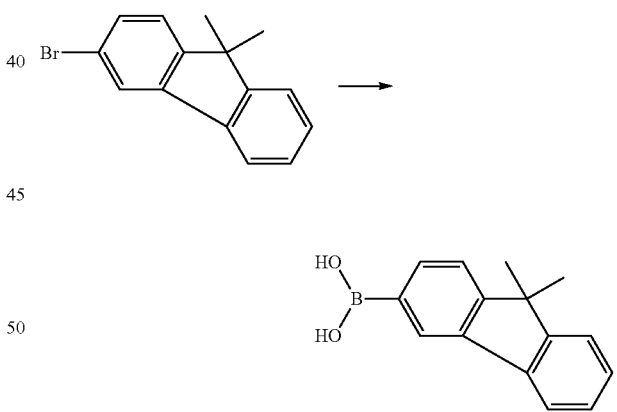

70 g (259 mmol) of 3-bromo-9,9-dimethyl-9H-fluorene are dissolved in 1500 ml of dry THF, 135 ml (337 mmol) of a 2.5 M solution of n-butyllithium in cyclohexane are added dropwise at −70° C., and, after 1 h, 37 ml of trimethyl borate (336 mmol) are added dropwise. The mixture is allowed to come to room temperature over the course of 1 h, and the solvent is removed. The residue, which is uniform according to $^1$H-NMR, is employed in the subsequent reaction without further purification. The yield is 55 g (230 mmol), corresponding to 90% of theory.

Precursors E and F are obtained analogously:

| Ex. | Starting material 1 | Product | Yield |
|---|---|---|---|
| E | 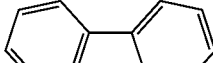 | 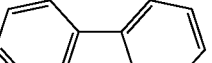 | 88% |
| F |  1161009-88-6 | 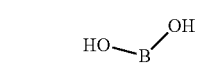 | 69% |

Precursor G:
3-(4-Bromophenyl)-9,9-dimethyl-9H-fluorene

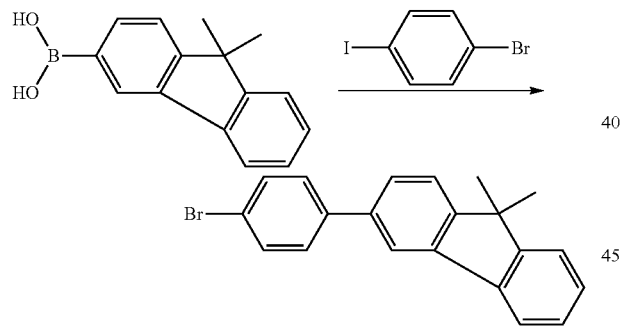

45 g (190 mmol) of 9,9-dimethyl-9,9'-spirobifluorene-3-boronic acid, 53 g (190 mmol) of iodobromobenzene and 13 g (123 mmol) of sodium carbonate are suspended in 180 ml of toluene, 180 ml of dioxane and 60 ml of water. 3.0 mg (2.6 mmol) of Pd(PPh$_3$)$_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum. The purity is 99.9%. The yield is 51 g (147 mmol), corresponding to 78% of theory.

Precursors H and I are obtained analogously:

| Ex. | Starting material 1 | Product | Yield |
|---|---|---|---|
| H | 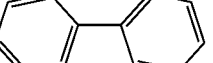 | 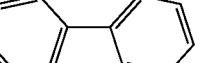 | 81% |

| Ex. | Starting material 1 | Product | Yield |
|---|---|---|---|
| I | | | 66% |

Precursor J: Synthesis of (9,9-dimethyl-9H-fluoren-3-yl)phenylamine

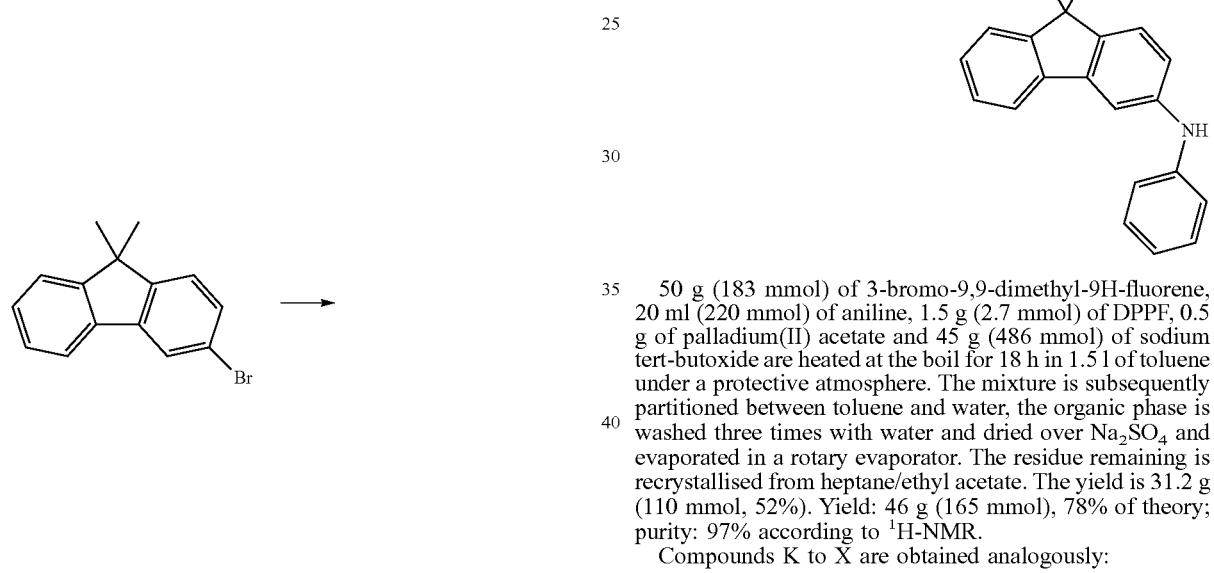

50 g (183 mmol) of 3-bromo-9,9-dimethyl-9H-fluorene, 20 ml (220 mmol) of aniline, 1.5 g (2.7 mmol) of DPPF, 0.5 g of palladium(II) acetate and 45 g (486 mmol) of sodium tert-butoxide are heated at the boil for 18 h in 1.5 l of toluene under a protective atmosphere. The mixture is subsequently partitioned between toluene and water, the organic phase is washed three times with water and dried over $Na_2SO_4$ and evaporated in a rotary evaporator. The residue remaining is recrystallised from heptane/ethyl acetate. The yield is 31.2 g (110 mmol, 52%). Yield: 46 g (165 mmol), 78% of theory; purity: 97% according to $^1$H-NMR.

Compounds K to X are obtained analogously:

| Ex. | Starting material 1 | Starting material 2 | Product | Yield |
|---|---|---|---|---|
| K | | 3315-50-2 | | 81% |

| Ex. | Starting material 1 | Starting material 2 | Product | Yield |
|---|---|---|---|---|
| L | 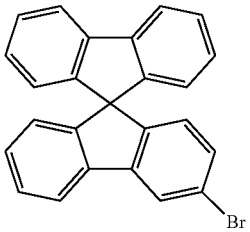 [SMILES: Brc1ccc2c(c1)-c1ccccc1C21c2ccccc2-c2ccccc21] | 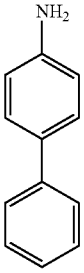<br>3315-50-2 | 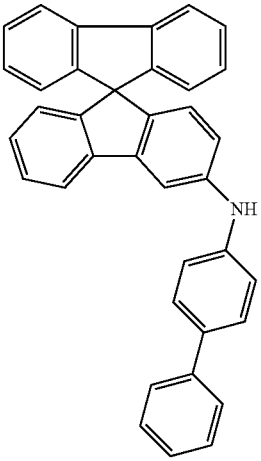 [SMILES: c1ccc(-c2ccc(Nc3ccc4c(c3)-c3ccccc3C43c4ccccc4-c4ccccc43)cc2)cc1] | 85% |
| M | 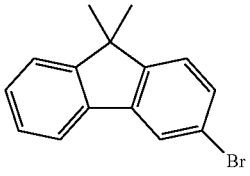 [SMILES: CC1(C)c2ccccc2-c2cc(Br)ccc21] | 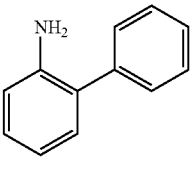<br>90-41-5 | 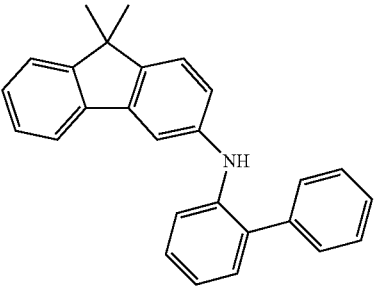 [SMILES: CC1(C)c2ccccc2-c2cc(Nc3ccccc3-c3ccccc3)ccc21] | 73% |
| N | 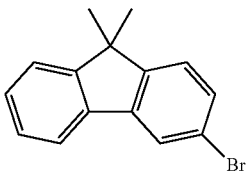 [SMILES: CC1(C)c2ccccc2-c2cc(Br)ccc21] | 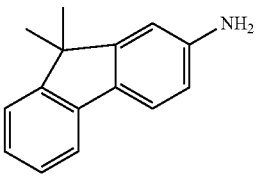<br>108714-73-4 | 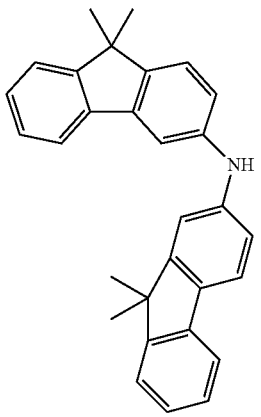 [SMILES: CC1(C)c2ccccc2-c2cc(Nc3ccc4c(c3)C(C)(C)c3ccccc3-4)ccc21] | 75% |

-continued
| Ex. | Starting material 1 | Starting material 2 | Product | Yield |
|---|---|---|---|---|
| O | 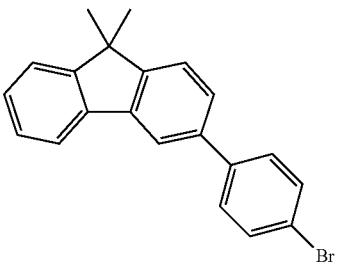 [SMILES: CC1(C)c2ccccc2-c2cc(-c3ccc(Br)cc3)ccc21] | 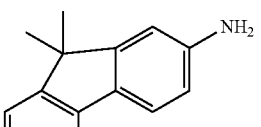 | 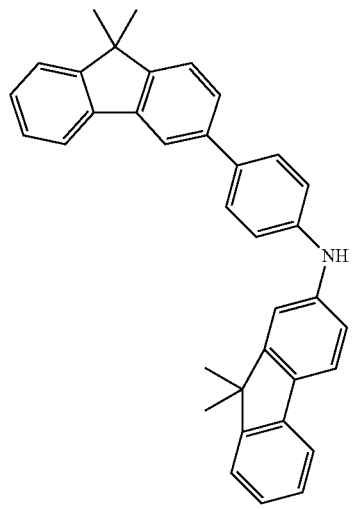 [SMILES: CC1(C)c2ccccc2-c2cc(-c3ccc(Nc4ccc5c(c4)C(C)(C)c4ccccc4-5)cc3)ccc21] | 70% |
| P | 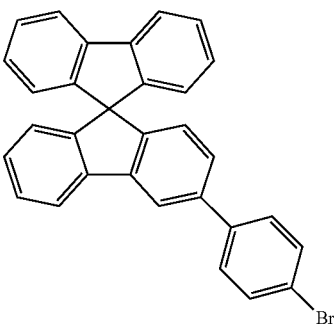 [SMILES: Brc1ccc(-c2ccc3c(c2)-c2ccccc2C32c3ccccc3-c3ccccc32)cc1] | 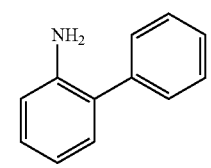 [SMILES: Nc1ccccc1-c1ccccc1] | 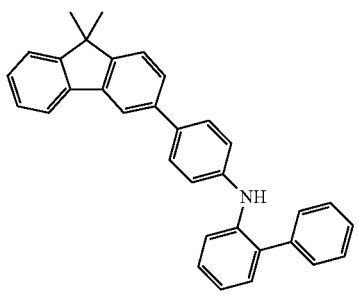 [SMILES: CC1(C)c2ccccc2-c2cc(-c3ccc(Nc4ccccc4-c4ccccc4)cc3)ccc21] | 71% |
| Q | 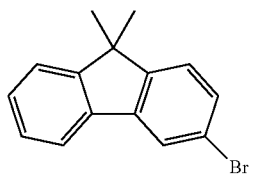 [SMILES: CC1(C)c2ccccc2-c2cc(Br)ccc21] | 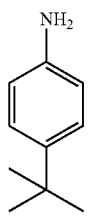 | 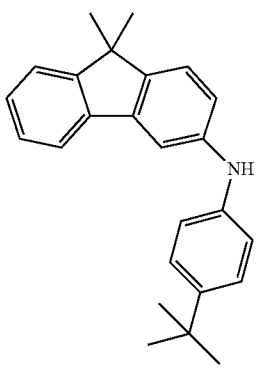 [SMILES: CC(C)(C)c1ccc(Nc2ccc3c(c2)-c2ccccc2C3(C)C)cc1] | 86% |
| R | 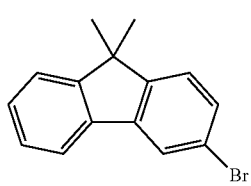 | 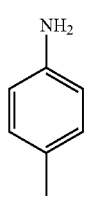 | 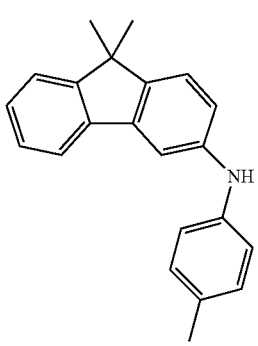 | 89% |

-continued

| Ex. | Starting material 1 | Starting material 2 | Product | Yield |
|---|---|---|---|---|
| S | 942615-32-9 | | | 72% |
| T | 1225053-54-2 | | | 75% |
| U | 942615-32-9 | 3315-50-2 | | 79% |

| Ex. | Starting material 1 | Starting material 2 | Product | Yield |
|---|---|---|---|---|
| V | 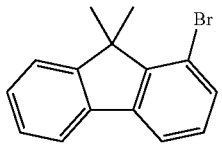<br>942615-32-9 | 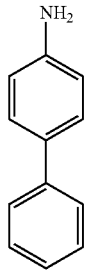<br>3315-50-2 | 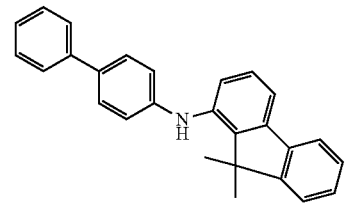 [SMILES: CC1(C)c2ccccc2-c2cccc(Nc3ccc(-c4ccccc4)cc3)c21] | 72% |
| W | 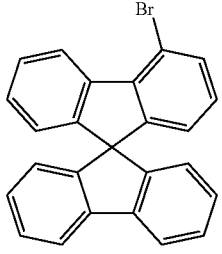 [SMILES: Brc1cccc2c1-c1ccccc1C21c2ccccc2-c2ccccc21] | 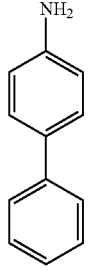<br>3315-50-2 | 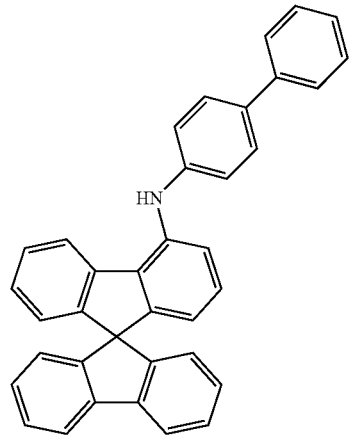 [SMILES: c1ccc(-c2ccc(Nc3cccc4c3-c3ccccc3C43c4ccccc4-c4ccccc43)cc2)cc1] | 70% |
| X | 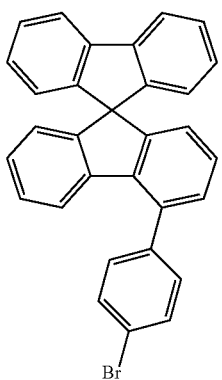 [SMILES: Brc1ccc(-c2cccc3c2-c2ccccc2C32c3ccccc3-c3ccccc32)cc1] | 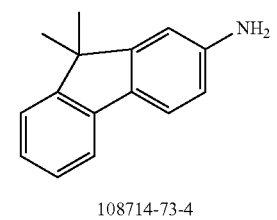 [SMILES: CC1(C)c2ccccc2-c2ccc(N)cc21]<br>108714-73-4 | 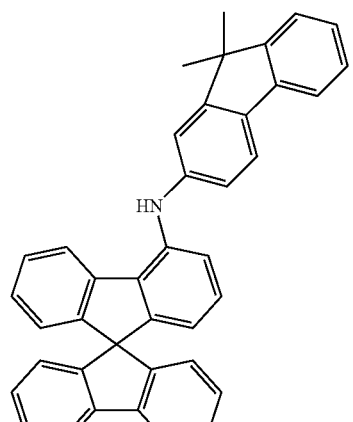 | 65% |

Example Compound 1

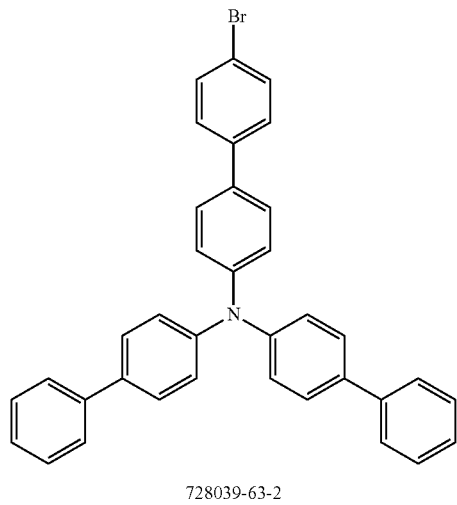

728039-63-2

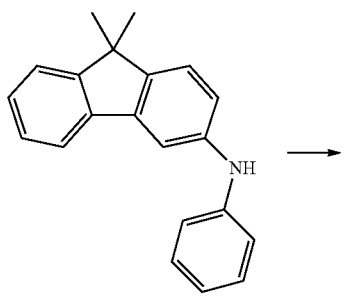

+

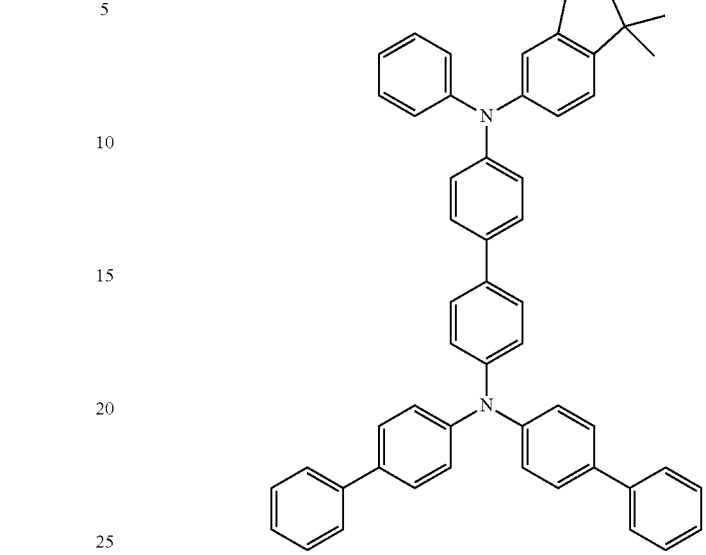

A degassed solution of 48 g (87 mmol) of bisbiphenyl-4-yl-(4'-bromo-biphenyl-4-yl)amine and 23 g (80 mmol) of (9,9-dimethyl-9H-fluoren-3-yl)-phenylamine in 1000 ml of dioxane is saturated with $N_2$ for 1 h. Then firstly 0.9 ml (4.3 mmol) of $P(tBu)_3$, then 0.48 g (2.1 mmol) of palladium(II) acetate are added to the solution. 12.6 g (131 mmol) of NaOtBu in the solid state is subsequently added. The reaction mixture is heated under reflux for 18 h. After cooling to room temperature, 1000 ml of water are carefully added. The organic phase is washed with 4×50 ml of water, dried over $MgSO_4$, and the solvent is removed in vacuo. The pure product is obtained by recrystallisation and final sublimation. Yield: 46 g (61 mmol), 71% of theory, purity according to HPLC 99.9%.

Compounds 2 to 18 are obtained analogously:

| Ex. | Starting material 1 | Starting material 2 | Product | Yield |
|---|---|---|---|---|
| 2 | ![sm1] | ![sm2] 212385-73-4 | ![prod] | 83% |

-continued

| Ex. | Starting material 1 | Starting material 2 | Product | Yield |
|---|---|---|---|---|
| 3 | | 1028648-25-0 | | 80% |
| 4 | | 1028647-93-9 | | 84% |
| 5 | | 728039-63-2 | | 80% |

-continued

| Ex. | Starting material 1 | Starting material 2 | Product | Yield |
|---|---|---|---|---|
| 6 | | 765271-17-8 | | 77% |
| 7 | | 1028647-93-9 | | 72% |
| 8 | | 1028648-25-0 | | 65% |

-continued

| Ex. | Starting material 1 | Starting material 2 | Product | Yield |
|---|---|---|---|---|
| 9 | | 1028647-93-9 | | 84% |
| 10 | | 1028647-93-9 | | 78% |
| 11 | | 308144-66-3 | | 69% |

-continued
| Ex. | Starting material 1 | Starting material 2 | Product | Yield |
|---|---|---|---|---|
| 12 | 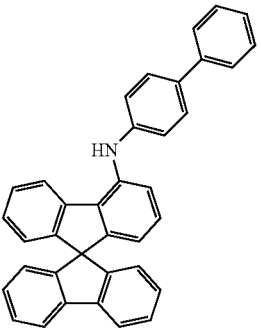 [SMILES: c1ccc(-c2ccc(Nc3cccc4c3-c3ccccc3C43c4ccccc4-c4ccccc43)cc2)cc1] | 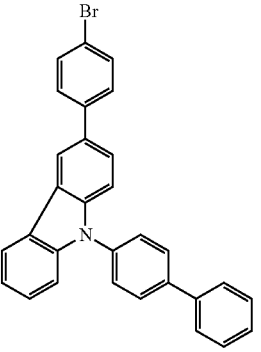 1028648-25-0 | 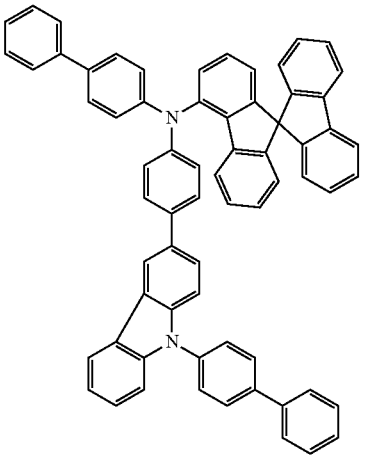 [SMILES: c1ccc(-c2ccc(N(c3ccc(-c4ccc5c(c4)c4ccccc4n5-c4ccc(-c5ccccc5)cc4)cc3)c3cccc4c3-c3ccccc3C43c4ccccc4-c4ccccc43)cc2)cc1] | 63% |
| 13 | 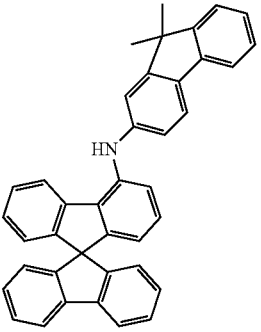 [SMILES: CC1(C)c2ccccc2-c2ccc(Nc3cccc4c3-c3ccccc3C43c4ccccc4-c4ccccc43)cc21] | 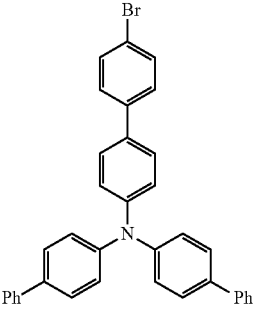 728039-63-2 | 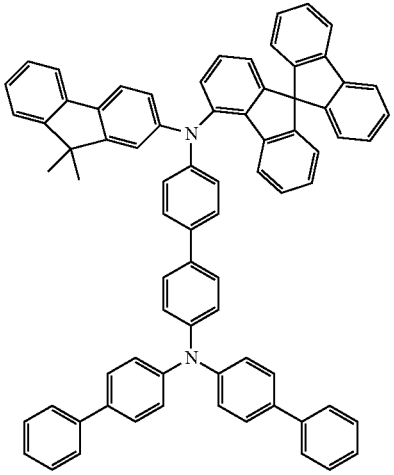 [SMILES: CC1(C)c2ccccc2-c2ccc(N(c3ccc(-c4ccc(N(c5ccc(-c6ccccc6)cc5)c5ccc(-c6ccccc6)cc5)cc4)cc3)c3cccc4c3-c3ccccc3C43c4ccccc4-c4ccccc43)cc21] | 73% |
| 14 | 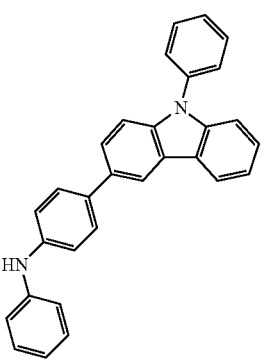 1072194-21-8 | 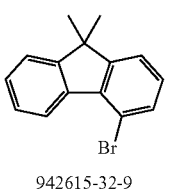 [SMILES: CC1(C)c2ccccc2-c2c(Br)cccc21] 942615-32-9 | 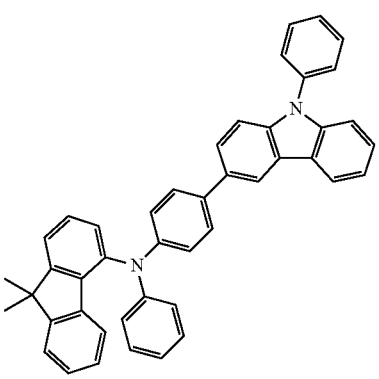 [SMILES: CC1(C)c2ccccc2-c2c(N(c3ccccc3)c3ccc(-c4ccc5c(c4)c4ccccc4n5-c4ccccc4)cc3)cccc21] | 76% |

US 9,773,979 B2
247                                                                                       248
-continued
| Ex. | Starting material 1 | Starting material 2 | Product | Yield |
|---|---|---|---|---|
| 15 | 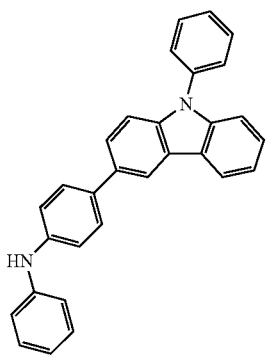 1072194-21-8 | 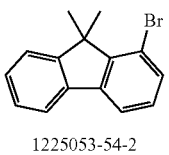 [SMILES: CC1(C)c2ccccc2-c2cccc(Br)c21] 1225053-54-2 | 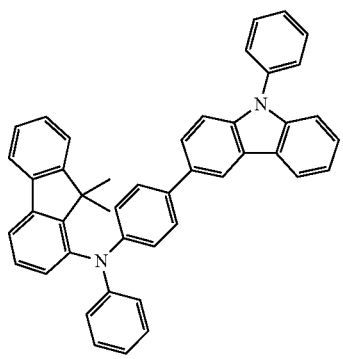 [SMILES: CC1(C)c2ccccc2-c2cccc(N(c3ccccc3)c3ccc(-c4ccc5c(c4)c4ccccc4n5-c4ccccc4)cc3)c21] | 77% |
| 16 | 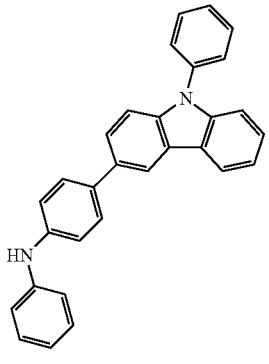 1072194-21-8 |  | 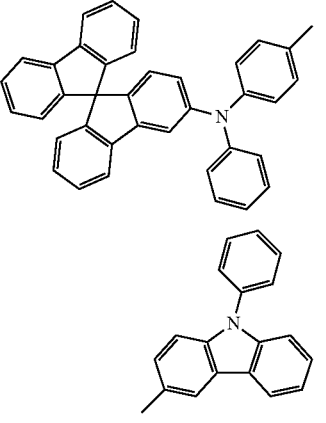 | 79% |
| 17 | 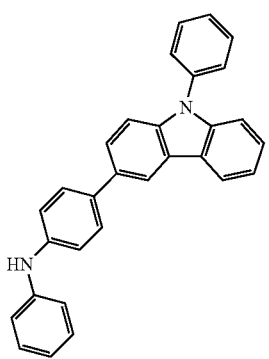 1072194-21-8 | 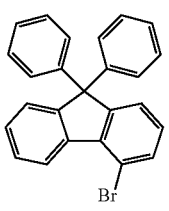 713125-22-5 | 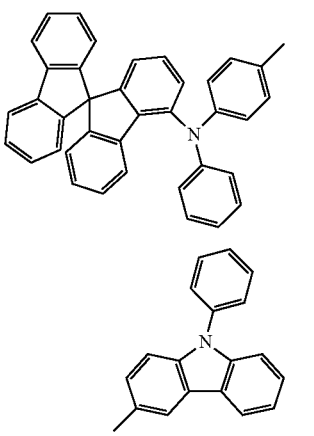 | 73% |

| Ex. | Starting material 1 | Starting material 2 | Product | Yield |
|---|---|---|---|---|
| 18 | 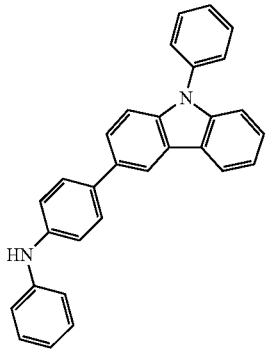 1072194-21-8 | 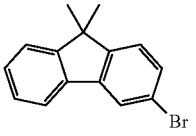 [SMILES: CC1(C)c2ccccc2-c2cc(Br)ccc21] | 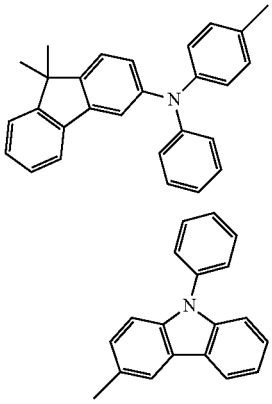 | 76% |

Device Examples

Production of OLEDs

OLEDs according to the invention and OLEDs in accordance with the prior art are produced by a general process in accordance with WO 2004/058911, which is adapted to the circumstances described here (layer-thickness variation, materials).

The data for various OLEDs are presented in Examples E1 to E16 below (see Tables 3 and 5 with device data and Tables 2 and 4 with the corresponding information on the device structures). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs basically have the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Tables 2 and 4. The materials required for the production of the OLEDs are shown in Table 1.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as H1:SEB1 (95%:5%) here means that material H1 is present in the layer in a proportion by volume of 95% and SEB1 is present in the layer in a proportion of 5%. The electron-transport layer may analogously also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m², and the CIE 1931x and y colour coordinates are calculated therefrom. The term U @ 1000 cd/m² in Table 3 and 5 denotes the voltage required for a luminous density of 1000 cd/m². Finally, EQE @ 1000 cd/m² denotes the external quantum efficiency at an operating luminous density of 1000 cd/m². LT80 @ 6000 cd/m² is the lifetime until the OLED at a luminance of 6000 cd/m² has dropped to 80% of the initial intensity, i.e. to 4800 cd/m². The device data for the various OLEDs are summarised in Table 3 and 5, while Tables 2 and 4 show the corresponding device structures.

Use of Compounds According to the Invention as Electron-Blocking Materials/Hole-Transport Materials in Fluorescent and Phosphorescent OLEDs Compounds according to the invention are particularly suitable as hole-transport material (HTM), as matrix material or as electron-blocking material (EBM) in OLEDs. They are suitable for use as individual materials in a layer, but also for use in a mixture with one or more further components in the hole-transport layer (HTL), electron-blocking layer (EBL) or emitting layer (EML).

Compared with devices comprising NPB as EBM (V1 and V5), the devices comprising compounds according to the invention (E1 to E16) exhibit both higher efficiencies and also improved lifetimes.

Compared with the material in accordance with the prior art HTMV1 (V2), in which the carbazole group and the fluorene group are connected directly to one another via an amino group, the compounds according to the invention exhibit similar or better efficiencies and significantly better lifetimes. Thus, the lifetime of the reference device V2 is virtually 10 times longer compared with E1 and E2 (blue-fluorescent devices), and the lifetime is also virtually doubled in the green-phosphorescent device (V6 compared with E9 and E10).

The advantage of a 3-fluorene substitution compared with a 2-fluorene substitution is readily evident in the comparison between HTMV2 and HTM6. Better efficiencies and better lifetimes are evident in the blue-fluorescent devices (V3 and E6) and in particular in the green-phosphorescent devices (V7 and E14). The same is also readily evident in the comparison of HTMV3 (V8) against HTM7 (E15) and HTM8 (E16). Here too, a significantly improved efficiency and lifetime is evident, in particular in the case of green-phosphorescent devices.

The devices discussed above were merely emphasised by way of example. Similar effects can also be observed in the case of the other devices which are not discussed explicitly, as can be seen from the tables with the device data. In general, the devices denoted by V1 to V8 are comparative examples comprising compounds in accordance with the prior art. The devices denoted by E1 to E16 comprise compounds in accordance with the present invention and are thus examples according to the invention.

TABLE 1

Structures of the materials used

HIL1

HIL2

NPB

TABLE 1-continued
Structures of the materials used
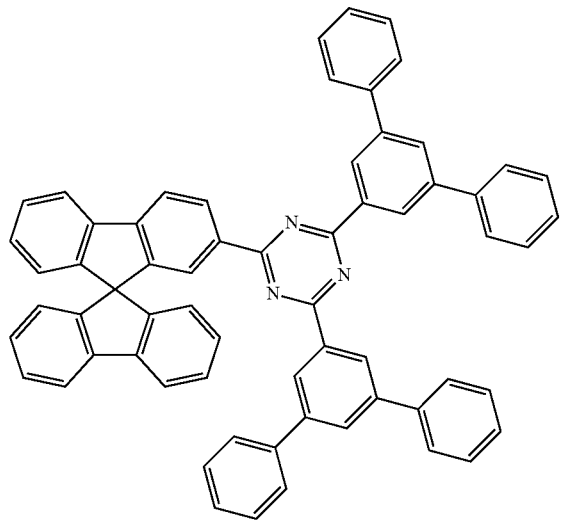 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM1
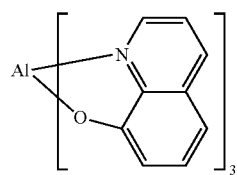
Alq3
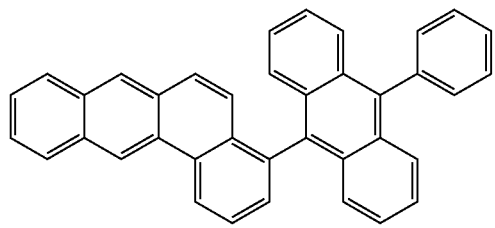 [SMILES: c1ccc(-c2c3ccccc3c(-c3cccc4c3ccc3cc5ccccc5cc34)c3ccccc23)cc1]
H1
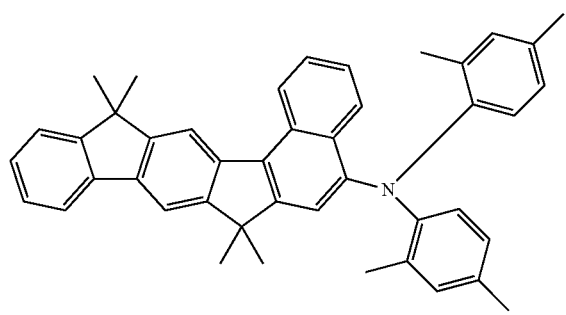 [SMILES: Cc1ccc(N(c2ccc(C)cc2C)c2cc3c(c4ccccc24)-c2cc4c(cc2C3(C)C)-c2ccccc2C4(C)C)c(C)c1]
SEB1
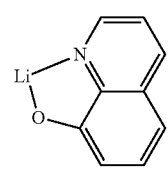
LiQ TABLE 1-continued
Structures of the materials used
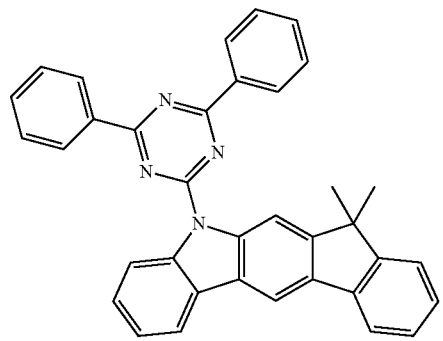 [SMILES: CC1(C)c2ccccc2-c2cc3c4ccccc4n(-c4nc(-c5ccccc5)nc(-c5ccccc5)n4)c3cc21]
H2
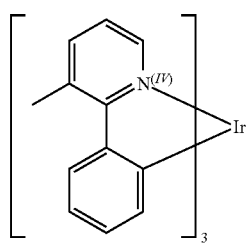
Irpy
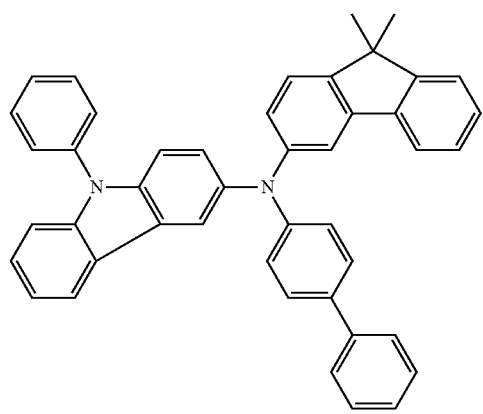 [SMILES: CC1(C)c2ccccc2-c2cc(N(c3ccc(-c4ccccc4)cc3)c3ccc4c(c3)c3ccccc3n4-c3ccccc3)ccc21]
HTMV1
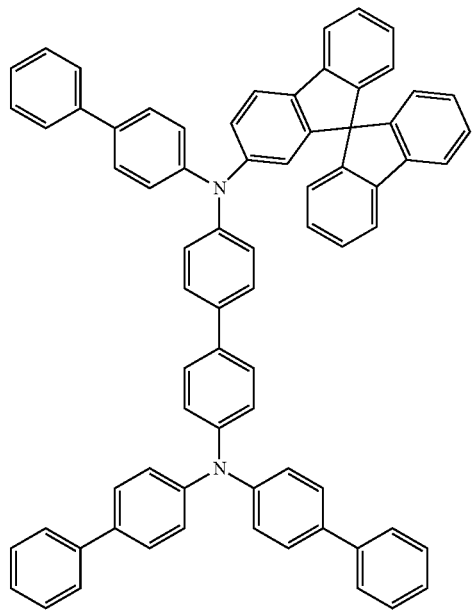 [SMILES: c1ccc(-c2ccc(N(c3ccc(-c4ccccc4)cc3)c3ccc(-c4ccc(N(c5ccc(-c6ccccc6)cc5)c5ccc6c(c5)C5(c7ccccc7-c7ccccc75)c5ccccc5-6)cc4)cc3)cc2)cc1]
HTMV2

TABLE 1-continued
Structures of the materials used
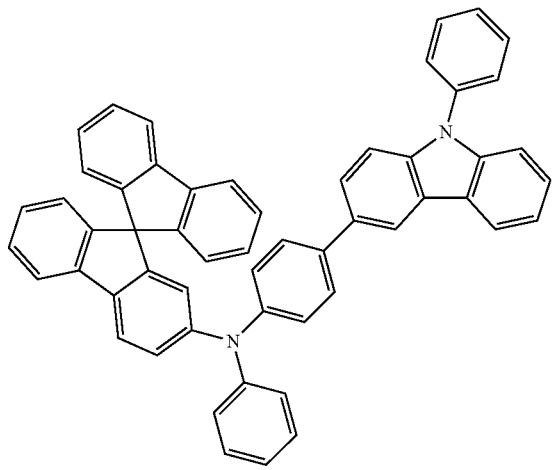 [SMILES: c1ccc(N(c2ccc(-c3ccc4c(c3)c3ccccc3n4-c3ccccc3)cc2)c2ccc3c(c2)C2(c4ccccc4-c4ccccc42)c2ccccc2-3)cc1]
HTMV3
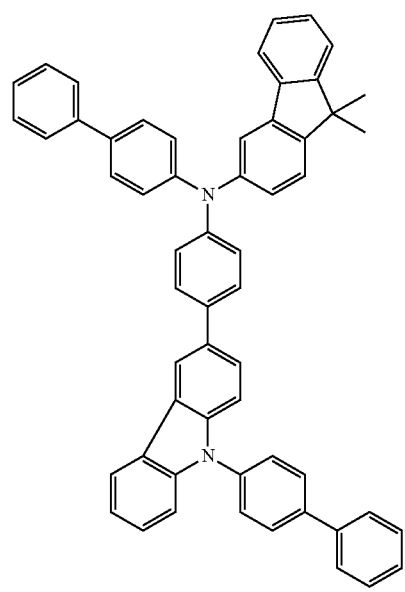
HTM1
(compound 3)

TABLE 1-continued
Structures of the materials used
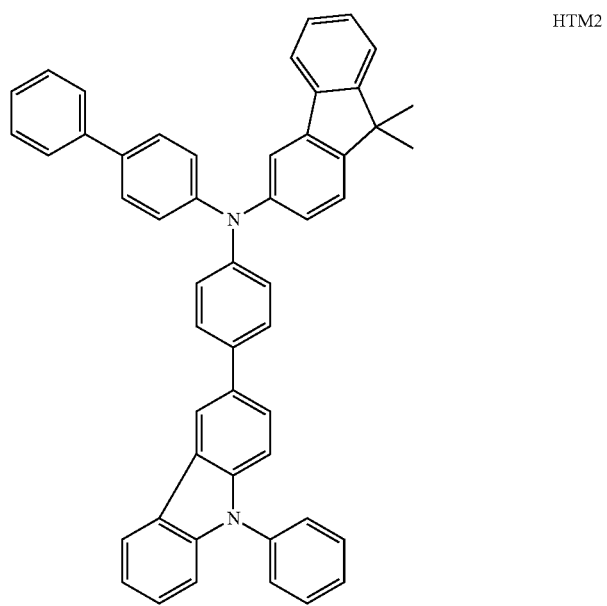
HTM2
(compound 4)
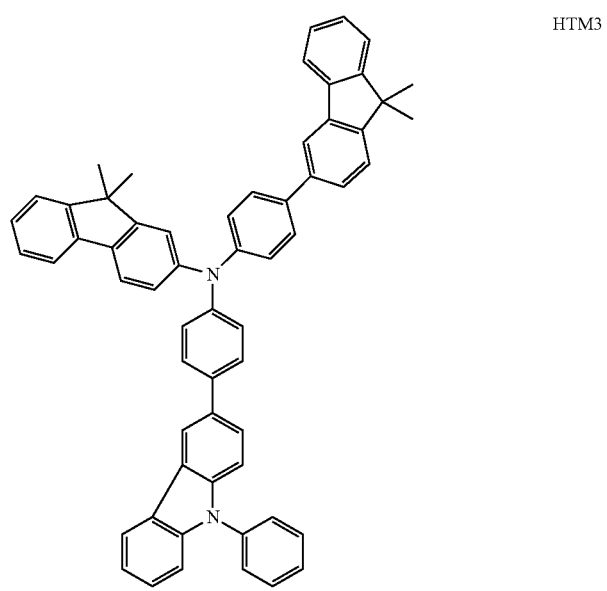
HTM3
(compound 7)

TABLE 1-continued
Structures of the materials used
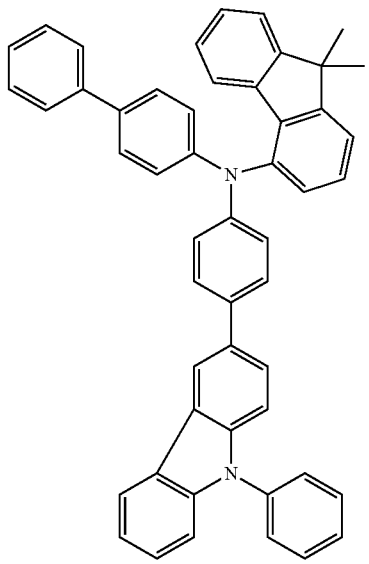
HTM4
(compound 9)
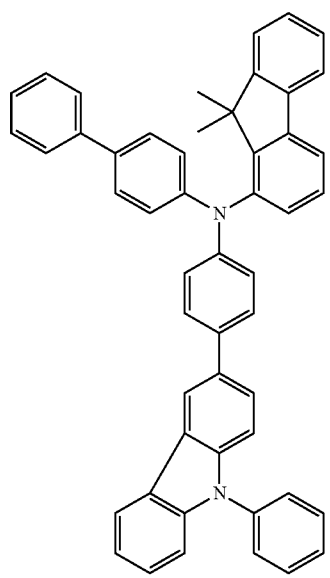
HTM5
(compound 10)

TABLE 1-continued
Structures of the materials used
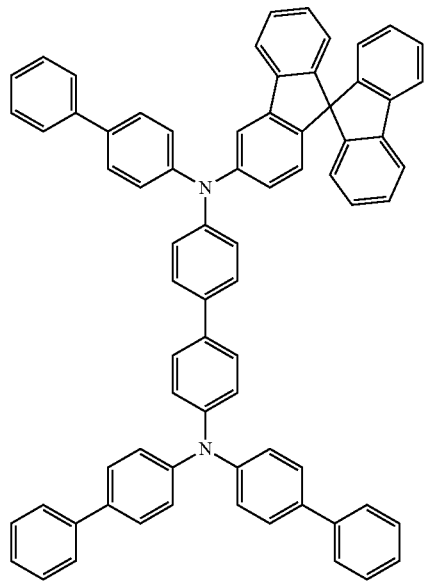
HTM6
(compound 5)
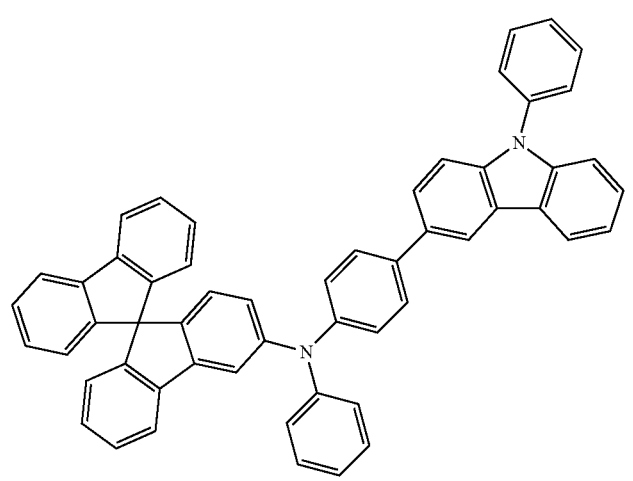
HTM7
(compound 16)

TABLE 1-continued

Structures of the materials used

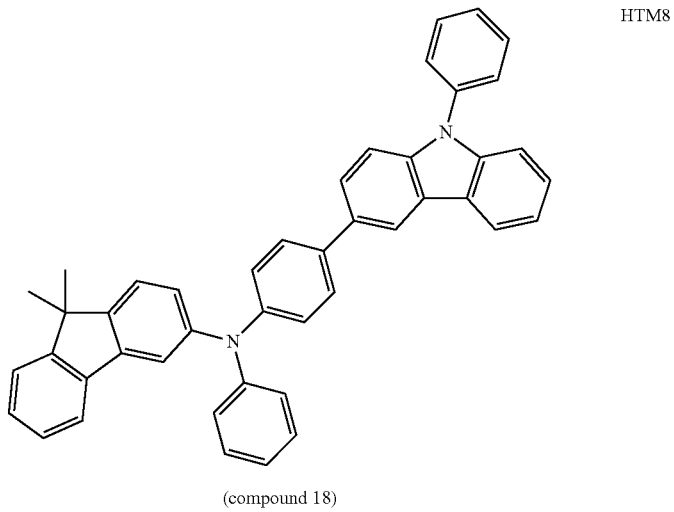

(compound 18)

HTM8

TABLE 2

Structure of the OLEDs

| Ex. | IL Thickness/ nm | HTL Thickness/ nm | IL Thickness/ nm | HTL2 Thickness/ nm | EBL Thickness/ nm | EML Thickness/ nm | ETL Thickness/ nm |
|---|---|---|---|---|---|---|---|
| V1 | HIL1 5 nm | HIL2 140 nm | HIL1 5 nm | | NPB 20 nm | H1(95%):SEB1(5%) 20 nm | ETM1(50%):LiQ(50%) 30 nm |
| V2 | HIL1 5 nm | HIL2 140 nm | HIL1 5 nm | | HTMV1 20 nm | H1(95%):SEB1(5%) 20 nm | ETM1(50%):LiQ(50%) 30 nm |
| V3 | HIL1 5 nm | HIL2 140 nm | HIL1 5 nm | | HTMV2 20 nm | H1(95%):SEB1 (5%) 20 nm | ETM1(50%):LiQ(50%) 30 nm |
| V4 | HIL1 5 nm | HIL2 140 nm | HIL1 5 nm | | HTMV3 20 nm | H1(95%):SEB1(5%) 20 nm | ETM1(50%):LiQ(50%) 30 nm |
| E1 | HIL1 5 nm | HIL2 140 nm | HIL1 5 nm | | HTM1 20 nm | H1(95%):SEB1(5%) 20 nm | ETM1(50%):LiQ(50%) 30 nm |
| E2 | HIL1 5 nm | HIL2 140 nm | HIL1 5 nm | | HTM2 20 nm | H1(95%):SEB1(5%) 20 nm | ETM1(50%):LiQ(50%) 30 nm |
| E3 | HIL1 5 nm | HIL2 140 nm | HIL1 5 nm | | HTM3 20 nm | H1(95%):SEB1(5%) 20 nm | ETM1(50%):LiQ(50%) 30 nm |
| E4 | HIL1 5 nm | HIL2 130 nm | HIL1 5 nm | NPB 10 nm | HTM4 20 nm | H1(95%):SEB1(5%) 20 nm | ETM1(50%):LiQ(50%) 30 nm |
| E5 | HIL1 5 nm | HIL2 130 nm | HIL1 5 nm | NPB 10 nm | HTM5 20 nm | H1(95%):SEB1(5%) 20 nm | ETM1(50%):LiQ(50%) 30 nm |
| E6 | HIL1 5 nm | HIL2 140 nm | HIL1 5 nm | | HTM6 20 nm | H1(95%):SEB1(5%) 20 nm | ETM1(50%):LiQ(50%) 30 nm |
| E7 | HIL1 5 nm | HIL2 140 nm | HIL1 5 nm | | HTM7 20 nm | H1(95%):SEB1(5%) 20 nm | ETM1(50%):LiQ(50%) 30 nm |
| E8 | HIL1 5 nm | HIL2 140 nm | HIL1 5 nm | | HTM8 20 nm | H1(95%):SEB1(5%) 20 nm | ETM1(50%):LiQ(50%) 30 nm |

TABLE 3

Data for the OLEDs

| Ex. | U @ 1000 cd/m2 V | EQE @ 1000 cd/m2 % | LT80 @ 6000 cd/m² [h] | CIE x | y |
|---|---|---|---|---|---|
| V1 | 4.7 | 4.8 | 70 | 0.14 | 0.17 |
| V2 | 4.4 | 6.5 | 10 | 0.14 | 0.16 |
| V3 | 4.6 | 5.9 | 60 | 0.14 | 0.16 |
| V4 | 4.5 | 6.7 | 90 | 0.14 | 0.16 |
| E1 | 4.5 | 6.8 | 105 | 0.14 | 0.16 |
| E2 | 4.4 | 6.9 | 110 | 0.14 | 0.16 |
| E3 | 4.5 | 6.8 | 105 | 0.14 | 0.15 |
| E4 | 4.6 | 7.0 | 120 | 0.14 | 0.16 |
| E5 | 4.6 | 6.9 | 110 | 0.14 | 0.16 |
| E6 | 4.5 | 6.6 | 80 | 0.14 | 0.16 |
| E7 | 4.5 | 6.8 | 100 | 0.14 | 0.16 |
| E8 | 4.5 | 6.9 | 95 | 0.14 | 0.16 |

TABLE 4

Structure of the OLEDs

| Ex. | HTL Thickness/ nm | IL Thickness/ nm | HTL2 Thickness/ nm | EBL Thickness/nm | EML Thickness/ nm | ETL Thickness/ nm |
|---|---|---|---|---|---|---|
| V5 | HIL2 70 nm | HIL1 5 nm | | NPB 90 nm | H2(88%):Irpy(12%) 30 nm | ETM1(50%):LiQ(50%) 40 nm |
| V6 | HIL2 70 nm | HIL1 5 nm | | HTMV1 90 nm | H2(88%):Irpy(12%) 30 nm | ETM1(50%):LiQ(50%) 40 nm |
| V7 | HIL2 70 nm | HIL1 5 nm | | HTMV2 90 nm | H2(88%):Irpy(12%) 30 nm | ETM1(50%):LiQ(50%) 40 nm |
| V8 | HIL2 70 nm | HIL1 5 nm | | HTMV3 90 nm | H2(88%):Irpy(12%) 30 nm | ETM1(50%):LiQ(50%) 40 nm |
| E9 | HIL2 70 nm | HIL1 5 nm | | HTM1 90 nm | H2(88%):Irpy(12%) 30 nm | ETM1(50%):LiQ(50%) 40 nm |
| E10 | HIL2 70 nm | HIL1 5 nm | | HTM2 90 nm | H2(88%):Irpy(12%) 30 nm | ETM1(50%):LiQ(50%) 40 nm |
| E11 | HIL2 70 nm | HIL1 5 nm | | HTM3 90 nm | H2(88%):Irpy(12%) 30 nm | ETM1(50%):LiQ(50%) 40 nm |
| E12 | HIL2 70 nm | HIL1 5 nm | NPB 10 nm | HTM4 80 nm | H2(88%):Irpy(12%) 30 nm | ETM1(50%):LiQ(50%) 40 nm |
| E13 | HIL2 70 nm | HIL1 5 nm | NPB 10 nm | HTM5 80 nm | H2(88%):Irpy(12%) 30 nm | ETM1(50%):LiQ(50%) 40 nm |
| E14 | HIL2 70 nm | HIL1 5 nm | | HTM6 90 nm | H2(88%):Irpy(12%) 30 nm | ETM1(50%):LiQ(50%) 40 nm |
| E15 | HIL2 70 nm | HIL1 5 nm | | HTM7 90 nm | H2(88%):Irpy(12%) 30 nm | ETM1(50%):LiQ(50%) 40 nm |
| E16 | HIL2 70 nm | HIL1 5 nm | | HTM8 90 nm | H2(88%):Irpy(12%) 30 nm | ETM1(50%):LiQ(50%) 40 nm |

TABLE 5

Data for the OLEDs

| Ex. | U @ 1000 cd/m2 V | Efficiency @ 1000 cd/m2 % | LT80 @ 8000 cd/m² [h] | CIE x | y |
|---|---|---|---|---|---|
| V5 | 3.6 | 14.4 | 85 | 0.32 | 0.63 |
| V6 | 3.4 | 16.8 | 70 | 0.33 | 0.64 |
| V7 | 3.4 | 15.6 | 120 | 0.33 | 0.64 |
| V8 | 3.5 | 16.7 | 135 | 0.33 | 0.63 |
| E9 | 3.3 | 17.6 | 155 | 0.34 | 0.62 |
| E10 | 3.3 | 17.8 | 160 | 0.33 | 0.63 |
| E11 | 3.4 | 17.0 | 145 | 0.33 | 0.64 |
| E12 | 3.5 | 17.5 | 155 | 0.34 | 0.63 |
| E13 | 3.5 | 17.8 | 160 | 0.34 | 0.63 |
| E14 | 3.4 | 16.4 | 145 | 0.33 | 0.63 |
| E15 | 3.5 | 17.6 | 155 | 0.33 | 0.64 |
| E16 | 3.4 | 17.8 | 150 | 0.33 | 0.63 |

The invention claimed is:

1. A compound of formulae (II-A), (II-B) or (III-C) or formula (III)

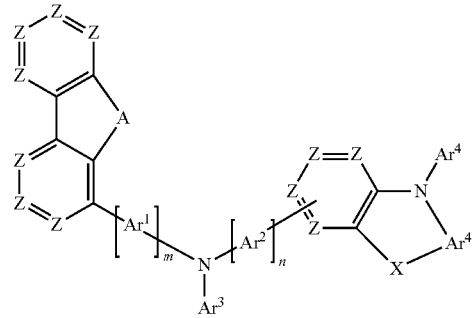

formula (II-A)

-continued

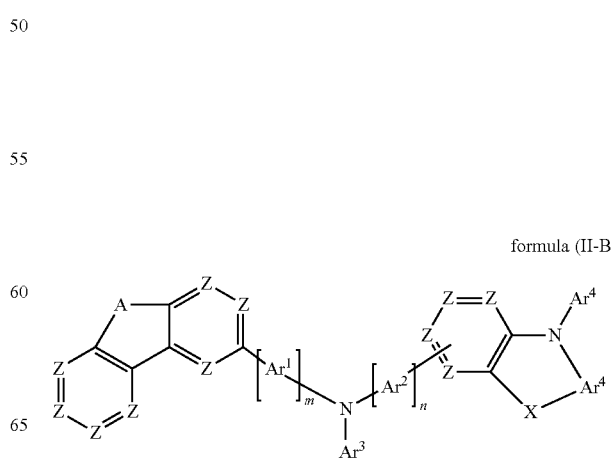

formula (II-B)

-continued formula (II-C)

formula (III)

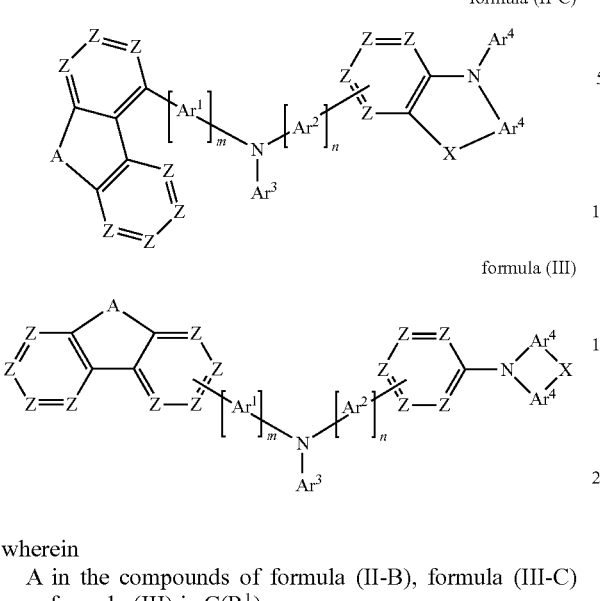

wherein
A in the compounds of formula (II-B), formula (III-C) formula (III) is $C(R^1)_2$ or

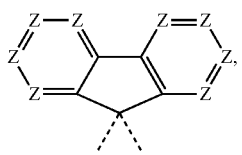

wherein
in the formula (III), the group $Ar^1$ or the nitrogen atom is bonded to the fluorene ring system in the I position, in the 3-position, or in the 4-position, and in the compounds of formula (II-A), A is

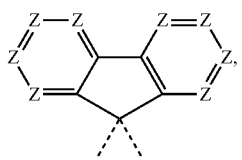

where the dashed lines represent the bonds emanating from the group A;
  Z is, identically or differently on each occurrence, $CR^1$, or, if a group is bonded in the relevant position, C;
  $Ar^1, Ar^3$ is, identically or differently on each occurrence, an aromatic or heteroaromatic ring system having 5 to 30 aromatic ring atoms, optionally substituted by one or more radicals $R^1$;
  $Ar^2$ is, identically or differently on each occurrence, an arylene group having 6 to 30 aromatic ring atoms or a heteroarylene group having 5 to 14 aromatic ring atoms, optionally substituted by one or more radicals $R^1$;
  $Ar^4$ is on each occurrence, phenyl, optionally substituted by one or more radicals $R^1$;
  X is selected from the group consisting of a single bond, $C(R^1)_2$, C=O, $Si(R^1)_2$, $NR^1$, O, S, S=O, and $S(=O)_2$;
  $R^1$ is, identically or differently on each occurrence, H, D, F, Cl, Br, I, $B(OR^2)_2$, CHO, $C(=O)R^2$, $CR^2=C(R^2)_2$, CN, $C(=O)OR^2$, $C(=O)N(R^2)_2$, $Si(R^2)_3$, $N(R^2)_2$, $NO_2$, $P(=O)(R^2)_2$, $OSO_2R^2$, $OR^2$, $S(=O)R^2$, $S(=O)_2R^2$, a straight-chain alkyl, alkoxy, or thioalkyl group having 1 to 20 C atoms, a branched or cyclic alkyl, alkoxy, or thioalkyl group having 3 to 20 C atoms, or an alkenyl or tilkynyl group having 2 to 20 C atoms, wherein the above-mentioned groups are optionally substituted by one or more radicals $R^2$, and wherein one or more $CH_2$ groups in the above-mentioned groups are optionally replaced by $-R^2C=CR^2-$, $-C\equiv C-$, $Si(R^2)_2$, C=O, C=S, $C=NR^2$, $-C(=O)O-$, $-C(=O)NR^2-$, $NR^2$, $P(=O)(R^2)$, $-O-$, $-S-$, SO, or $SO_2$, and wherein one or more H atoms in the above-mentioned groups are optionally replaced by D, F, Cl, Br, I, CN, or $NO_2$, an aromatic or heteroaromatic ring system having 5 to 30 aromatic ring atoms, optionally substituted by one or more radicals $R^2$, or an aryloxy or heteroaryloxy group having 5 to 30 aromatic ring atoms, optionally substituted by one or more radicals $R^2$;
  $R^2$ is, identically or differently on each occurrence, H, D, F, Cl, Br, I, $B(OR^3)_2$, CHO, $C(=O)R^3$, $CR^3=C(R^3)_2$, CN, $C(=O)OR^3$, $C(=O)N(R^3)_2$, $Si(R^3)_3$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy, or thioalkyl group having 1 to 20 C atoms, a branched or cyclic alkyl, alkoxy, or thioalkyl group having 3 to 20 C atoms, or an alkenyl or alkynyl group having 2 to 20 C atoms, wherein the above-mentioned groups are optionally substituted by one or more radicals $R^3$, and wherein one or more $CH_2$ groups in the above-mentioned groups are optionally replaced by $-R^3C=CR^3-$, $-C\equiv C-$, $Si(R^3)_2$, C=O, C=S, $C=NR^3$, $-C(=O)O-$, $-C(=O)NR^3-$, $NR^3$, $P(=O)(R^3)$, $-O-$, $-S-$, SO, or $SO_2$, and wherein one or more H atoms in the above-mentioned groups are optionally replaced by D, F, Cl, Br, I, CN, or $NO_2$, an aromatic or heteroaromatic ring system having 5 to 30 aromatic ring atoms, optionally substituted by one or more radicals $R^3$, or an aryloxy or heteroaryloxy group having 5 to 30 aromatic ring atoms, optionally substituted by one or more radicals $R^3$, wherein two or more radicals $R^2$ optionally define a ring system;
  $R^3$ is, identically or differently on each occurrence, H, D, F, or an aliphatic, aromatic or heteroaromatic organic radical having 1 to 20 C atoms, wherein one or more H atoms are optionally replaced by D or F; wherein two or more substituents $R^3$ optionally define a ring system;
  m is 0, 1, 2, or 3, wherein when m=0, the group is not present;
  n is 0, 1, 2, or 3, wherein when n=0, the group is not present;
    wherein n in formulae (II-A), (II-B) or (II-C) must be 1 if the group X represents a single bond; and with the proviso that the compound does not contain a heteroaryl group which contains more than 14 aromatic ring atoms.

2. The compound of claim 1, wherein the group $Ar^1$ or, in the case where m=0, the group $N(Ar^3)$, is bonded to the fluorenyl ring system in the 3-position.

3. The compound of claim 1, wherein A is $C(R^1)_2$.

4. The compound of claim 1, wherein $Ar^1$ represents an aromatic ring system having 6 to 12 aromatic ring atoms, optionally substituted by one or more radicals $R^1$.

5. The compound of claim 1, wherein $Ar^2$ represents a phenylene group, optionally substituted by one or more radicals $R^1$.

6. The compound of claim 1, wherein the group X is selected from the group consisting of a single bond, $C(R^1)_2$, O, and S.

7. The compound of claim 1, wherein m is zero.

8. The compound of claim 1, wherein n is 1 or 2.

9. The compound of claim 1, with the proviso that no condensed aryl group having more than 14 aromatic ring atoms is present in the compound.

10. The compound of claim 1, wherein the compound cannot be represented by a mirror-symmetrical structural formula.

11. An oligomer, polymer, or dendrimer, containing one or more compounds of claim 1, wherein the bonds to the oligomer, polymer, or dendrimer, are optionally localised at any desired positions in formula (II), or formula (III), that are substituted by $R^1$.

12. A formulation comprising at least one compound of claim 1 and at least one solvent.

13. A formulation comprising at least one polymer, oligomer, or dendrimer of claim 11 and at least one solvent.

14. An electronic device comprising at least one compound of claim 1.

15. An electronic device comprising at least one polymer, oligomer, or dendrimer, of claim 11.

16. The electronic device of claim 14, wherein said electronic device is selected from the group consisting of organic integrated circuit, organic field-effect transistor, organic thin-film transistor, organic light-emitting transistor, organic solar cell, organic optical detector, organic photoreceptor, organic field-quench device, light-emitting electrochemical cell, organic laser diode, and organic electroluminescent device.

17. The electronic device of claim 15, wherein said electronic device is selected from the group consisting of organic integrated circuit, organic field-effect transistor, organic thin-film transistor, organic light-emitting transistor, organic solar cell, organic optical detector, organic photoreceptor, organic field-quench device, light-emitting electrochemical cell, organic laser diode, and organic electroluminescent device.

18. The electronic device of claim 14, wherein the electronic device is an organic electroluminescent device, and wherein the compound is employed in one or more of the following functions:
- as hole-transport material in a hole-transport or hole-injection layer,
- as matrix material in an emitting layer,
- as electron-blocking material,
- as exciton-blocking material,
- as material for an interlayer.

19. The electronic device of claim 15 wherein the electronic device is an organic electrolutninescent device, and wherein the polymer, oligomer, or dendrimer, is employed in one or more of the following functions:
- as hole-transport material in a hole-transport or hole-injection layer,
- as matrix material in an emitting layer,
- as electron-blocking material,
- as exciton-blocking material,
- as material for an interlayer.

* * * * *